(12) United States Patent
Bennett et al.

(10) Patent No.: US 8,680,076 B2
(45) Date of Patent: Mar. 25, 2014

(54) METHODS OF TREATMENT, IMPROVEMENT AND PREVENTION USING HALOARYL SUBSTITUTED AMINOPURINES

(75) Inventors: Brydon L. Bennett, San Diego, CA (US); Brian Edwin Cathers, San Diego, CA (US); Kristen Lee Jensen-Pergakes, San Diego, CA (US); Heather Raymon, San Diego, CA (US); Weilin Xie, San Diego, CA (US); Jaman May Maroni, Watchung, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 217 days.

(21) Appl. No.: 13/277,282

(22) Filed: Oct. 20, 2011

(65) Prior Publication Data

US 2012/0129807 A1    May 24, 2012

Related U.S. Application Data

(60) Provisional application No. 61/406,219, filed on Oct. 25, 2010, provisional application No. 61/509,638, filed on Jul. 20, 2011.

(51) Int. Cl.
*A61K 31/69* (2006.01)
*A61K 31/5377* (2006.01)
*A61K 31/551* (2006.01)
*A61K 31/52* (2006.01)

(52) U.S. Cl.
USPC ..... 514/64; 514/218; 514/234.2; 514/252.11; 514/252.16; 514/263.2; 514/263.4; 514/263.22; 514/263.23; 514/263.24

(58) Field of Classification Search
USPC .............. 514/64, 218, 234.2, 252.11, 252.16, 514/263.2, 263.4, 263.22, 263.23, 262.24
See application file for complete search history.

(56) References Cited

U.S. PATENT DOCUMENTS

| | | | |
|---|---|---|---|
| 7,521,446 | B2 | 4/2009 | Albers et al. |
| 7,723,340 | B2 | 5/2010 | Albers et al. |
| 7,759,342 | B2 | 7/2010 | Bennett et al. |
| 2009/0048275 | A1 | 2/2009 | Beauchamps et al. |
| 2009/0275564 | A1 | 11/2009 | Albers et al. |
| 2010/0249066 | A1 | 9/2010 | Bennett et al. |
| 2012/0100213 | A1 | 4/2012 | Bhat et al. |

FOREIGN PATENT DOCUMENTS

| | | |
|---|---|---|
| WO | WO 03/047570 A1 | 6/2003 |
| WO | WO 2006/076595 A1 | 7/2006 |
| WO | WO 2007/127382 A1 | 11/2007 |
| WO | WO 2008/057252 A2 | 5/2008 |
| WO | WO 2011/071491 A1 | 6/2011 |

OTHER PUBLICATIONS

He et al., 2010, "Mechanisms of transforming growth factor beta(1)/Smad signalling mediated by mitogen-activated protein kinase pathways in keloid fibroblasts", Br J Dermatol., 162(3):538-546.
Javelaud, 2003, "Disruption of basal JNK activity differentially affects key fibroblast functions important for wound healing", J Biol Chem., 278(27):24624-24628.
Ma et al., 1998, "Inhibition of ultraviolet C irradiation-induced AP-1 activity by aspirin is through inhibition of JNKs but not erks or P38 MAP kinase", Int J Oncol., 12(3):565-568.
Silvers et al., 2003, "The role of JNK and p38 MAPK activities in UVA-induced signaling pathways leading to AP-1 activation and c-Fos expression", Neoplasia, 5(4):319-329.
Wu et al., 2006, "(+)-Catechin prevents ultraviolet B-induced human keratinocyte death via inhibition of JNK phosphorylation", Life Sci., 79(8):801-807.
Davis et al., 1994, "MAPKs: new JNK expands the group," Trends Biochem. Sci,. 9(11):470-3.
Derijard et al., 1994, "JNK1: a protein kinase stimulated by UV light and Ha-Ras that binds and phosphorylates the c-Jun activation domain," Cell; 76(6):1025-37.
Dunn et al., 2002, "Molecular mechanism and biological functions of c-Jun N-terminal kinase signalling via the c-Jun transcription factor," Cell Signal; 14(7):585-93.
Einspahr et al., 2008, "Cross-Validation of Murine UV Signal Transduction Pathways in Human Skin," Photochem. Photobiol.; 84(2):463-76.
Fanger et al., 1997, "MEKKs, GCKs, MLKs, PAKs, TAKs, and tpls: upstream regulators of the c-Jun amino-terminal kinases?" Curr. Opin. Genet. Dev.; 7(1):67-74.
Fisher et al., 1998, "Retinoic Acid Inhibits Induction of c-Jun Protein by Ultraviolet Radiation That Occurs Subsequent to Activation of Mitogen-Activated Protein Kinase Pathways in Human Skin in Vivo," J. Clin Invest.; 101(6): 1432 — 40.
Hachulla et al., 2010, "Diagnosis and classification of systemic sclerosis," Clin Rev Allergy Immunol.; 40(2):78-83.
Hibi et al., 1993, "Identification of an oncoprotein- and UV-responsive protein kinase that binds and potentiates the c-Jun activation domain," Genes Dev.; 7(11):2135-48.
Hildesheim et al., 2002, "Gadd45a protects against UV irradiation-induced skin tumors, and promotes apoptosis and stress signaling via MAPK and p53," Cancer Res.; 62(24):7305-15.
Ichijo H, 1999, "From receptors to stress-activated MAP kinases," Oncogene, 18(45):6087-93.
Ip et al., 1998, " Signal transduction by the c-Jun N-terminal kinase (JNK)-from inflammation to development," Curr. Opin. Cell Biol.; 10(2):205-19.

(Continued)

*Primary Examiner* — Raymond Henley, III
(74) *Attorney, Agent, or Firm* — Jones Day

(57) ABSTRACT

Provided herein are Aminopurine Compounds having the following structure:

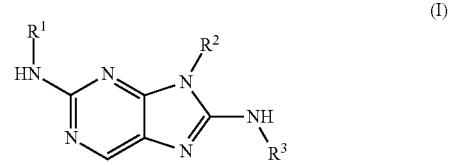

(I)

Figure 1:
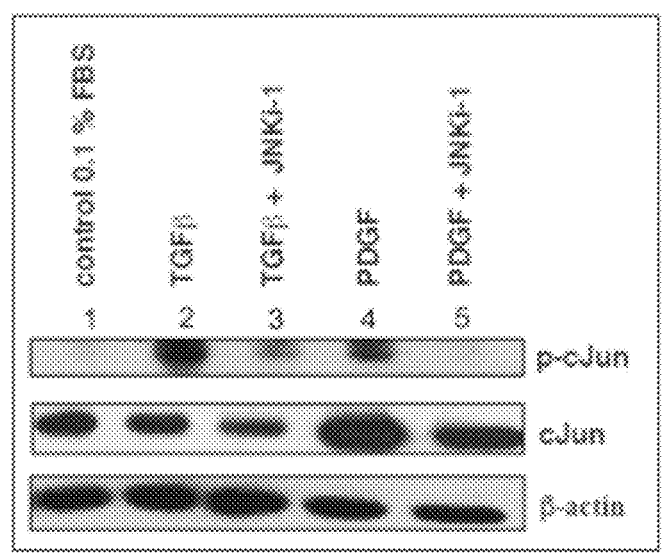

wherein $R^1$, $R^2$ and $R^3$ are as defined herein, compositions comprising an effective amount of an Aminopurine Compound and methods for treating or preventing scleroderma, keloids, UV injury, or sunburn, and methods for improving or preventing scar formation.

18 Claims, 32 Drawing Sheets

(56) References Cited

OTHER PUBLICATIONS

Kyriakis et al., 1994, "The stress-activated protein kinase subfamily of c-Jun kinases," Nature; 369(6476):156-60.

Kyriakis et al., 2001, "Mammalian mitogen-activated protein kinase signal transduction pathways activated by stress and inflammation," Physiol. Rev., 81(2):807-869.

Kyriakis JM, 2000, "MAP kinases and the regulation of nuclear receptors," Sci. STKE 2000(48):pe1, pp. 1-4.

Li et al., 1999, "Regulation of IL-4 expression by the transcription factor JunB during T helper cell differentiation," EMBO J., 18(2):420-32.

Merryman et al., 1998, "Transforming growth factor-beta enhances the ultraviolet-mediated stress response in p53−/−keratinocytes," Int. J. Oncol., 13(4):781-89.

Mutou et al., 2010, "Immune Response Pathways in Human Keratinocyte (HaCat) Cells are Induced by Ultraviolet B via p38 Mitogen-activated Protein Kinase Activation," J. Health Science, 56(6):675-83.

Potts JF, 1990, "Sunlight, sunburn, and sunscreens—Preventing and remedying problems from 'too much fun in the sun'," Postgrad. Med.; 87(8):52-61.

Schramek H, 2002, "MAP kinases: from intracellular signals to physiology and disease," News Physiol. Sci.; 17:62-7.

Schwabe et al., 2003, "c-Jun-N-terminal kinase drives cyclin D1 expression and proliferation during liver regeneration," Hepatology; 37(4):824-32.

Seger et al., 1995, "The MAPK signaling cascade," FASEB J.; 9(9):726-35.

Shi-Wen et al., 2009, "Requirement of transforming growth factor beta-activated kinase 1 for transforming growth factor beta-induced alpha-smooth muscle actin expression and extracellular matrix contraction in fibroblasts," Arthritis Rheum., 60(1):234-41.

Whitmarsh et al., 1999, "Signal transduction by MAP kinases: Regulation by phosphorylation-dependent switches," Sci. STKE 1999(1):pe1, pp. 1-3.

Xie et al., 1998, "Crystal structure of JNK3: a kinase implicated in neuronal apoptosis," Structure; 6(8):983-91.

Yang et al., 1998, "Differentiation of CD4+ T cells to Th1 cells requires MAP kinase JNK2," Immunity; 9(4):575-85.

Yang et al., 2003, "C-Jun NH(2)-terminal kinase mediates proliferation and tumor growth of human prostate carcinoma," Clin. Cancer Res.; 9W:391-401.

A    Study A

B    Study B

C    Study C

A. Vehicle

B. Compound JNKi-1 60mg/kg

A. Vehicle

B. Dexamethasone

C. Compound JNKi-1 60mg/kg

METHODS OF TREATMENT, IMPROVEMENT AND PREVENTION USING HALOARYL SUBSTITUTED AMINOPURINES

1. CROSS-REFERENCE TO RELATED APPLICATIONS

This application claims the benefit of U.S. Provisional Application No. 61/406,219, filed Oct. 25, 2010, and claims the benefit of U.S. Provisional Application No. 61/509,638, filed Jul. 20, 2011, the entire contents of each of which are incorporated herein by reference.

2. FIELD

Provided herein are methods for treating or preventing scleroderma, keloids, UV injury, or sunburn, and methods for improving or preventing scar formation, comprising administering an effective amount of certain amino-substituted purine compounds to a patient in need thereof. Also provided herein are methods for measuring the inhibition of c-Jun N-terminal kinase (JNK) in skin using immunohistochemistry. Further provided herein is an assay based on UVB-irradiation and measurement of phospho c-Jun immunoreactivity useful for evaluating dose-response relationships of JNK inhibitors and identifying and selecting patient populations sensitive or insensitive to JNK inhibitors.

3. BACKGROUND

JNK is a ubiquitously expressed serine/threonine kinase belonging, together with ERK (extracellular-regulated kinase) and p38, to the family of mitogen-activated protein kinases (MAPKs). (Kyriakis J M, *MAP kinases and the regulation of nuclear receptors*, Sci. STKE 2000 (48):pe1; Whitmarsh A J, Davis R J, *Signal transduction by MAP kinases: Regulation by phosphorylation-dependent switches*, Sci. STKE 1999 (1):pe1; Schramek H, *MAP kinases: from intracellular signals to physiology and disease*, News Physiol. Sci. 2002; 17:62-7; Ichijo H, *From receptors to stress-activated MAP kinases*, Oncogene 1999, 18(45):6087-93). MAPKs are important mediators of signal transduction from the cell surface to the nucleus, using phosphorylation cascades to generate a coordinated response by a cell to an external stimulus by phosphorylation of selected intracellular proteins, including transcription factors. Additionally, JNK also phosphorylates non-nuclear proteins, for example, IRS-1, and Bcl-2 family members. (Davis R J, *MAPKs: new JNK expands the group*, Trends Biochem. Sci. 1994; 9(11):470-3; Seger R, Krebs E G, *The MAPK signaling cascade*, FASEB J. 1995; 9(9):726-35; Fanger G R, Gerwins P, Widmann C, Jarpe M B, Johnson G L, *MEKKs, GCKs, MLKs, PAKs, TAKs, and tpls: upstream regulators of the c-Jun amino-terminal kinases?* Curr. Opin. Genet. Dev. 1997; 7(1):67-74).

JNK was first identified in the early 1990s, and the term is derived from cJun N-terminal kinase; its best-known substrate is the transcription factor cJun. (Hibi M, Lin A, Smeal T, Minden A, Karin M, *Identification of an oncoprotein-and UV-responsive protein kinase that binds and potentiates the c-Jun activation domain*, Genes Dev. 1993; 7(11):2135-48; Dunn C, Wiltshire C, MacLaren A, Gillespie D A, *Molecular mechanism and biological functions of c-Jun N-terminal kinase signalling via the c-Jun transcription factor*, Cell Signal 2002; 14(7):585-93; Ip Y T, Davis R J, *Signal transduction by the c-Jun N-terminal kinase (JNK)—from inflammation to development*, Curr. Opin. Cell Biol. 1998; 10(2):205-19). JNK is also known as SAPKα, stress-activated protein kinase α, since JNK is activated upon exposure of cells to proinflammatory cytokines, growth factors, and environmental stress, such as UV-irradiation or heat shock. (Hibi M, Lin A, Smeal T, Minden A, Karin M, *Identification of an oncoprotein-and UV-responsive protein kinase that binds and potentiates the c-Jun activation domain*, Genes Dev. 1993; 7(11):2135-48; Ip Y T, Davis R J, *Signal transduction by the c-Jun N-terminal kinase (JNK)—from inflammation to development*, Curr. Opin. Cell Biol. 1998; 10(2):205-19; Derijard B, Hibi M, Wu I H, Barrett T, Su B, Deng T, Karin M, Davies R J, *JNK1: a protein kinase stimulated by UV light and Ha-Ras that binds and phosphorylates the c-Jun activation domain*, Cell 1994; 76(6):1025-37; Kyriakis J M, Banerjee P, Nikolakaki E, Dai T, Rubie E A, Ahmad M F, Avruch J, Woodgett J R, *The stress-activated protein kinase subfamily of c-Jun kinases*, Nature 1994; 369(6476):156-60).

Because of the variety of stress responses in which JNK is involved, a single pathway for JNK activation does not appear to exist. Many stimulants cause JNK activation through more than one mechanism. Depending on the cell type and state, JNK can be involved in processes as divergent as apoptosis (Kyriakis J M, Avruch J, *Mammalian mitogen-activated protein kinase signal transduction pathways activated by stress and inflammation*, Physiol. Rev. 2001; 81(2):807-869; Xie X, Gu Y, Fox T, Coll J T, Fleming M A, Markland W, Caron P R, Wilson K P, Su M S, *Crystal structure of JNK3: a kinase implicated in neuronal apoptosis*, Structure 1998; 6(8):983-91), cell proliferation (Yang Y M, Bost F, Charbono W, Dean N, McKay R, Rhim J S, Depatie C, Mercola D, *C-Jun NH(2)-terminal kinase mediates proliferation and tumor growth of human prostate carcinoma*, Clin. Cancer Res. 2003; 9(1):391-401; Schwabe R F, Bradham C A, Uehara T, Hatano E, Bennett B L, Schoonhoven R, Brenner D A, *c-Jun-N-terminal kinase drives cyclin D1 expression and proliferation during liver regeneration*, Hepatology 2003; 37(4):824-32), and cell differentiation (Li B, Tournier C, Davis R J, Flavell R A, *Regulation of IL-4 expression by the transcription factor JunB during T helper cell differentiation*, EMBO J. 1999; 18(2):420-32; Yang D D, Conze D, Whitmarsh A J, Barrett T, Davis R J, Ricón M, Flavell R A, *Differentiation of CD4+ T cells to Th1 cells requires MAP kinase JNK2*, Immunity 1998; 9(4):575-85); hence, JNK is an essential regulator of physiological and pathological processes.

Scleroderma

Scleroderma is a rare disease with a stable incidence of approximately 19 cases per 1 million persons. The exact cause of scleroderma is unknown. Abnormalities involve autoimmunity and alteration of endothelial cell and fibroblast function. Systemic scleroderma usually begins with skin thickening, usually of the fingers, accompanied by Raynaud's phenomenon. Raynaud's disease typically precedes further manifestations of systemic scleroderma. Early in the disease the affected skin may be puffy and soft. The usual location of greatest skin thickening and hardening is the face, hands and fingers. Sclerodactyly is frequently present. Tendon friction rubs are often palpable on exam and can be painful. With more advanced disease, digital ulcers and auto-amputation may occur. Gastrointestinal dismotility is a feature, often manifested by heartburn, or by diarrhea with malabsorption or pseudo-obstruction. New onset hypertension or renal insufficiency are manifestations of the associated vascular injury. Heart failure or arrhythmia are also possible due to cardiac fibrosis. (Hachulla E, Launay D, *Diagnosis and classification of systemic sclerosis*, Clin Rev Allergy Immunol 2010; 40(2):78-83).

The major manifestations of scleroderma and in particular of systemic sclerosis are inappropriate excessive collagen synthesis and deposition, endothelial dysfunction, spasm, collapse and obliteration by fibrosis. In terms of diagnosis, an important clinical parameter is skin thickening proximal to the metacarpophalangeal joints. Raynaud's phenomenon is a frequent, almost universal component of scleroderma. It is diagnosed by color changes of the skin upon cold exposure. Ischemia and skin thickening are symptoms of Raynaud's disease.

UV Injury and Sunburn

The skin is one of the largest body organs and functions as one of its major interfaces with the environment, including solar radiation. Exposure to solar radiation has the beneficial effects of stimulating the cutaneous synthesis of vitamin D and providing radiant warmth. (McStay, C M Elahi E J, *Sunburn, eMedicine—Online Medical Reference Textbook* (last modified May 18, 2010) (online), (retrieved on 2010-08-30). Retrieved from the internet: <URL: http://emedicine.medscape.com/article/773203-overview>). Unfortunately, when the skin is subjected to excessive radiation in the ultraviolet range, deleterious effects, such as sunburn, occur. Sunburn is an acute cutaneous inflammatory reaction that follows excessive exposure of the skin to ultraviolet radiation (UVR). The inflammatory response occurs within 2-6 hours after exposure and peaks at 20-24 hours with symptoms such as erythema, warmth, tenderness, edema, and blistering (severe cases). Acute UVR injury will also lead to apoptosis of keratinocytes resulting in skin injury and skin remodeling. (Merryman, J. I., Neilsen, N. and Stanton, D. D., *Transforming growth factor-beta enhances the ultraviolet-mediated stress response in p53−/−keratinocytes*, Int. J. Oncol. 1998; 13(4): 781-9) Chronic UVR exposure to the skin may lead to melanoma and squamous cell carcinomas of the skin. (Hildesheim J, Bulavin D V, Anver M R, et al., *Gadd45a protects against UV irradiation-induced skin tumors, and promotes apoptosis and stress signaling via MAPK and p53*, Cancer Res. 2002; 62(24):7305-15).

Severity of sunburn is related to duration of exposure, skin type and amount of protection. Potts J F, *Sunlight, Sunburn, and Sunscreens*, Postgrad. Med. 1990; 87:52-61. Factors influencing the cutaneous response to UVR depend on interactions among many other factors besides exposure time and dose. Wavelengths of the radiation source, skin characteristics such as pigmentation, hydration and skin thickness, and external factors such as wind, temperature and humidity all effect the response. Reflection off snow and sand may also lead to increased exposure. Some medications are known to be sensitizing to ultraviolet radiation. Tricyclic antidepressants, antihistamines, anti-infectives, antineoplastic agents, antipsychotic agents, diuretics, hypoglycemic agents, nonsteroidal anti-inflammatory drugs, and sunscreens all may decrease an individual's tolerance for sun exposure.

Current treatment for sunburn includes the systemic administration of aspirin or nonsteroidal anti-inflammatory drugs (NSAIDs) to inhibit the cyclooxygenase pathway and thereby reduce prostaglandin production. NSAIDs work best if administered within the first several hours after exposure. Systemic corticosteroids are often employed and probably shorten the course of the pain that accompanies severe sunburn. Corticosteroids should not be given to patients with severe, second-degree burns because they increase the risk of infection. Topical steroids show minimal, if any benefit.

Over-the-counter topical remedies include anesthetics such as lidocaine hydrochloride, benzocaine, and pramoxine hydrochloride. Skin soothing ingredients such as aloe vera, tocopheryl acetate (Vitamin E), menthol, camphor, eucalyptus oil, and calamine are also popular ingredients known in the art. Home topical remedies include taking a cool bath with oatmeal or baking soda; and spreading the juice of a cut potato, lavender essential oil, or chamomile on the burn.

While these topical remedies may help soothe the skin or temporarily relieve the pain associated with sunburn, they are not a treatment for the underlying inflammation that defines sunburn. Non-steroidal anti-inflammatories must be given systemically soon after exposure to be effective. Moreover, patients with allergies to NSAIDs, sensitive stomachs, or potential negative drug interactions may not be able to tolerate this treatment.

Current sunburn prevention methods include wearing protective clothing and avoidance of the sun during midday. But these methods restrict the outdoor activities, such as swimming, of a person wanting to avoid sunburn. Topical products for the prevention of sunburn fall into two categories: physical barriers and chemical absorbers. Chemical sunscreens are generally aromatic compounds conjugated with a carbonyl group. After application, the chemical sunscreen components diffuse into the stratum corneum and adsorb or conjugate with various proteins. Product effectiveness is determined by the depth of penetration, binding affinity for different proteins, and duration of protection. These chemicals absorb radiation in the UV spectrum. Chemical sunscreens have the disadvantages of possibly staining clothing and causing contact dermatitis. Moreover, recently concerns have been raised regarding the mutagenic properties of the most popular chemical sunscreens p-amino-benzoic acid (PABA) and PABA esters. Physical blockers, such as zinc oxide, talc, and titanium dioxide, reflect or scatter UVR. Many consumers find these products messy to apply and cosmetically unappealing.

Thus, a method for treating or preventing UV injury or sunburn is needed.

Scar Formation

Wounds caused by trauma or surgery are accompanied by an initial inflammatory response which is a natural response of the body and a first step of the wound healing process. The initial inflammatory response is followed by the formation of fibrous tissue, more commonly referred to as scar tissue, by proliferation of fibroblasts, and differentiation of fibroblasts to myofibroblasts, which produce collagen, mucopolysaccharides, and gylcosaminoglycans at the wound site. A certain amount of inflammation is required in the early healing stages in order to clear away the cellular and protein debris that accumulates at the wound to avoid infection and/or chronic inflammation. The second stage of wound healing involves a repair process which entails the influx and proliferation of fibrous tissue, due in part by the production of collagen and other substances by the fibroblasts, resulting in the formation of dense fibrous connective tissue that is visually seen as a scar.

The process of wound healing broadly comprises a regeneration phase and a repair phase, the differentiation between the two based on the resultant tissue. In regeneration, specialized tissues are replaced by the proliferation of surrounding undamaged specialized cells. In repair, lost tissue is replaced by granulation tissue which matures to form scar tissue. The repair phase involves the generation of the repair material, which for the majority of musculoskeletal injuries, involves the production of scar (collagen) material. Generation of repair material occurs fairly soon after injury, typically within 24-48 hours, and continues for a period of several weeks after injury, the time period depending in part on the amount of vasculature in the injured tissue. During this period, the bulk of the scar material is formed, with scar formation being evident and ultimately complete with a functional scar is achieved.

As mentioned above, inflammation is a normal and necessary prerequisite to healing. The inflammatory events involve both a vascular cascade of events and a cellular cascade of events. These occur in parallel and are significantly interlinked. The inflammatory cascade involves production of chemical mediators that make an active contribution to the healing process. For example, the cellular cascade involves emigration of neutrophils, monocytes, lymphocytes, eosinophils, basophils, to the wounded area and production of chemical mediators. The inflammatory response results in a vascular response, by production of a cellular and fluid exudate, with resulting edema. The course of the inflammatory response will depend upon the number of cells destroyed, the original causation of the process and the tissue condition at the time of insult.

Following the inflammation phase, the wound repair begins, with scar formation resulting. In some subjects, the scar tissue formation process results in what is referred to as hypertrophic or keloid scars. A keloid scar is a raised, firm, thickened red scar that exceeds the boundary of the injury and may grow for a prolonged period of time. A keloid scar occurs when the tissue response is out of proportion to the amount of scar tissue required for normal repair and healing. The increase in scar size is due to deposition of an increased amount of collagen into the tissue. Keloid development has been associated with different types of skin injury including surgery, ear piercing, laceration, burns, vaccination or inflammatory process. Common sites are earlobes and the upper trunk and extremities.

Scar formation is both a cosmetic problem and can in some cases be a medical problem. For example, scars on the face following an injury or surgery undesirable and can negatively impact a person. In some cases, keloid development occurs and a visible, undesirable scar results. Moreover, intra-abdominal adhesions results in a very significant morbidity and mortality in every surgery practice. Treatment of pelvic adhesions following surgery is often performed, and repeat surgery can greatly aggravate scarring.

There remains a need for a treatment to prevent scar formation, to reduce excessive scar formation and to prevent development of adhesions. Mechanical barriers are currently used to prevent adhesion formation, and these are only minimally effective clinically. Keloids have been treated with injection of corticosteroid into the scar, by laser therapy, and by administration of pharmacologic agents that interfere with collagen synthesis. Methods for improving the appearance of scars and for prevention excessive scarring and adhesions, without the inhibition of wound healing, are needed.

Measurement of Inhibition of c-Jun Terminal Kinase in Skin.

Previous studies have measured levels of IL-10, TNF-α, and NO in cells exposed to UVB irradiation either with or without specific inhibitors, demonstrating that UVB induced the production of those proinflammatory mediators, purportedly via activation of the p38 MAPK signalling pathway (Mutou Y, Tsukimoto M, Homma T, Kojima S, *Immune Response Pathways in Human Keratinocyte (HaCat) Cells are Induced by Ultraviolet B via p38 Mitogen-activated Protein Kinase Activation*, J. Health Science 2010; 56(6):675-83). Additionally, the induction of c-Jun protein and phosphorylation after UV irradiation of human skin has been reported (Fisher G, Talwar H, Lin J, Lin P, McPhillips F, Wang Z, Li X, Wan Y, Kang S, and Voorhees J, *Retinoic Acid Inhibits Induction of c-Jun Protein by Ultraviolet Radiation That Occurs Subsequent To Activation Of Mitogen-Activated Protein Kinase Pathways In Human Skin In Vivo*, J. Clin Invest. 1998; 101(6):1432-40 and Einspahr J, Bowden T, Alberts D, McKenzie N, Saboda K, Warneke J, Salasche S, Ranger-Moore J, Lewandrowski C, Nagle R, Nickoloff B, Brooks, C, Dong Z, and Stratton S, *Cross-Validation of Murine UV Signal Transduction Pathways in Human Skin*, Photochem. Photobiol. 2008; 84(2):463-76).

Clinical markers are needed to evaluate the biological effects of drug candidates. The methods set forth herein allow for the evaluation of the biological effects of JNK inhibitors and, accordingly, are useful in a clinical setting, such as by providing a straight-forward avenue for following the in vivo activity of a JNK inhibitor, and for assessing the sensitivity of a particular patient population to treatment with JNK inhibitors, in particular oral JNK inhibitors.

Citation or identification of any reference in Section 2 of this application is not to be construed as an admission that the reference is prior art to the present application.

4. SUMMARY

Provided herein are uses of compounds having the following formula (I):

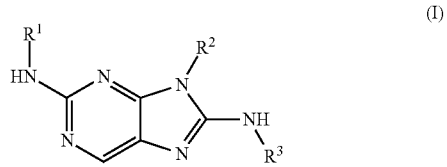

and pharmaceutically acceptable salts, solid forms, clathrates, solvates, hydrates, stereoisomers, tautomers and prodrugs thereof, wherein $R^1$, $R^2$ and $R^3$ are as defined herein.

In a particular embodiment, tautomers of compounds of formula (I) have the following structure:

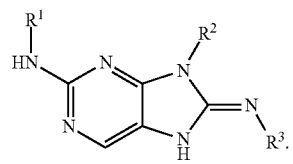

A compound of formula (I) or a pharmaceutically acceptable salt, solid form, clathrate, solvate, hydrate, stereoisomer, tautomer or prodrug thereof (each being referred to herein as an "Aminopurine Compound") is useful for treating or preventing scleroderma, keloids, UV injury, or sunburn, and for improving or preventing scar formation.

Further provided herein are uses of compositions or dosage forms comprising an effective amount of an Aminopurine Compound and uses of compositions comprising an effective amount of an Aminopurine Compound and a pharmaceutically acceptable carrier, diluent or vehicle. The compositions are useful for treating or preventing scleroderma, keloids, UV injury, or sunburn, and for improving or preventing scar formation.

Further provided herein are methods for treating or preventing scleroderma, keloids, UV injury, or sunburn, and methods for improving or preventing scar formation, comprising administering an effective amount of an Aminopurine Compound to a patient in need of the treating, improving or preventing.

Also provided herein are methods for evaluating the effect of an Aminopurine Compound in a patient, comprising UVB-irradiation of a patient's skin, Aminopurine Compound administration, and measurement of phospho c-Jun expression in skin using immunohistochemistry. In one embodiment, the Aminopurine Compound is in combination with inhibitors of MAP kinase. In one embodiment, the effect of the Aminopurine Compound is the dose-response relationship of the Aminopurine Compound in a patient. In some embodiments, the Aminopurine Compound is administered orally. In some embodiments, the Aminopurine Compound is JNKi-1. In one embodiment, provided herein are methods for identifying patient populations who are sensitive to an Aminopurine Compound comprising employing a method for detecting JNK inhibition provided herein.

Provided herein are methods for evaluating inhibition of JNK in a patient by measuring certain biomarkers in the patient's skin. In one embodiment, provided herein are methods of measuring inhibition of JNK in a patient by exposing a first portion of said patient's skin to UVB irradiation, obtaining a sample of said first portion of said patient's skin, measuring the amount of phosphorylated c-Jun in said first portion of said patient's skin, administering an Aminopurine Compound to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein a decreased level of phosphorylated c-Jun in said second portion of said patient's skin relative to said first portion of said patient's skin indicates inhibition of JNK.

In another embodiment, methods for determining a dose-response relationship for the administration of an Aminopurine Compound in a patient are provided. The methods comprise administering to said patient varying doses (e.g., an initial dose and anywhere from 2 to 20 additional doses of differing amounts) of said Aminopurine Compound and determining the amount of JNK inhibition in said patient resulting from each dose of said Aminopurine Compound, comprising exposing a first portion of said patient's skin to UVB irradiation, obtaining a sample of said first portion of said patient's skin, measuring the amount of phosphorylated c-Jun in said first portion of said patient's skin, administering a dose of said Aminopurine Compound to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein the decrease in the level of phosphorylated c-Jun in said second portion of said patient's skin relative to said first portion of said patient's skin is proportional to the inhibition of JNK.

In yet another embodiment, provided herein are methods for determining whether a patient is sensitive to an Aminopurine Compound, comprising exposing a first portion of said patient's skin to UVB irradiation, obtaining a sample of said first portion of said patient's skin, measuring the amount of phosphorylated c-Jun in said first portion of said patient's skin, administering said Aminopurine Compound to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein a decrease in the level of phosphorylated c-Jun in said second portion of said patient's skin relative to said first portion of said patient's skin indicates that said patient is sensitive to said Aminopurine Compound.

In other embodiments, methods for determining the effective amount of an Aminopurine Compound for the treatment or management of a disease or condition associated with JNK in a patient are provided, which comprise administering to said patient varying doses (e.g., an initial dose and anywhere from 2 to 20 additional doses of differing amounts) of said Aminopurine Compound and determining the amount of JNK inhibition in said patient resulting from each dose of said Aminopurine Compound, comprising exposing a first portion of said patient's skin to UVB irradiation, obtaining a sample of said first portion of said patient's skin, measuring the amount of phosphorylated c-Jun in said first portion of said patient's skin, administering a dose of said Aminopurine Compound to said patient, exposing a second portion of said patient's skin to UVB irradiation, obtaining a sample of said second portion of said patient's skin, measuring the amount of phosphorylated c-Jun in said second portion of said patient's skin, and comparing the levels of phosphorylated c-Jun in said first portion of said patient's skin and said second portion of said patient's skin, wherein a decrease in the level of phosphorylated c-Jun in said second portion of said patient's skin relative to said first portion of said patient's skin is indicative of the administration of an effective amount of said Aminopurine Compound.

In yet another embodiment, a method for monitoring patient compliance with Aminopurine Compound therapy is provided. The method comprises measuring the level of phospho c-Jun or c-Jun expressed in a sample of the patient's skin after administration of an Aminopurine Compound and determining if the expression level is increased or decreased in the sample of the patient's skin compared to the expression level prior to administration of an Aminopurine Compound, wherein decreased expression indicates patient compliance with the Aminopurine Compound therapy.

The present embodiments can be understood more fully by reference to the detailed description and examples, which are intended to exemplify non-limiting embodiments.

5. DETAILED DESCRIPTION

5.1 Definitions

An "alkyl" group is a saturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. An alkyl group can be substituted or unsubstituted. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine;

N-oxide; hydrazine; hydrazide; hydrazone; azide; isocyanate; isothiocyanate; cyanate; thiocyanate; $B(OH)_2$ or $O(alkyl)$ aminocarbonyl.

An "alkenyl" group is a straight chain or branched noncyclic hydrocarbon having from 2 to 10 carbon atoms, typically from 2 to 8 or 2 to 6 carbon atoms, and including at least one carbon-carbon double bond. Representative straight chain and branched ($C_2$-$C_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

An "alkoxy" group is an —O-(alkyl) group, wherein alkyl is defined above, including —$OCH_3$, —$OCH_2CH_3$, —$O(CH_2)_2CH_3$, —$O(CH_2)_3CH_3$, —$O(CH_2)_4CH_3$, —$O(CH_2)_5CH_3$, and the like.

An "alkoxyalkyl" group is a -(alkylene)-O-(alkyl) group, wherein each alkyl is independently an alkyl group defined above, including —$CH_2OCH_3$, —$CH_2OCH_2CH_3$, —$(CH_2)_2OCH_2CH_3$, —$(CH_2)_2O(CH_2)_2CH_3$, and the like.

An "alkylamino" group is a mono-alkylamino or di-alkylamino group, such as —$NH(C_{1-6}alkyl)$, —$N(C_{1-6}alkyl)(C_{1-6}alkyl)$, —$NH(C_{3-10}cycloalkyl)$, —$N(C_{3-10}cycloalkyl)(C_{3-10}cycloalkyl)$, or —$N(C_{1-6}alkyl)(C_{3-10}cycloalkyl)$ wherein each $C_{1-6}alkyl$ and $C_{3-10}cycloalkyl$ is independently as defined herein, including, but not limited to, —$NHCH_3$, —$NHCH_2CH_3$, —$NH(CH_2)_2CH_3$, —$NH(CH_2)_3CH_3$, —$NH(CH_2)_4CH_3$, —$NH(CH_2)_5CH_3$, —$N(CH_3)_2$, —$N(CH_2CH_3)_2$, —$N((CH_2)_2CH_3)_2$, and —$N(CH_3)(CH_2CH_3)$.

An "aminocarbonyl" group is a —$C(O)NR_2$ group, wherein each R is independently hydrogen or a $C_{1-6}alkyl$ group defined above, wherein each $C_{1-6}alkyl$ group can be optionally substituted.

An "acylamino" group is a —NRC(O)R group, wherein each R is independently hydrogen or a $C_{1-6}alkyl$ group defined above, wherein each $C_{1-6}alkyl$ group can be optionally substituted An "aminoalkyl" group is a $C_{1-6}alkyl$ group substituted with one or more $NR_2$ groups, wherein R is hydrogen or a $C_{1-6}alkyl$ group defined above, wherein each $C_{1-6}alkyl$ group can be optionally further substituted.

An "alkanesulfonylamino" group is a —NR—$SO_2$—$C_{1-6}$ alkyl group, wherein R is hydrogen or an alkyl group defined above, wherein each alkyl group can be optionally substituted.

A "cycloalkyl" group is a cyclic alkyl group having a single cyclic ring or multiple condensed or bridged rings which can be optionally substituted with from 1 to 3 alkyl groups. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantanyl and the like. In one embodiment, the cycloalkyl group has from 3 to 10 carbon atoms A cycloalkyl group can be substituted or unsubstituted. Such substituted cycloalkyl groups include, by way of example, cyclohexanone and the like.

A "carboxyl" or "carboxy" is a —COOH group.

A "halogen" is fluorine, chlorine, bromine or iodine.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo(d)imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocyclylalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo-(1,4)dioxinyl, and benzo(1,3)dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo(1,3)dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below. Additional non-limiting examples include the following:

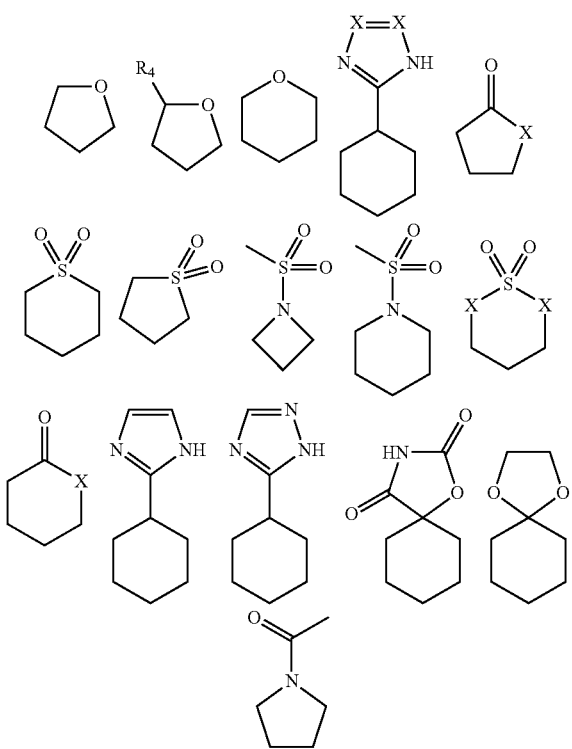

including stereoisomers, tautomers and enantiomers thereof, wherein each occurrence of X is independently $CH_2$, O, S or N and $R^4$ is H, substituted or unsubstituted alkyl, substituted or unsubstituted aryl, substituted or unsubstituted cycloalkyl, substituted or unsubstituted heterocycle or substituted or unsubstituted heteroaryl. A heteroaryl group can be substituted or unsubstituted. A heterocycle group can be substituted or unsubstituted.

A "heterocyclocarbonyl" group is a —C(O)-heterocycle group, wherein heterocycle is as described herein, wherein the heterocycle group can be optionally substituted.

A "hydroxyalkyl" group is an alkyl group as described above substituted with one or more hydroxy groups.

In one embodiment, when the groups described herein are said to be "substituted," they may be substituted with one or more suitable substituents Examples of substituents are those found in the exemplary compounds and embodiments disclosed herein, as well as halogen (chloro, iodo, bromo, or fluoro); $C_{1-6}$ alkyl; $C_{2-6}$ alkenyl; $C_{2-6}$ alkynyl; hydroxyl; $C_{1-6}$ alkoxy; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); $B(OH)_2$; carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); O-lower alkyl; O-aryl; aryl; aryl-lower alkyl; $CO_2CH_3$; $CONH_2$; $OCH_2CONH_2$; $NH_2$; $SO_2NH_2$; $OCHF_2$; $CF_3$; or $OCF_3$. In a particular embodiment, substituents include halogen (e.g., chloro, bromo, iodo or fluoro), alkoxy (e.g., methoxy, —O—$(CH_2)_2$-piperidine or ethoxy), cyano, hydroxy, aryl (e.g., phenyl), $CF_3$, alkyl (e.g., methyl), amino (e.g., $NH_2$), amido (e.g., —NH—C(O)CH$_3$, —NH—C(O)CH$_2$CH$_3$, —C(O)-pyrrolidine, —NH—C(O)CH(CH$_3$)$_2$, —NH—C(O)CH$_2$CH(CH$_3$)$_2$, —NH—C(O)CH$_2$N(CH$_3$)$_2$, —N(CH$_3$)—C(O)CH$_3$, —NHC(O)CH$_3$, —C(O)NH$_2$, —C(O)-(4-methyl)-piperazine, —C(O)—NH—(CH$_2$)$_2$-piperidine, —C(O)—NH—CH$_2$—CHOH—CH$_2$OH, —C(O)-(4-hydroxyethyl)-piperazine, —C(O)-piperidine-pyrrolidine, —C(O)—NH-piperidine, —C(O)-(4-ethyl)-piperazine, —C(O)—NHCH$_3$, —C(O)—N(CH$_3$)$_2$, —C(O)—NH-cyclopropyl, —C(O)—NH—CH$_2$—CH$_2$OH, —C(O)-(3-hydroxy)-pyrrolidine, —C(O)-(2-hydroxymethyl)-pyrrolidine, —C(O)-(4-hydroxy)-piperadine, —C(O)-piperidine, —C(O)—NH-isopropyl, —C(O)-morpholine, —C(O)—NH-cyclobutyl, —C(O)—NH-hydroxyisopropyl or —C(O)—NH-ethyl), dialkylamino (e.g., —N(CH$_3$)$_2$), sulfonamido (e.g., —NH—S(O)$_2$CH$_3$), carboxy, hydroxyalkyl (e.g., —CH$_2$OH, —(CH$_2$)$_2$OH or t-BuOH), heterocycloalkyl (e.g., —(CH$_2$)$_2$-piperidine or —(CH$_2$)$_2$-pyrrolidine), alkylamino (e.g., —NHCH$_3$), arylalkyl (e.g., —CH$_2$-phenyl or —CH(CH$_3$)-phenyl), heterocyclyl (e.g., morpholine), alkoxycarbonyl (e.g., —C(O)OCH$_2$CH$_3$), sulfonyl (e.g., —S(O)$_2$CH$_3$), carbonylalkoxy (e.g., —O—C(O)—(CH$_2$)$_2$COOH), acyl (e.g., —C(O)CH$_3$), cycloalkyl (e.g., cyclopropyl), heteroaryl (e.g., pyridine or thiophene), oxygen (=O) or $B(OH)_2$. In one embodiment, "alkyl" groups can be substituted with one or substituents set forth in the definition of "alkyl" provided herein.

"JNK" means a protein or an isoform thereof expressed by a JNK 1, JNK 2, or JNK 3 gene (Gupta, S., Barrett, T., Whitmarsh, A. J., Cavanagh, J., Sluss, H. K., Derijard, B. and Davis, R. J. *The EMBO J.* 15:2760-2770 (1996)).

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Aminopurine Compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein, the term "solid form(s)" and related terms herein refer to solid forms of the Aminopurine Compounds having different physical properties as a result of the order of the molecules in the crystal lattice. The differences in physical properties exhibited by solid forms affect pharmaceutical parameters such as storage stability, compressibility and density (important in formulation and product manufacturing), and dissolution rates (an important factor in determining bioavailability). Differences in stability can result from changes in chemical reactivity (e.g., differential oxidation, such that a dosage form discolors more rapidly when comprised of one solid form than when comprised of another solid form) or mechanical changes (e.g., tablets crumble on storage as a kinetically favored solid form converts to thermodynamically more stable solid form) or both (e.g., tablets of one solid form are more susceptible to breakdown at high humidity). As a result of solubility/dissolution differences, in the extreme case, some solid form transitions may result in lack of potency or, at the other extreme, toxicity. In addition, the physical properties of the crystal may be important in processing, for example, one solid form might be more likely to form solvates or might be difficult to filter and wash free of impurities (i.e., particle shape and size distribution might be different between one solid form relative to the other).

As used herein and unless otherwise indicated, the term "clathrate" means an Aminopurine Compound, or a salt thereof, in the form of a crystal lattice that contains spaces (e.g., channels) that have a guest molecule (e.g., a solvent or water) trapped within or a crystal lattice wherein an Aminopurine Compound is a guest molecule.

As used herein and unless otherwise indicated, the term "hydrate" means an Aminopurine Compound, or a salt thereof, that further includes a stoichiometric or non-stoichiometric amount of water bound by non-covalent intermolecular forces.

As used herein and unless otherwise indicated, the term "solvate" means an Aminopurine Compound, or a salt thereof, that further includes a stoichiometric or non-stoichiometric amount of a solvent bound by non-covalent intermolecular forces.

As used herein and unless otherwise indicated, the term "prodrug" means an Aminopurine Compound derivative that can hydrolyze, oxidize, or otherwise react under biological conditions (in vitro or in vivo) to provide an active compound, particularly an Aminopurine Compound. Examples of prodrugs include, but are not limited to, derivatives and metabolites of an Aminopurine Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of an Aminopurine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Aminopurine Compounds can have chiral centers and can occur as racemates, individual enantiomers or diastereomers, and mixtures thereof. All such isomeric forms are included within the embodiments disclosed herein, including mixtures thereof. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

As used herein and unless otherwise indicated, the term "tautomer" refers to isomeric forms of a compound that can be in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

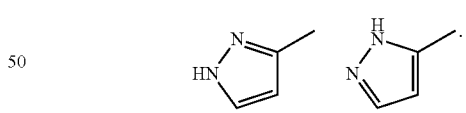

It should also be noted the Aminopurine Compounds include E and Z isomers, or a mixture thereof, and cis and trans isomers or a mixture thereof. In certain embodiments, the Aminopurine Compounds are isolated as either the E or Z isomer. In other embodiments, the Aminopurine Compounds are a mixture of the E and Z isomers.

It should also be noted the Aminopurine Compounds can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Aminopurine Compounds as described herein, whether radioactive or not, are intended to be encompassed within the scope of the embodiments provided herein. In some embodiments, there are provided isotopologues of the Aminopurine Compounds, for example, the isotopologues are deuterium, carbon-13, or nitrogen-15 enriched Aminopurine Compounds. In certain embodiments, isotopologues of the Aminopurine Compounds included those set forth in PCT/US2009/067313, filed Dec. 8, 2009, the entire contents of which are incorporated by reference herein.

"Treating" as used herein, means an alleviation, in whole or in part, of symptoms associated with a disorder or condition (e.g., scleroderma, keloids, UV injury, or sunburn, as described herein), or slowing, or halting of further progression or worsening of those symptoms.

"Preventing" as used herein, means the prevention of the onset, recurrence or spread, in whole or in part, of the disease or condition (e.g., scleroderma, keloids, UV injury, sunburn, or scar formation as described herein), or a symptom thereof.

"Improving" as used herein in connection with scar formation or keloid formation, means reducing the size, visibility or noticeability of the scar or keloid or generally improving the appearance of the scar or keloid.

The term "effective amount" in connection with an Aminopurine Compound means an amount capable of treating, improving or preventing a disease or condition disclosed herein, such as scleroderma, keloids, UV injury, sunburn or scar formation.

The term "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a patient is a human having or at risk for having scleroderma, UV injury, sunburn or scar formation or a symptom thereof.

As used herein "UVA" refers to electro-magnetic radiation that is in the region of the ultraviolet spectrum which extends from about 320 nm to about 400 nm in wavelength.

As used herein "UVB" refers to electro-magnetic radiation that is in the region of the ultraviolet spectrum which extends form about 280 nm to about 320 nm.

As used herein "overall survival" refers to the time from randomization until death from any cause, and is measured in the intent-to-treat population. Overall survival can be evaluated in randomized controlled studies.

As used herein "objective response rate" refers to the proportion of patients with reduced predefined scleroderma symptoms at the end of a predefined period of time. Response duration is usually measured from the time of initial response until documented scleroderma progression.

As used herein "time to progression" means the time from randomization until objective scleroderma progression. In certain embodiments, time to progression does not include deaths.

As used herein "progression-free survival" means the time from randomization until objective scleroderma progression or death.

As used herein "time-to-treatment failure" means any endpoint(s) measuring time from randomization to discontinuation of treatment for any reason, including disease progression, treatment toxicity, and death.

As used herein "mortality" means a measure of the number of deaths in a given population.

As used herein "respiratory mortality" means patients who die from acute hypoxemia or other specific respiratory deterioration resulting in death such as need for mechanical ventilation leading to death, respiratory arrest, or any other event in a subject deemed to be respiratory in nature.

As used herein "respiratory hospitalization" means those hospitalized for deterioration in pulmonary status as documented by patient hospital admission notes or other medical opinion.

As used herein "modified Rodnan skin score" means a validated numerical scoring system to assess dermal skin thickness.

As used herein "skin thickness" means hard or indurated skin that can be evaluated using a variety of techniques including durometer and mRSS As used herein "skin induration" means skin that is hardened, red, inflamed, thickened or tender.

As used herein "dermatology quality of life index" means an evaluation of quality or life related to the skin symptoms for a patient having scleroderma.

As used herein "pulmonary function" means any measurement of forced expiratory flow, forced vital capacity, FEV 25-75%, lung volumes or vital capacity.

As used herein "carbon monoxide diffusing capacity" means an assessment of the uptake of carbon monoxide across the alveolar-capillary membrane. It can be a proxy for the measurement of the lungs ability to transfer oxygen from the lungs to the blood stream.

As used herein "Mahler Dyspnea index" means an instrument that provides clinical measurement of shortness of breath.

As used herein "Saint George's Respiratory Questionnaire score" means an instrument that measures quality of life in patients with pulmonary disease.

As used herein "UCLA scleroderma clinical trial consortium gastrointestinal tract score" means a questionnaire administered to patients having scleroderma to evaluate gastrointestinal symptoms associated with scleroderma (systemic sclerosis).

As used herein "flow-mediated dilatation" means any measurement of vascular endothelial function in a patient having scleroderma.

As used herein "six minute walk distance" means any evaluation of the distance a patient having scleroderma can walk within 6 minutes or any standardized procedure to evaluate ability to walk for a fixed period of time or distance.

The term "likelihood" generally refers to an increase in the probability of an event. The term "likelihood" when used in reference to the effectiveness of a patient response generally contemplates an increased probability that the symptoms of a disease or condition associated with JNK will be lessened or decreased.

The term "predict" generally means to determine or tell in advance. When used to "predict" the effectiveness of Aminopurine Compound treatment, for example, the term "predict" can mean that the likelihood of the outcome of the treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the efficacy of a treatment for a disease or condition associated with JNK" refers to tracking the effectiveness in treating a patient. Similarly, the term "monitoring," when used in connection with patient compliance, either individually, or in a clinical trial, refers to the tracking or confirming that the patient is actually following the treatment regimen being tested as prescribed.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

5.2 Brief Description of the Drawings

FIG. 1: Effect of Compound JNKi-1 treatment on pro-fibrotic cytokine activated JNK pathway dermal SSc-fibroblasts, as demonstrated by Western Blot analysis of phosphorylation of the JNK target cJun. Incubation with TGFβ (lane 2) or PDGF (lane 4) increased the protein level of p-cJun compared to unstimulated fibroblasts (lane 1). Pre-treatment of fibroblasts with Compound JNKi-1 reduced the stimulatory effects of TGFβ (lane 3) and in particular of PDGF (lane 5). Equal loading of proteins was confirmed by quantification of β-actin. (p-cJun=phosphorylated cJun).

Figure 2:
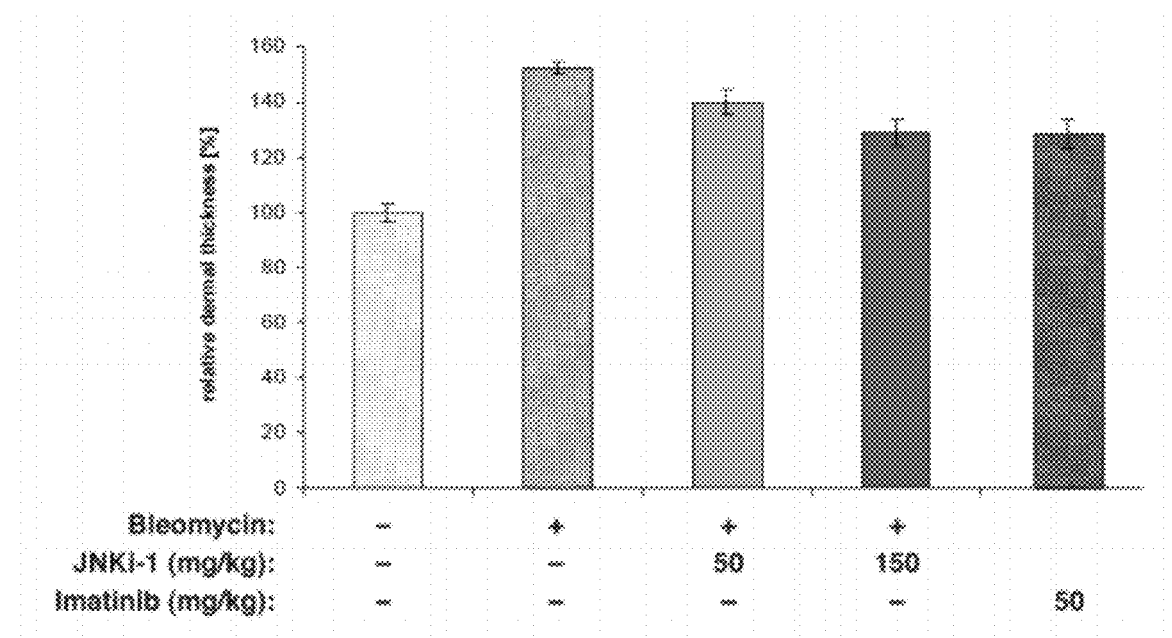

FIG. 2: Effect of Compound JNKi-1 treatment on dermal thickness in bleomycin-induced skin fibrosis mouse model. Each bar represents data from a group of 10 mice. Dermal thickness was measured by hematoxylin and eosin (H & E) staining of skin biopsies. The data shows that dermal thickness was decreased dose-dependently by treatment with compound JNKi-1.

Figure 3:
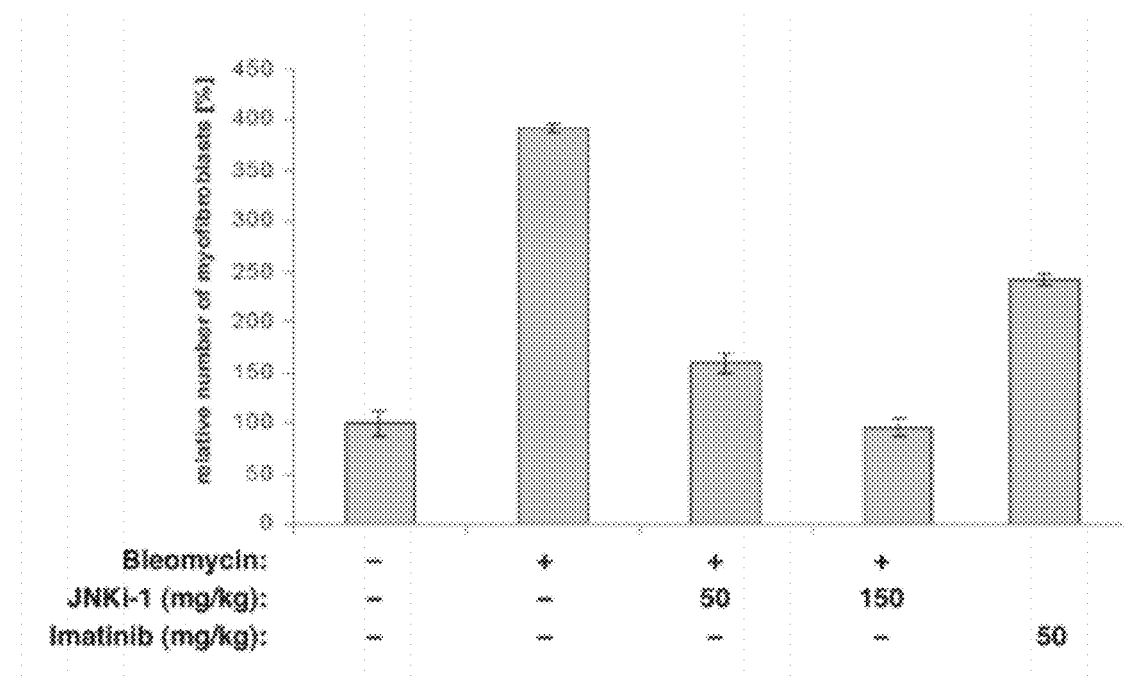

FIG. 3: Effect of Compound JNKi-1 treatment on the accumulation of myofibroblasts in lesional skin of the bleomycin-induced skin fibrosis mouse model. Each bar represents data from a group of 10 mice. Myofibroblasts were quantified by immunohistochemical (IHC) staining of skin biopsies for α-SMA. The data shows that the numbers of myofibroblasts was significantly decreased by treatment with compound JNKi-1.

Figure 4:
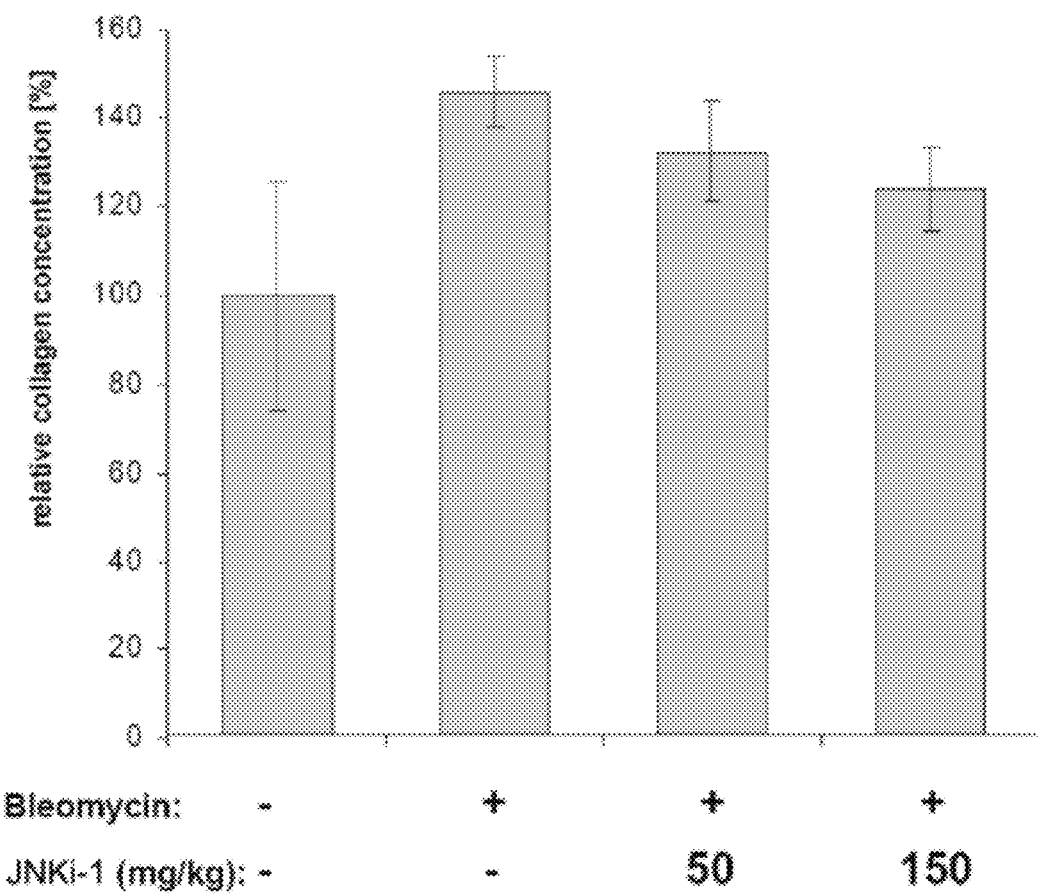

FIG. 4: Effect of Compound JNKi-1 on the accumulation of collagen in lesional skin of the bleomycin-induced skin fibrosis mouse model. Each bar represents data from a group of 10 mice. The total collagen content was quantified by hydroxyproline assay. The data shows that the collagen content in lesional skin was reduced dose-dependently by treatment with compound JNKi-1.

Figure 5:
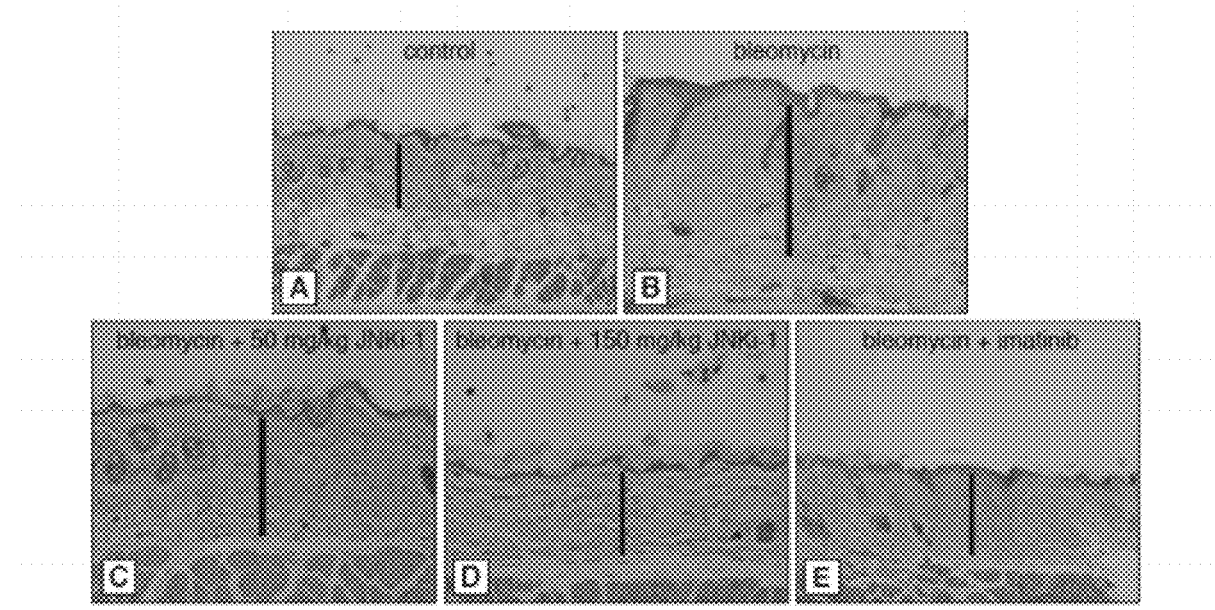

FIG. 5: Effect of Compound JNKi-1 treatment on the prevention of dermal thickness in the mouse model of bleomycin-induced fibrosis. Dermal fibrosis with dense accumulation of collagen bundles in the dermis was induced in mice by subcutaneous injections of bleomycin resulting in an increase in dermal thickness compared to mice receiving sodium chloride injections (A and B). Dermal thickening was reduced dose dependently by treatment with Compound JNKi-1 (C and D) and was comparable to that observed with imatinib (E). Representative skin sections stained with H & E are shown at 100-fold magnification.

Figure 6:
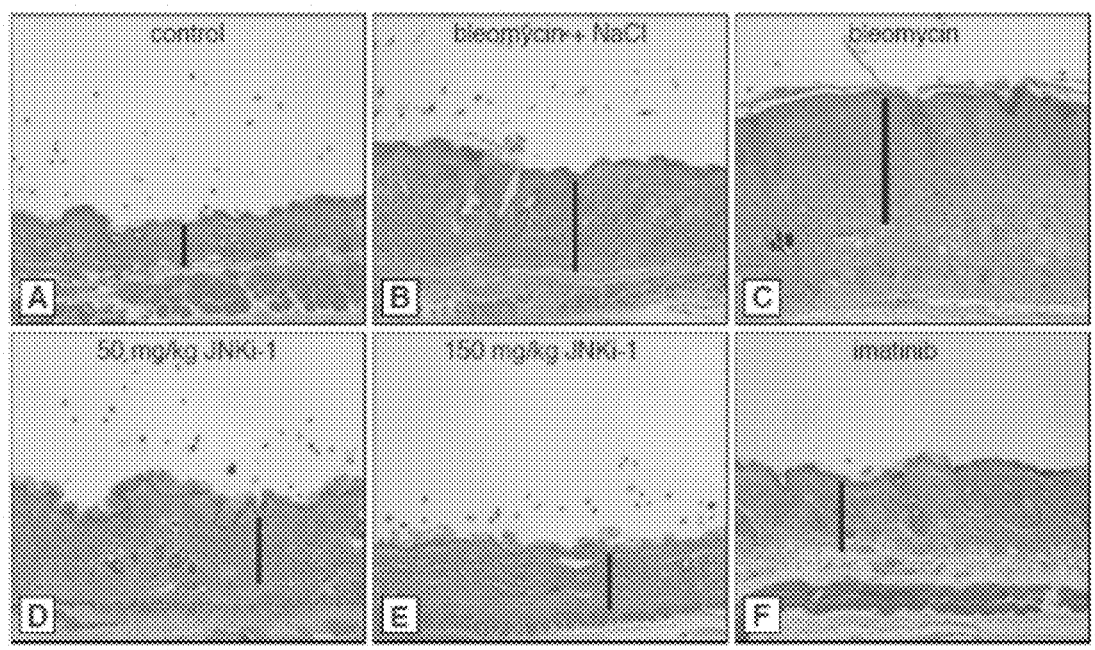

FIG. 6: Effect of Compound JNKi-1 treatment on induced regression of pre-existing accumulation of collagen (manifested as dermal thickening) in the mouse model of bleomycin-induced pre-established dermal fibrosis. Bleomycin challenge for 3 weeks followed by NaCl injections for another 3 weeks (B) increased dermal thickening compared to mice receiving NaCl injections for 6 weeks (A). The dermal thickening was further increased upon continuous bleomycin challenge for 6 weeks (C). Compound JNKi-1 for the last 3 weeks upon continuous bleomycin treatment stopped further progression of dermal thickening (D and E), whereas doses of 150 mg/kg induced regression of dermal thickening in lesional skin (E) and was more pronounced than imatinib (F). Representative skin sections stained with H & E are shown at 100-fold magnification.

Figure 7:
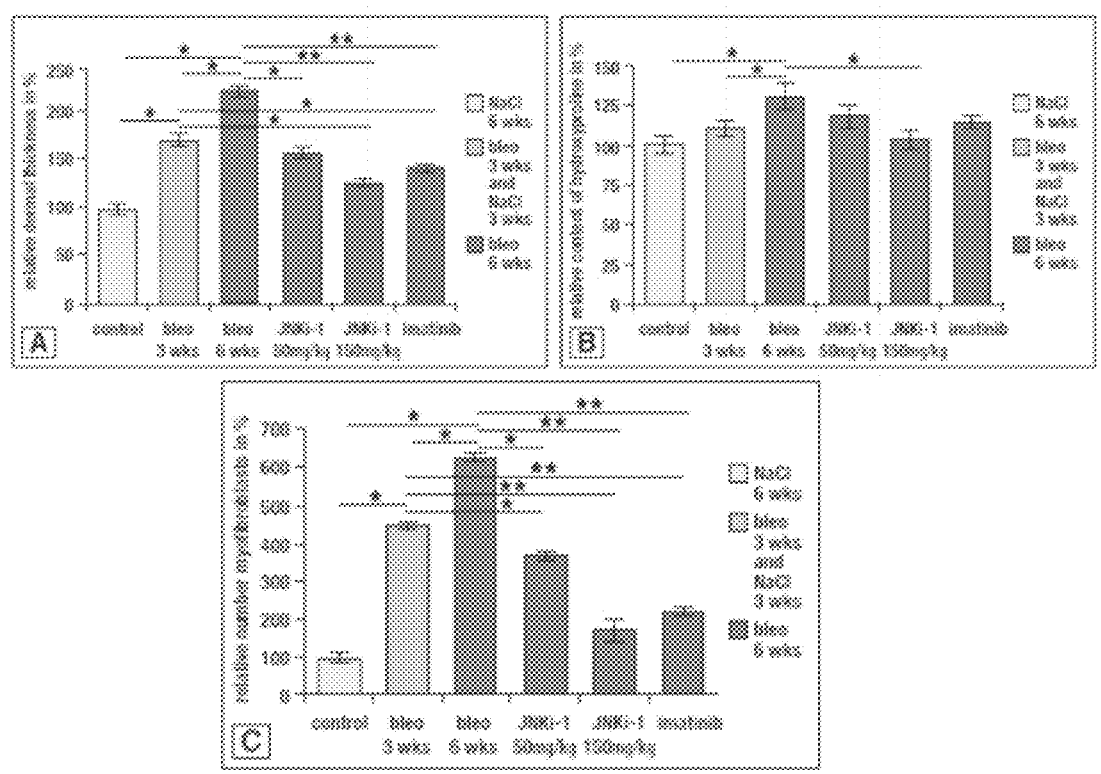

FIG. 7: Effect of Compound JNKi-1 treatment on induced regression of experimental fibrosis using a therapeutic treatment paradigm. Treatment with Compound JNKi-1 for the last 3 weeks upon continuous challenge did not only stop further progression of fibrosis (as compared to mice treated with bleomycin for 6 weeks), but also induced regression of fibrosis and reduced dermal thickening (A), myofibroblast counts (B), and hydroxyproline content (C) dose-dependently below the levels of mice challenged with bleomycin for 3 weeks. The level of mice receiving sodium chloride injections for 6 weeks was defined as 100%; other results were normalized to this value. Data represent the mean±SEM. *, p<0.05; **, p<0.01.

Figure 8:
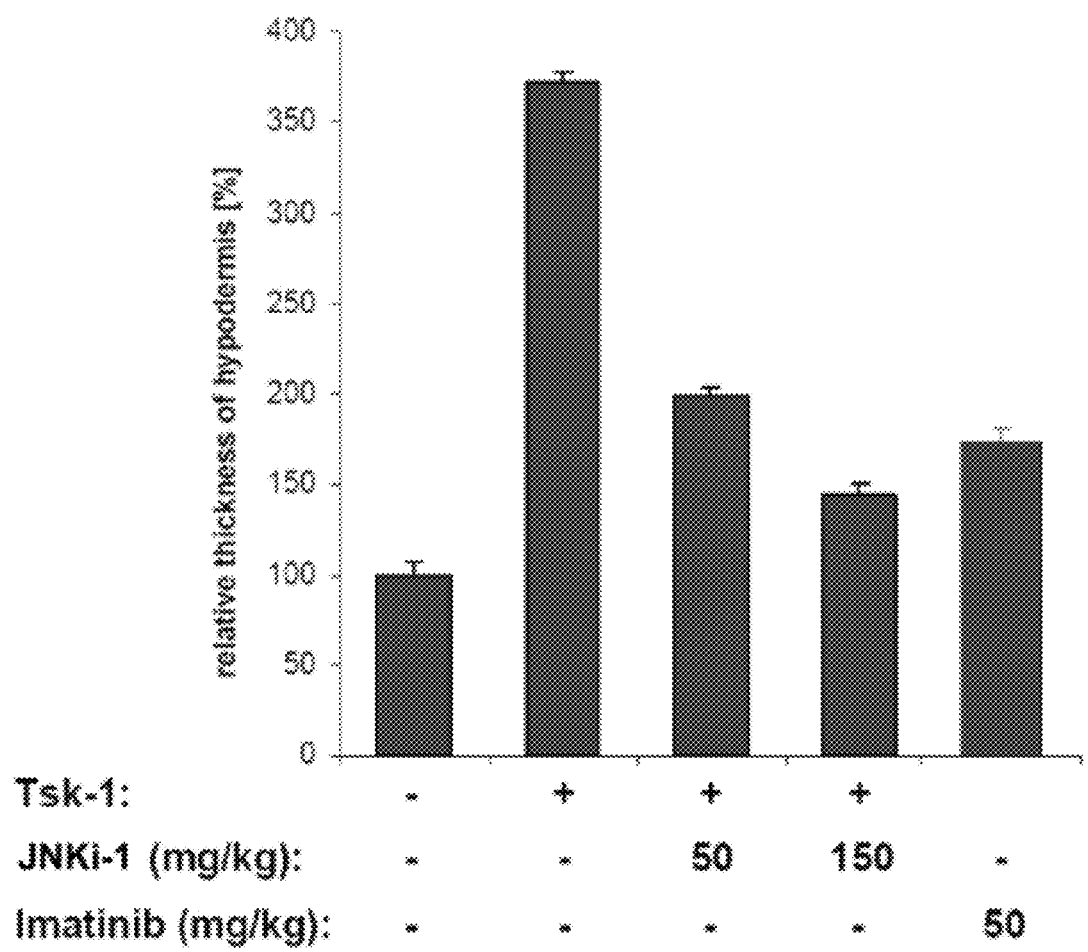

FIG. 8: Antifibrotic effects of Compound JNKi-1 treatment in the Tsk-1 Mouse Model. The dermal thickness in control mice not carrying the TSK-1 mutation (first column) was considered as 100%, other results were normalized to this value. Dermal thickness was measured by H & E staining of skin biopsies.

Figure 9:
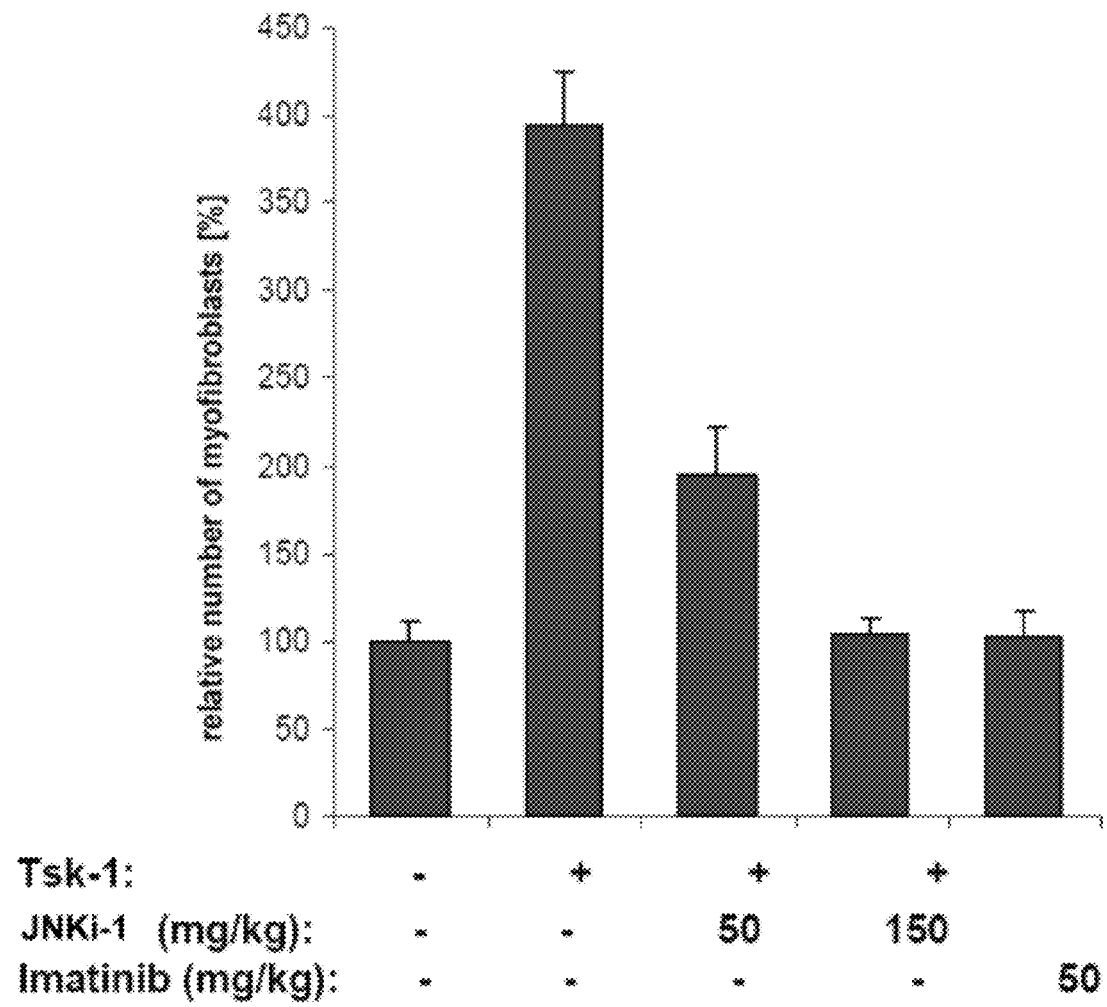

FIG. 9: Effect of Compound JNKi-1 treatment on the accumulation of myofibroblasts in Tsk-1 Mice. The number of myofibroblasts in control mice not carrying the TSK-1 mutation (first column) was considered as 100%, other results were normalized to this value. Myofibroblasts were quantified by IHC staining of skin biopsies for α-SMA.

Figure 10:
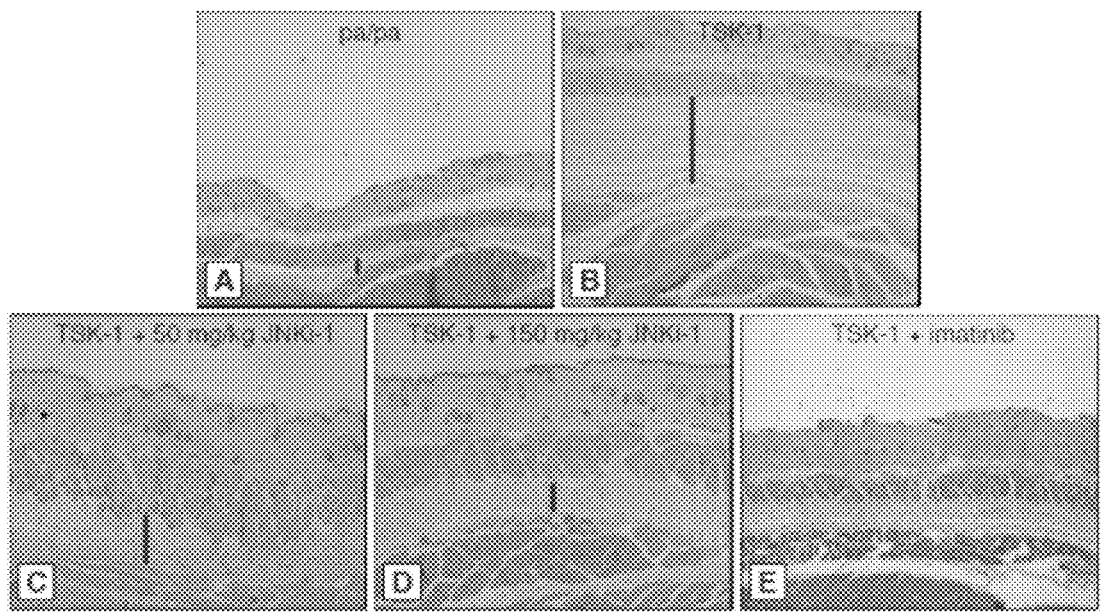

FIG. 10: Effect of Compound JNKi-1 treatment on hypodermal thickening of TSK-1 mice. TSK-1 mice generate hypodermal thickening compared to pa/pa mice not carrying the mutation (A and B). Treatment of TSK-1 mice with Compound JNKi-1 dose dependently reduced these histological changes (C and D). Reduction of hypodermal thickening upon treatment with 150 mg/kg effects of Compound JNKi-1 was more pronounced than treatment with imatinib (E). Representative skin sections stained with H & E are shown at 40-fold magnification.

Figure 11:
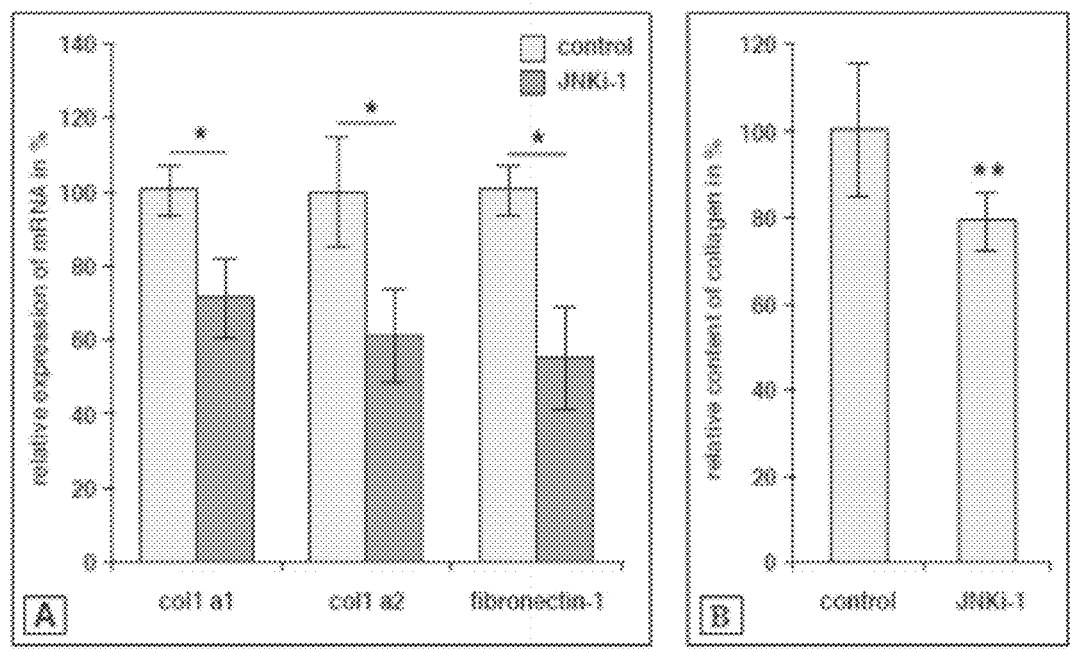

FIG. 11: Effect of Compound JNKi-1 treatment on basal production of extracellular matrix (ECM) components in dermal fibroblasts from SSc patients. Incubation of dermal SSc-fibroblasts with Compound JNKi-1 for 24 hours reduced expression of col1 a1, col1 a2, and fibronectin-1 mRNA (A) and the release of protein into supernatants (B). The levels of mock-treated fibroblasts were defined as 100%; other results were normalized to this value. Data represent the mean±SEM. *, p<0.05; **, p<0.01.

Figure 12:
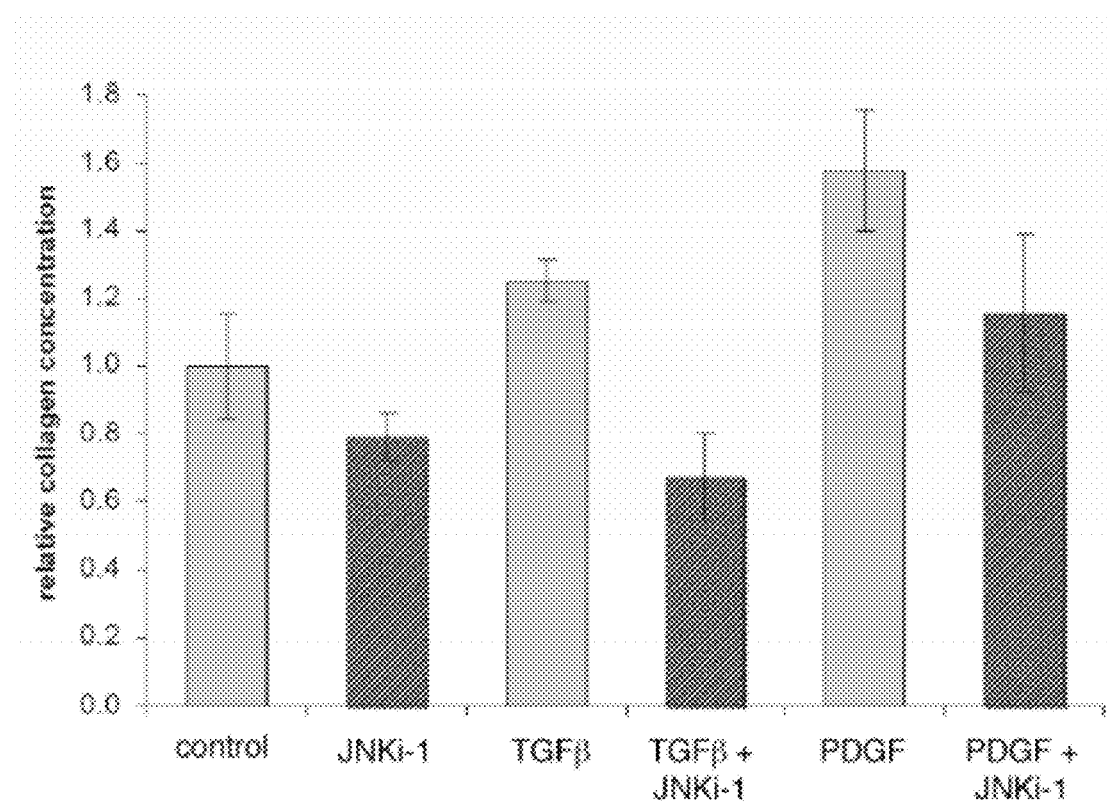

FIG. 12: Effect of Compound JNKi-1 treatment on systemic scleroderma fibroblast viability, demonstrating that Compound JNKi-1 does not exert its inhibitory effects indirectly by reducing cell viability.

Figure 13:
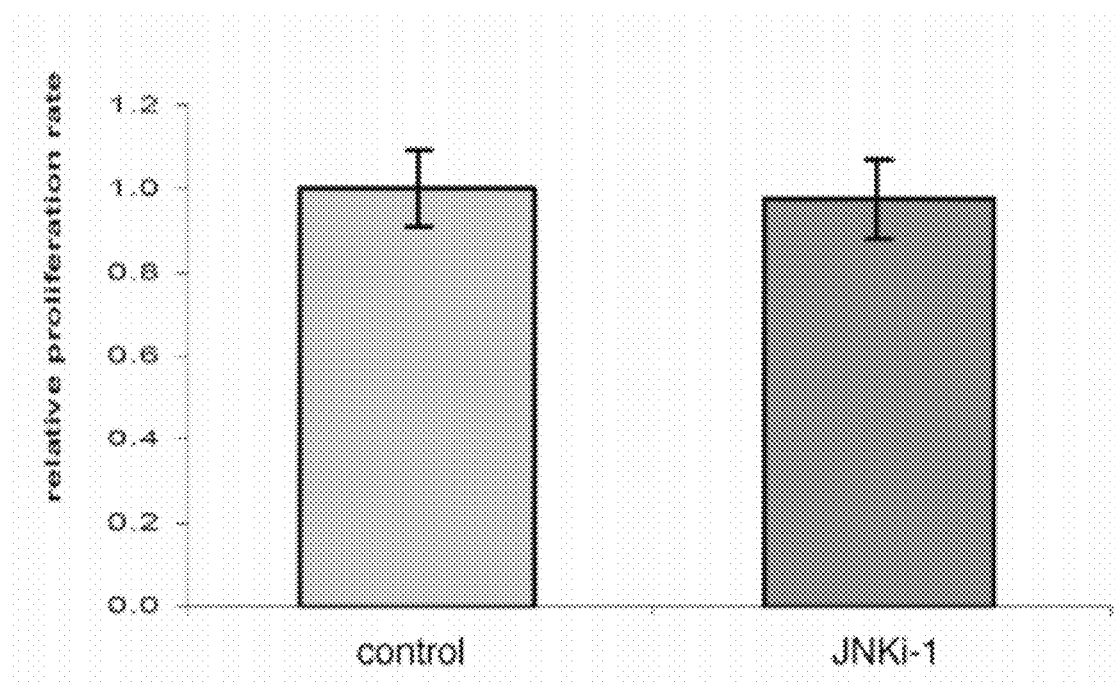

FIG. 13: Effect of Compound JNKi-1 treatment on TGF-β and PDGF-induced total collagen secretion, demonstrating that Compound JNKi-1 modestly inhibited both TGF-β and PDGF-induced total collagen secretion.

Figure 14:
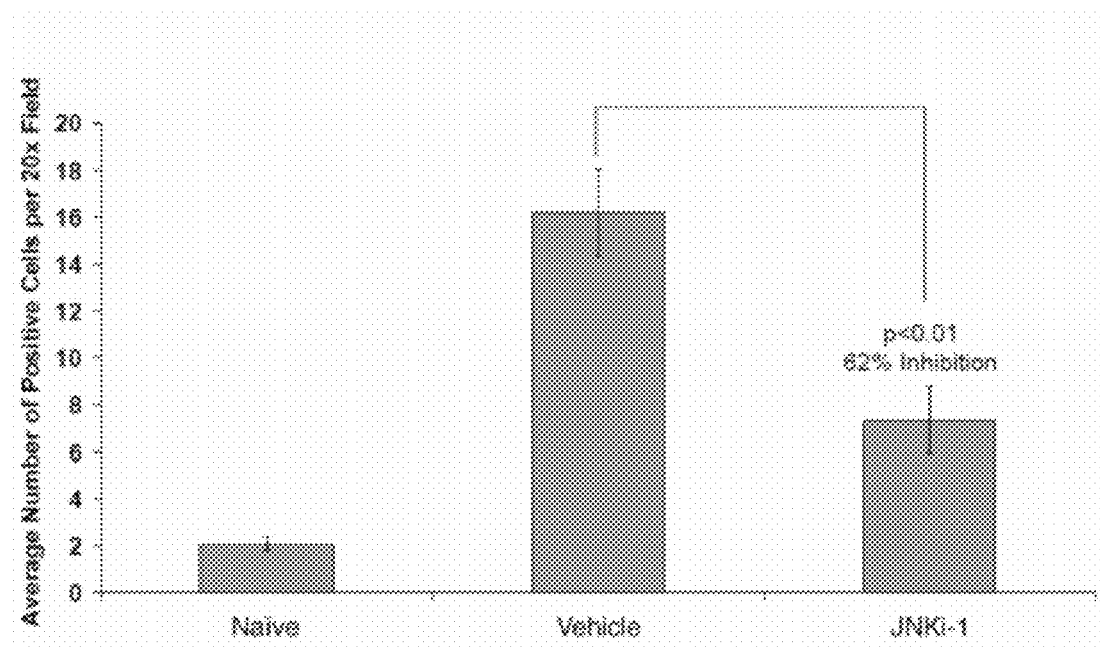

FIG. 14: Effect of Compound JNKi-1 treatment on UVB-induced TUNEL labeling in mouse epidermis 24 hr post UVB stimulation. The study results demonstrate that Compound JNKi-1, administered orally prior to UVB exposure, can inhibit apoptotic cell death within the epidermis of SKH-1 mice.

Figure 15:
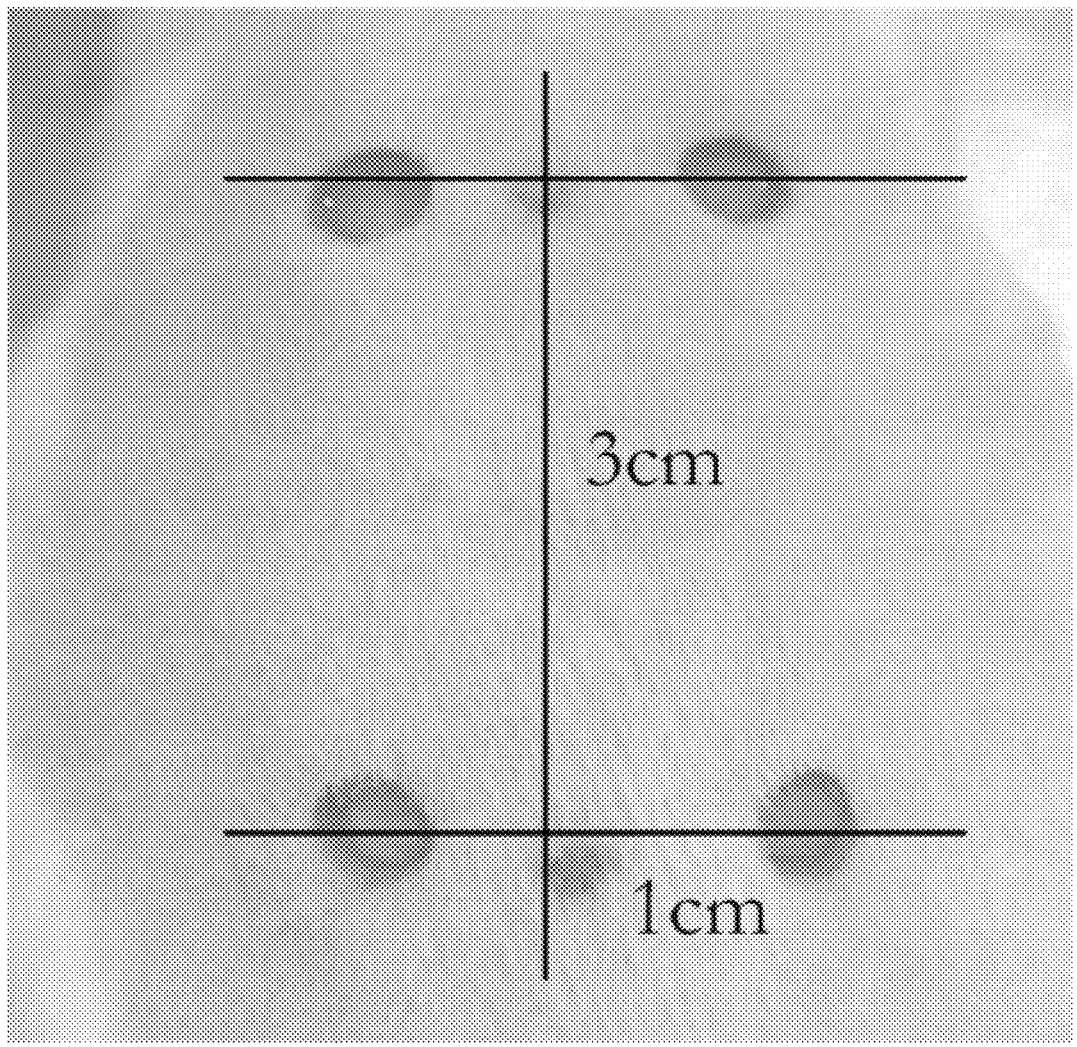

FIG. 15: Excisional wound procedure, showing the four points marked on the animal's back 1 cm at either side of the midline. A biopsy punch (6 mm diameter) was aligned vertically over the center of a mark and the epidermis, dermis and panniculus carnosus were removed.

Figure 16:
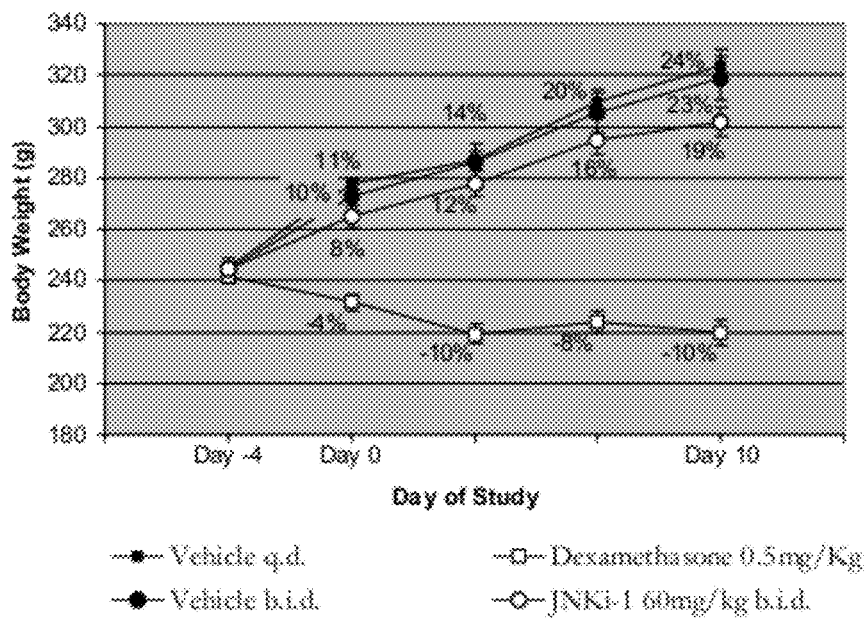

FIG. 16: Effect of treatment with Compound JNKi-1 treatment on body weight in the wound healing model, demonstrating that body weight gain was comparable between vehicle and Compound JNKi-1 treated groups. Study A shown as representative of three experiments.

Figure 17:
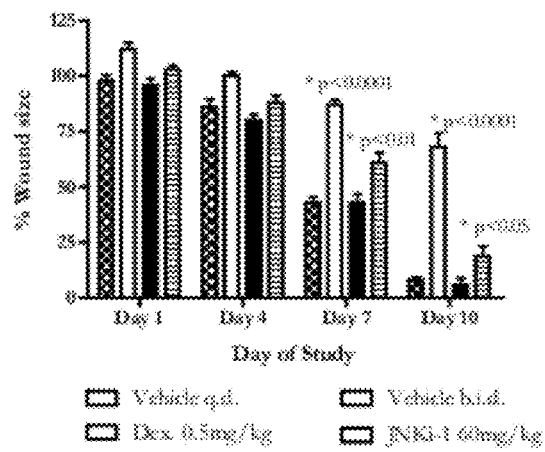
Figure 17:
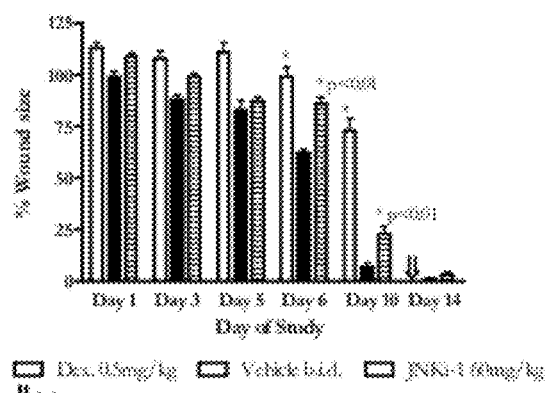
Figure 17:
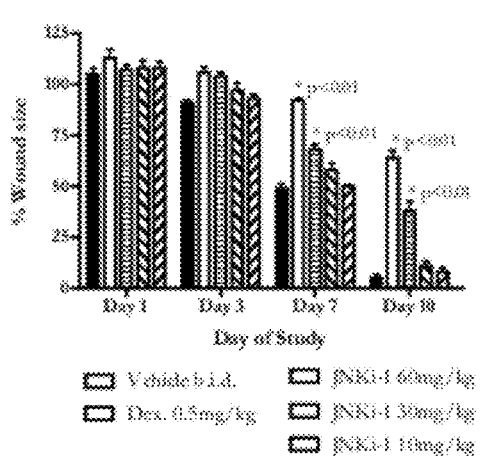

FIG. 17: Effect of Compound JNKi-1 treatment on wound size in 3 experiments (Studies A, B and C), demonstrating that a delay in wound healing was observed in rats dosed with Compound JNKi-1 at 60 mg/kg b.i.d (panel A), but that no difference was observed in rats dosed with Compound JNKi-1 at 30 or 10 mg/kg (panel C). Complete skin repair was achieved by day 14 post wounding in all Compound JNKi-1 treated groups (panel B).

Figure 18:
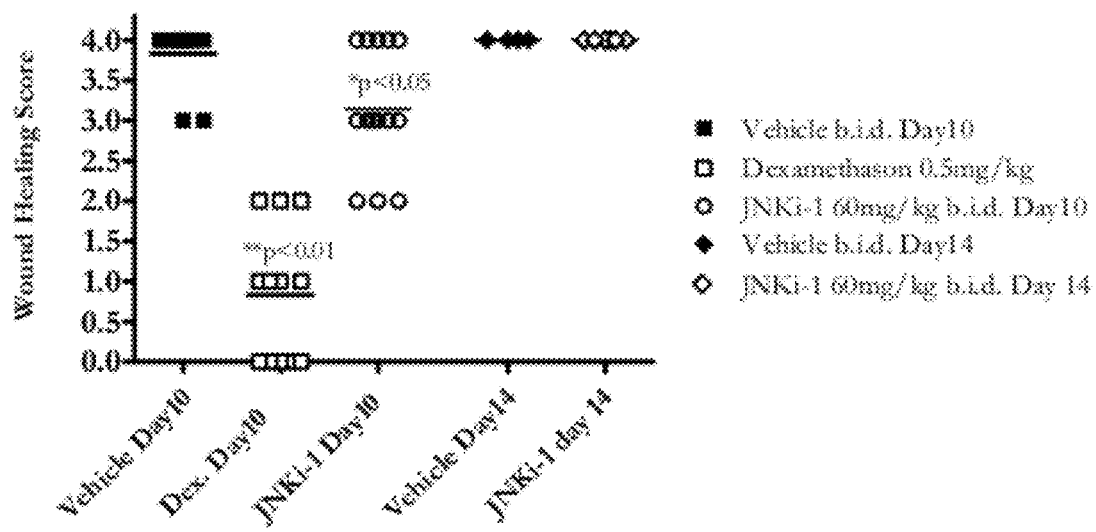
Figure 18:
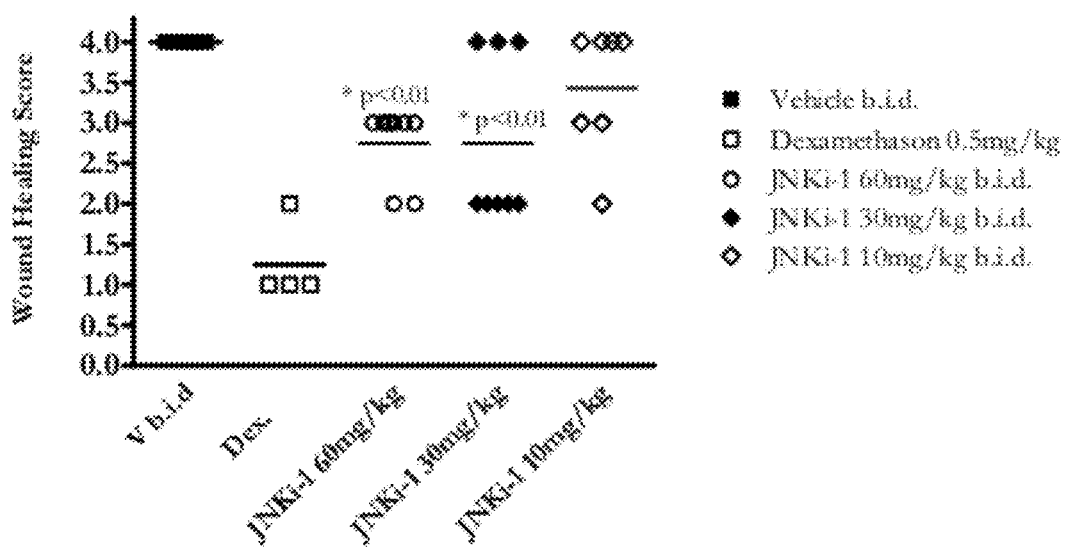

FIG. 18: Effect of Compound JNKi-1 treatment on healing score results (panel A: Combined Data for Study A and Study B; panel B: Study C), demonstrating that in the Compound JNKi-1 treated group, only 5 out of 14 rats had completely healed by day 10 but by day 14 all animals receiving Compound JNKi-1 had fully healed (panel A). In Study C, both 30 and 60 mg/kg doses showed a significant delay in healing compare to vehicle control group. None of the rats treated at 60 mg/kg had completely healed by day 10 and 5 out of 8 rats treated at 30 mg/kg displayed both incomplete re-epithelialization and collagen remodeling. No significant effect was observed in the group that received Compound JNKi-1 at 10 mg/kg (panel B).

Figure 19:
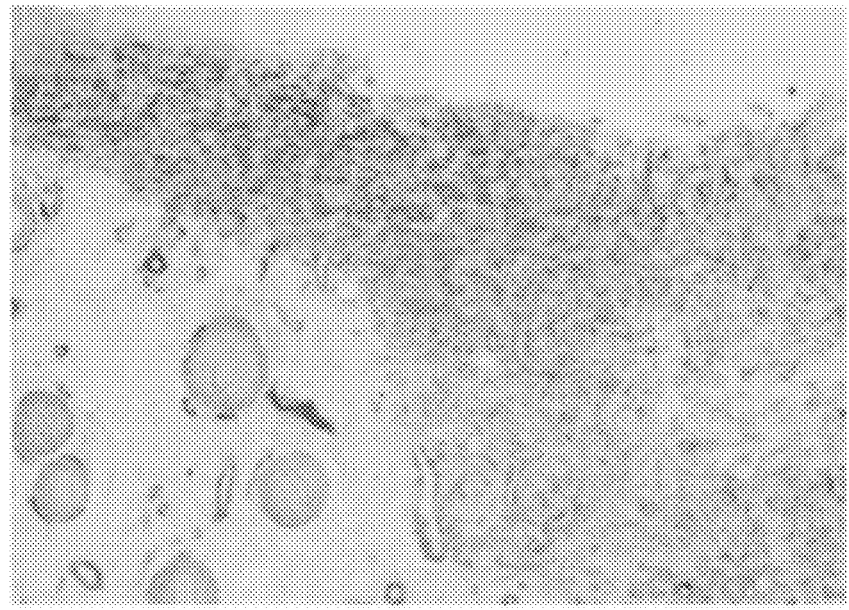
Figure 19:
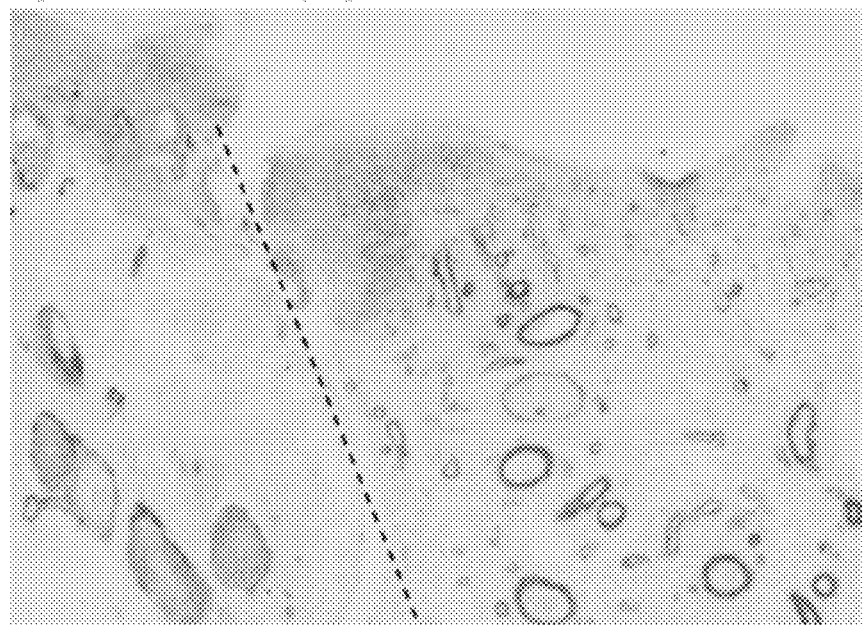

FIG. 19: Effect of Compound JNKi-1 treatment on myofibroblast migration into the wound gap, as measured by alpha-SMA staining on tissue sections 5 days post wounding, demonstrating that treatment with Compound JNKi-1 resulted in reduced myofibroblast migration (panel B) at the wound edges compared to the vehicle treated animals (panel A).

Figure 20:
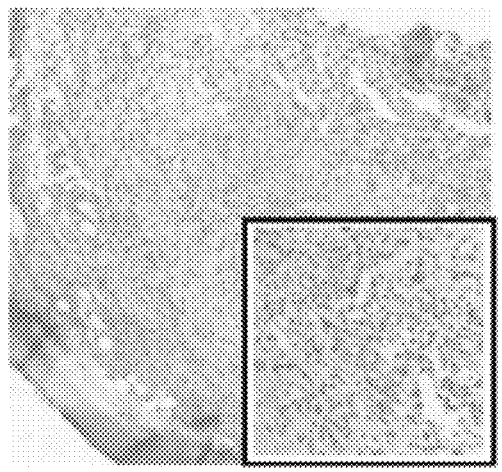
Figure 20:
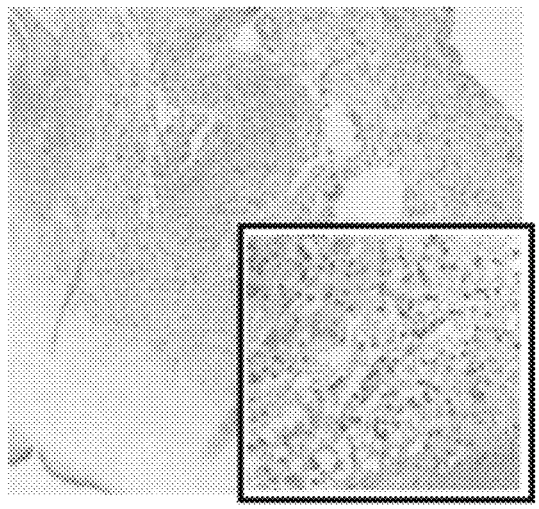
Figure 20:
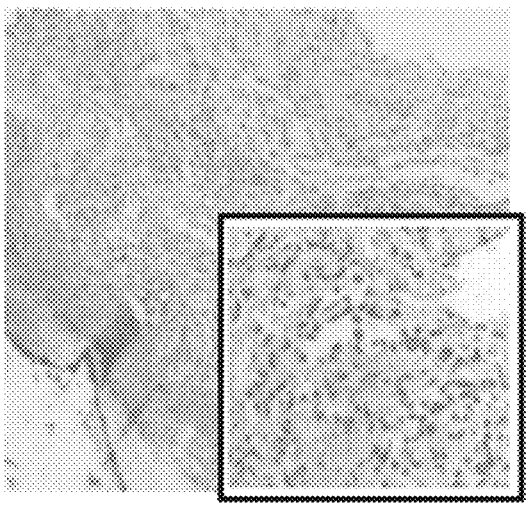

FIG. 20: Effect of Compound JNKi-1 treatment on neutrophil migration into the wound gap, as measured by anti-myeloperoxidase (MPO) staining on skin sections, demonstrating that on day 1 post wounding, treatment with Compound JNKi-1 did not affect inflammatory cell infiltration during response to tissue damage (panel C).

Figure 21:
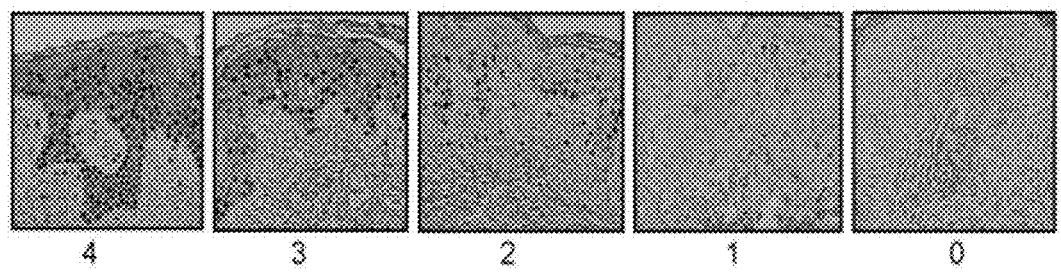

FIG. 21: Representative immunostaining images for the IHC subjective scoring parameters. The percentage of epithelial cJun positive nuclei was determined, and a score was awarded based on the following table: Score=0: 0-19% positive nuclei; Score=1: 20-39% positive nuclei; Score=2: 40-59% positive nuclei; Score=3: 60-79% positive nuclei; Score=4: 80-100% positive nuclei.

Figure 22:
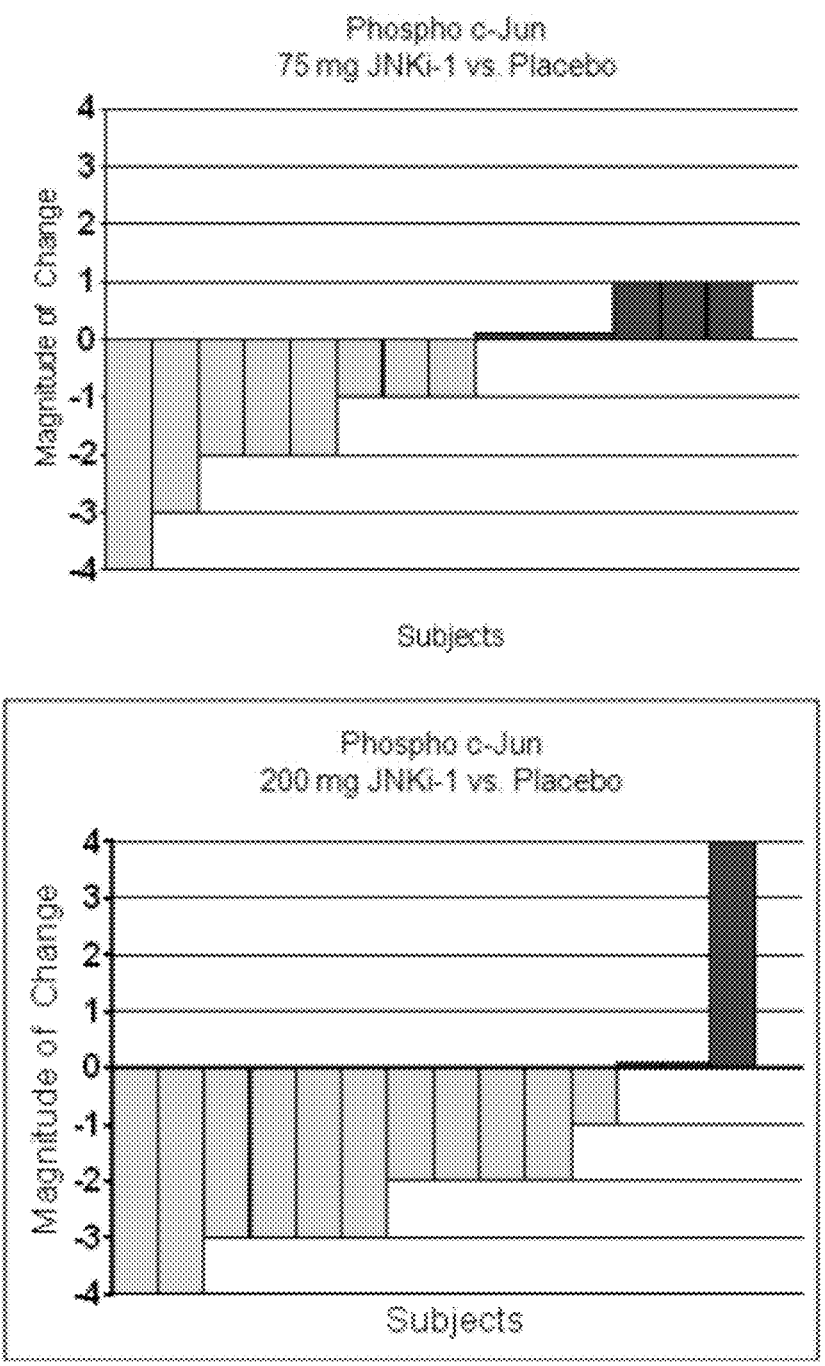

FIG. 22: Effect of JNKi-1 treatment on phospho c-Jun subjective scores. At the 75 mg dose, 8/14 subjects showed decreased p-cJun scoring, while at 200 mg 11/14 subjects showed decreased p-cJun scoring.

Figure 23:
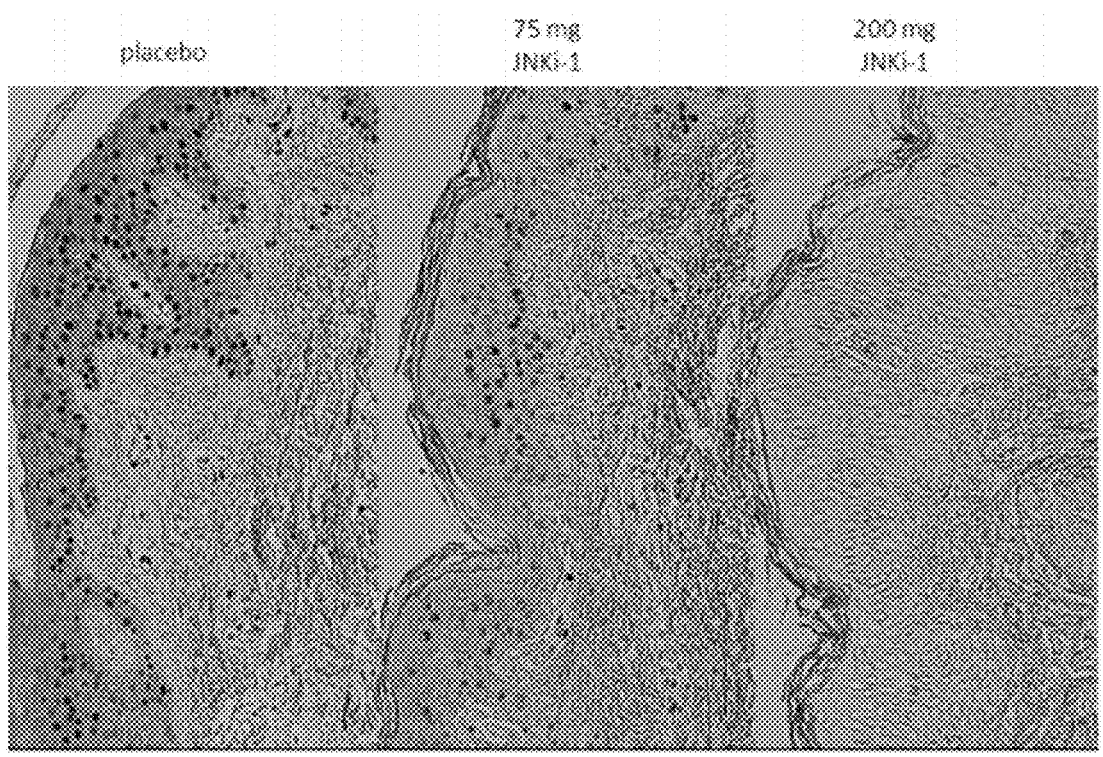

FIG. 23: Effect of JNKi-1 treatment on phospho c-Jun immunostaining of skin biopsy for representative patient.

Figure 24:
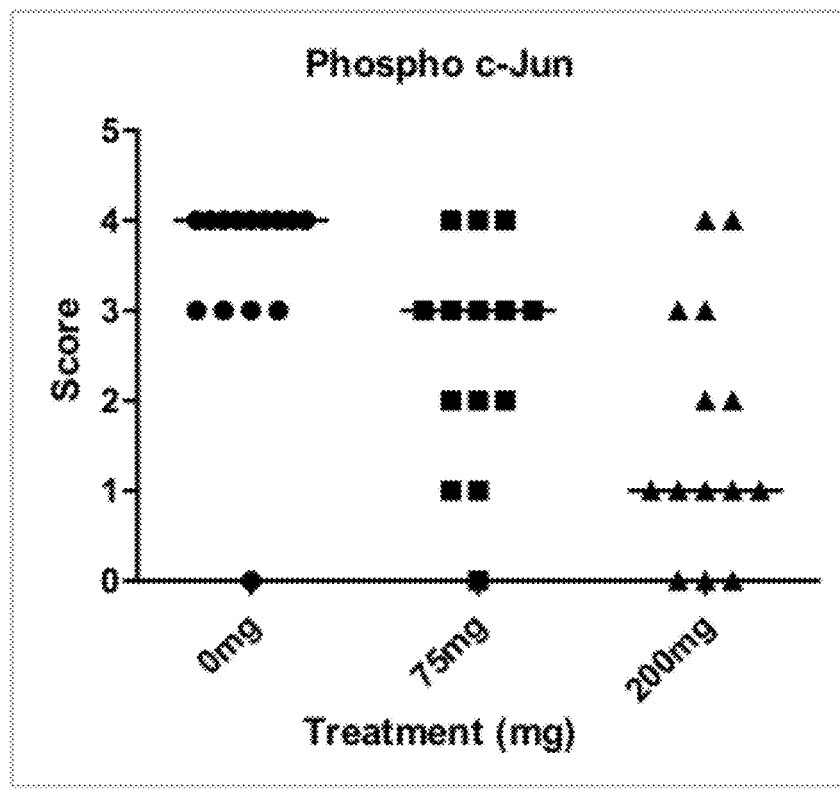

FIG. 24: Dose-response and magnitude of inhibition of phospho c-Jun scoring following treatment with 75 mg or 200 mg JNKi-1, compared to placebo treatment. The median subjective score was reduced from 4 in the placebo treated group to 3 in the 75 mg treatment group to 1 in the 200 mg treatment group.

Figure 25:
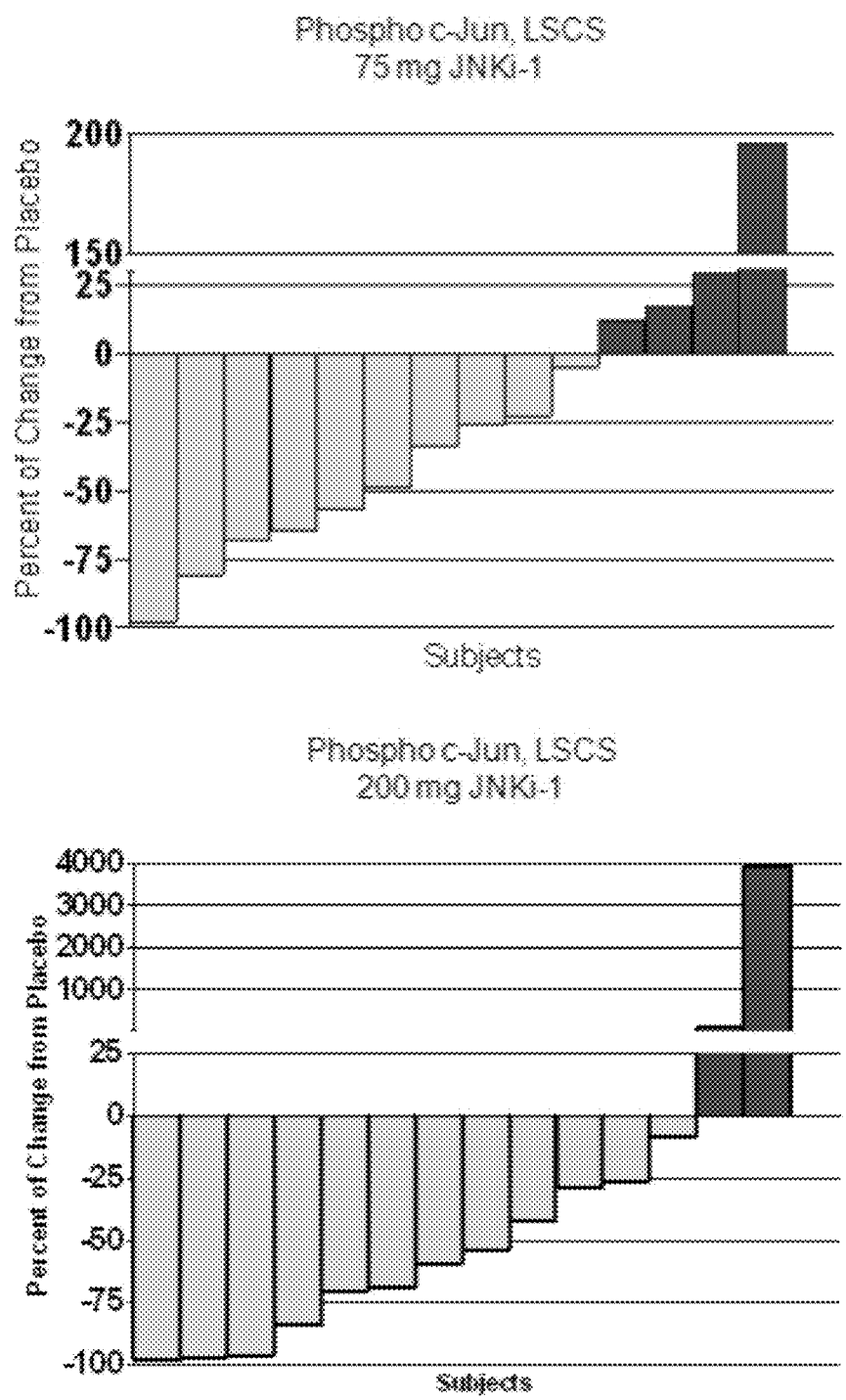

FIG. 25: Effect of JNKi-1 treatment on phospho c-Jun scoring as measured by laser scanning cytometry, showing similar results to subjective scoring.

Figure 26:
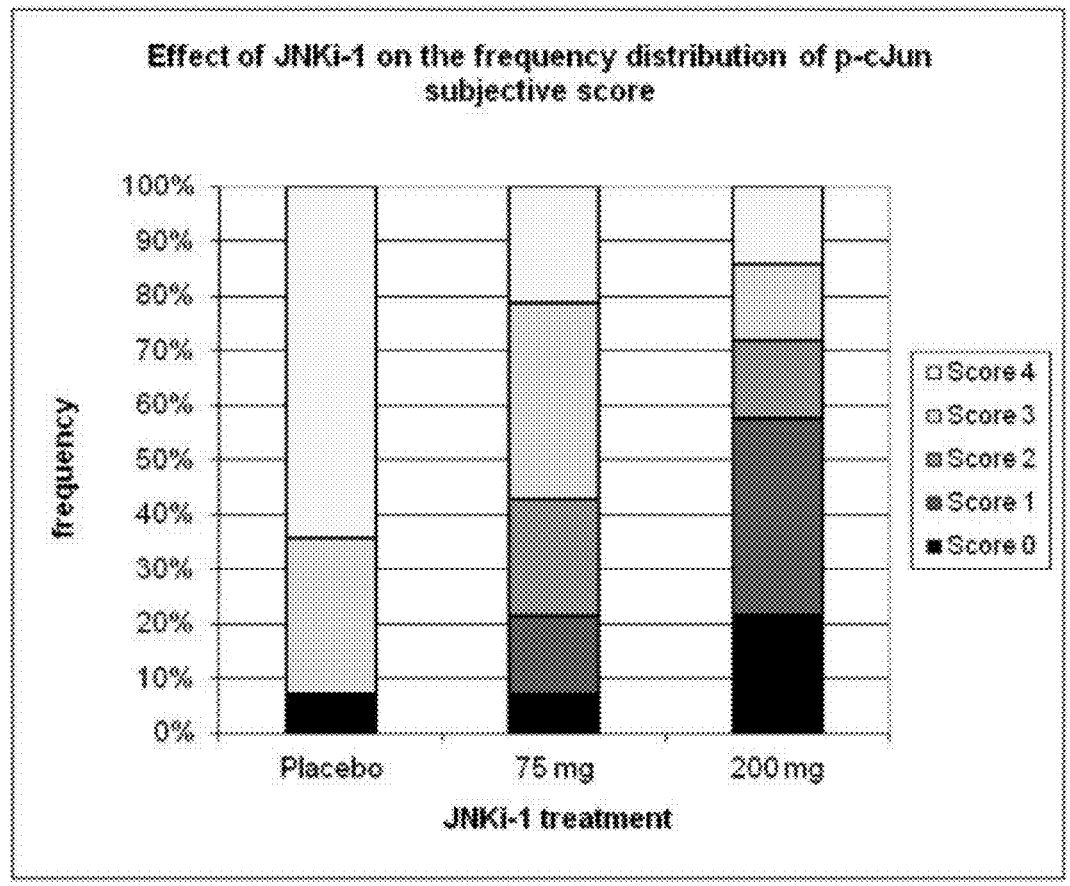

FIG. 26: Effect of JNKi-1 treatment on the frequency distribution of phospho c-Jun subjective scores, showing that following treatment fewer subjects had high p-cJun scores.

Figure 27:
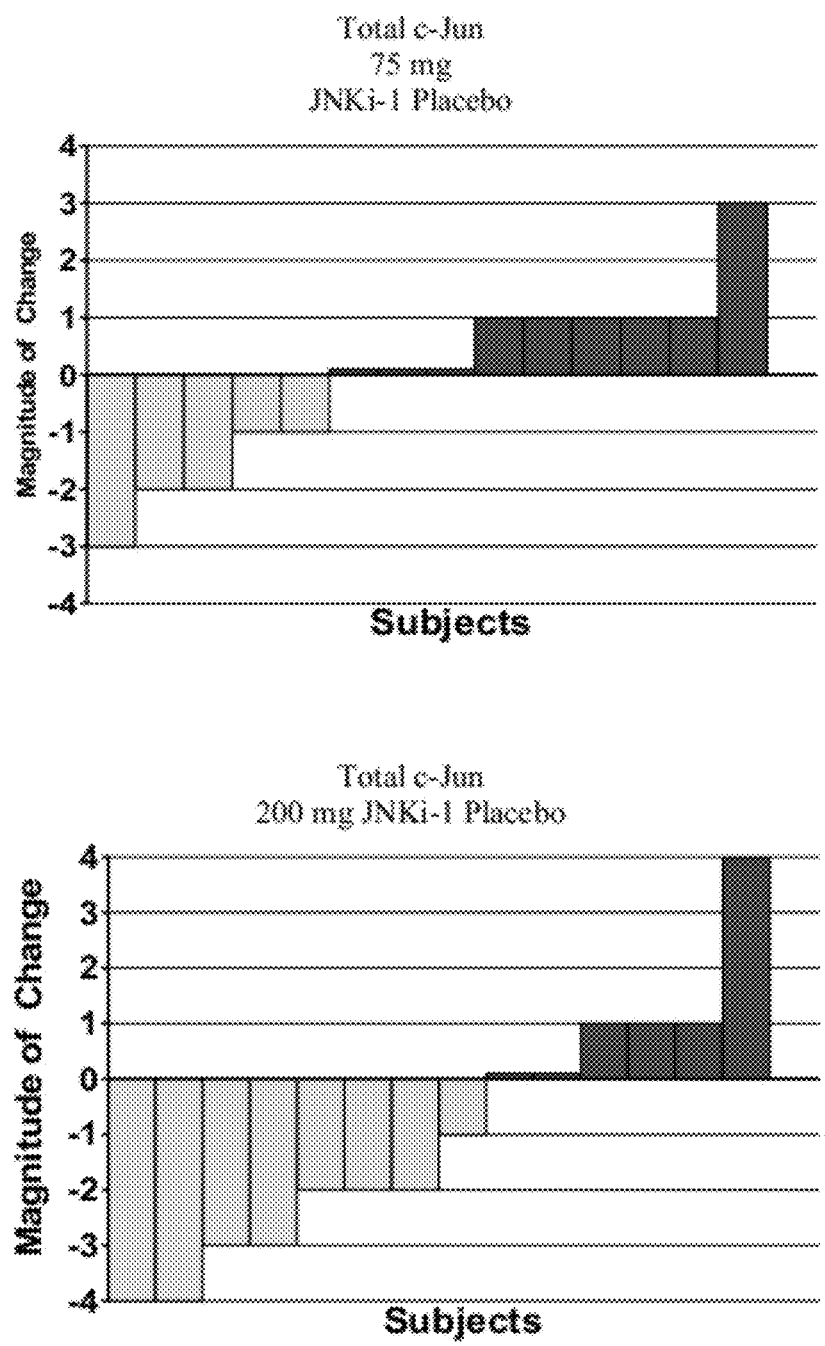

FIG. 27: Effect of JNKi-1 treatment on c-Jun subjective scores. At the 75 mg dose, 5/14 subjects showed decreased cJun scoring, while at 200 mg 8/14 subjects showed decreased cJun scoring FIG. 28: Effect of JNKi-1 treatment on c-Jun immunostaining of skin biopsy for representative Patient 15.

Figure 29:
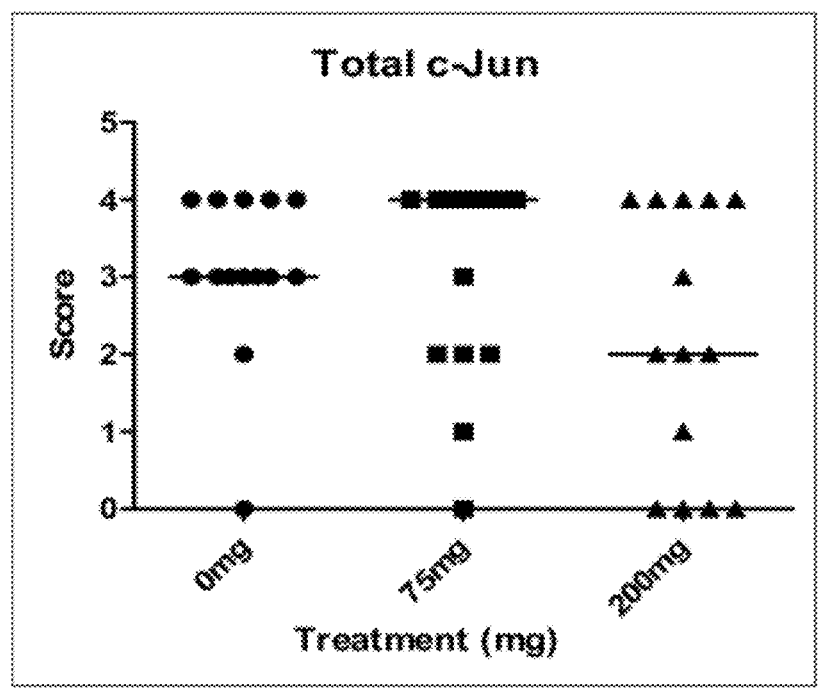

FIG. 29: Dose-response and magnitude of inhibition of c-Jun scoring following treatment with 75 mg or 200 mg JNKi-1, compared to placebo treatment. The median subjective score was reduced from 4 in the placebo treated group to 2 in the 200 mg treatment group.

Figure 30:
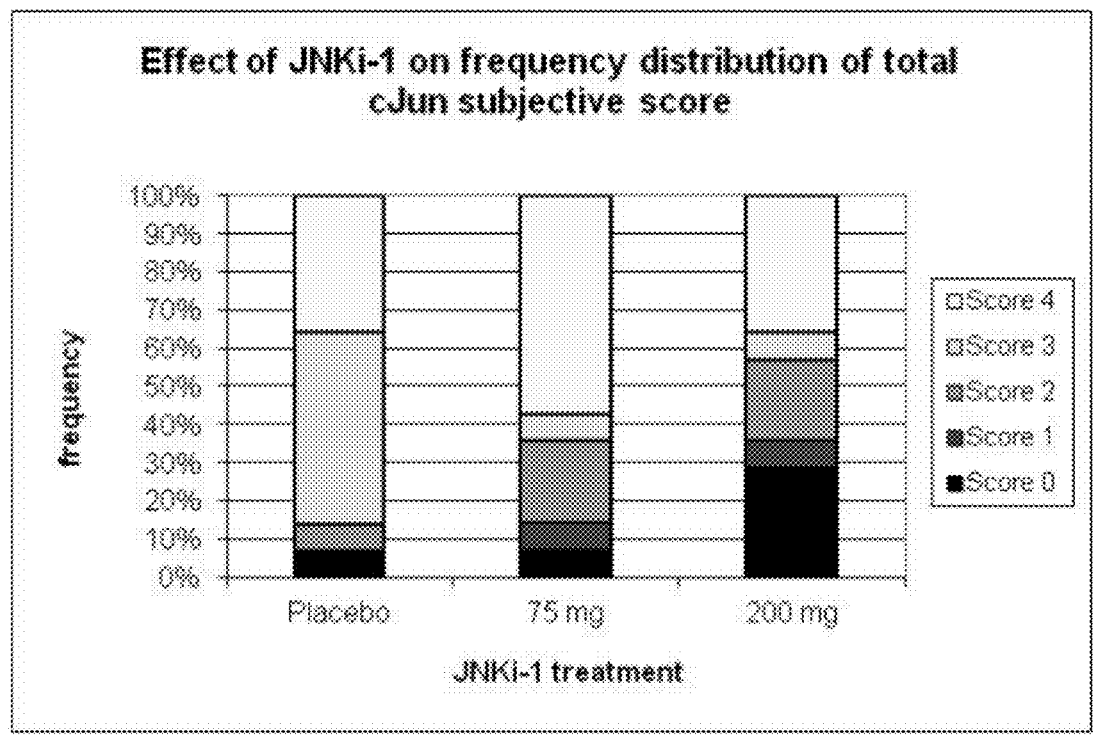

FIG. 30: Effect of JNKi-1 treatment on the frequency distribution of c-Jun subjective scores, showing that following treatment with 200 mg JNKi-1 fewer subjects had high cJun scores.

Figure 31:
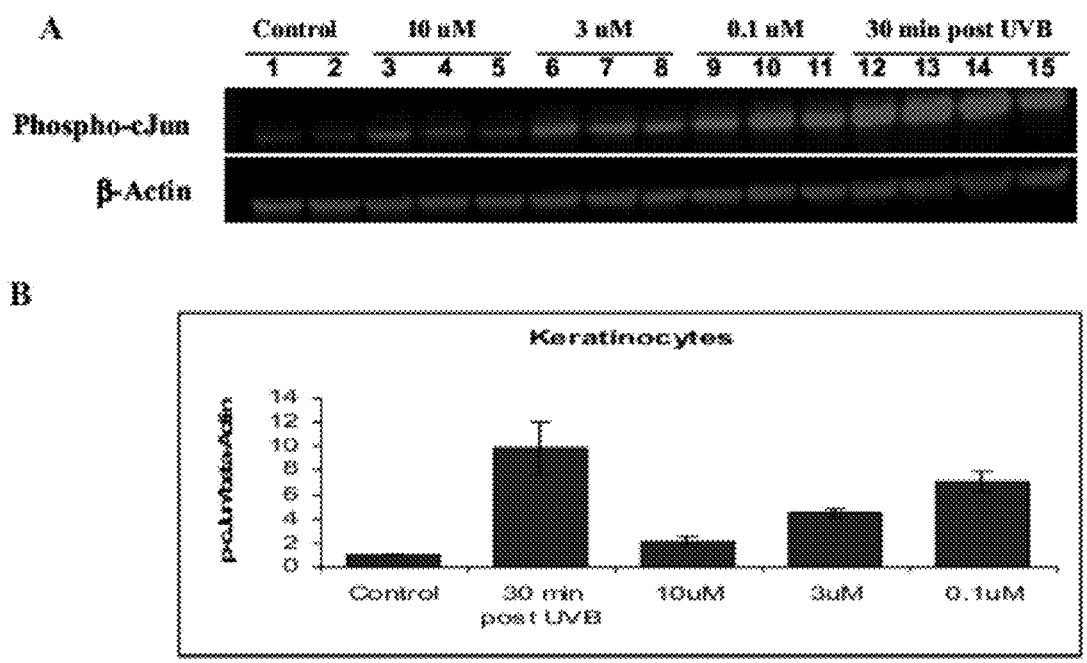

FIG. 31: Effect of JNKi-1 on c-Jun phosphorylation in nHEK cells is shown by Western blot analysis (panel A). Quantitation of Western blot is shown in panel B. The results show that JNKi-1 strongly Inhibits UVB-Induced JNK Activation in normal Human Epithelial Keratinocytes.

Figure 32:
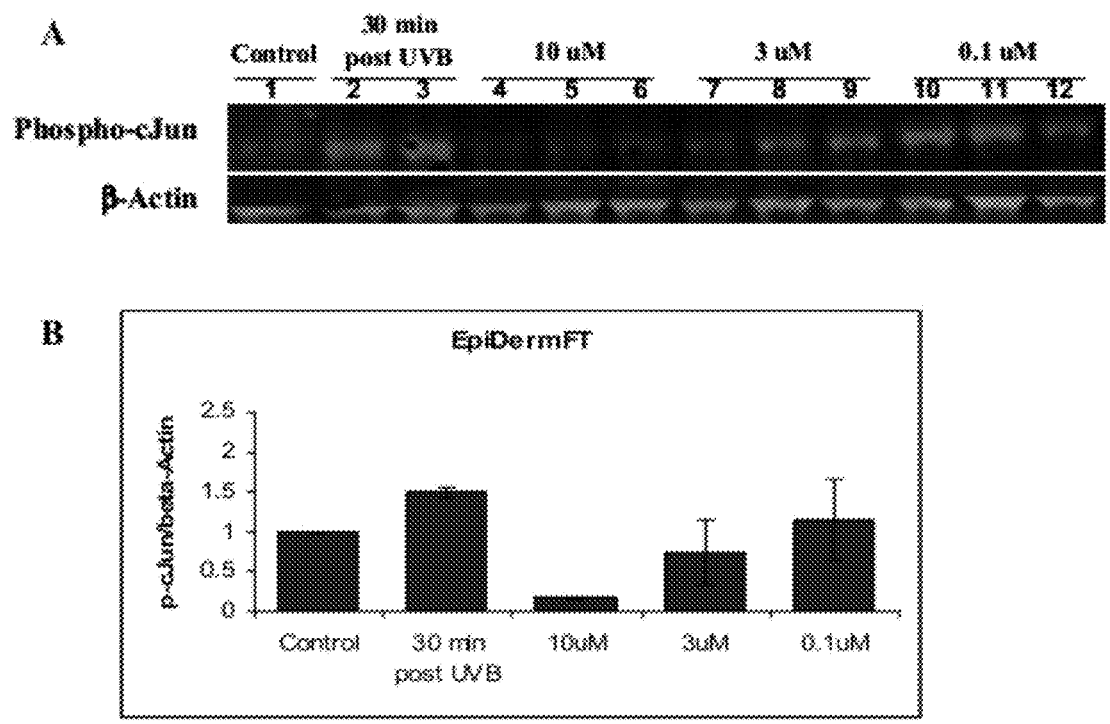

FIG. 32: Effect of JNKi-1 on c-Jun phosphorylation in the EpiDermFT™ skin model is shown by Western blot analysis (panel A). Quantitation of Western blot is shown in panel B. The results indicate that JNKi-1 strongly Inhibits UVB-Induced JNK Activation in EpiDermFT™.

5.3 Aminopurine Compounds

Provided herein are Aminopurine Compounds having the following formula (I):

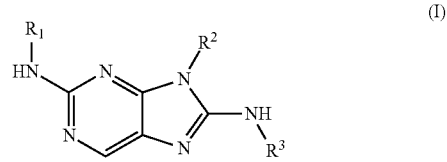

and pharmaceutically acceptable salts, solid forms, clathrates, solvates, hydrates, stereoisomers, tautomers, enantiomers and prodrugs thereof, wherein:

$R^1$ is substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl;

$R^2$ is H, substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl; and $R^3$ is aryl substituted with one or more halogens or $C_{3-10}$heteroaryl substituted with one or more halogens, wherein the aryl or $C_{3-10}$heteroaryl group is optionally further substituted with one or more $C_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

In a particular embodiment, tautomers of compounds of formula (I) have the following structure:

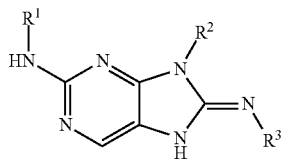

and include pharmaceutically acceptable salts, solid forms, clathrates, solvates, hydrates, stereoisomers, enantiomers and prodrugs thereof, wherein $R^1$-$R^3$ are as defined above.

In one embodiment, the Aminopurine Compounds of formula (I) are those wherein $R^1$ is substituted or unsubstituted aryl.

In another embodiment, the Aminopurine Compounds of formula (I) are those wherein $R^1$ is substituted or unsubstituted phenyl.

In another embodiment, the Aminopurine Compounds of formula (I) are those wherein $R^1$ is substituted phenyl, in one embodiment alkoxy substituted phenyl, in one embodiment p-alkoxy substituted phenyl, and in one embodiment p-methoxy substituted phenyl.

In another embodiment, the Aminopurine Compounds of formula (I) are those wherein $R^1$ is m-alkoxy substituted phenyl, in one embodiment m-methoxy substituted phenyl.

In another embodiment, the Aminopurine Compounds of formula (I) are those wherein $R^1$ is trifluoromethyl substituted phenyl, in one embodiment p-trifluoromethyl substituted phenyl.

In another embodiment, the Aminopurine Compounds of formula (I) are those wherein $R^1$ is $C_{1-6}$alkyl, in one embodiment isopropyl.

In another embodiment, the Aminopurine Compounds of formula (I) are those wherein $R^1$ is p-halo substituted phenyl, in one embodiment p-fluoro substituted phenyl.

In another embodiment, the Aminopurine Compounds of formula (I) are those wherein $R^1$ is p-$C_{1-6}$alkyl substituted phenyl, in one embodiment p-methyl substituted phenyl.

In another embodiment, the Aminopurine Compounds of formula (I) are those wherein $R^1$ is o-halo substituted phenyl, in one embodiment o-fluoro substituted phenyl.

In another embodiment, the Aminopurine Compounds of formula (I) are those wherein $R^1$ is m,p-dihalo substituted phenyl, in one embodiment m,p-dichloro substituted phenyl.

In another embodiment, the Aminopurine Compounds of formula (I) are those wherein $R^1$ is m-cyano substituted phenyl.

In another embodiment, the Aminopurine Compounds of formula (I) are those wherein $R^1$ is p-$C_{3-10}$heterocycle substituted phenyl, in one embodiment p-morpholino substituted phenyl.

In another embodiment, the Aminopurine Compounds of formula (I) are those wherein $R^1$ is p-sulfonyl substituted phenyl.

In another embodiment, the Aminopurine Compounds of formula (I) are those wherein $R^1$ is $C_{3-10}$heteroaryl, in one embodiment pyridine or pyridinone.

In another embodiment, the Aminopurine Compounds of formula (I) are those wherein $R^1$ is $C_{3-10}$heterocycle, in one embodiment piperidine, piperidin-2-one, pyrrolidinone or tetrahydropyran.

In another embodiment, the Aminopurine Compounds of formula (I) are those wherein $R^1$ is N-substituted piperidine, in one embodiment N-sulfonyl substituted piperidine.

In another embodiment, the Aminopurine Compounds of formula (I) are those wherein $R^1$ is $C_{3-10}$cycloalkyl, in one embodiment cyclohexyl, cyclopentyl or cyclopropyl.

In another embodiment, the Aminopurine Compounds of formula (I) are those wherein $R^1$ is substituted $C_{3-10}$cycloalkyl, in one embodiment $C_{3-10}$cycloalkyl substituted with one or more $C_{1-6}$alkyl, hydroxy, hydroxyalkyl, alkoxy, alkoxyalkyl, amino, alkylamino, carboxy, heterocyclocarbonyl, aminocarbonyl, cyano, acylamino, alkanesulfonylamino, tetrazolyl, triazolyl or imidazolyl groups.

In another embodiment, the Aminopurine Compounds of formula (I) are those wherein $R^1$ is substituted $C_{3-10}$cycloalkyl, in one embodiment $C_{3-10}$cycloalkyl substituted with one or more alkyl, hydroxy, hydroxyalkyl, alkoxy, alkoxyalkyl, amino, aminoalkyl, amido, amidoalkyl, carboxy, heterocyclocarbonyl, sulfonamide or sulfonaminoalkyl groups. Cyclohexyl and cyclopentyl are particular $C_{3-10}$cycloalkyl groups.

In another embodiment, the Aminopurine Compounds of formula (I) are those wherein $R^1$ is cyclohexyl substituted with one or more alkyl, hydroxy, hydroxyalkyl, alkoxy, alkoxyalkyl, amino, aminoalkyl, amido, amidoalkyl, carboxy, heterocyclocarbonyl, sulfonamide or sulfonaminoalkyl groups.

In another embodiment, the Aminopurine Compounds of formula (I) are those wherein $R^1$ is $C_{1-6}$alkyl, in one embodiment methyl, ethyl, propyl (e.g., n-propyl or isopropyl) or butyl (e.g., isobutyl).

In another embodiment, the Aminopurine Compounds of formula (I) are those wherein $R^1$ is substituted $C_{1-6}$alkyl, in one embodiment phenyl, hydroxy, $C_{3-10}$cycloalkyl, or oxirane substituted $C_{1-6}$alkyl.

In another embodiment, the Aminopurine Compounds of formula (I) are those wherein $R^1$ is benzyl.

In another embodiment, the Aminopurine Compounds of formula (I) are those wherein $R^1$ is substituted $C_{1-6}$alkyl, in one embodiment $C_{3-10}$heterocycle (e.g., piperidine or pyrrolidine substituted $C_{1-6}$alkyl.

In another embodiment, the Aminopurine Compounds of formula (I) are those wherein $R^2$ is substituted or unsubstituted $C_{1-6}$alkyl, substituted or unsubstituted aryl, substituted or unsubstituted $C_{3-10}$heterocycle or substituted or unsubstituted $C_{3-10}$heteroaryl.

In another embodiment, the Aminopurine Compounds of formula (I) are those wherein $R^2$ is substituted or unsubstituted $C_{3-10}$cycloalkyl, in one embodiment cyclohexyl, cyclopentyl, cyclobutyl or cyclopropyl. Cyclohexyl and cyclopentyl are specific $C_{3-10}$cycloalkyl groups. In one embodiment, $C_{3-10}$cycloalkyl substitutents include $C_{1-6}$alky, hydroxy, hydroxyalkyl, alkoxy, alkoxyalkyl, amino, aminoalkyl, amido, amidoalkyl, carboxy, heterocyclocarbonyl, sulfonamide and sulfonaminoalkyl groups.

In another embodiment, the Aminopurine Compounds of formula (I) are those wherein $R^2$ is cyclohexyl or cyclopentyl substituted with one or more $C_{1-6}$alkyl, hydroxy, hydroxyalkyl, alkoxy, alkoxyalkyl, amino, aminoalkyl, amido, amidoalkyl, carboxy, heterocyclocarbonyl, sulfonamide or sulfonaminoalkyl groups.

In another embodiment, the Aminopurine Compounds of formula (I) are those wherein $R^2$ is cyclohexyl or cyclopentyl substituted with one or more $C_{1-6}$alkyl, hydroxy, hydroxyalkyl, alkoxy, alkoxyalkyl, amino, alkylamino, carboxy, heterocyclocarbonyl, aminocarbonyl, cyano, acylamino, alkanesulfonylamino, tetrazolyl, triazolyl or imidazolyl groups.

In another embodiment, the Aminopurine Compounds of formula (I) are those wherein $R^2$ is $C_{1-6}$alkyl, in one embodiment butyl (e.g., n-butyl, isobutyl or t-butyl), propyl (e.g., isopropyl), ethyl or methyl.

In another embodiment, the Aminopurine Compounds of formula (I) are those wherein $R^2$ is substituted $C_{1-6}$alkyl, in one embodiment cyano, $C_{3-10}$cycloalkyl or hydroxy substituted $C_{1-6}$alkyl.

In another embodiment, the Aminopurine Compounds of formula (I) are those wherein $R^2$ is substituted $C_{1-6}$alkyl, in one embodiment $C_{3-10}$heterocycle (e.g., piperidine or pyrrolidine) hydroxy or amido substituted $C_{1-6}$alkyl.

In another embodiment, the Aminopurine Compounds of formula (I) are those wherein $R^2$ is aryl, in one embodiment phenyl.

In another embodiment, the Aminopurine Compounds of formula (I) are those wherein $R^2$ is $C_{3-10}$heterocycle, in one embodiment piperidine, piperidin-2-one, tetrahydropyran, tetrahydrofuran or azetidine.

In another embodiment, the Aminopurine Compounds of formula (I) are those wherein $R^2$ is $C_{3-10}$heterocycle, in one embodiment a sulfur containing $C_{3-10}$heterocycle, including but not limited to 4-(1,1-dioxo)thiopyrianyl and 3-(1,1-dioxo)thiofuranyl. In a particular embodiment, $R^2$ is a sulfur, sulfonyl or sulfonamido containing $C_{3-10}$heterocycle.

In another embodiment, the Aminopurine Compounds of formula (I) are those wherein $R^2$ is substituted $C_{3-10}$heterocycle, in one embodiment acetyl substituted piperidine.

In another embodiment, the Aminopurine Compounds of formula (I) are those wherein $R^2$ is substituted or unsubstituted 3-oxetanyl, 3-tetrahydrofuranyl, 4-tetrahydropyranyl, 4-piperidinyl, 4-(1-acy)-piperidinyl, 4-(1-alkanesulfonyl)piperidinyl, 3-pyrrolidinyl, 3-(1-acyl)pyrrolidinyl or 3-(1-alkanesulfonyl)pyrrolidinyl.

In another embodiment, the Aminopurine Compounds of formula (I) are those wherein $R^3$ is o-halo substituted phenyl, in one embodiment o-fluoro or chloro substituted phenyl.

In another embodiment, the Aminopurine Compounds of formula (I) are those wherein $R^3$ is m-halo substituted phenyl, in one embodiment m-fluoro or chloro substituted phenyl.

In another embodiment, the Aminopurine Compounds of formula (I) are those wherein $R^3$ is p-halo substituted phenyl, in one embodiment p-fluoro or chloro substituted phenyl.

In another embodiment, the Aminopurine Compounds of formula (I) are those wherein $R^3$ is m,p-dihalo substituted phenyl, in one embodiment m,p-difluoro or dichloro substituted phenyl.

In another embodiment, the Aminopurine Compounds of formula (I) are those wherein $R^3$ is o,m-dihalo substituted phenyl, in one embodiment o,m-difluoro substituted phenyl.

In another embodiment, the Aminopurine Compounds of formula (I) are those wherein $R^3$ is o,p-dihalo substituted phenyl, in one embodiment o,p-difluoro substituted phenyl, o-fluoro-p-bromo substituted phenyl or o-fluoro-p-chloro substituted phenyl.

In another embodiment, the Aminopurine Compounds of formula (I) are those wherein $R^3$ is o,o-dihalo substituted phenyl, in one embodiment o,o-difluoro substituted phenyl or o-chloro-o-fluoro substituted phenyl.

In another embodiment, the Aminopurine Compounds of formula (I) are those wherein $R^3$ is 2,4,6-trihalo substituted phenyl, in one embodiment trifluoro substituted phenyl.

In another embodiment, the Aminopurine Compounds of formula (I) are those wherein $R^3$ is o-halo substituted, in one embodiment o-fluoro or chloro substituted, and m-trifluoromethyl substituted phenyl.

In another embodiment, the Aminopurine Compounds of formula (I) are those wherein $R^3$ is halo substituted $C_{3-10}$heteroaryl, in one embodiment halo substituted pyridine.

In another embodiment, the Aminopurine Compounds of formula (I) are those wherein $R^2$ is not aminoethyl.

In another embodiment, the Aminopurine Compounds of formula (I) are those wherein $R^2$ is not a five-membered heterocyclic ring.

In another embodiment, the Aminopurine Compounds of formula (I) are those wherein $R^2$ is not a five-membered N-containing heterocyclic ring.

In another embodiment, the Aminopurine Compounds of formula (I) are those wherein $R^2$ is not a five-membered O-containing heterocyclic ring.

In another embodiment, the Aminopurine Compounds of formula (I) are those wherein $R^2$ is not 2-tetrahydrofuranyl.

In another embodiment, the Aminopurine Compounds of formula (I) are those wherein $R^2$ is not 2-pyrrolidinyl.

In a further embodiment, provided herein are Aminopurine Compounds of formula (I), and pharmaceutically acceptable salts, solid forms, clathrates, solvates, hydrates, stereoisomers, tautomers and prodrugs thereof, wherein:

$R^1$ is substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl;

$R^2$ is:

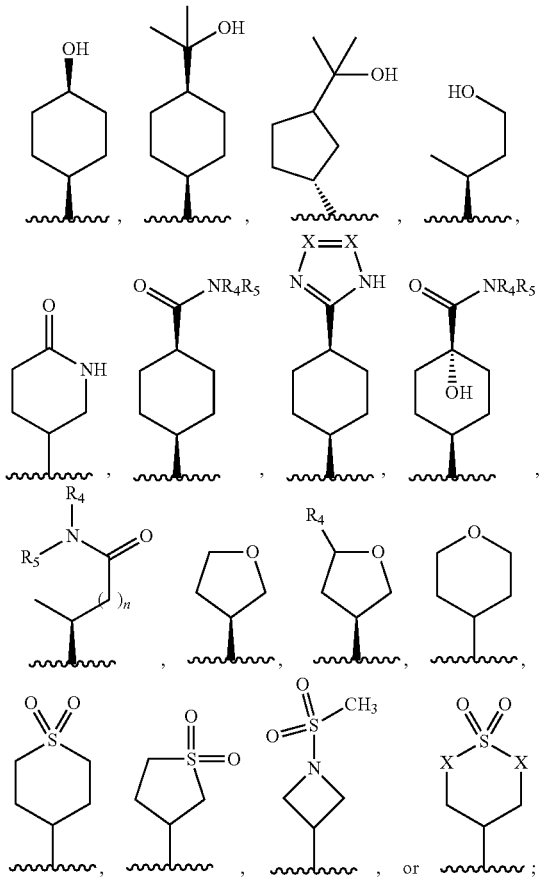

$R^3$ is aryl or $C_{3-10}$heteroaryl, each being substituted with one or more halogens;

X is at each occurrence independently CH$_2$, O, S or N;

R$^4$ and R$^5$ are at each occurrence independently H, substituted or unsubstituted C$_{1-6}$alkyl, substituted or unsubstituted aryl, substituted or unsubstituted C$_{3-10}$cycloalkyl, substituted or unsubstituted C$_{3-10}$heterocycle or substituted or unsubstituted C$_{3-10}$heteroaryl; or R$^4$ and R$^5$ taken together with the N atom to which they are attached form a substituted or unsubstituted 5-7 membered heterocycle; and n is at each occurrence independently an integer ranging from 0 to 3.

In a another embodiment, the Aminopurine Compounds of formula (I) are those wherein R$^3$ is:

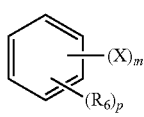

wherein:

X is at each occurrence independently F, Cl, Br or I;

R$_6$ is C$_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl;

m is an integer ranging from 1 to 5; and p is an integer ranging from 0 to 4.

In a further embodiment, p is an integer ranging from 1 to 4.

In a further embodiment, provided herein are Aminopurine Compounds having the following formula (II):

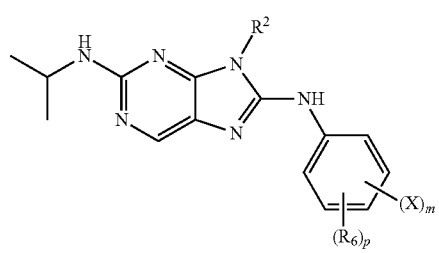

(II)

and pharmaceutically acceptable salts, solid forms, clathrates, solvates, hydrates, stereoisomers, tautomers, enantiomers and prodrugs thereof, wherein:

X is at each occurrence independently F, Cl, Br or I;

R$^2$ is:

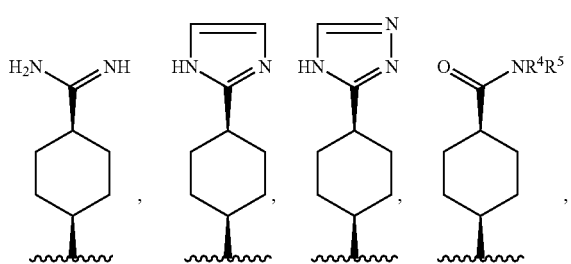

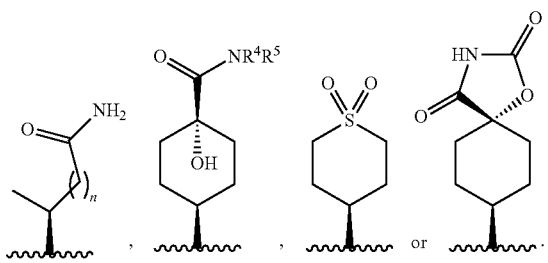

R$^4$ and R$^5$ are at each occurrence independently H, substituted or unsubstituted C$_{1-6}$alkyl, substituted or unsubstituted aryl, substituted or unsubstituted C$_{3-10}$cycloalkyl, substituted or unsubstituted C$_{3-10}$heterocycle or substituted or unsubstituted C$_{3-10}$heteroaryl; or R$^4$ and R$^5$ taken together with the N atom to which they are attached form a substituted or unsubstituted 5-7 membered heterocycle;

R$_6$ is C$_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl;

m is an integer ranging from 1 to 5;

n is at each occurrence independently an integer ranging from 0 to 3; and p is an integer ranging from 0-4.

In one embodiment, the Aminopurine Compounds of formula (II) are those wherein X is fluoro.

In another embodiment, the Aminopurine Compounds of formula (II) are those wherein X is fluoro and m is 3.

In another embodiment, p is 0.

In another embodiment, p is an integer ranging from 1 to 4.

In a further embodiment, provided herein are Aminopurine Compounds having the following formula (III):

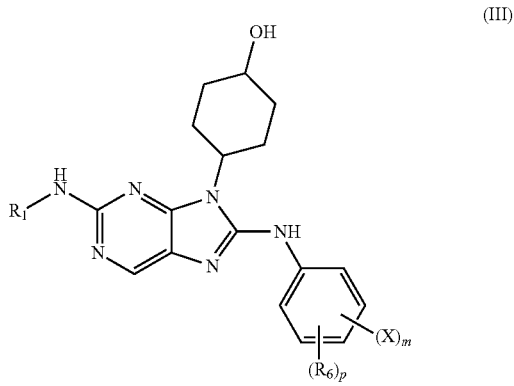

(III)

and pharmaceutically acceptable salts, solid forms, clathrates, solvates, hydrates, stereoisomers, tautomers, enantiomers and prodrugs thereof, wherein:

X is at each occurrence independently F, Cl, Br or I;

m is an integer ranging from 1 to 5;

p is an integer ranging from 0-4;

R¹ is:

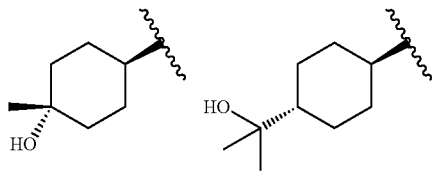

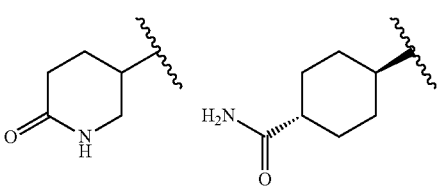

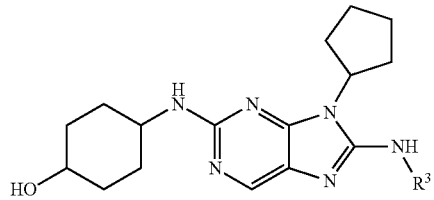

and

R₆ is C₁₋₆alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl.

In one embodiment, the Aminopurine Compounds of formula (III) are those wherein X is fluoro.

In another embodiment, the Aminopurine Compounds of formula (III) are those wherein X is fluoro and m is 3.

In another embodiment, p is 0.

In another embodiment, p is an integer ranging from 1 to 4.

In one embodiment, provided herein are Aminopurine Compounds having the following formula (IV):

(IV)

and pharmaceutically acceptable salts, solid forms, clathrates, solvates, hydrates, stereoisomers, tautomers, enantiomers and prodrugs thereof, wherein:
R³ is:

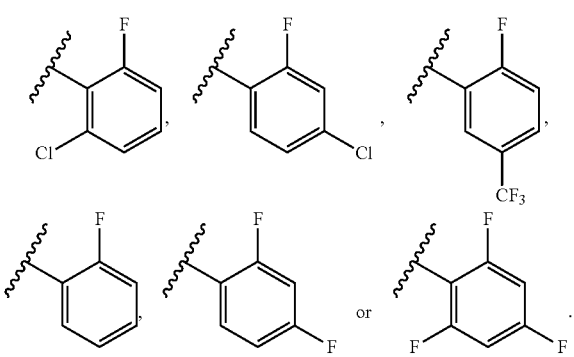

Representative Aminopurine Compounds are set forth in Table 1, below.

TABLE 1

Compound

TABLE 1-continued
Compound
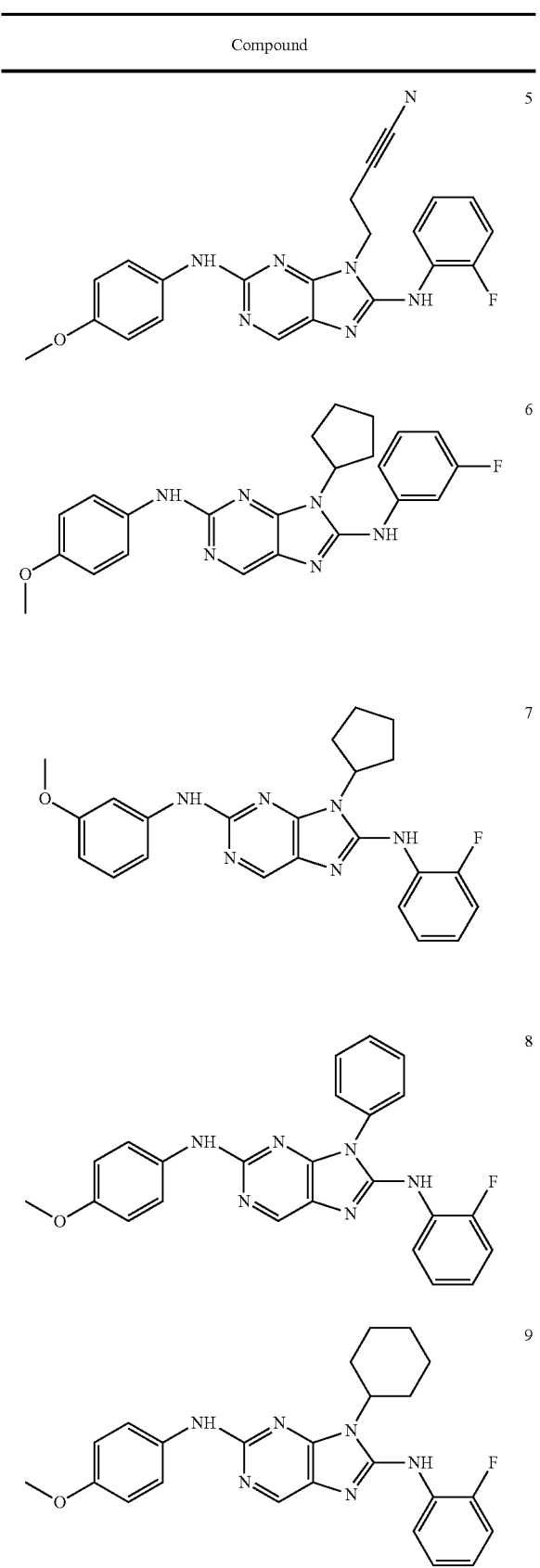
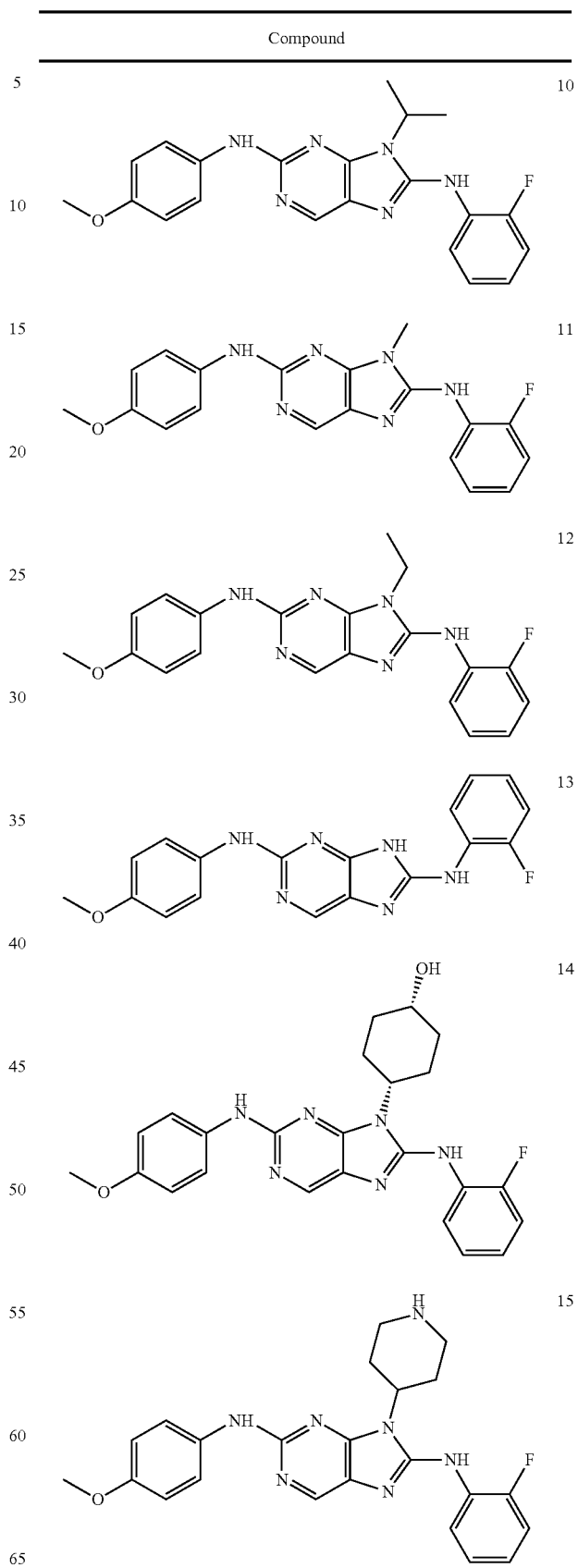

TABLE 1-continued

Compound

TABLE 1-continued
Compound
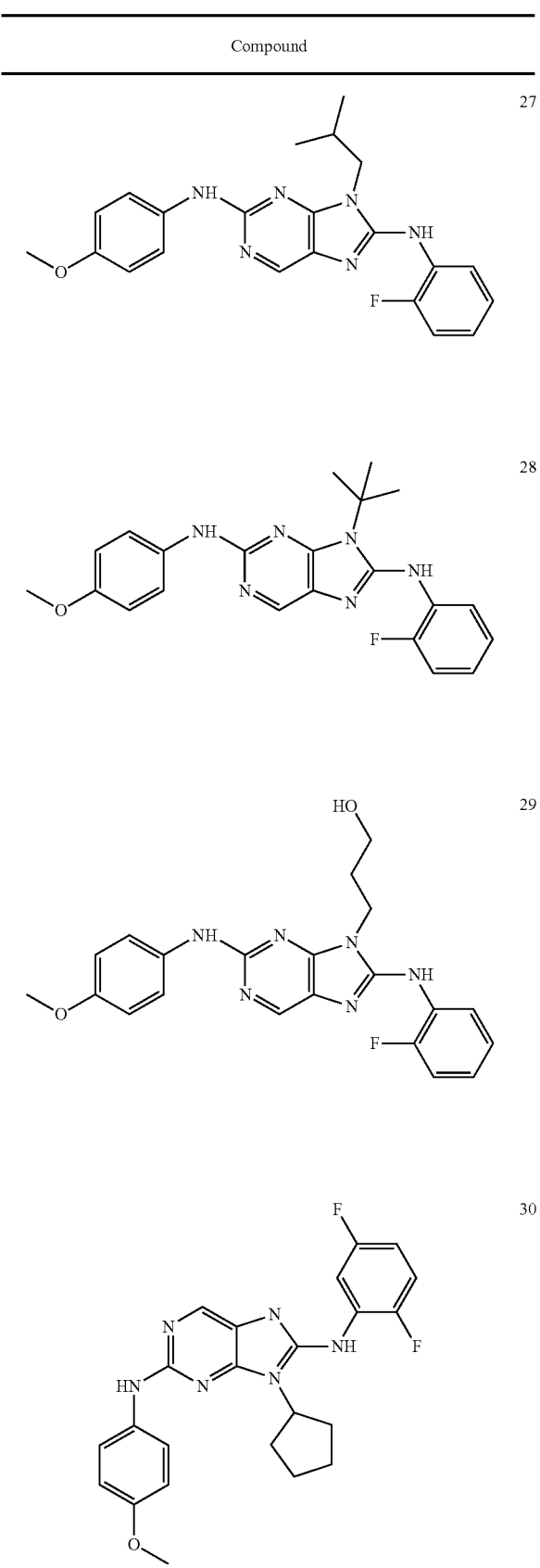
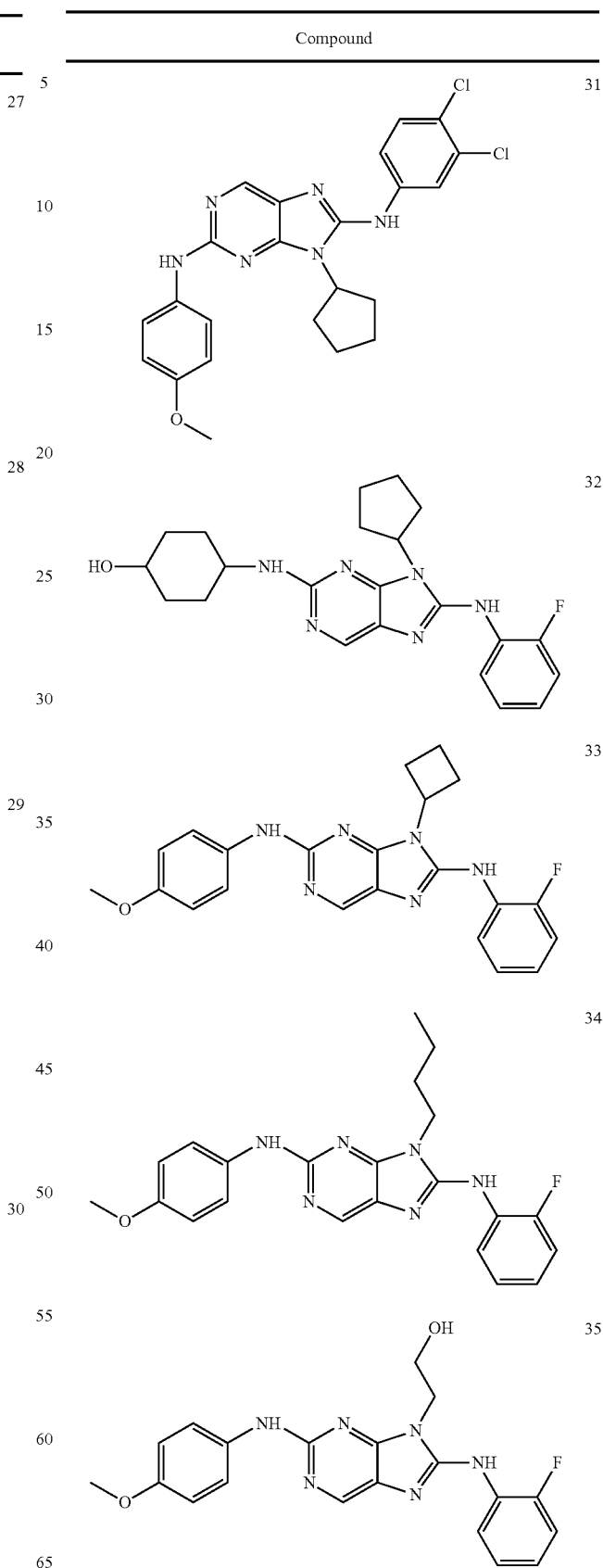

TABLE 1-continued
Compound
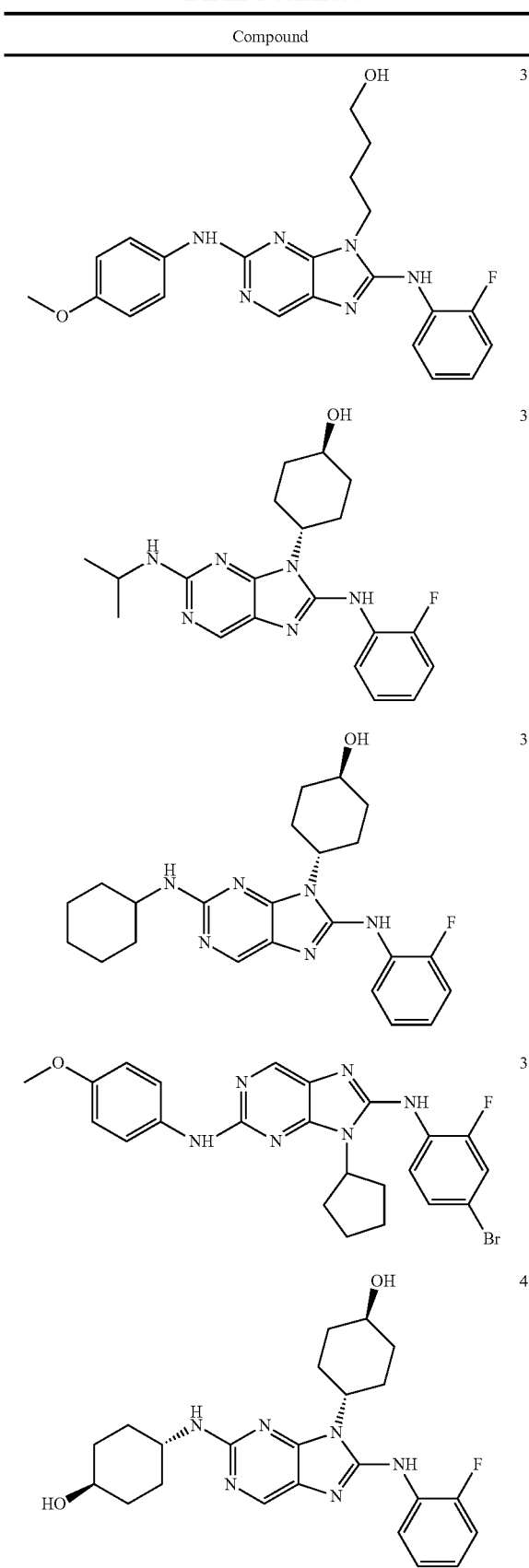
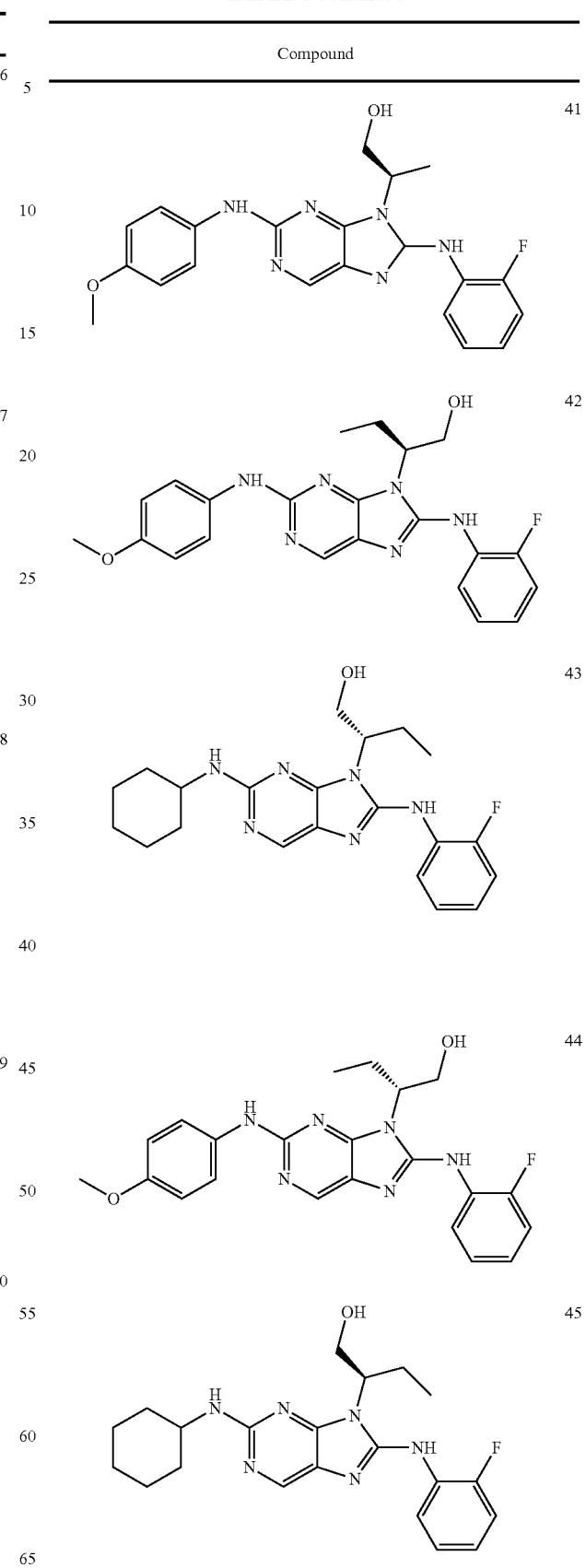

TABLE 1-continued

Compound 46, 47, 48, 49, 50, 51, 52, 53, 54, 55, 56

TABLE 1-continued

Compound

| 57 | 58 | 59 | 60 | 61 | 62 | 63 | 64 | 65 |

TABLE 1-continued
Compound
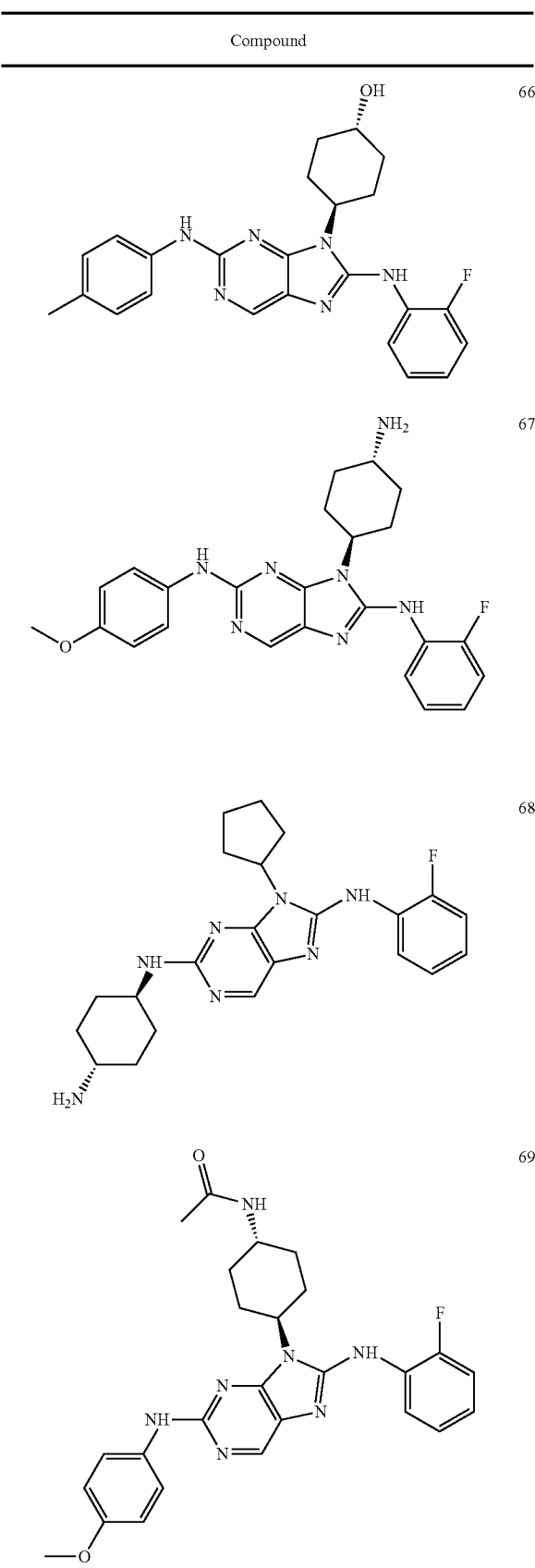
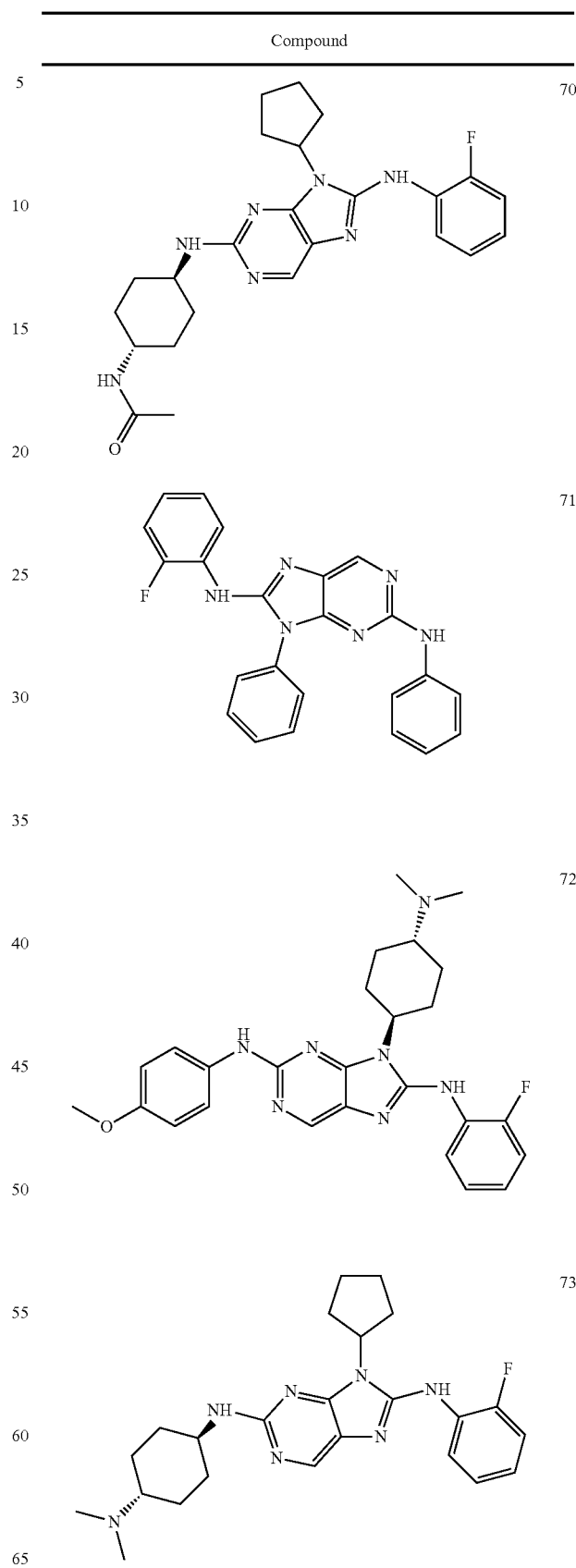

TABLE 1-continued
Compound
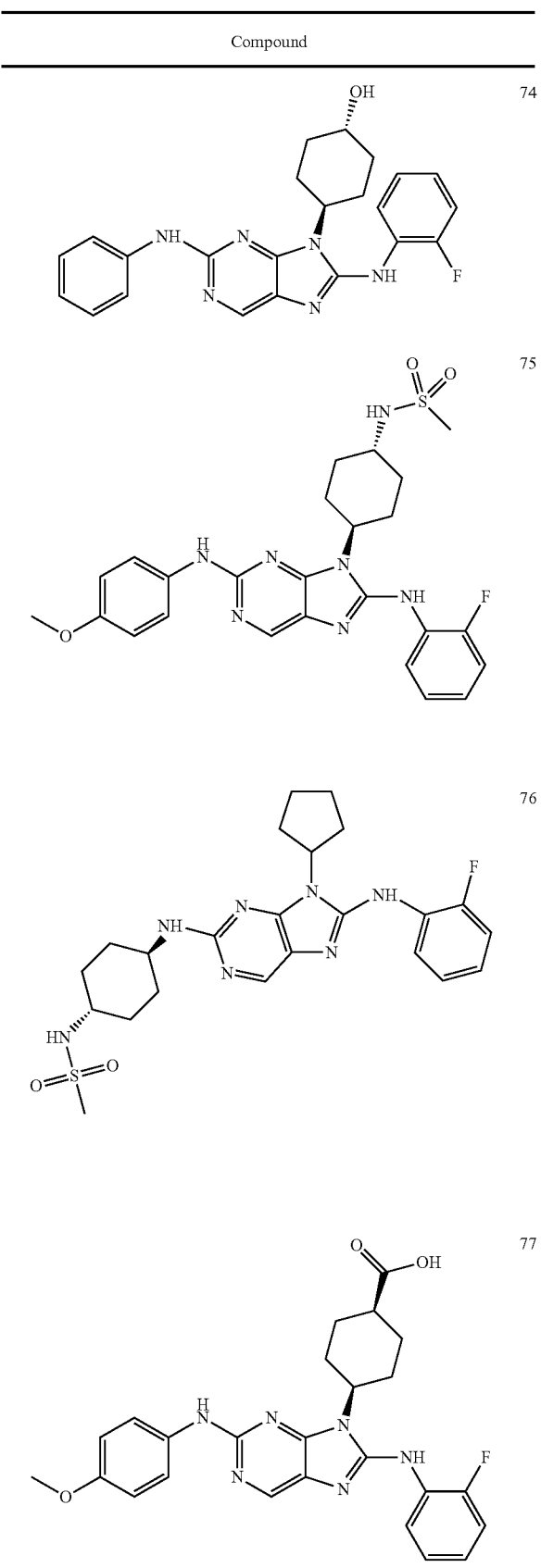
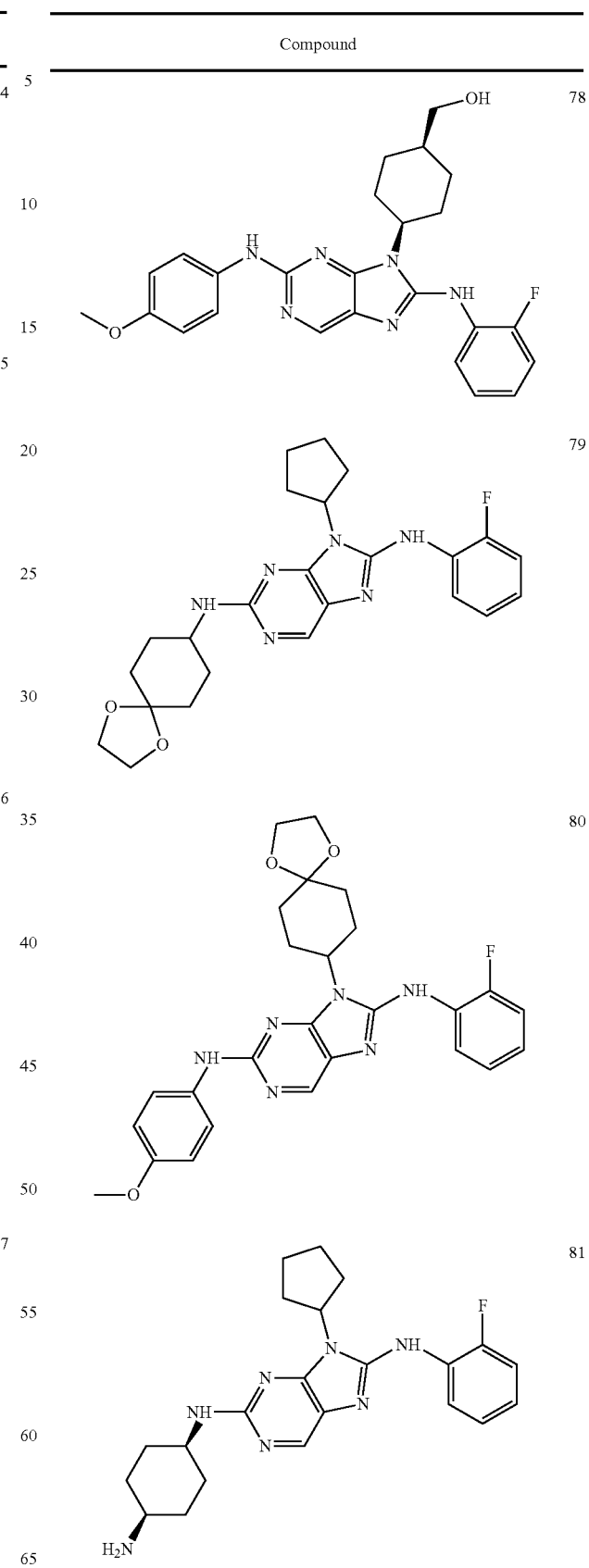

TABLE 1-continued

Compound

TABLE 1-continued
Compound
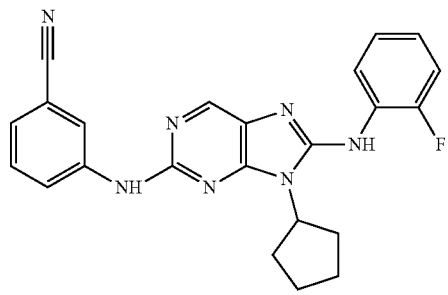 [SMILES: N#Cc1cccc(Nc2ncc3nc(Nc4ccccc4F)n(C4CCCC4)c3n2)c1]
93
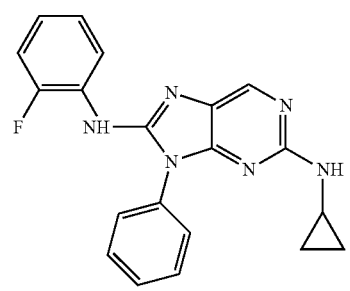 [SMILES: Fc1ccccc1Nc1nc2cnc(NC3CC3)nc2n1-c1ccccc1]
94
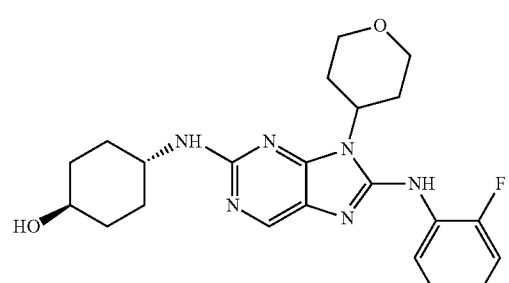
95
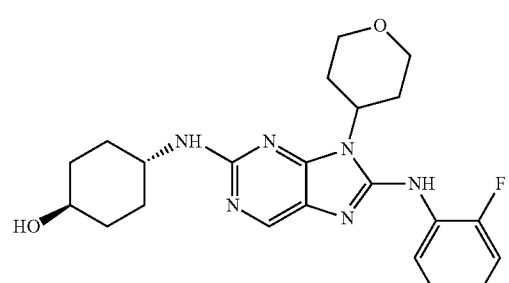
96
TABLE 1-continued
Compound
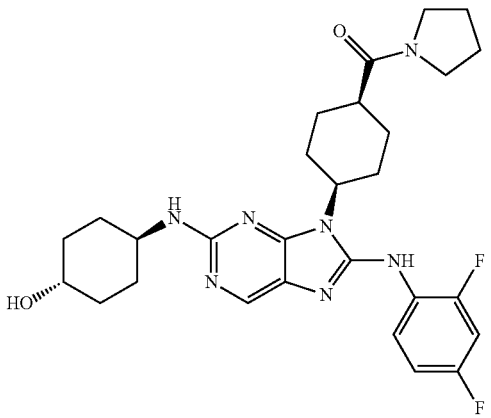 [SMILES: O=C([C@H]1CC[C@@H](n2c(Nc3ccc(F)cc3F)nc3cnc(N[C@H]4CC[C@H](O)CC4)nc32)CC1)N1CCCC1]
97
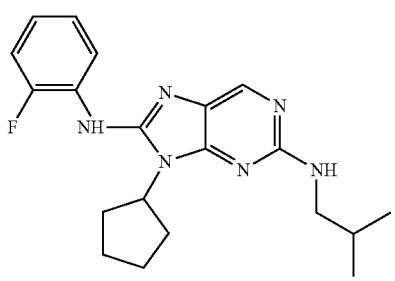 [SMILES: CC(C)CNc1ncc2nc(Nc3ccccc3F)n(C3CCCC3)c2n1]
98
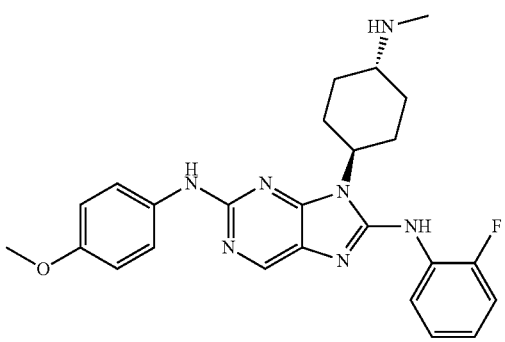 [SMILES: CN[C@H]1CC[C@H](n2c(Nc3ccccc3F)nc3cnc(Nc4ccc(OC)cc4)nc32)CC1]
99
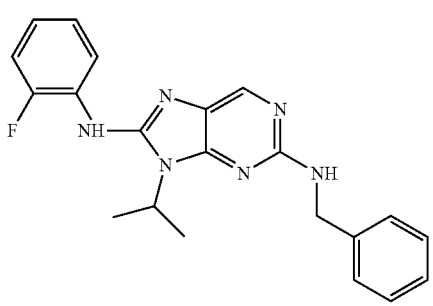 [SMILES: CC(C)n1c(Nc2ccccc2F)nc2cnc(NCc3ccccc3)nc21]
100

TABLE 1-continued
| Compound | |
|---|---|
| 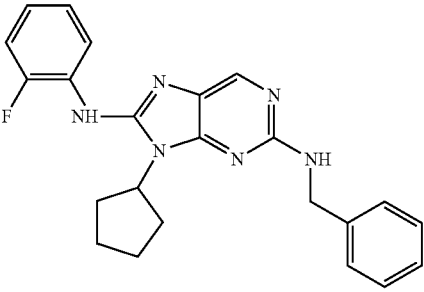 [SMILES: Fc1ccccc1Nc1nc2cnc(NCc3ccccc3)nc2n1C1CCCC1] | 101 |
| 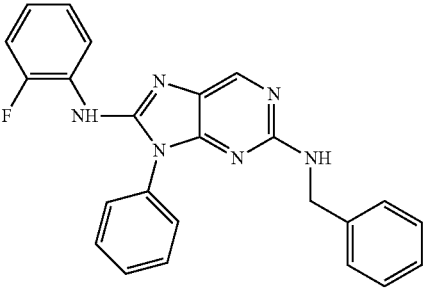 [SMILES: Fc1ccccc1Nc1nc2cnc(NCc3ccccc3)nc2n1-c1ccccc1] | 102 |
| 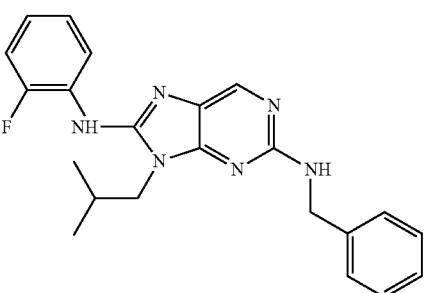 | 103 |
| 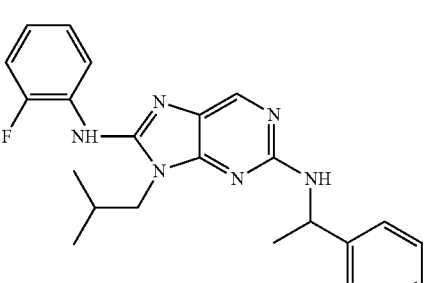 | 104 |
| 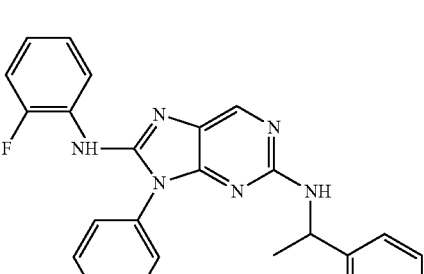 | 105 |
|  | 106 |
|  | 107 |
|  | 108 |
|  | 109 |
|  | 110 |

TABLE 1-continued
Compound
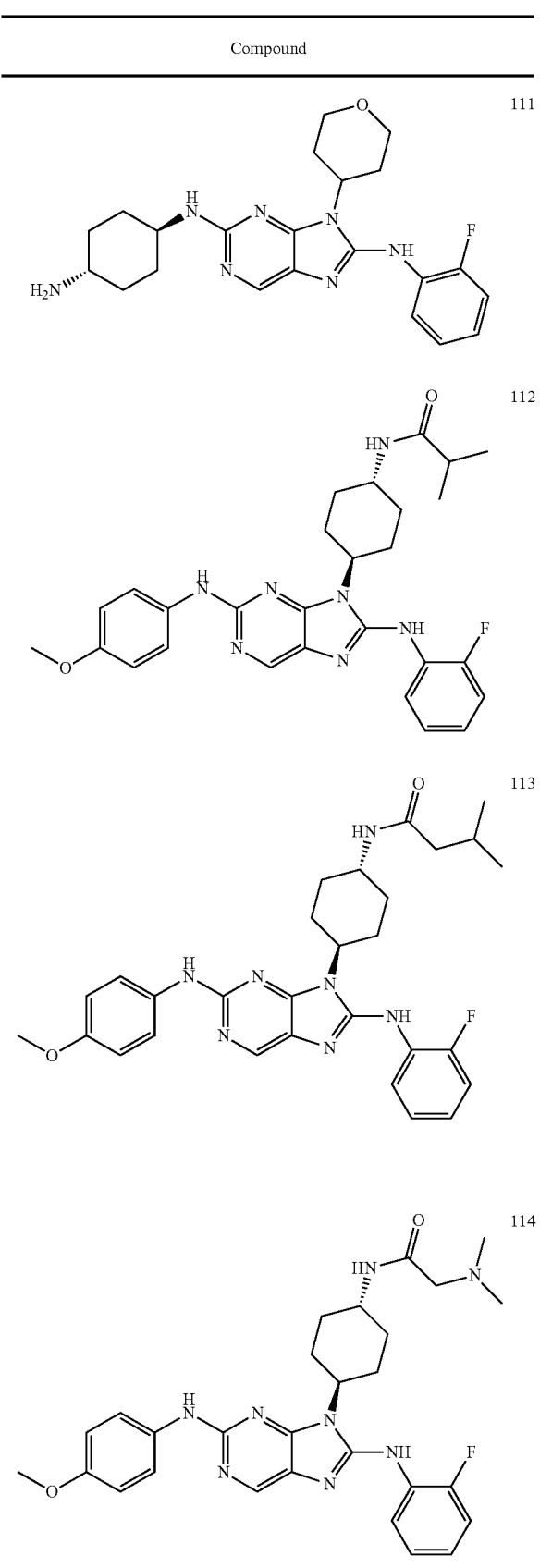
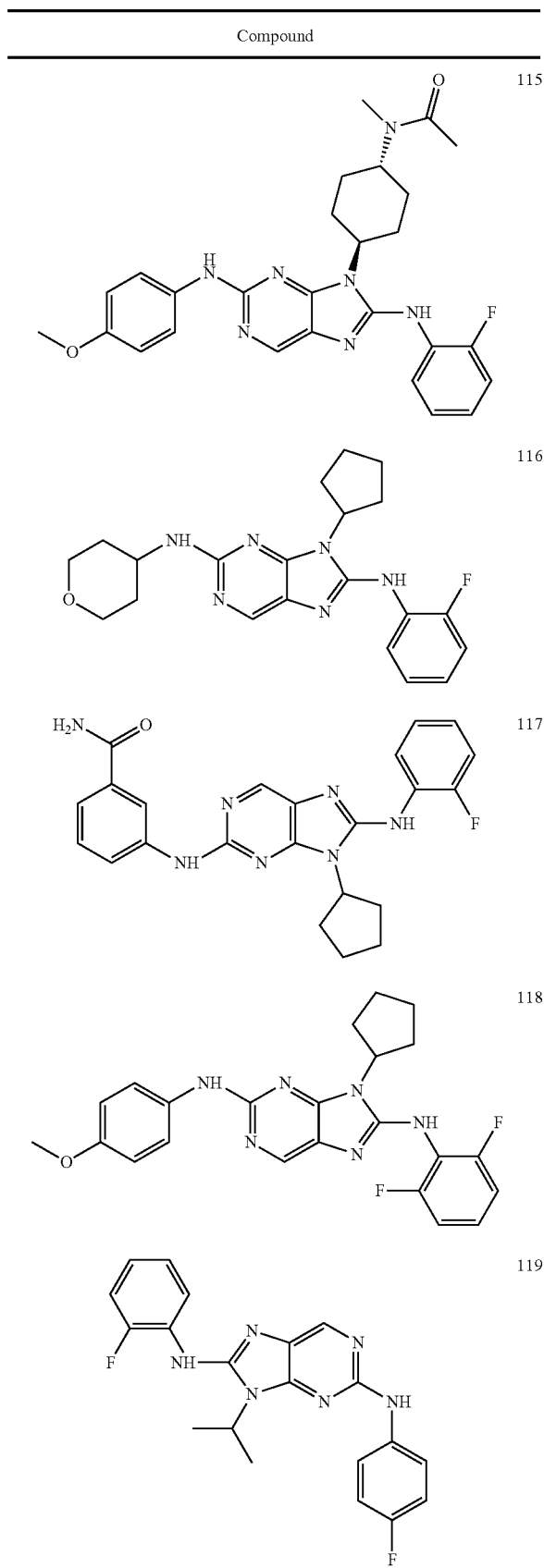

TABLE 1-continued
Compound
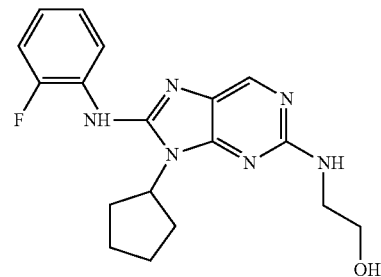 [SMILES: OCCNc1ncc2nc(Nc3ccccc3F)n(C3CCCC3)c2n1]
120
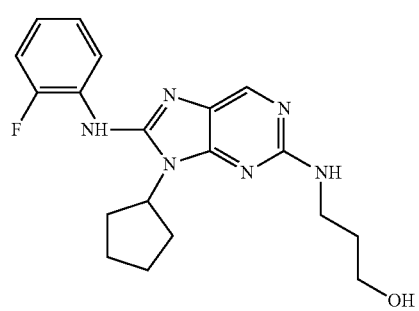 [SMILES: OCCCNc1ncc2nc(Nc3ccccc3F)n(C3CCCC3)c2n1]
121
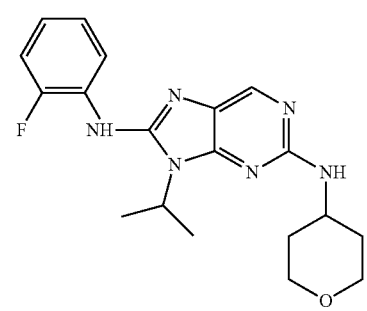 [SMILES: CC(C)n1c(Nc2ccccc2F)nc2cnc(NC3CCOCC3)nc21]
122
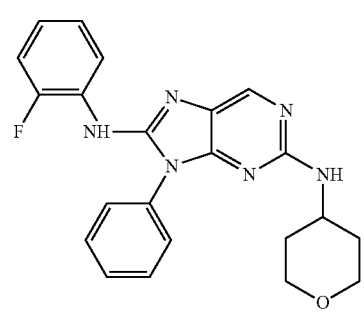 [SMILES: Fc1ccccc1Nc1nc2cnc(NC3CCOCC3)nc2n1-c1ccccc1]
123
TABLE 1-continued
Compound
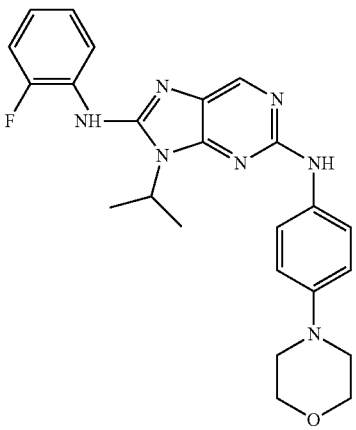 [SMILES: CC(C)n1c(Nc2ccccc2F)nc2cnc(Nc3ccc(N4CCOCC4)cc3)nc21]
124
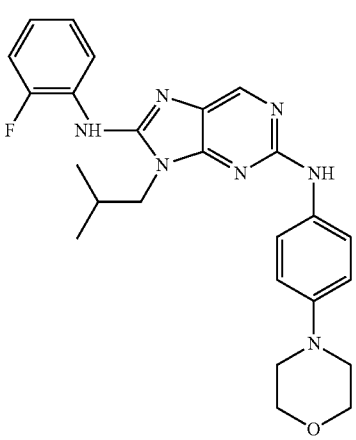 [SMILES: CC(C)Cn1c(Nc2ccccc2F)nc2cnc(Nc3ccc(N4CCOCC4)cc3)nc21]
125
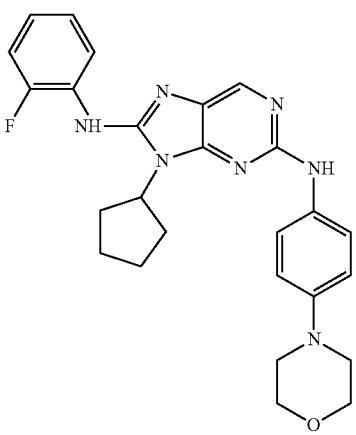 [SMILES: Fc1ccccc1Nc1nc2cnc(Nc3ccc(N4CCOCC4)cc3)nc2n1C1CCCC1]
126

TABLE 1-continued
Compound
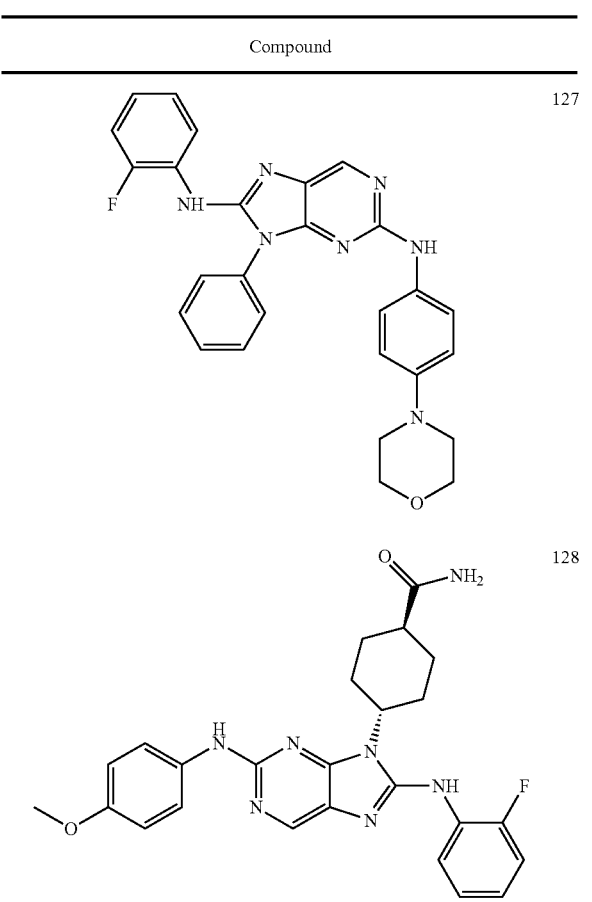
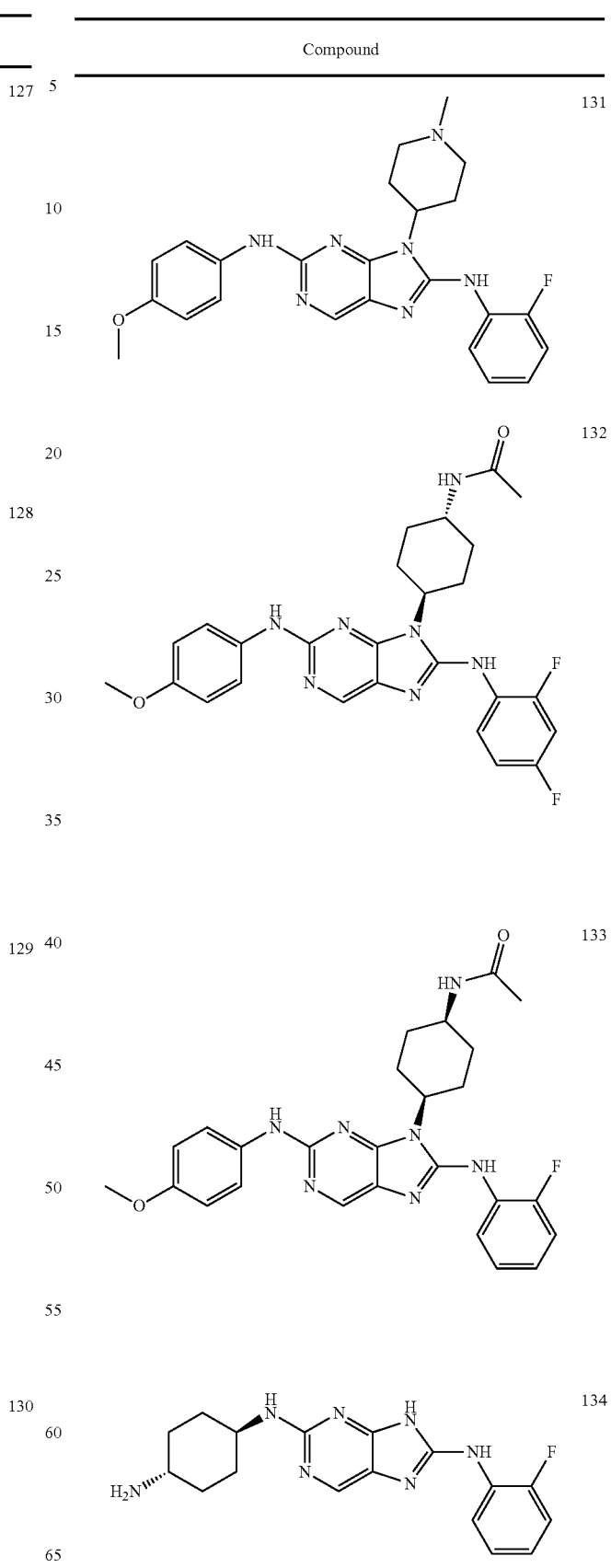

TABLE 1-continued

Compound

TABLE 1-continued
Compound
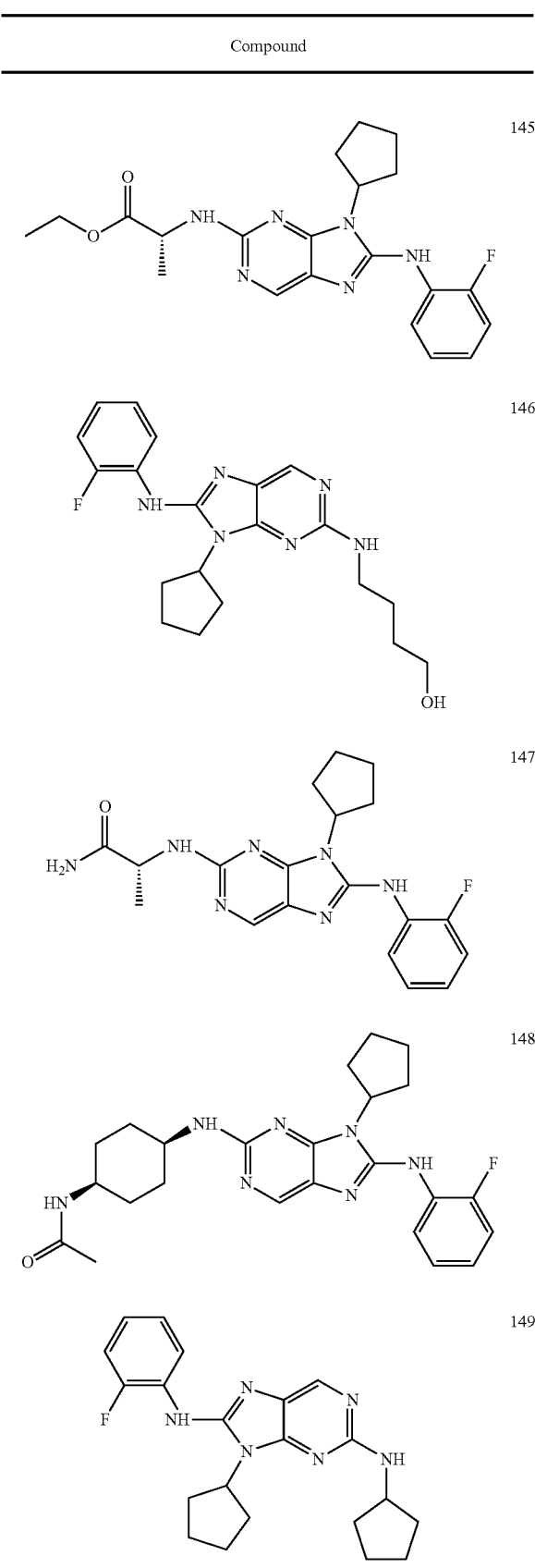
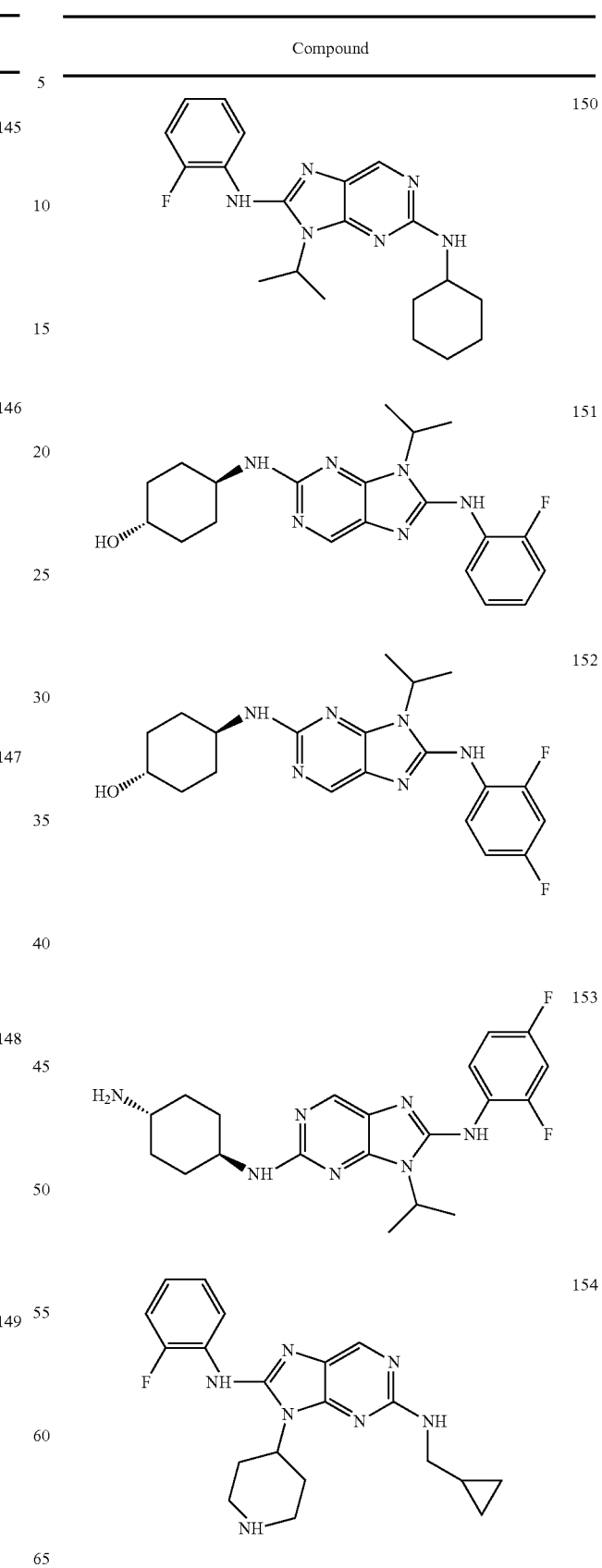

TABLE 1-continued
Compound
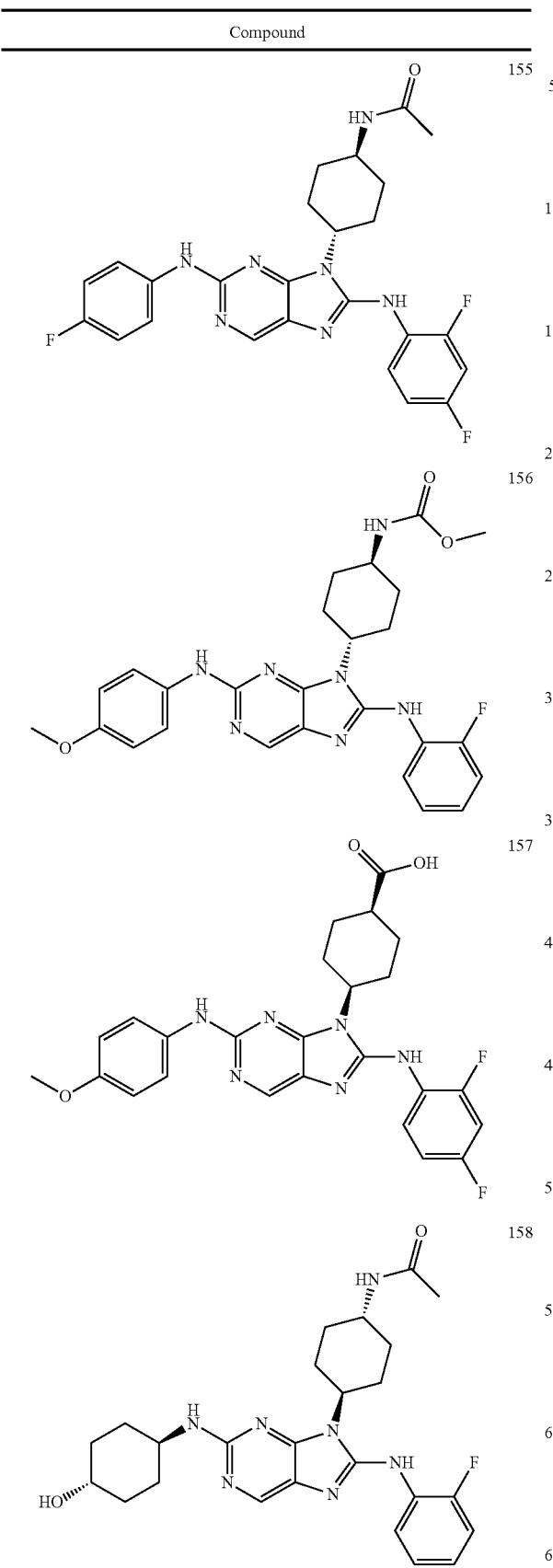
155
156
157
158
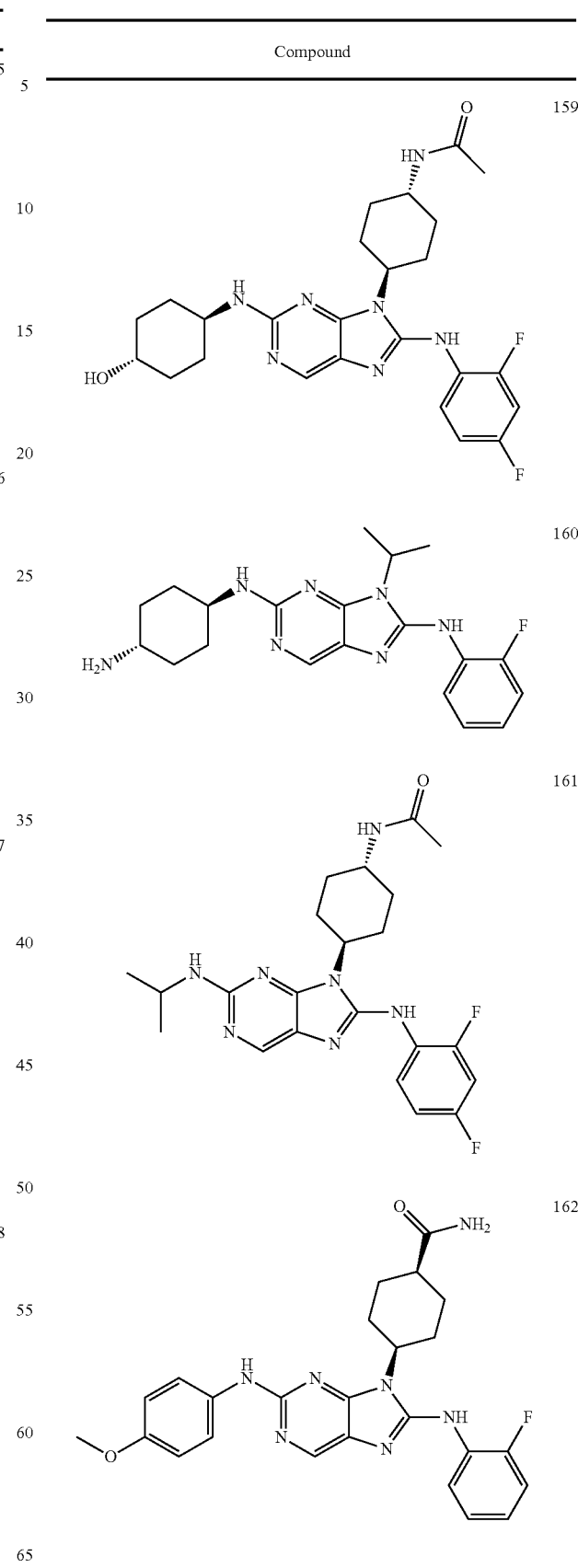
159
160
161
162

TABLE 1-continued
Compound
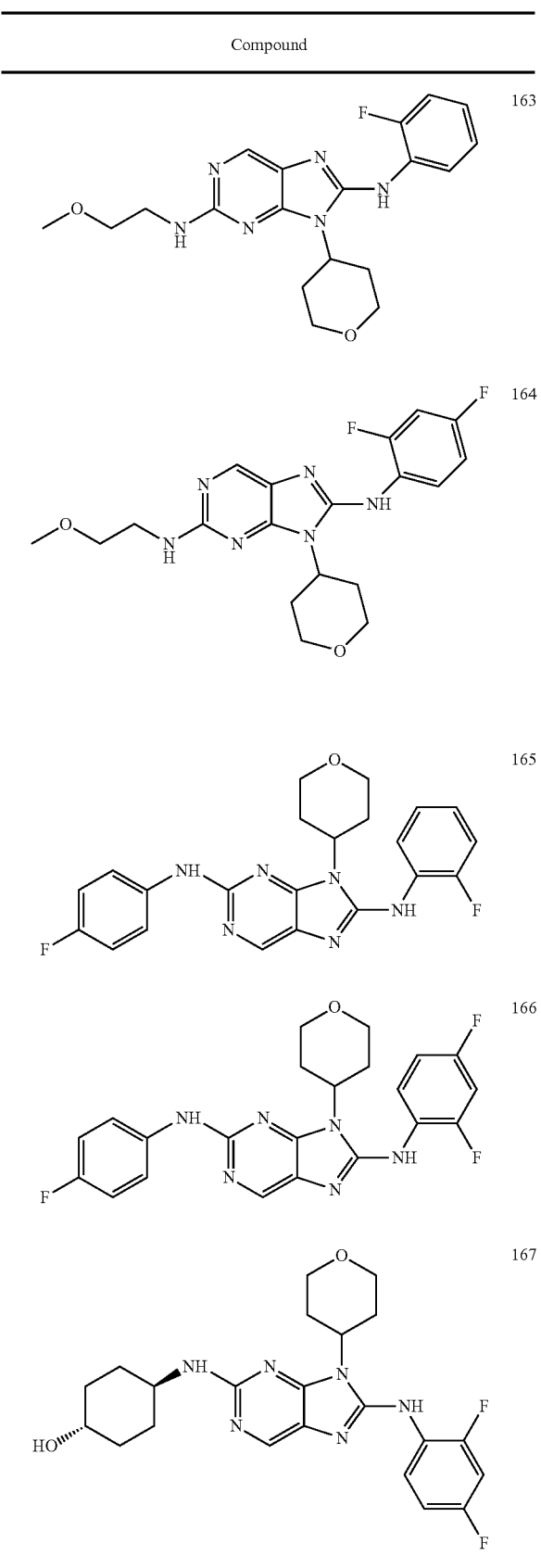
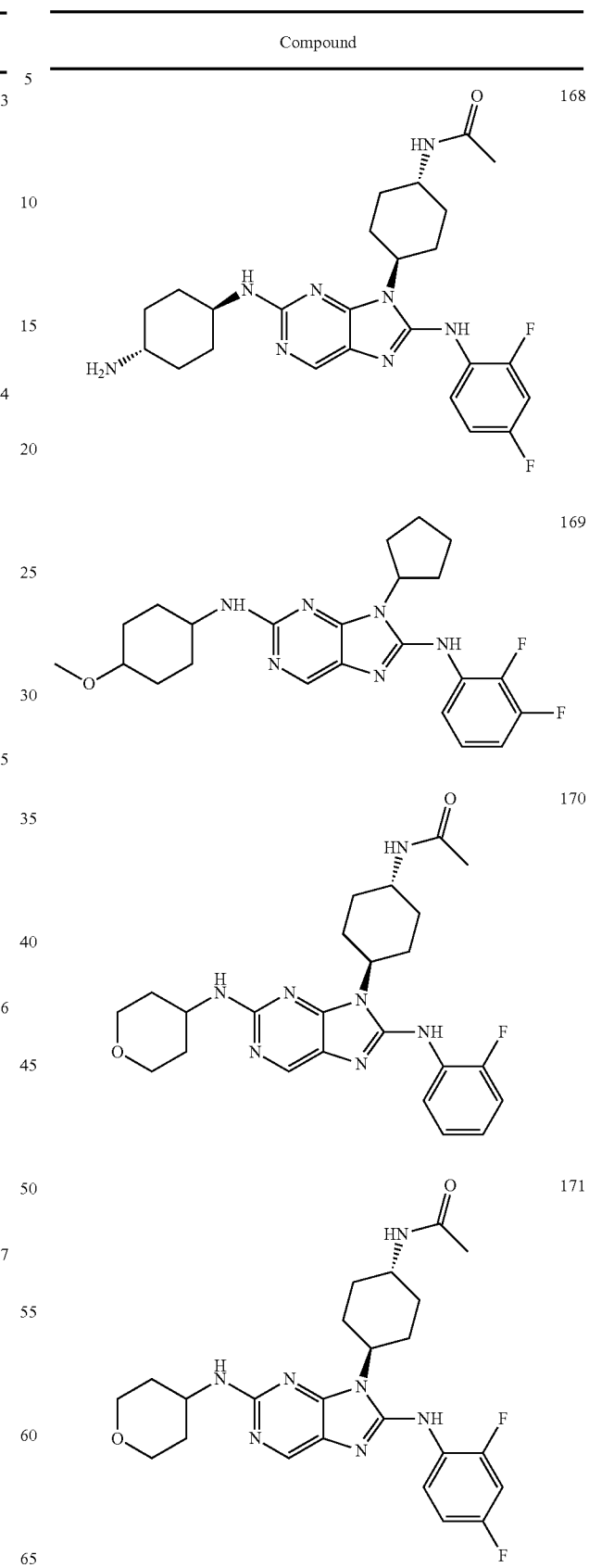

TABLE 1-continued
Compound
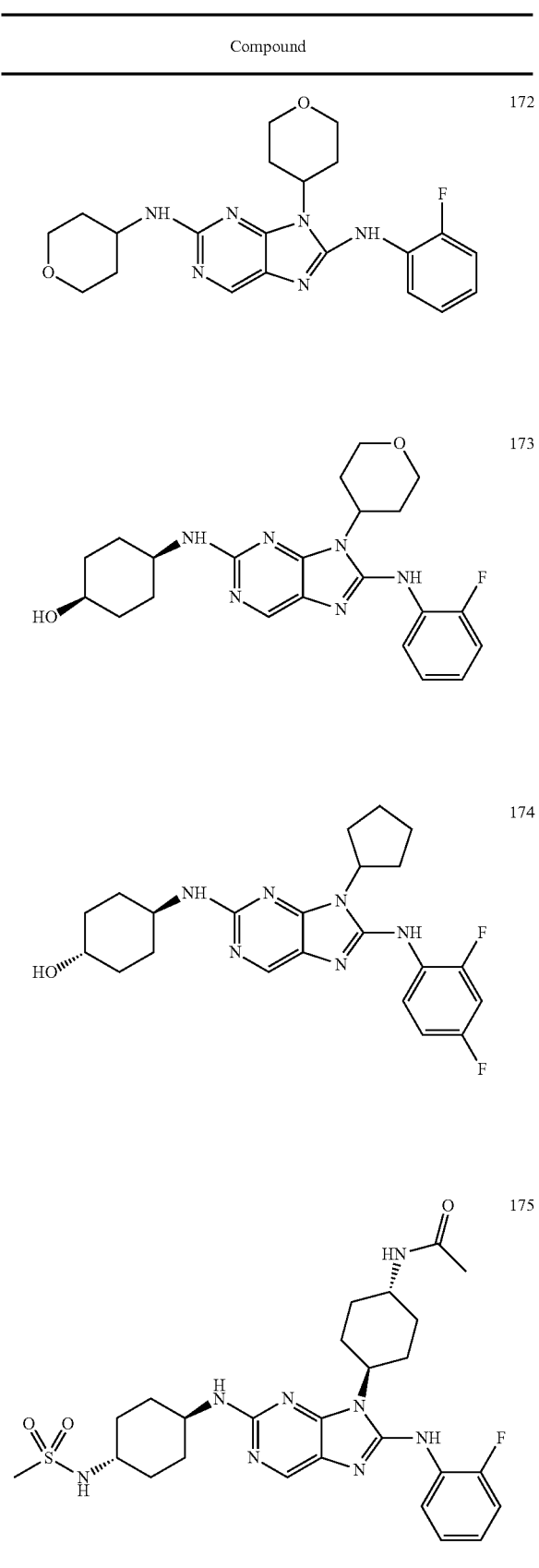
172
173
174
175
TABLE 1-continued
Compound
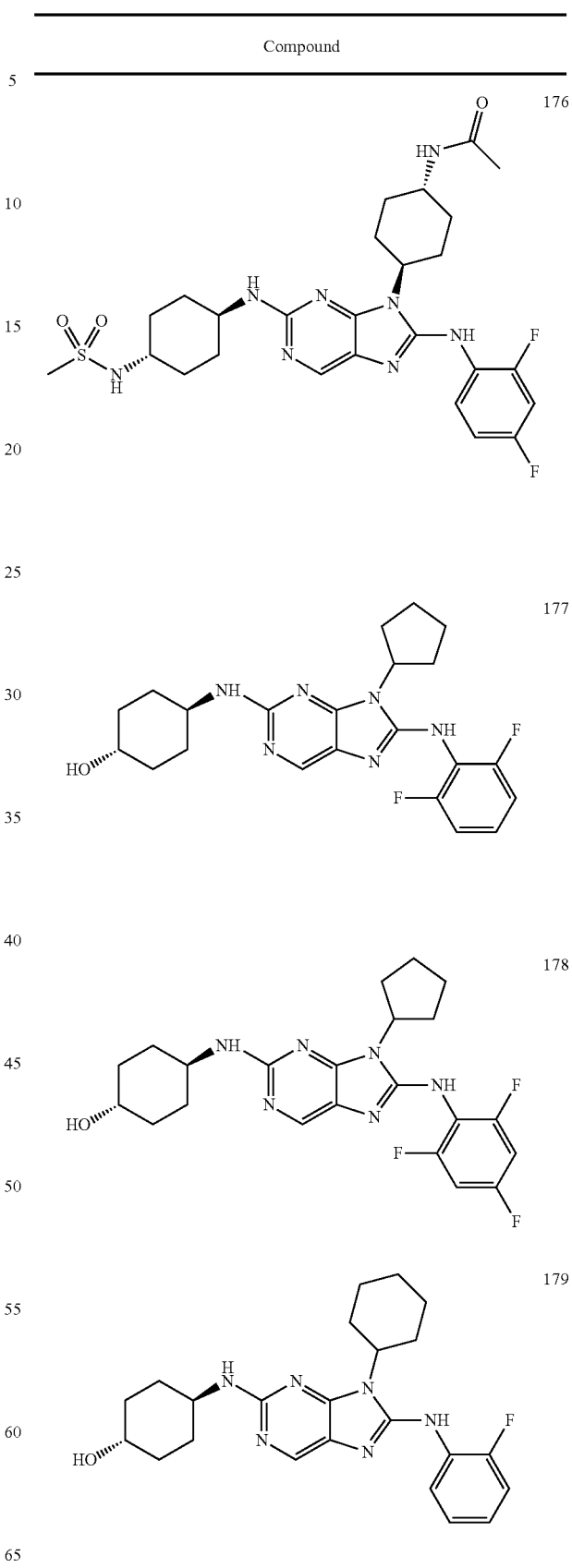
176
177
178
179

TABLE 1-continued
Compound
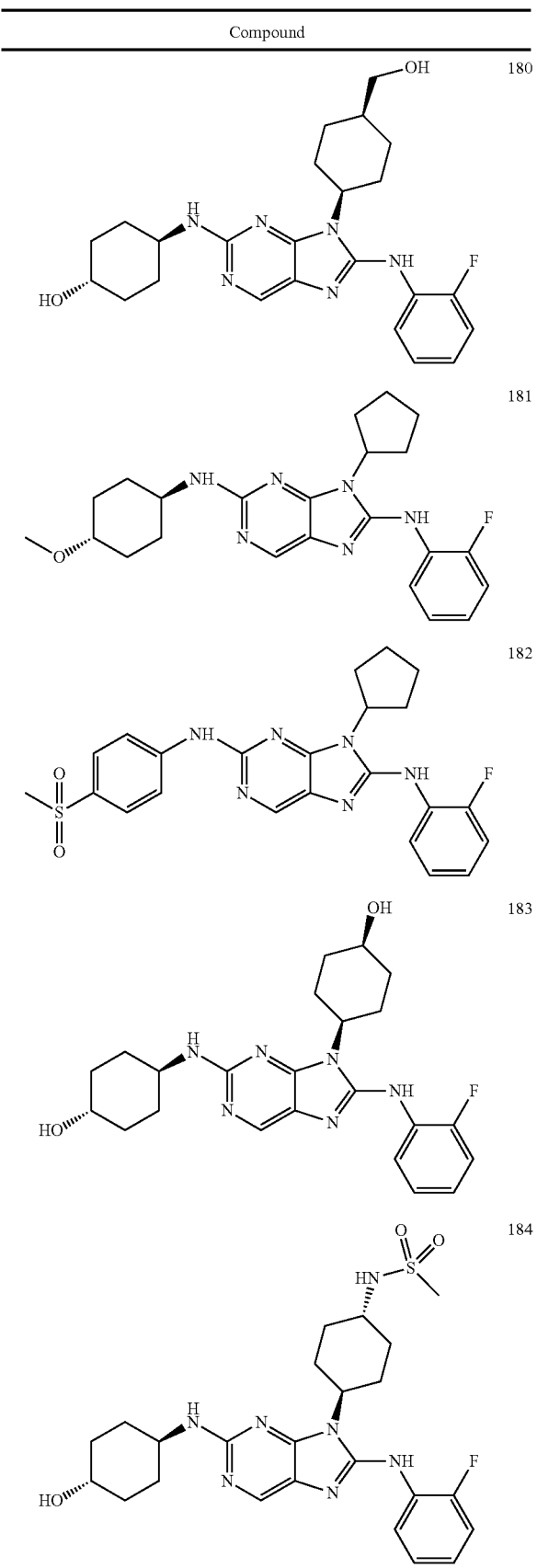
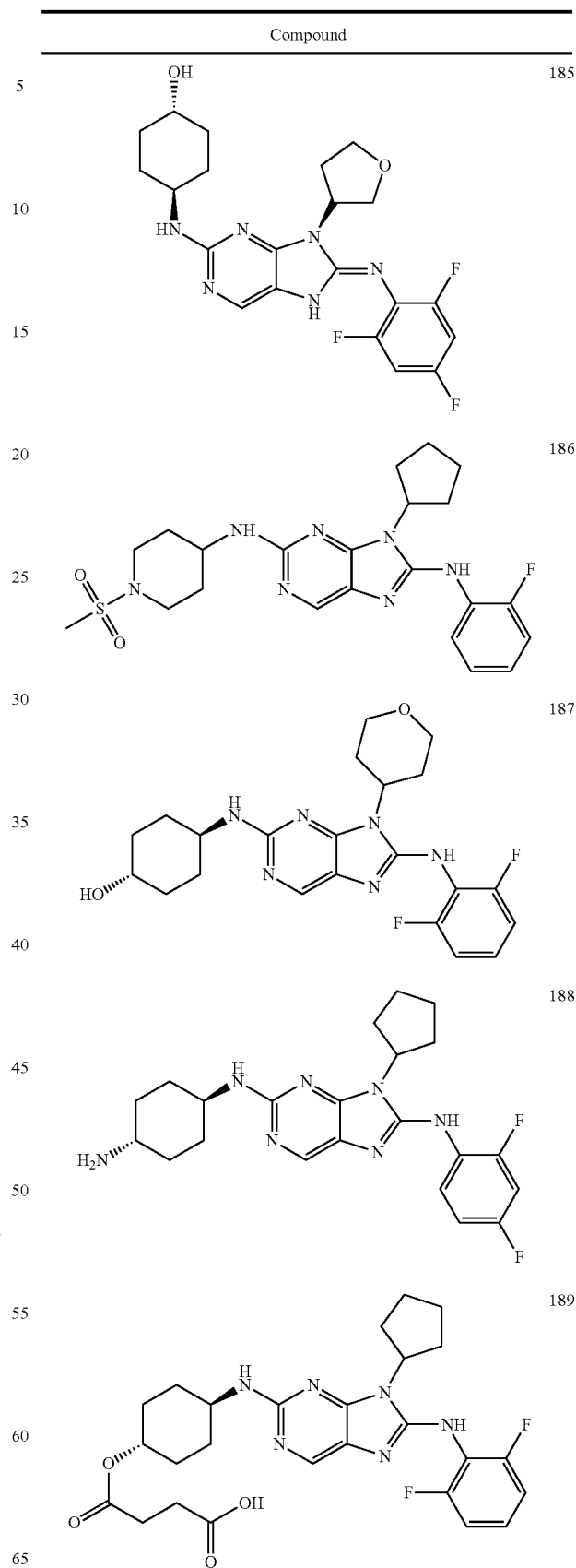

TABLE 1-continued

Compound

TABLE 1-continued
| Compound | | Compound | |
|---|---|---|---|
| 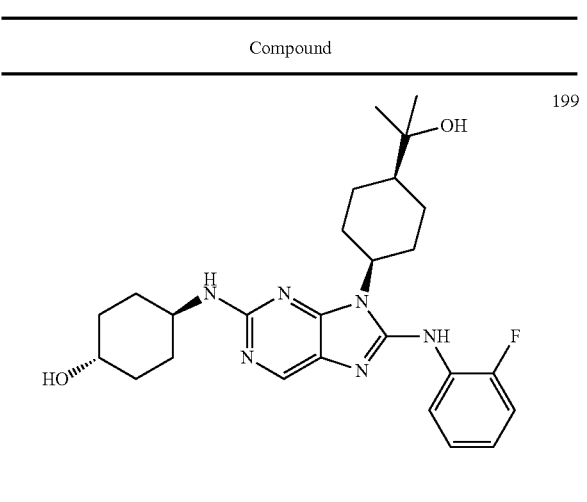 | 199 | 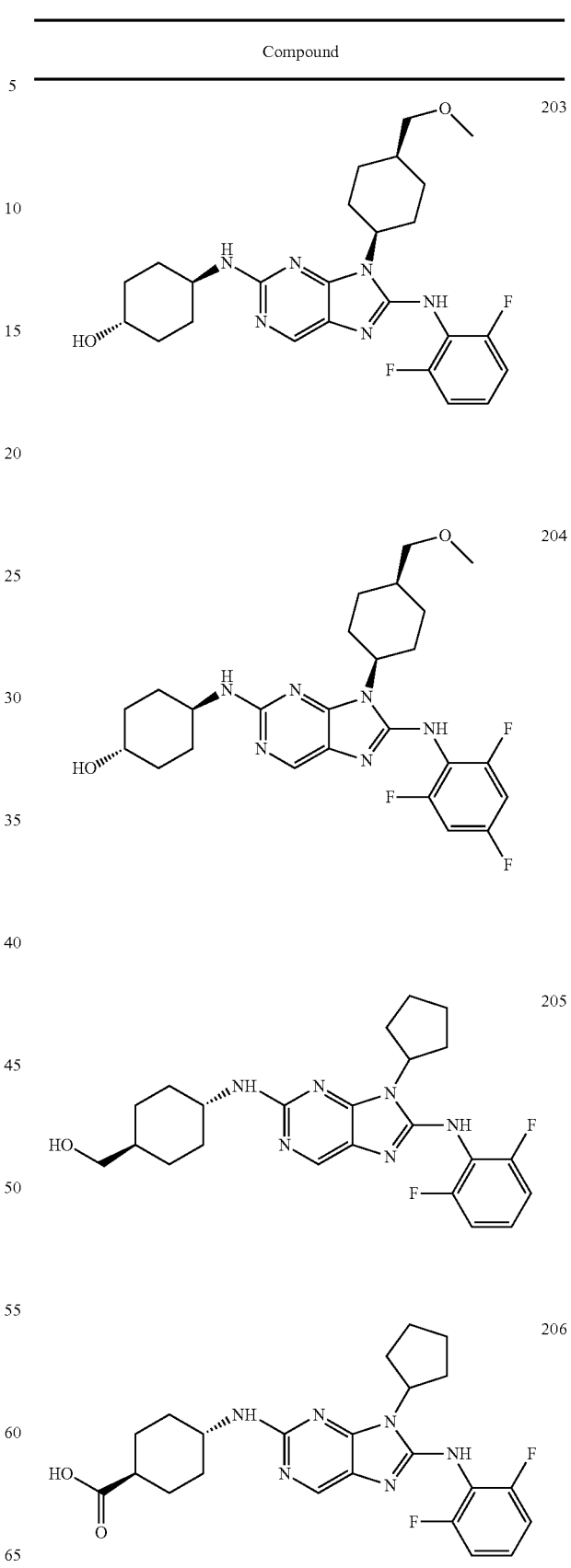 | 203 |
| | 200 | | 204 |
| | 201 | | 205 |
| | 202 | | 206 |

TABLE 1-continued
Compound
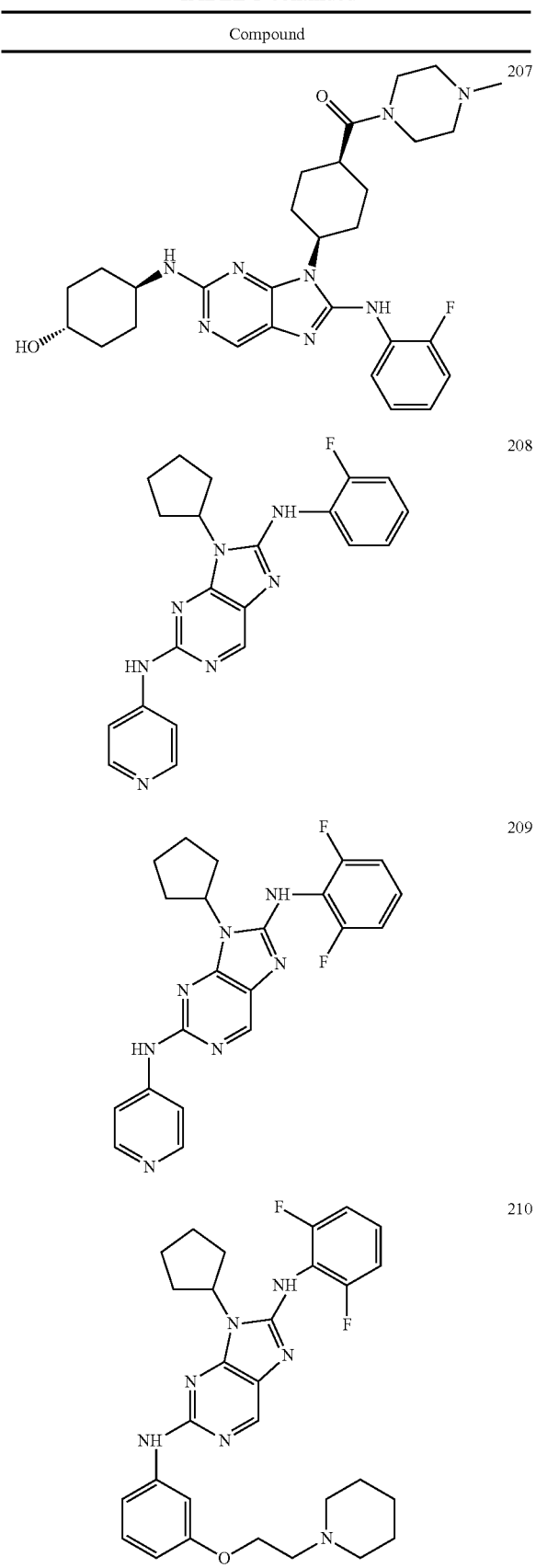
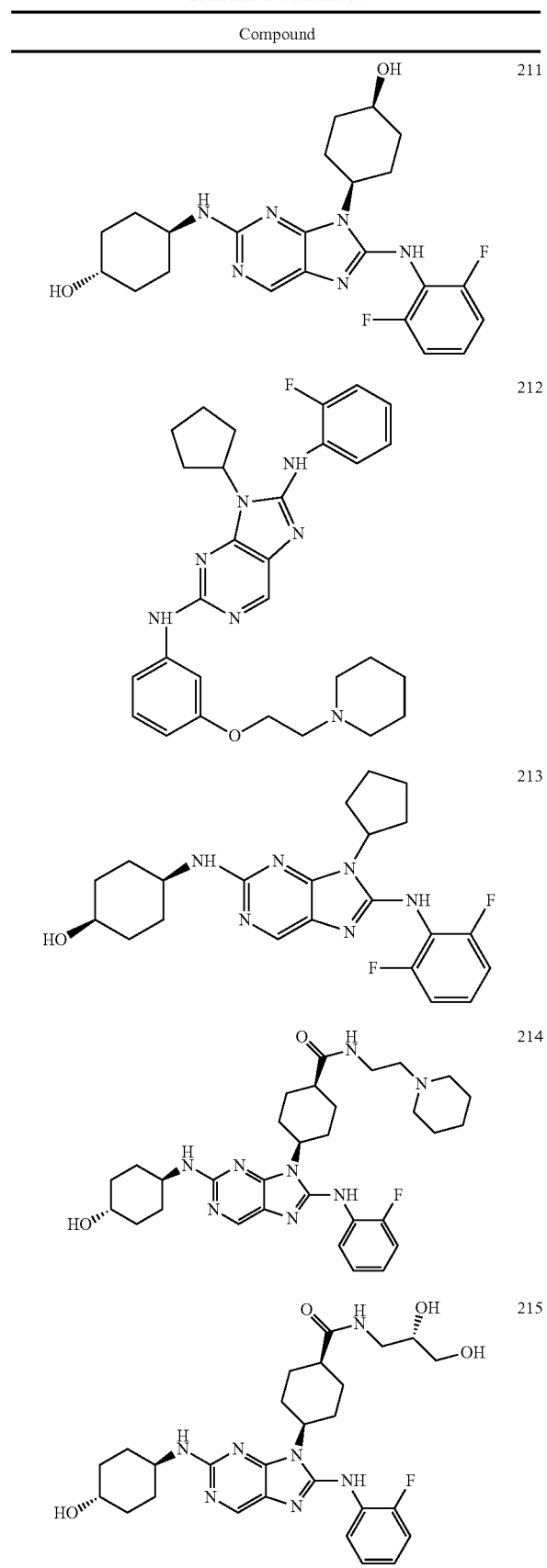

TABLE 1-continued

Compound

| No. | |
|---|---|
| 216 | (structure) |
| 217 | (structure) |
| 218 | (structure) |
| 219 | (structure) |
| 220 | (structure) |
| 221 | (structure) |
| 222 | (structure) |
| 223 | (structure) |
| 224 | (structure) |

TABLE 1-continued

Compound

225

226

227

228

229

230

231

232

233

TABLE 1-continued

Compound 234, 235, 236, 237, 238, 239, 240, 241

TABLE 1-continued
Compound
242
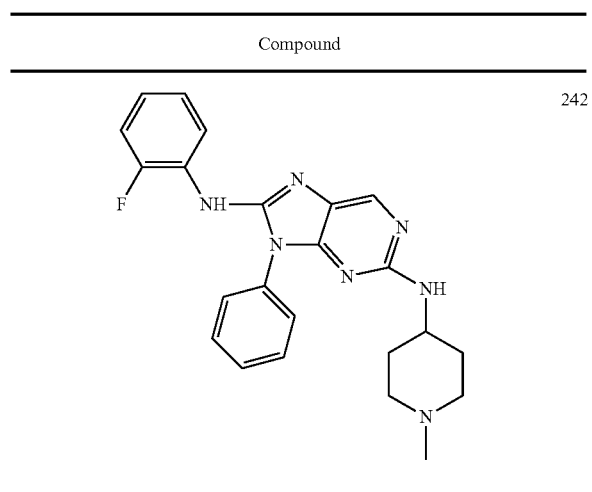
243
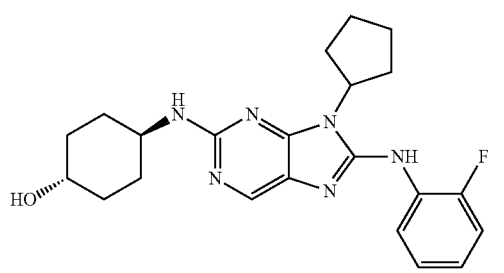 [SMILES: O[C@H]1CC[C@H](Nc2ncc3nc(Nc4ccccc4F)n(C4CCCC4)c3n2)CC1]
244
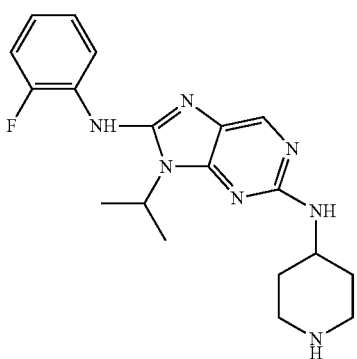 [SMILES: CC(C)n1c(Nc2ccccc2F)nc2cnc(NC3CCNCC3)nc21]
245
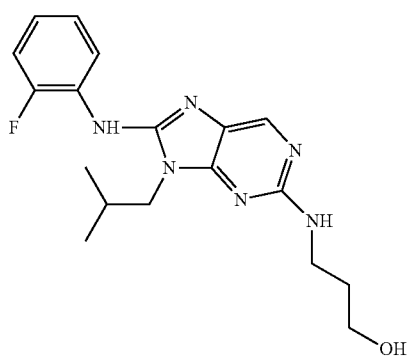 [SMILES: CC(C)Cn1c(Nc2ccccc2F)nc2cnc(NCCCO)nc21]
TABLE 1-continued
Compound
246
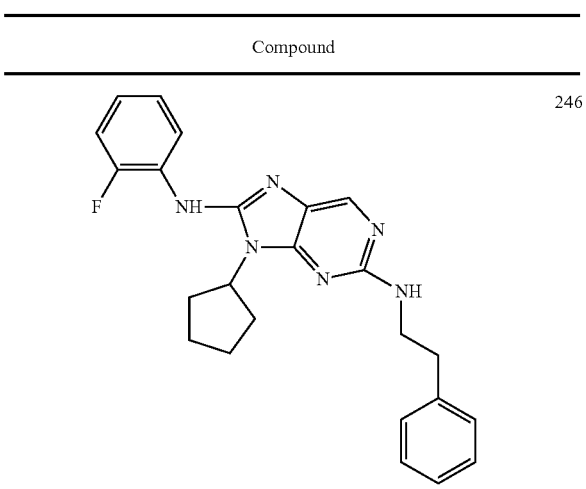
247
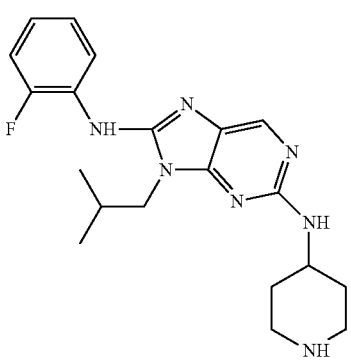 [SMILES: CC(C)Cn1c(Nc2ccccc2F)nc2cnc(NC3CCNCC3)nc21]
248
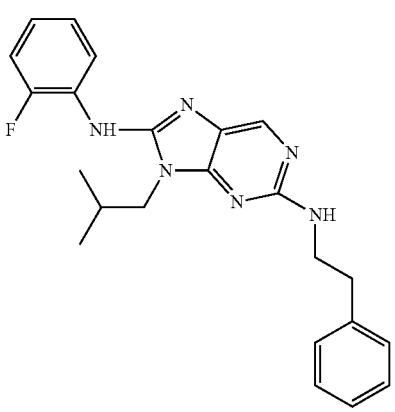 [SMILES: CC(C)Cn1c(Nc2ccccc2F)nc2cnc(NCCc3ccccc3)nc21]
249
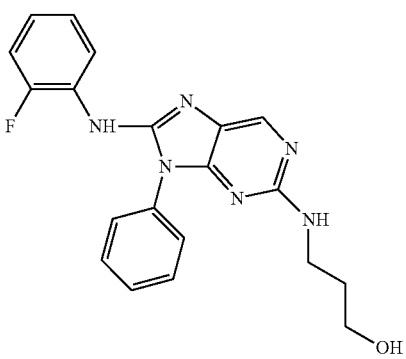 [SMILES: OCCCNc1ncc2nc(Nc3ccccc3F)n(-c3ccccc3)c2n1]

TABLE 1-continued
Compound
250
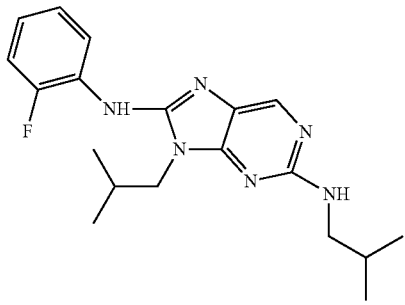 [SMILES: CC(C)CNc1ncc2nc(Nc3ccccc3F)n(CC(C)C)c2n1]
251
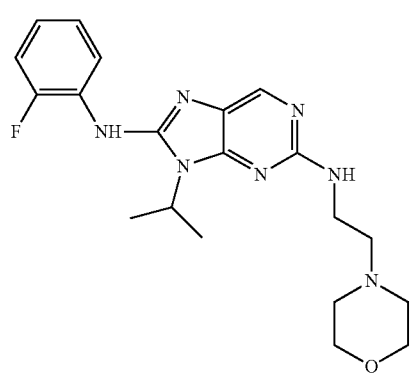 [SMILES: CC(C)n1c(Nc2ccccc2F)nc2cnc(NCCN3CCOCC3)nc21]
252
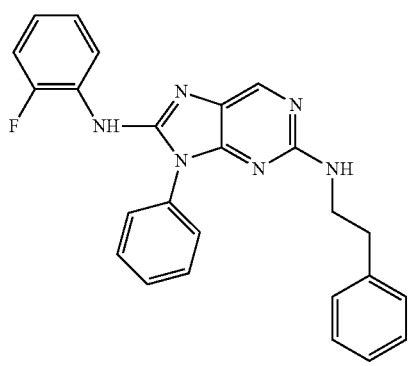 [SMILES: Fc1ccccc1Nc1nc2cnc(NCCc3ccccc3)nc2n1-c1ccccc1]
253
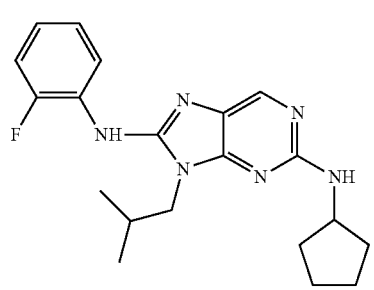 [SMILES: CC(C)Cn1c(Nc2ccccc2F)nc2cnc(NC3CCCC3)nc21]
TABLE 1-continued
Compound
254
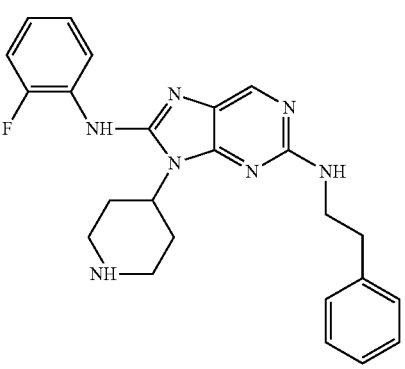 [SMILES: Fc1ccccc1Nc1nc2cnc(NCCc3ccccc3)nc2n1C1CCNCC1]
255
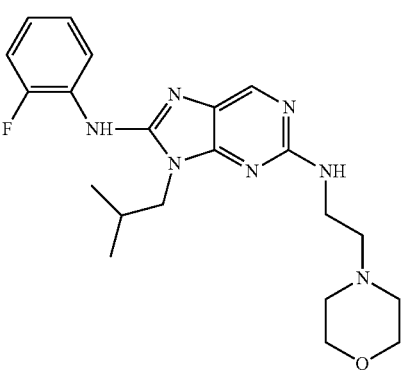 [SMILES: CC(C)Cn1c(Nc2ccccc2F)nc2cnc(NCCN3CCOCC3)nc21]
256
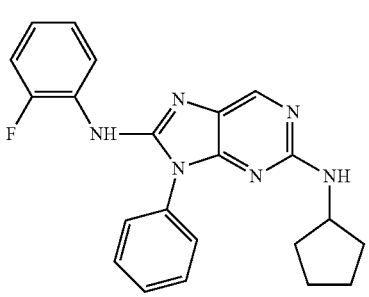 [SMILES: Fc1ccccc1Nc1nc2cnc(NC3CCCC3)nc2n1-c1ccccc1]
257

TABLE 1-continued
Compound
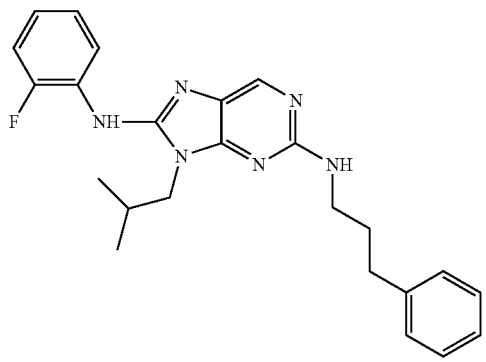 [SMILES: CC(C)Cn1c(Nc2ccccc2F)nc2cnc(NCCCc3ccccc3)nc21]
258
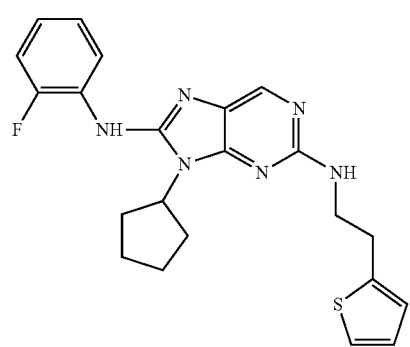 [SMILES: Fc1ccccc1Nc1nc2cnc(NCCc3cccs3)nc2n1C1CCCC1]
259
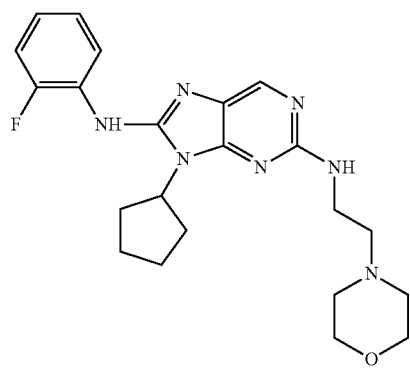 [SMILES: Fc1ccccc1Nc1nc2cnc(NCCN3CCOCC3)nc2n1C1CCCC1]
260
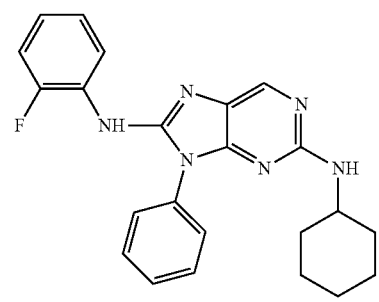 [SMILES: Fc1ccccc1Nc1nc2cnc(NC3CCCCC3)nc2n1-c1ccccc1]
261
TABLE 1-continued
Compound
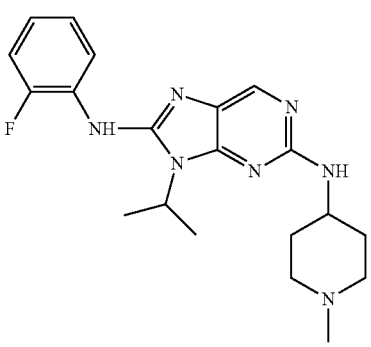 [SMILES: CC(C)n1c(Nc2ccccc2F)nc2cnc(NC3CCN(C)CC3)nc21]
262
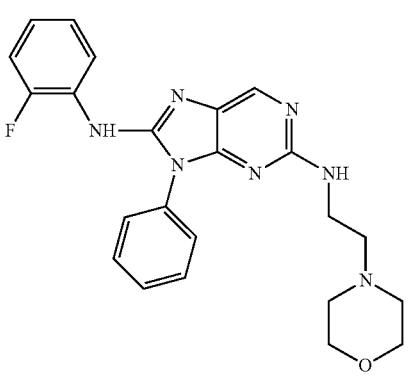 [SMILES: Fc1ccccc1Nc1nc2cnc(NCCN3CCOCC3)nc2n1-c1ccccc1]
263
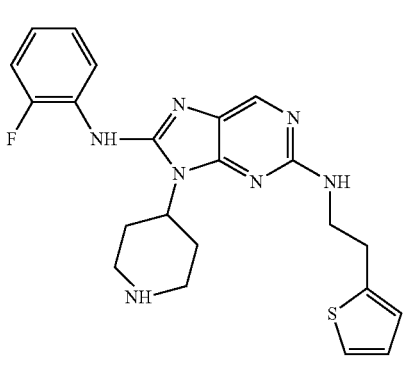 [SMILES: Fc1ccccc1Nc1nc2cnc(NCCc3cccs3)nc2n1C1CCNCC1]
264
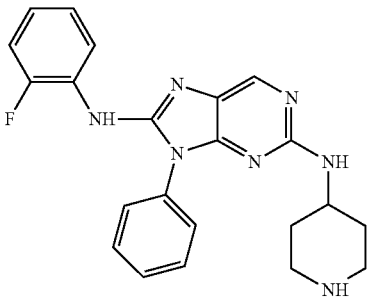 [SMILES: Fc1ccccc1Nc1nc2cnc(NC3CCNCC3)nc2n1-c1ccccc1]
265

TABLE 1-continued
Compound
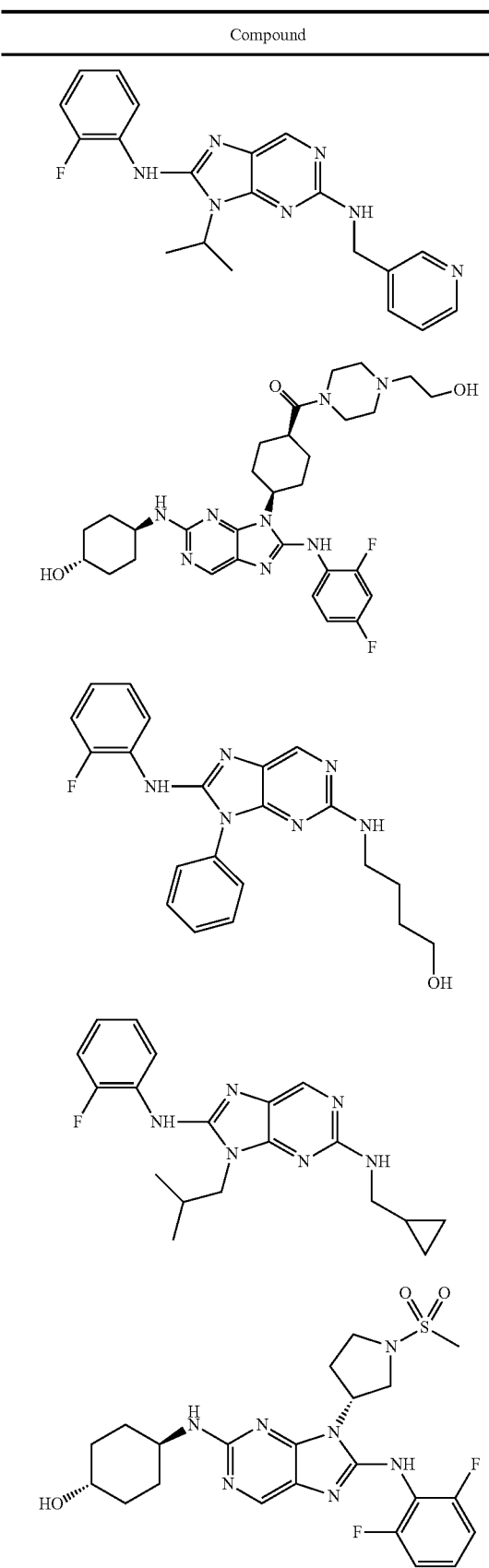
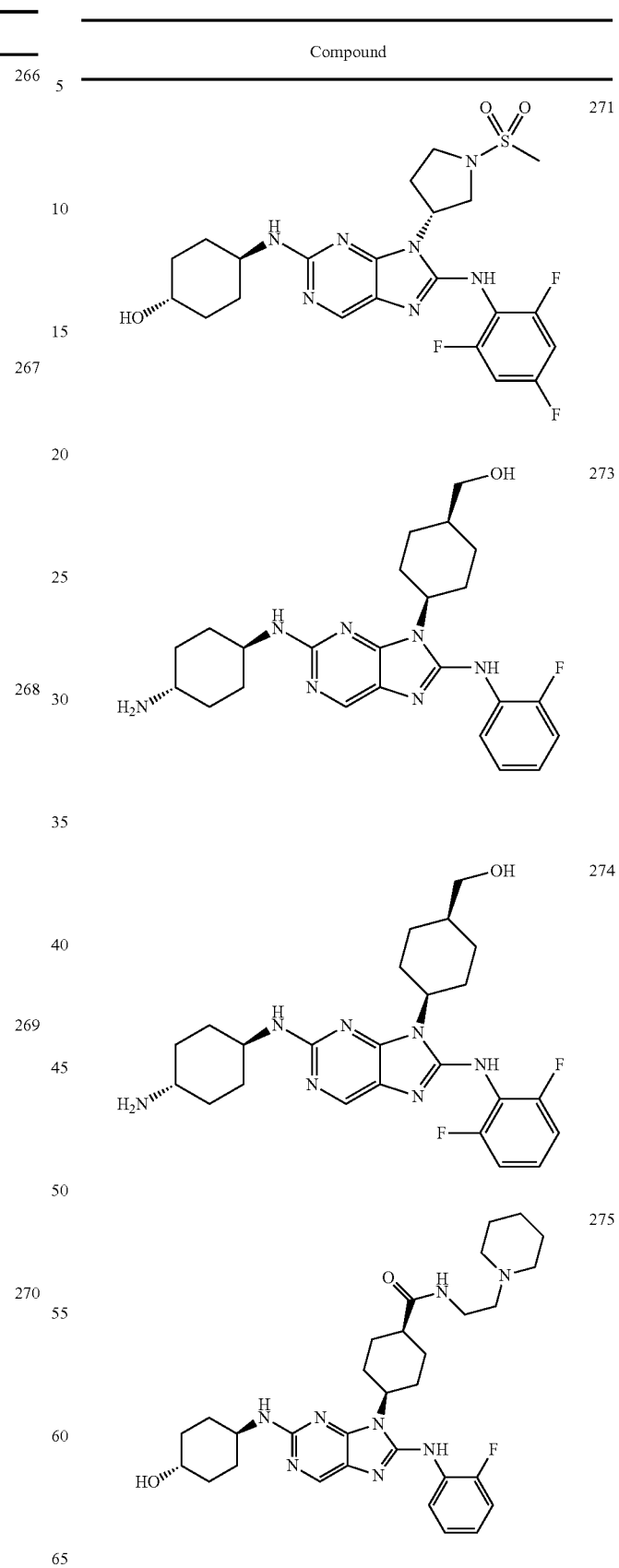

TABLE 1-continued

Compound

TABLE 1-continued
Compound
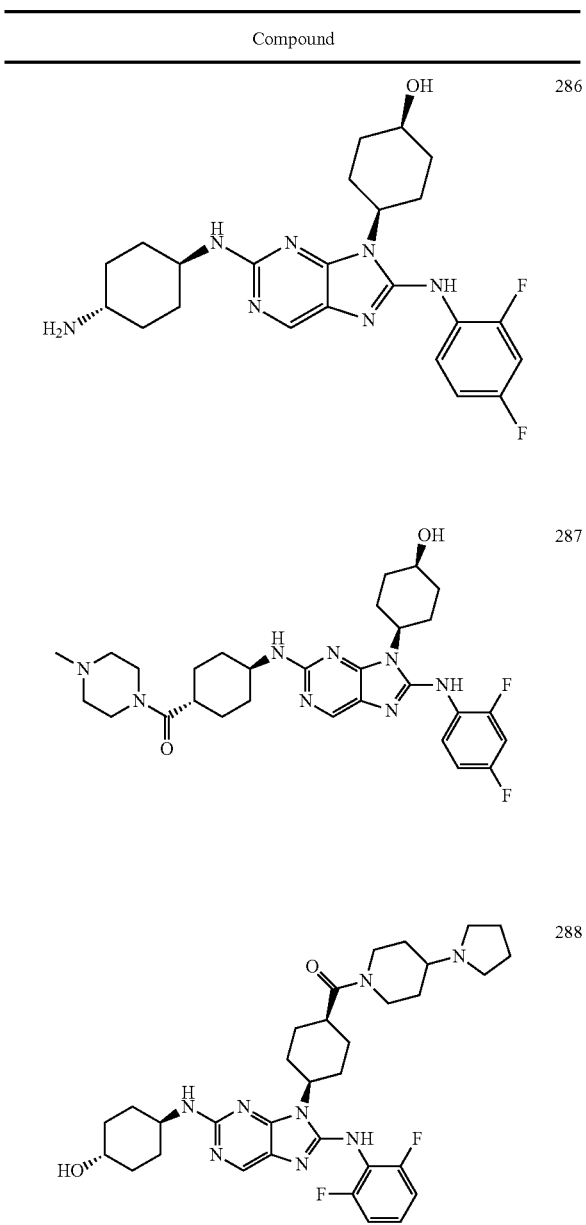
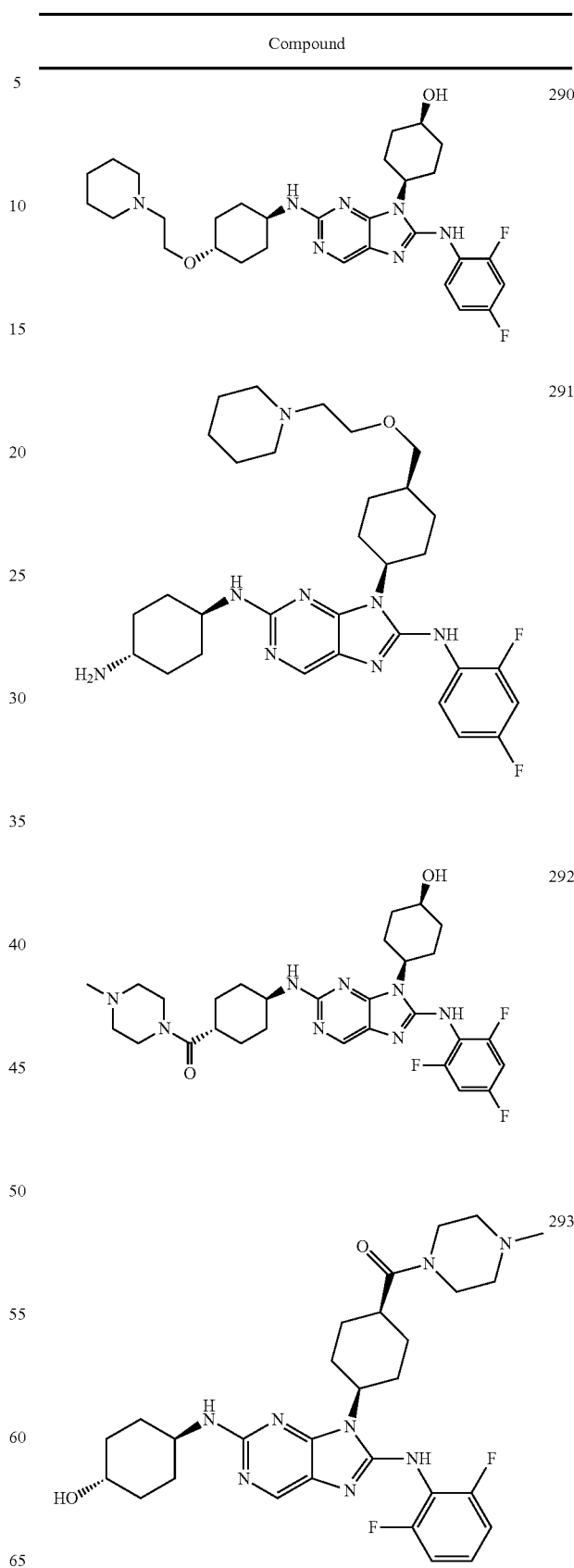

TABLE 1-continued
Compound
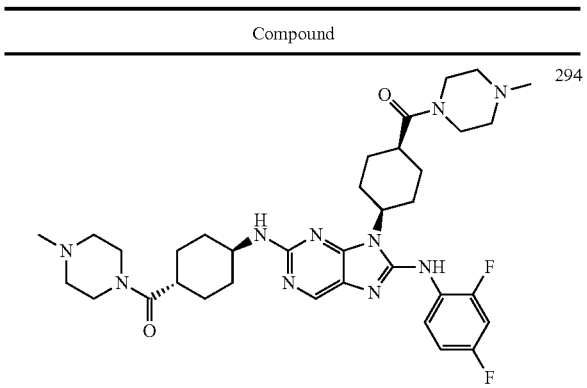
294
295
296
297
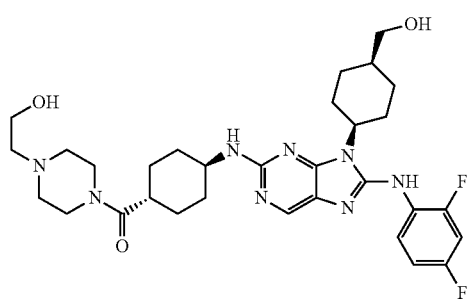 [SMILES: O=C([C@H]1CC[C@H](Nc2ncc3nc(Nc4ccc(F)cc4F)n([C@H]4CC[C@@H](CO)CC4)c3n2)CC1)N1CCN(CCO)CC1]
298
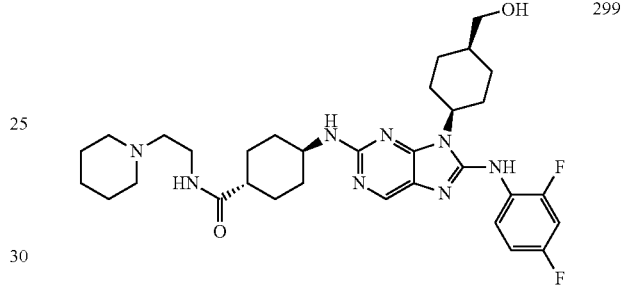
299
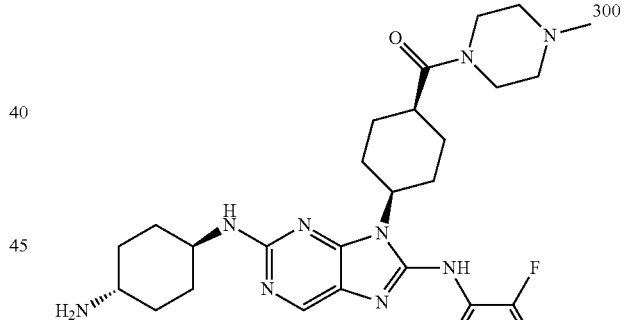
300
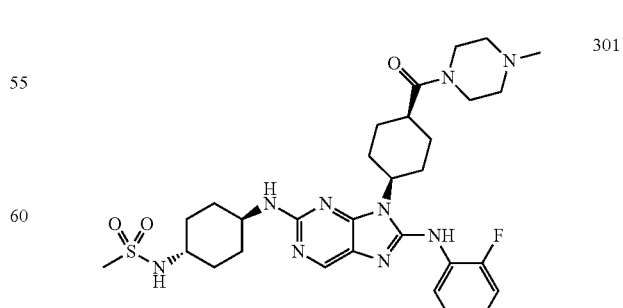
301

TABLE 1-continued
Compound
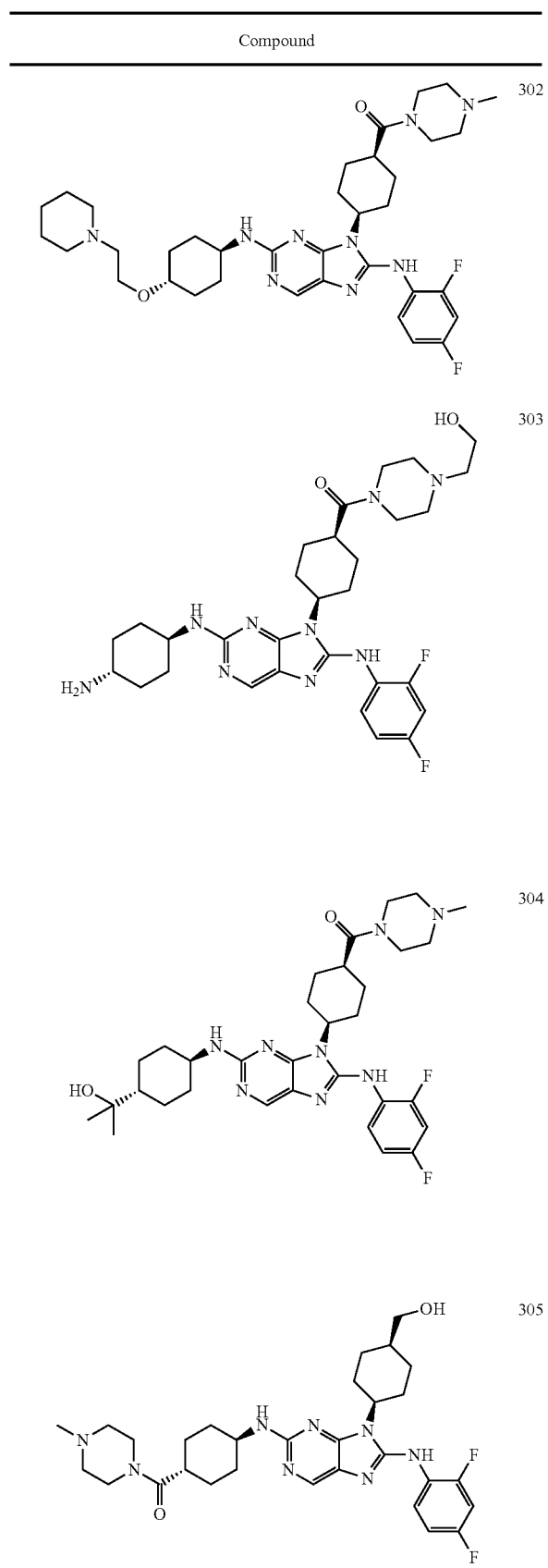
302
303
304
305
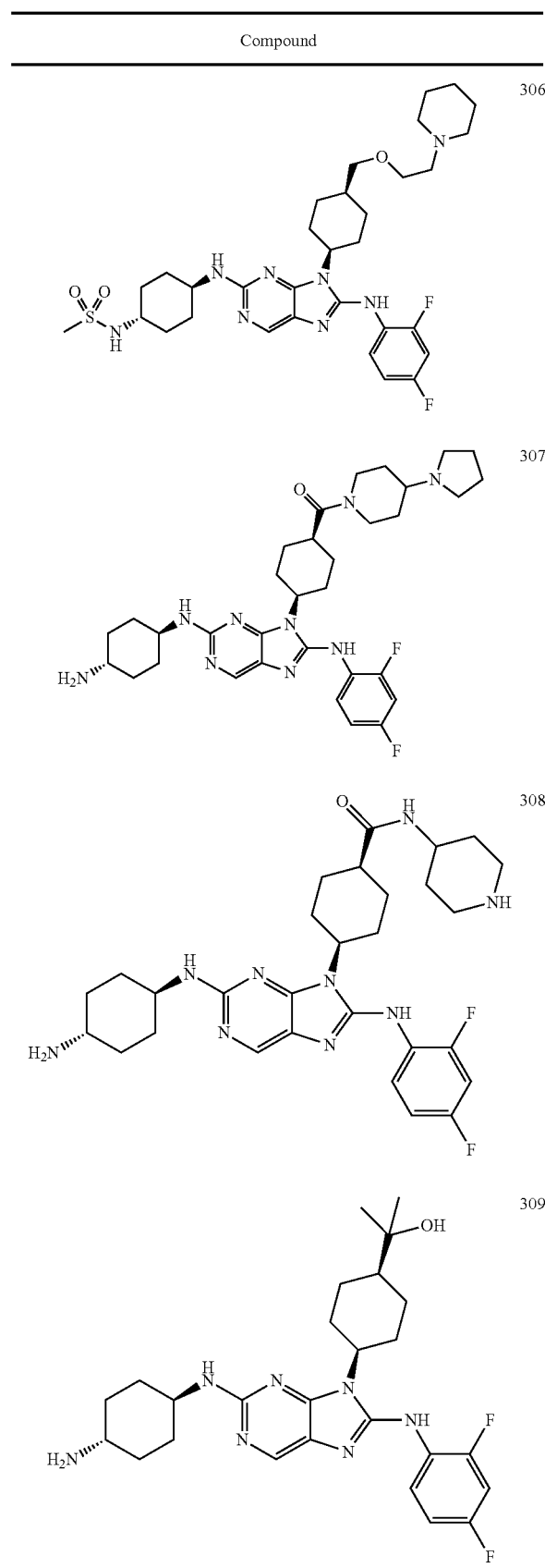
306
307
308
309

TABLE 1-continued
Compound
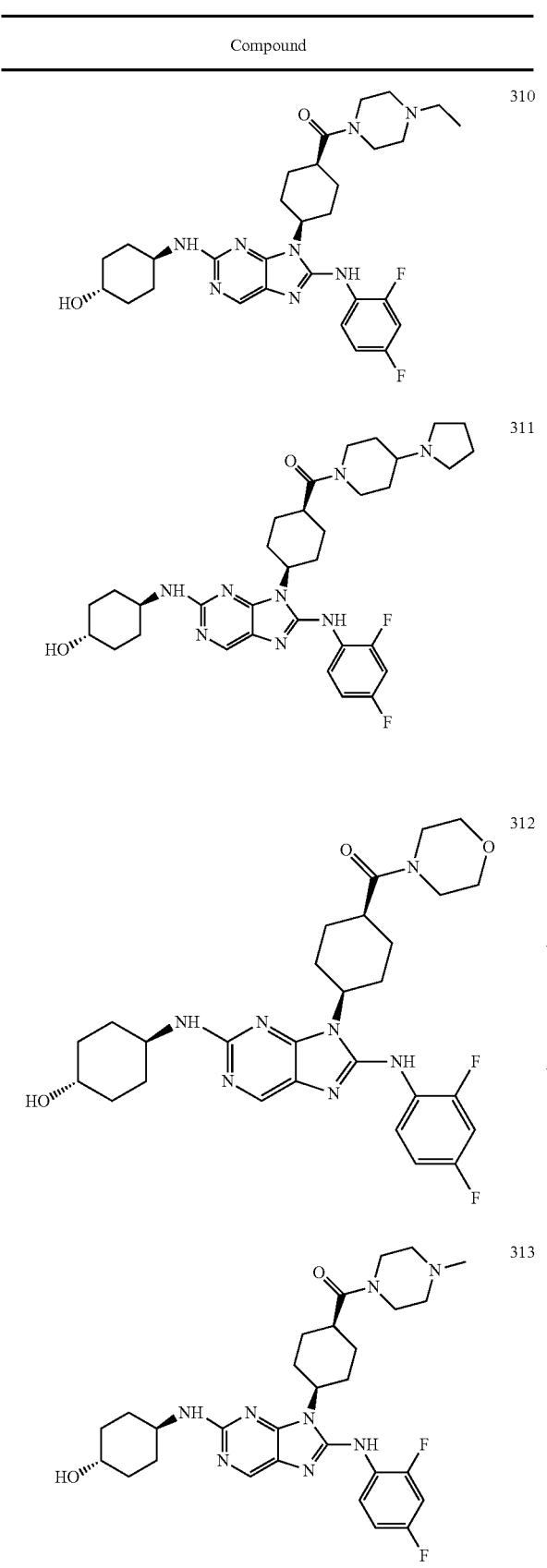
310
311
312
313
TABLE 1-continued
Compound
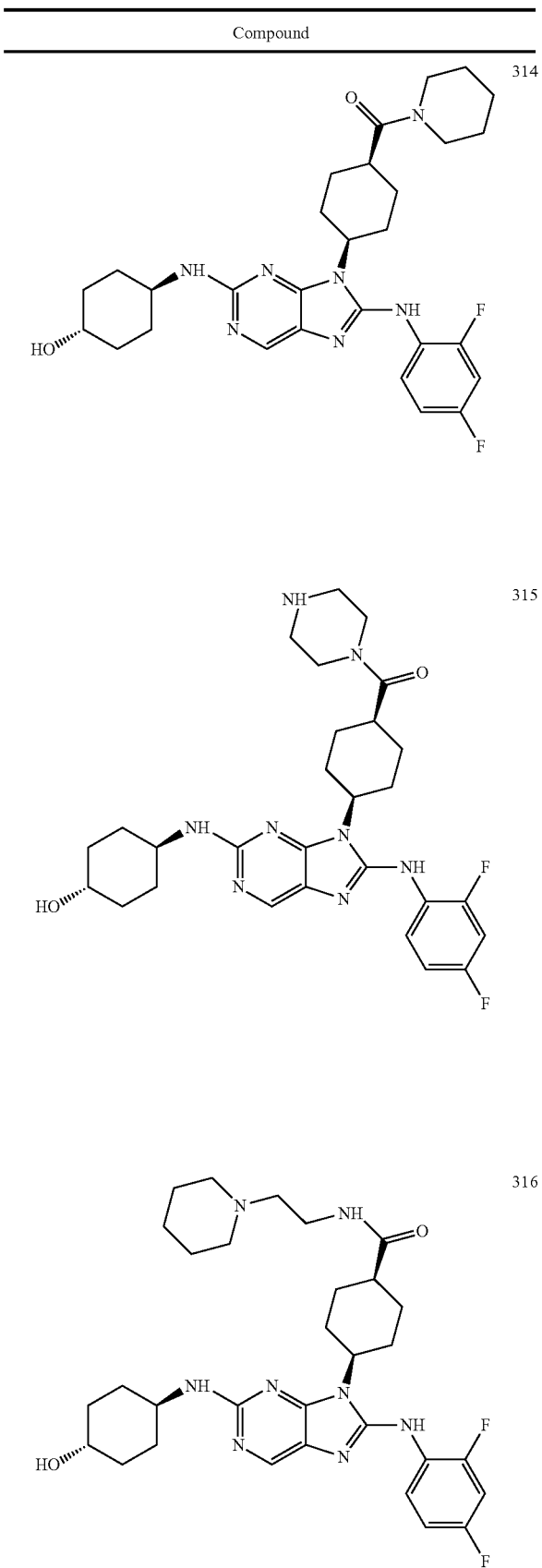
314
315
316

TABLE 1-continued
Compound
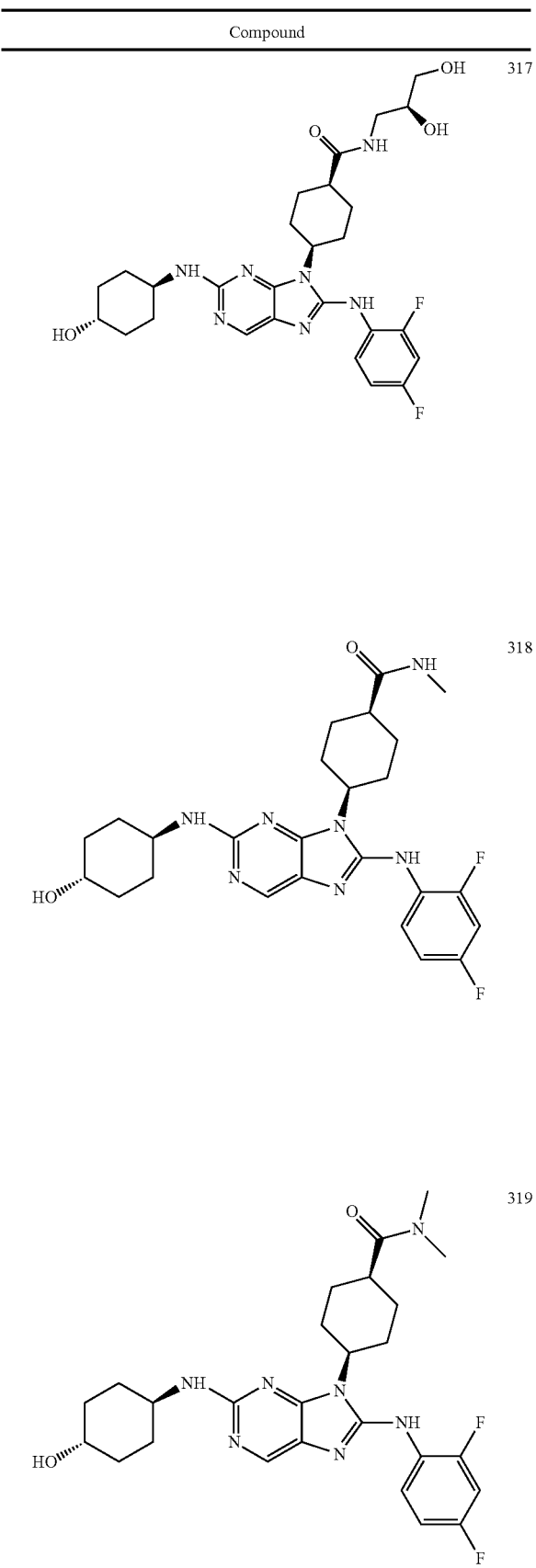
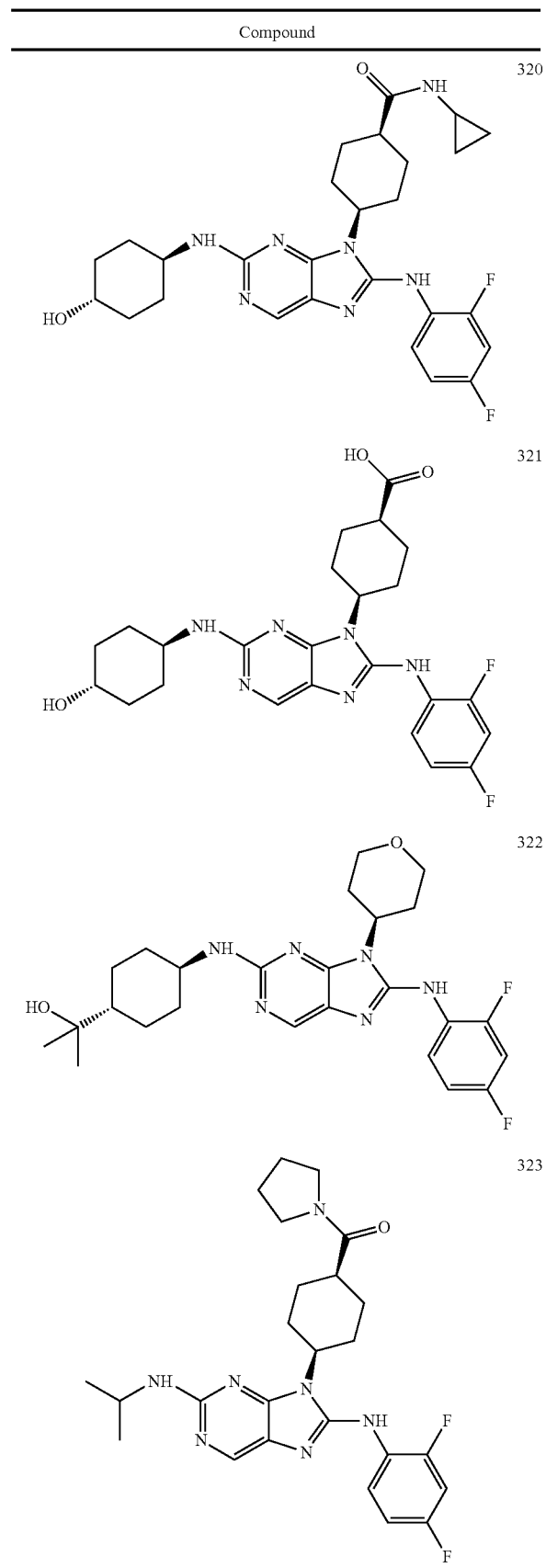

TABLE 1-continued

Compound

TABLE 1-continued
Compound
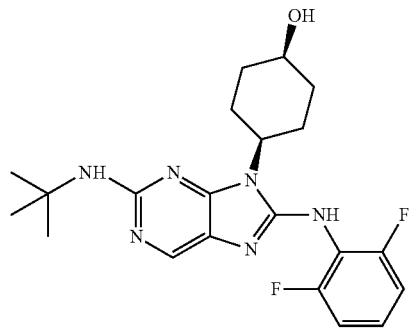 [SMILES: CC(C)(C)Nc1ncc2nc(Nc3c(F)cccc3F)n([C@H]3CC[C@@H](O)CC3)c2n1] 332
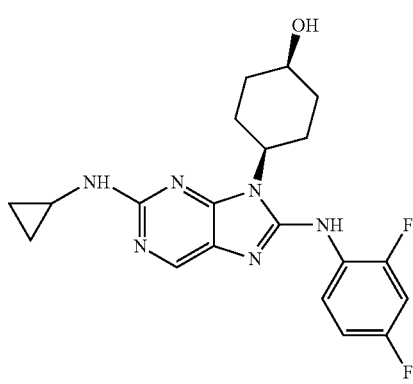 [SMILES: O[C@H]1CC[C@@H](n2c(Nc3ccc(F)cc3F)nc3cnc(NC4CC4)nc32)CC1] 333
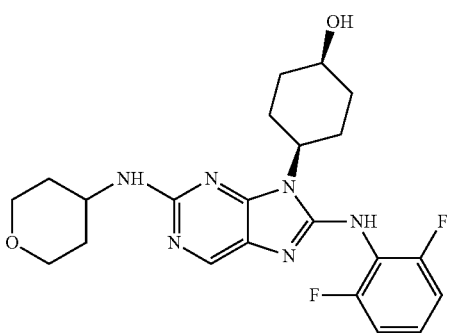 [SMILES: O[C@H]1CC[C@@H](n2c(Nc3c(F)cccc3F)nc3cnc(NC4CCOCC4)nc32)CC1] 334
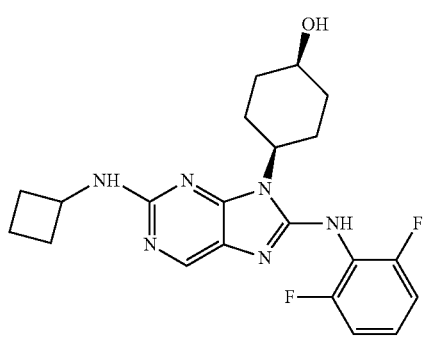 [SMILES: O[C@H]1CC[C@@H](n2c(Nc3c(F)cccc3F)nc3cnc(NC4CCC4)nc32)CC1] 335
TABLE 1-continued
Compound
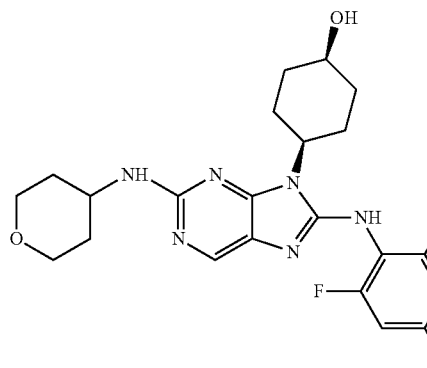 336
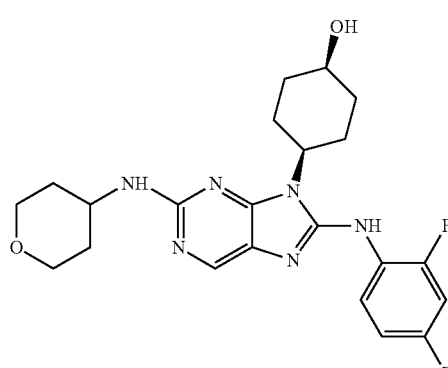 337
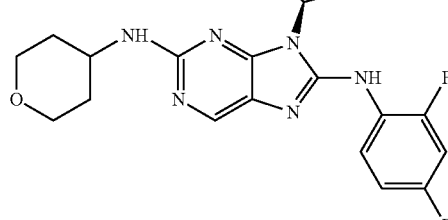 338
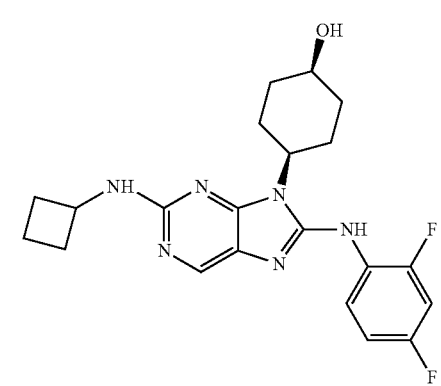 [SMILES: O[C@H]1CC[C@@H](n2c(Nc3ccc(F)cc3F)nc3cnc(NC4CCC4)nc32)CC1] 339

TABLE 1-continued
Compound
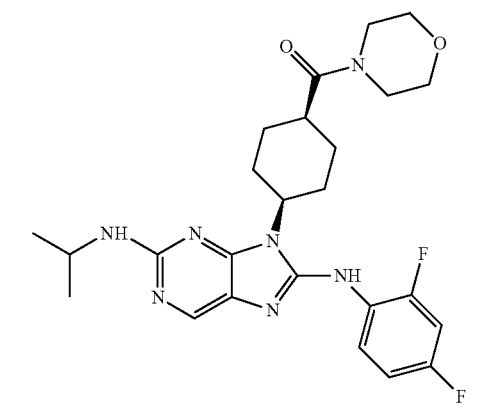 [SMILES: CC(C)Nc1ncc2nc(Nc3ccc(F)cc3F)n([C@H]3CC[C@@H](C(=O)N4CCOCC4)CC3)c2n1] 340
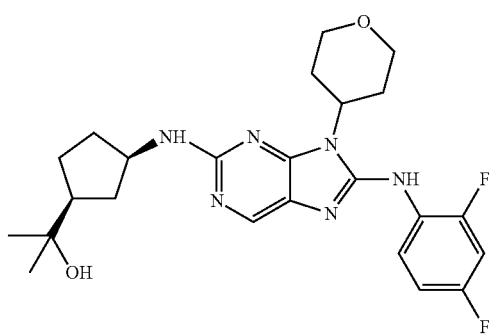 [SMILES: CC(C)(O)[C@H]1CC[C@@H](Nc2ncc3nc(Nc4ccc(F)cc4F)n(C4CCOCC4)c3n2)C1] 341
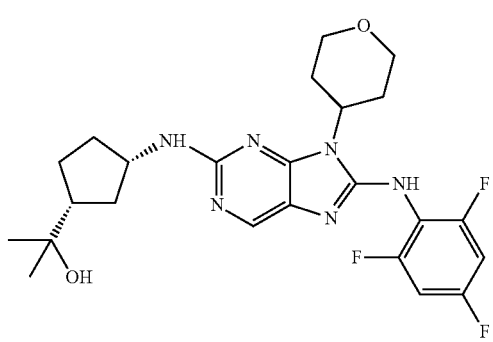 [SMILES: CC(C)(O)[C@@H]1CC[C@H](Nc2ncc3nc(Nc4c(F)cc(F)cc4F)n(C4CCOCC4)c3n2)C1] 342
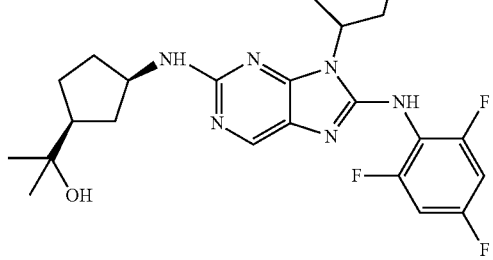 343
TABLE 1-continued
Compound
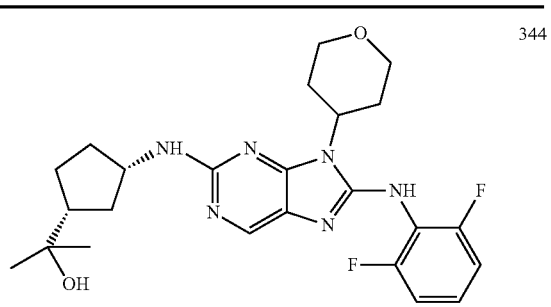 344
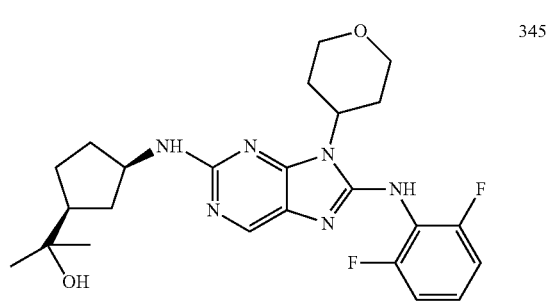 345
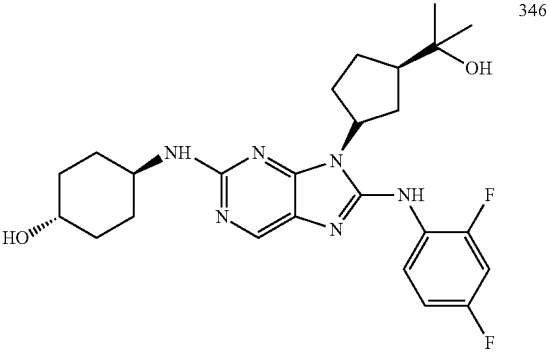 346
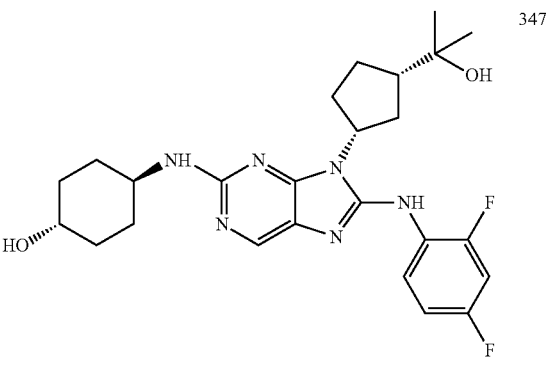 347

TABLE 1-continued
Compound
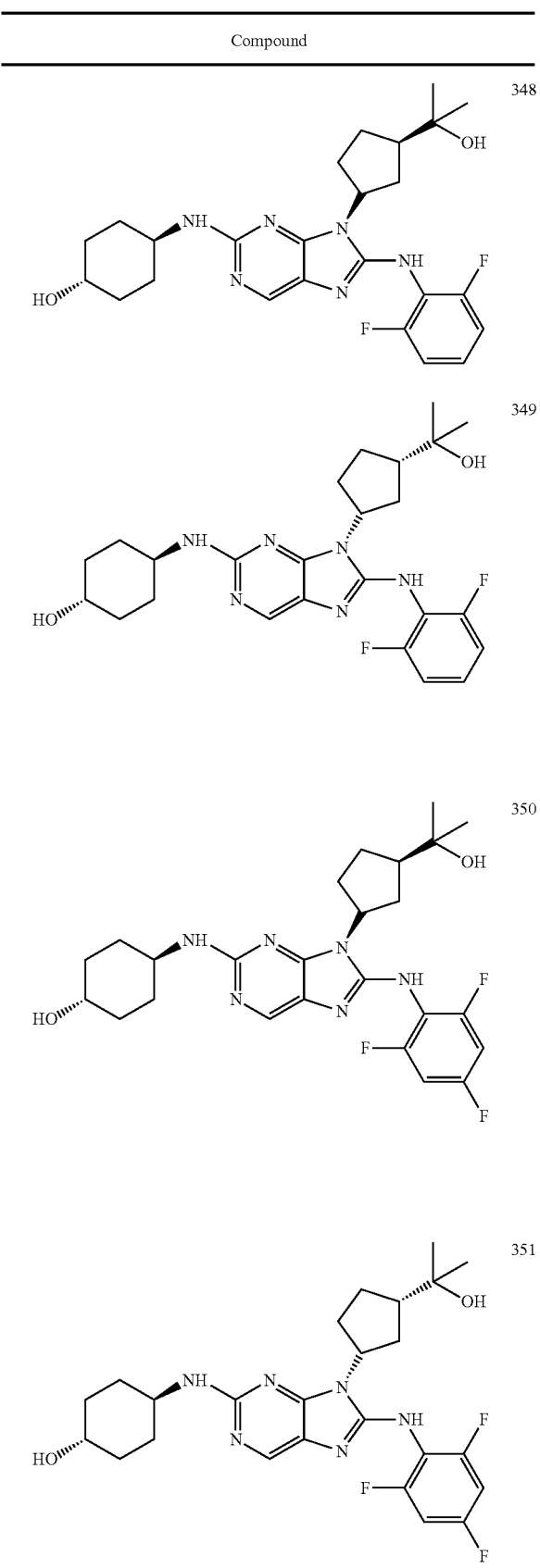
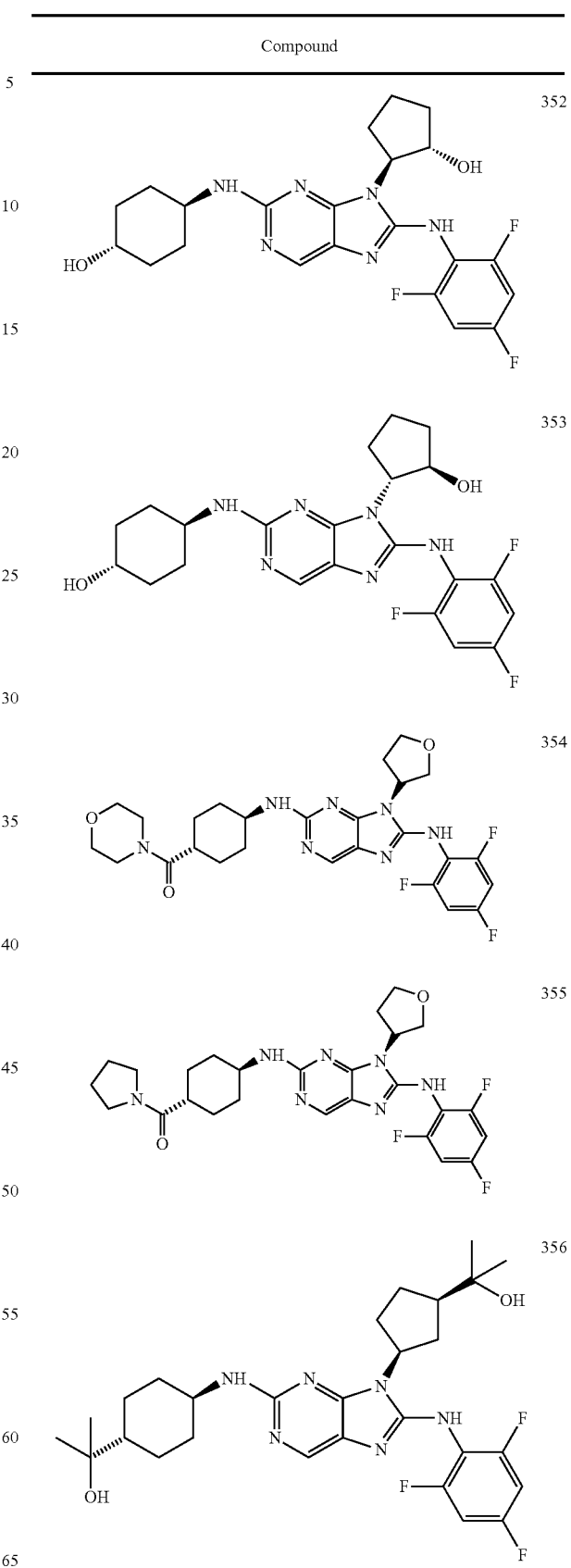

TABLE 1-continued
Compound
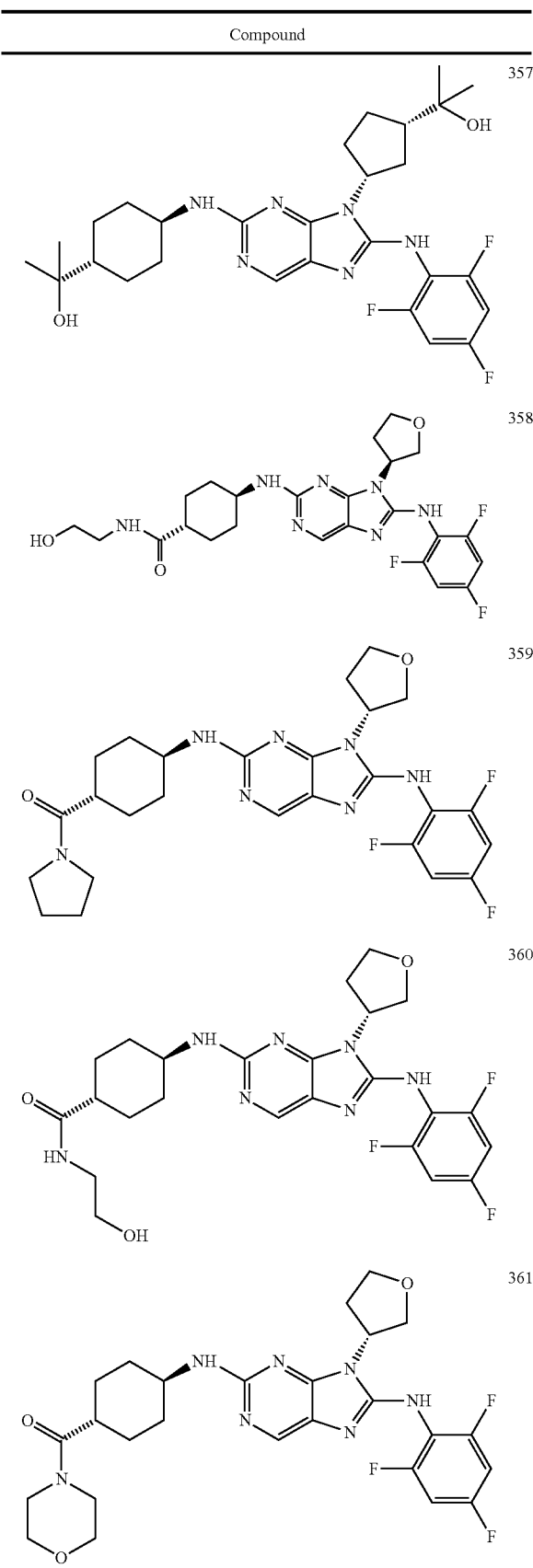
357
358
359
360
361
TABLE 1-continued
Compound
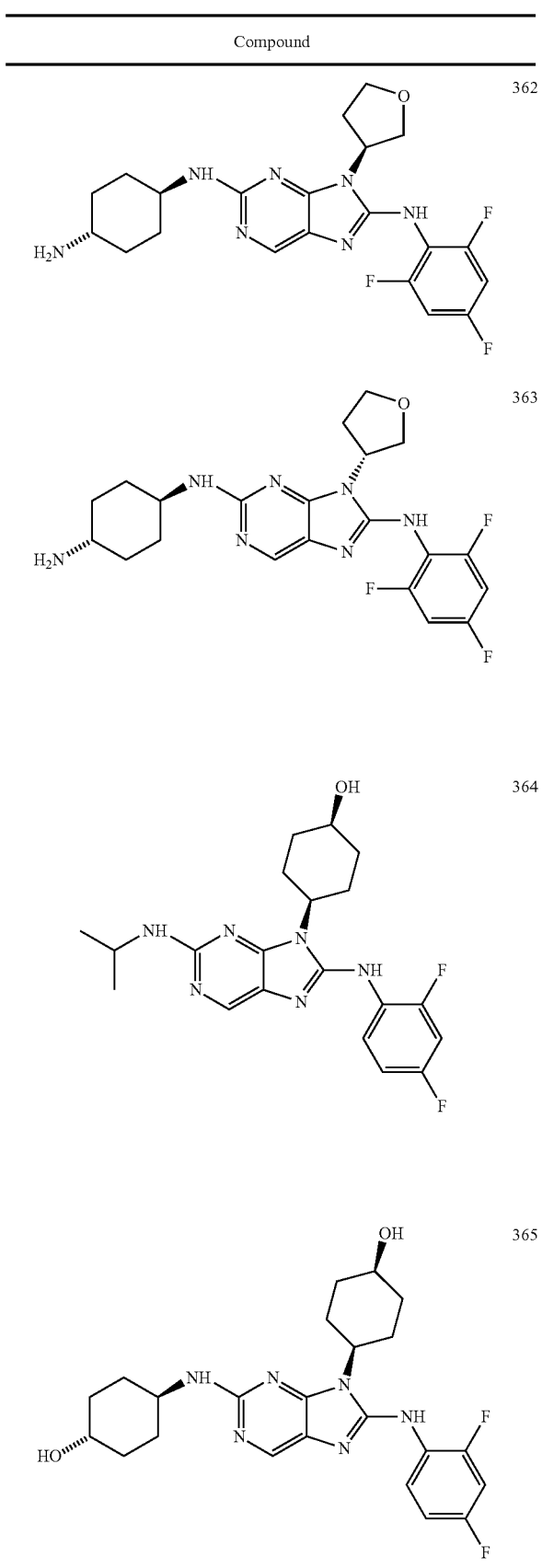
362
363
364
365

TABLE 1-continued
Compound
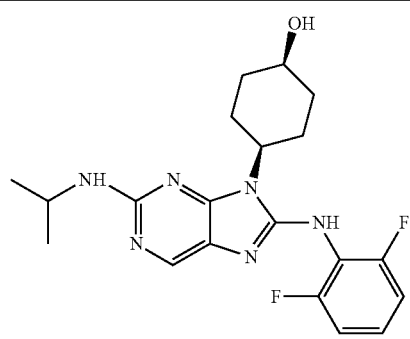 366
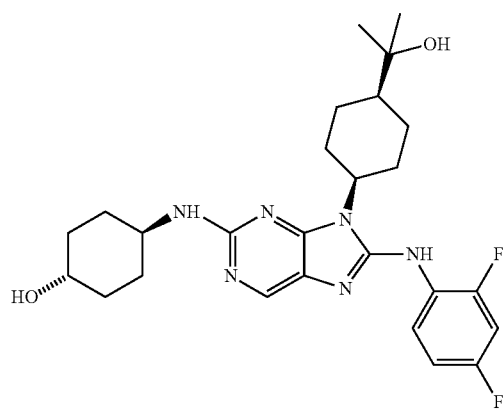 [SMILES: CC(C)(O)[C@H]1CC[C@@H](n2c(Nc3ccc(F)cc3F)nc3cnc(N[C@H]4CC[C@H](O)CC4)nc32)CC1] 367
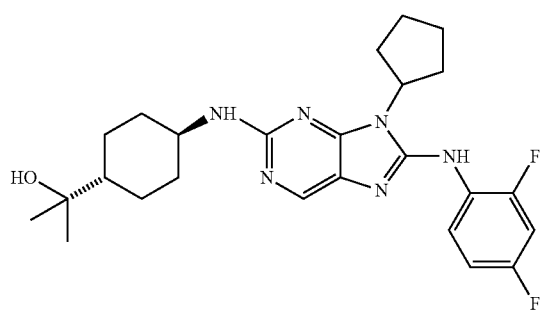 [SMILES: CC(C)(O)[C@H]1CC[C@H](Nc2ncc3nc(Nc4ccc(F)cc4F)n(C4CCCC4)c3n2)CC1] 368
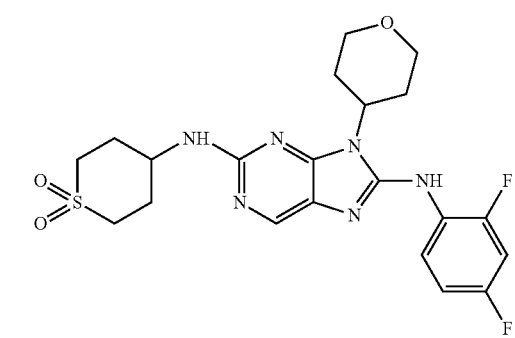 [SMILES: O=S1(=O)CCC(Nc2ncc3nc(Nc4ccc(F)cc4F)n(C4CCOCC4)c3n2)CC1] 369
TABLE 1-continued
Compound
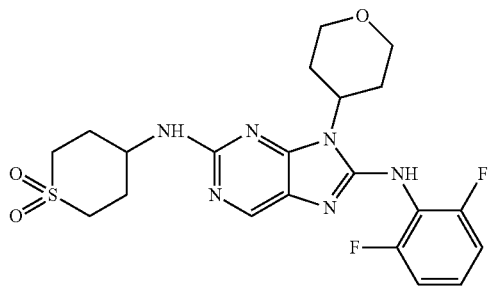 [SMILES: O=S1(=O)CCC(Nc2ncc3nc(Nc4c(F)cccc4F)n(C4CCOCC4)c3n2)CC1] 370
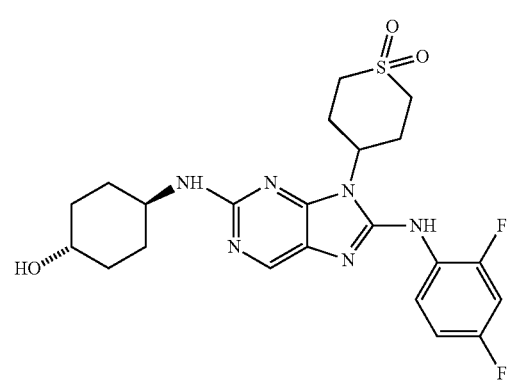 [SMILES: O=S1(=O)CCC(n2c(Nc3ccc(F)cc3F)nc3cnc(N[C@H]4CC[C@H](O)CC4)nc32)CC1] 371
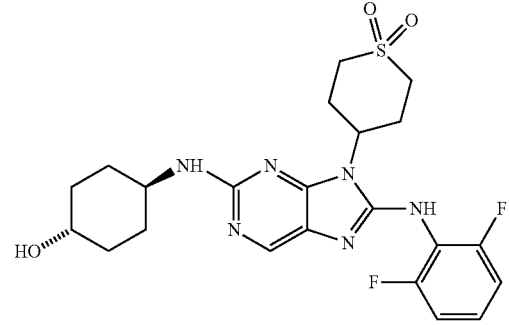 [SMILES: O=S1(=O)CCC(n2c(Nc3c(F)cccc3F)nc3cnc(N[C@H]4CC[C@H](O)CC4)nc32)CC1] 372
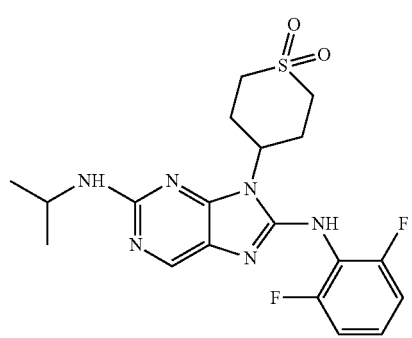 [SMILES: CC(C)Nc1ncc2nc(Nc3c(F)cccc3F)n(C3CCS(=O)(=O)CC3)c2n1] 373

TABLE 1-continued
Compound
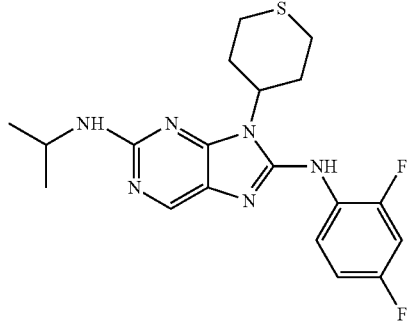 [SMILES: CC(C)Nc1ncc2nc(Nc3ccc(F)cc3F)n(C3CCSCC3)c2n1]
374
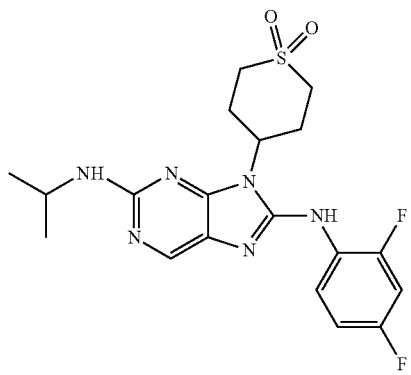 [SMILES: CC(C)Nc1ncc2nc(Nc3ccc(F)cc3F)n(C3CCS(=O)(=O)CC3)c2n1]
375
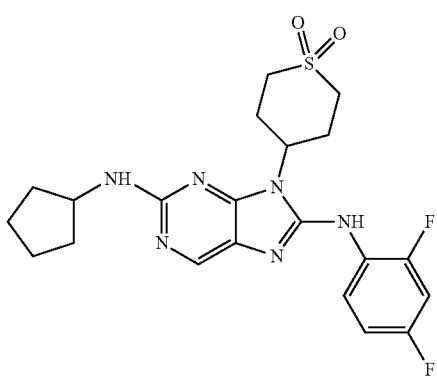 [SMILES: O=S1(=O)CCC(n2c(Nc3ccc(F)cc3F)nc3cnc(NC4CCCC4)nc32)CC1]
376
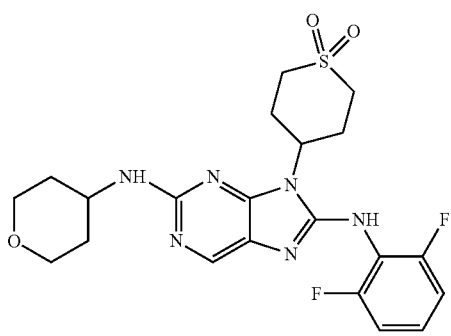 [SMILES: O=S1(=O)CCC(n2c(Nc3c(F)cccc3F)nc3cnc(NC4CCOCC4)nc32)CC1]
377
TABLE 1-continued
Compound
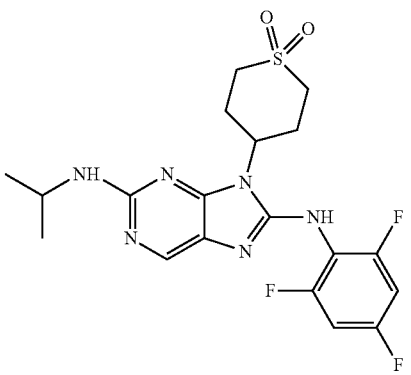 [SMILES: CC(C)Nc1ncc2nc(Nc3c(F)cc(F)cc3F)n(C3CCS(=O)(=O)CC3)c2n1]
378
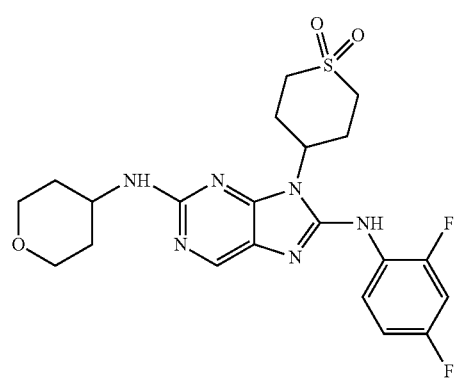 [SMILES: O=S1(=O)CCC(n2c(Nc3ccc(F)cc3F)nc3cnc(NC4CCOCC4)nc32)CC1]
379
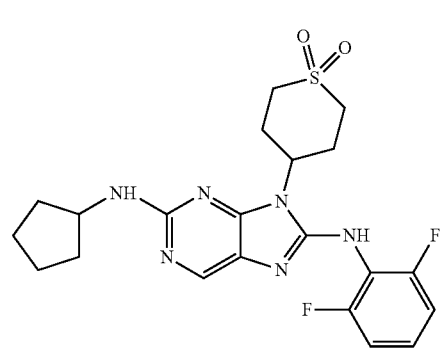 [SMILES: O=S1(=O)CCC(n2c(Nc3c(F)cccc3F)nc3cnc(NC4CCCC4)nc32)CC1]
380
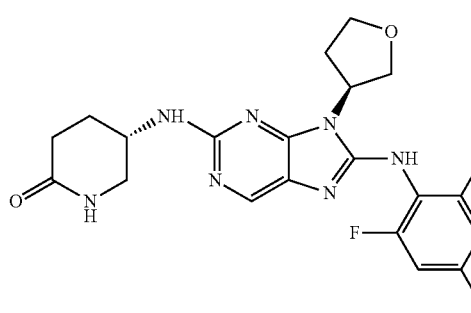
381

TABLE 1-continued

Compound

TABLE 1-continued

| Compound |
|---|
| 391 |
| 392 |
| 393 |
| 394 |
| 395 |
| 396 |
| 397 |

TABLE 1-continued
Compound
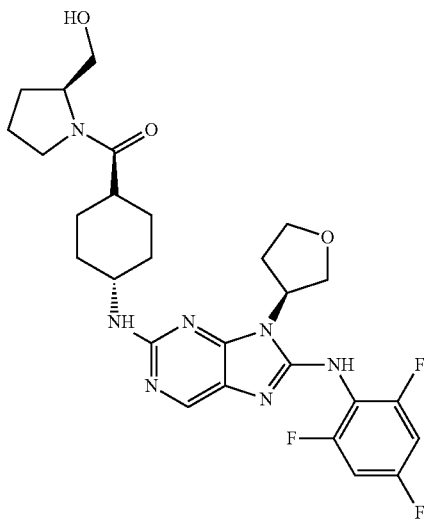
398
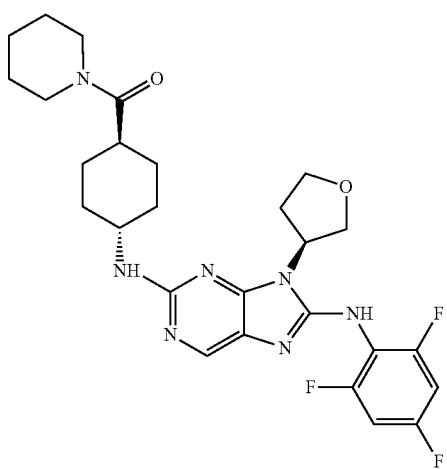 [SMILES: O=C([C@H]1CC[C@H](Nc2ncc3nc(Nc4c(F)cc(F)cc4F)n([C@H]4CCOC4)c3n2)CC1)N1CCCCC1]
399
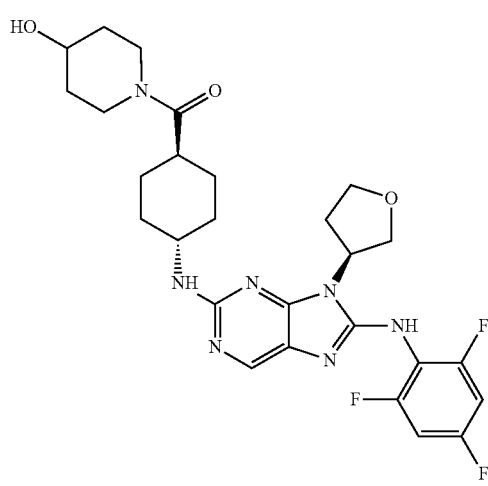 [SMILES: O=C([C@H]1CC[C@H](Nc2ncc3nc(Nc4c(F)cc(F)cc4F)n([C@H]4CCOC4)c3n2)CC1)N1CCC(O)CC1]
400
TABLE 1-continued
Compound
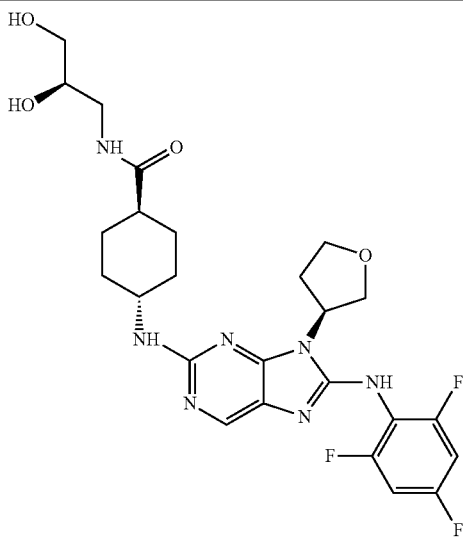
401
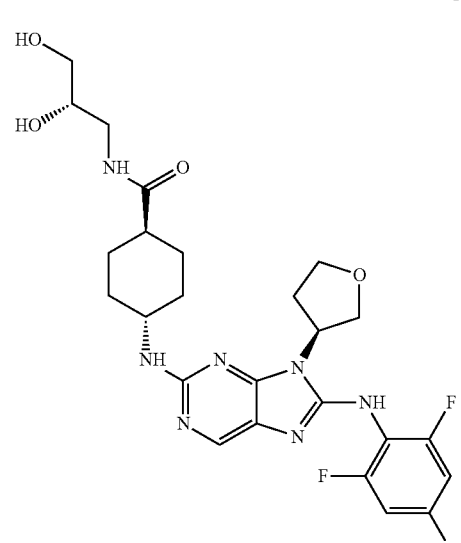
402
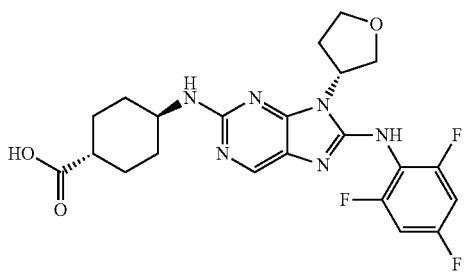 [SMILES: O=C(O)[C@H]1CC[C@H](Nc2ncc3nc(Nc4c(F)cc(F)cc4F)n([C@@H]4CCOC4)c3n2)CC1]
403
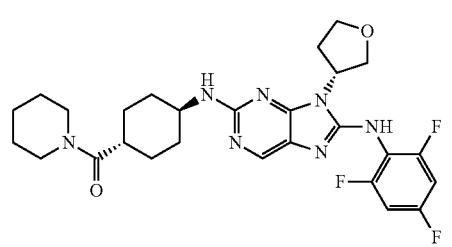 [SMILES: O=C([C@H]1CC[C@H](Nc2ncc3nc(Nc4c(F)cc(F)cc4F)n([C@@H]4CCOC4)c3n2)CC1)N1CCCCC1]
404

TABLE 1-continued
| Compound | |
|---|---|
| 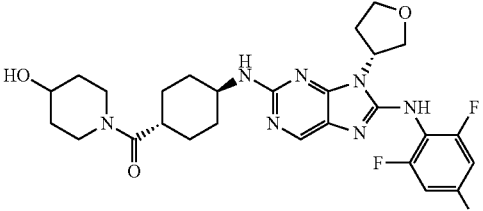 | 405 |
| 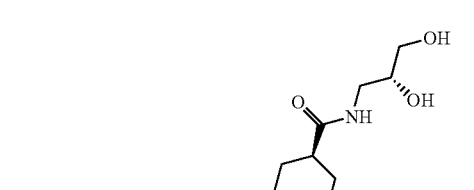 | 406 |
| 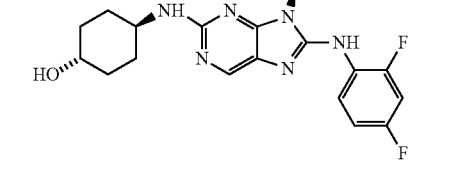 | 407 |
| 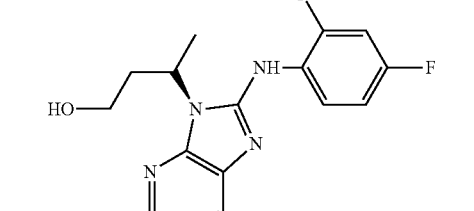 | 408 |
| 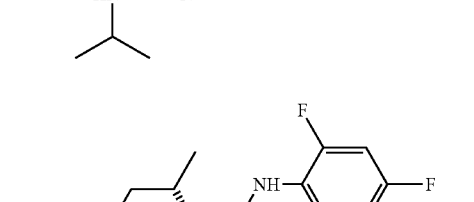 | 409 |
| 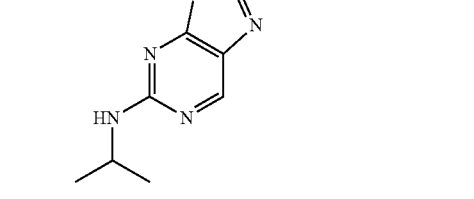 | 410 |
| 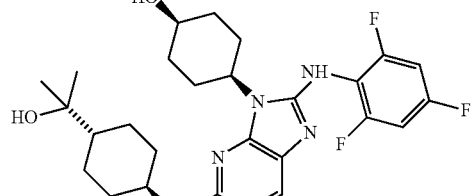 | 411 |
| 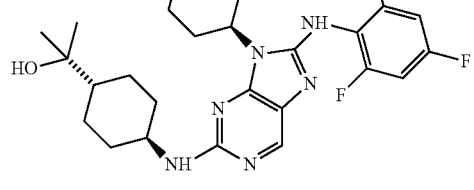 | 412 |

TABLE 1-continued
| Compound | |
|---|---|
| 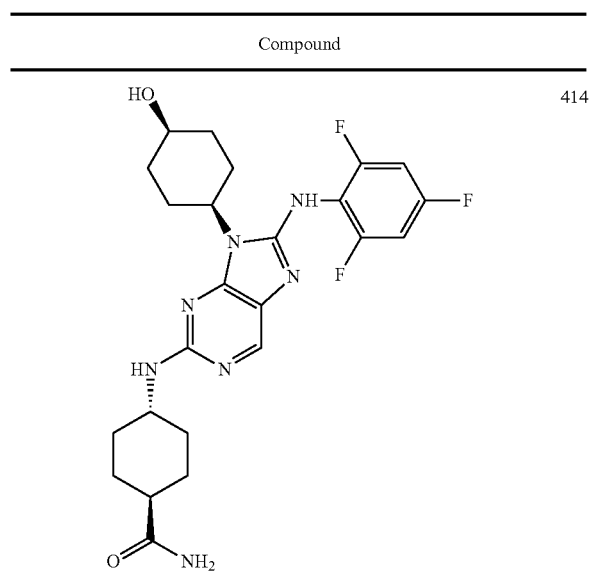 | 414 |
| 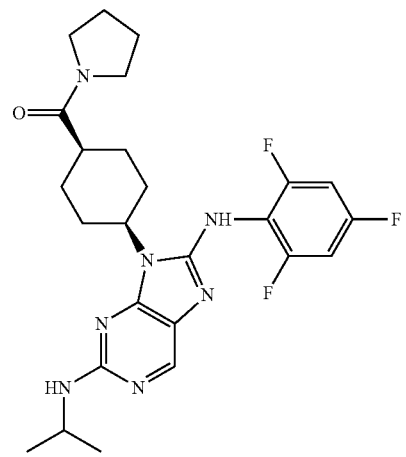 [SMILES: CC(C)Nc1ncc2nc(Nc3c(F)cc(F)cc3F)n([C@H]3CC[C@@H](C(=O)N4CCCC4)CC3)c2n1] | 415 |
| 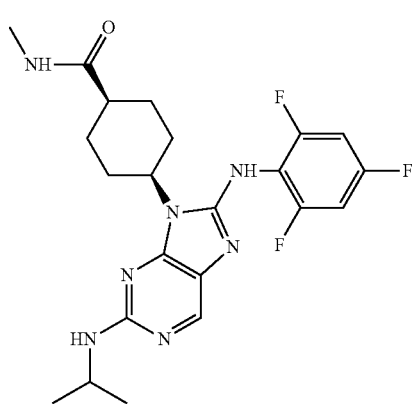 [SMILES: CNC(=O)[C@H]1CC[C@@H](n2c(Nc3c(F)cc(F)cc3F)nc3cnc(NC(C)C)nc32)CC1] | 416 |
TABLE 1-continued
| Compound | |
|---|---|
| 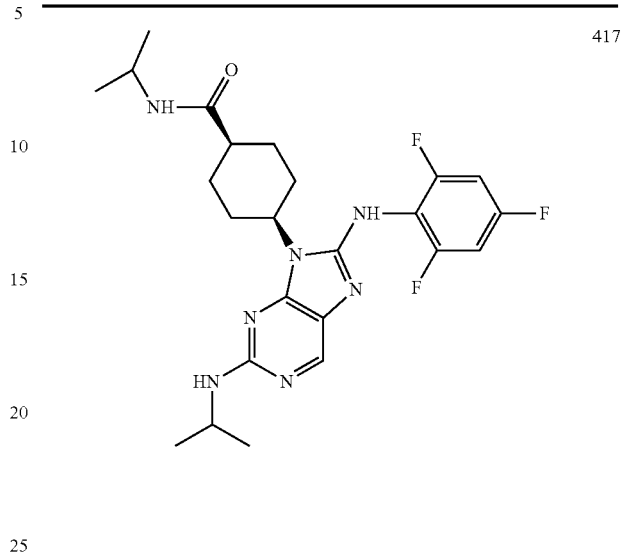 | 417 |
| 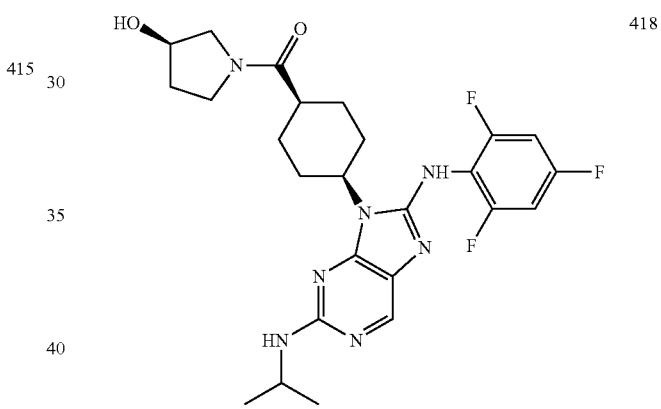 | 418 |
| 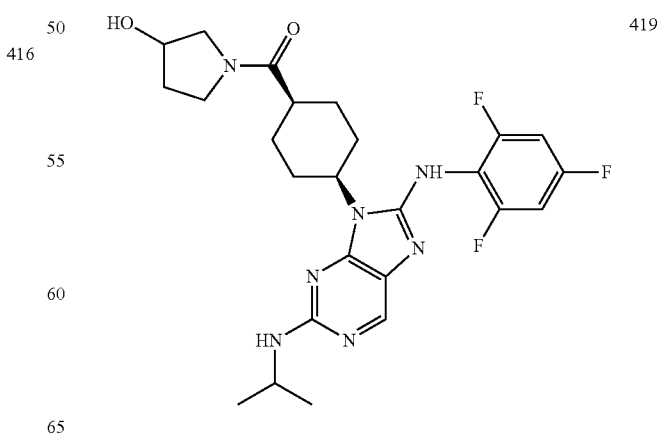 | 419 |

TABLE 1-continued
Compound
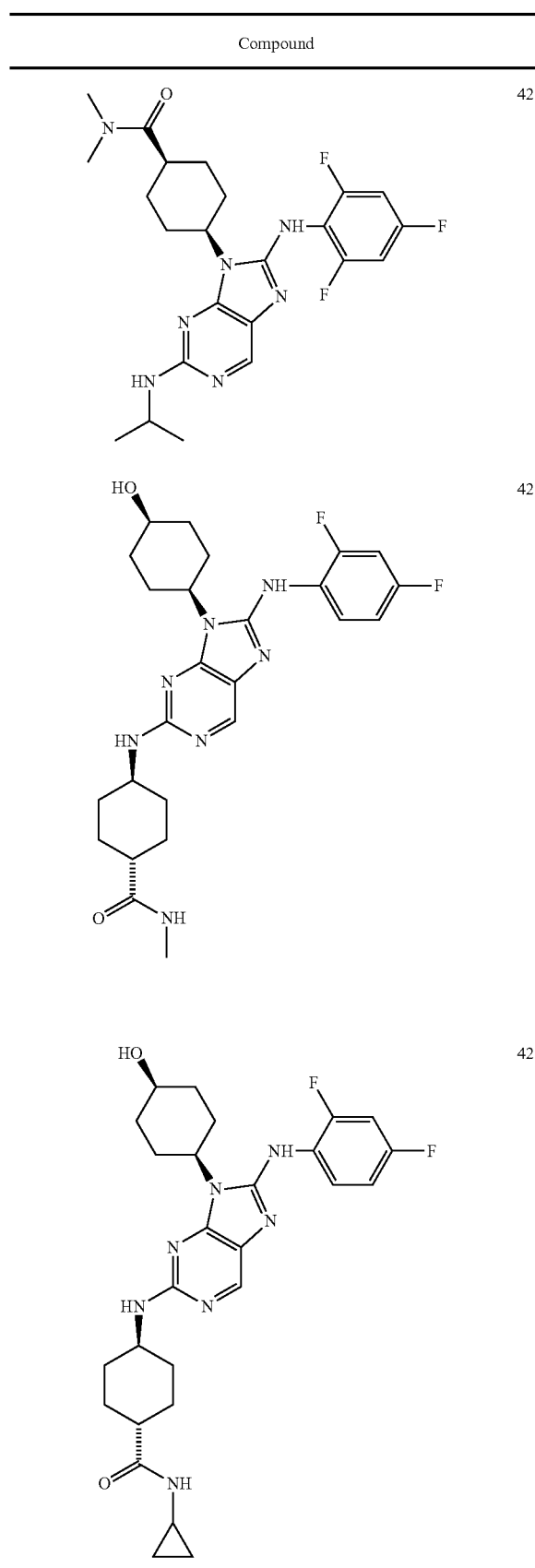
420
421
422
TABLE 1-continued
Compound
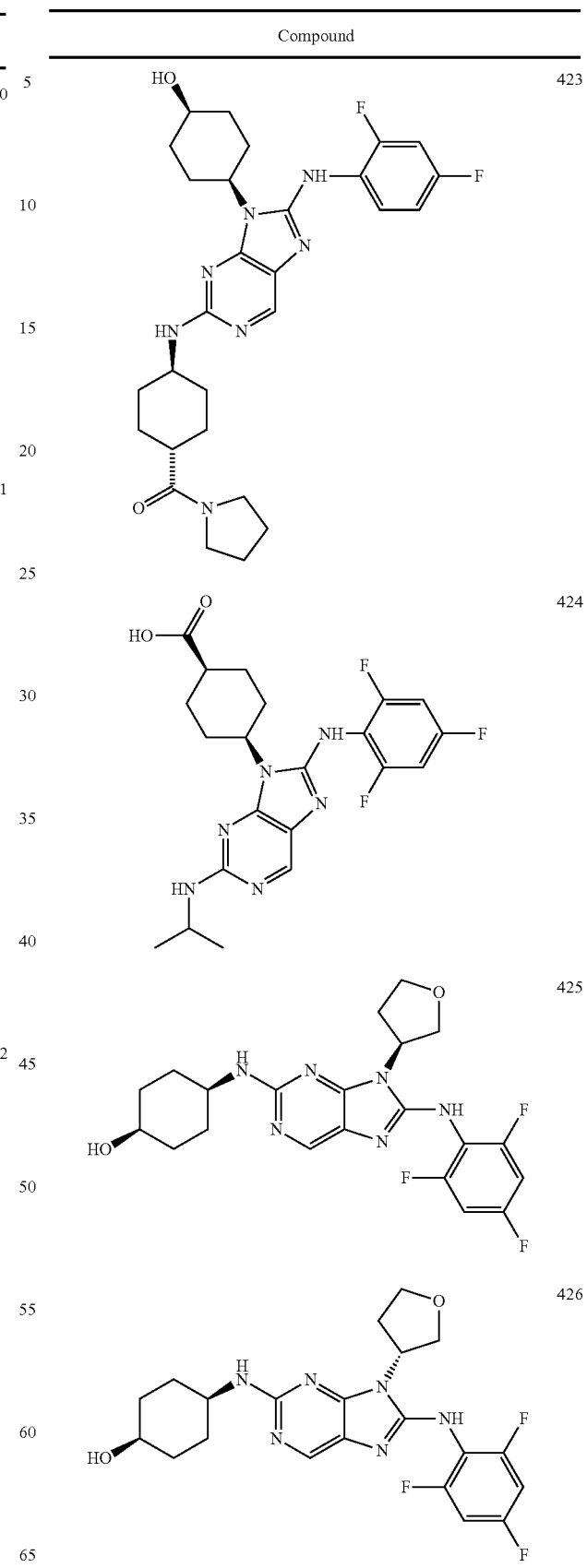
423
424
425
426

US 8,680,076 B2
TABLE 1-continued
Compound
427 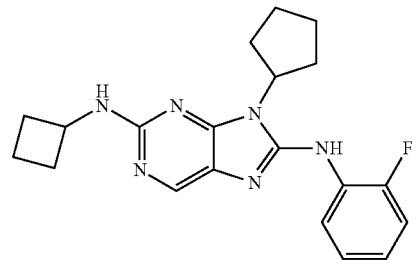 [SMILES: Fc1ccccc1Nc1nc2cnc(NC3CCC3)nc2n1C1CCCC1]
428 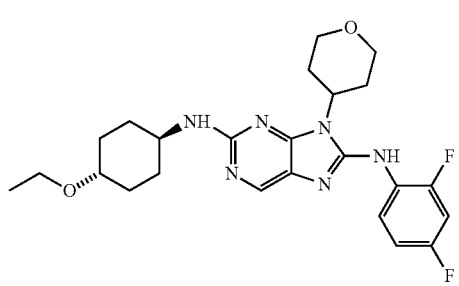 [SMILES: CCO[C@H]1CC[C@H](Nc2ncc3nc(Nc4ccc(F)cc4F)n(C4CCOCC4)c3n2)CC1]
429 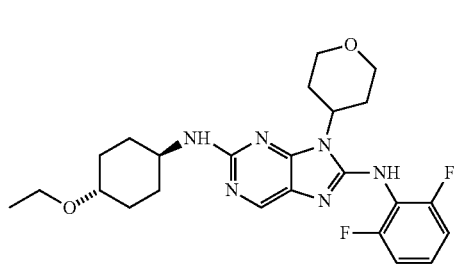 [SMILES: CCO[C@H]1CC[C@H](Nc2ncc3nc(Nc4c(F)cccc4F)n(C4CCOCC4)c3n2)CC1]
430 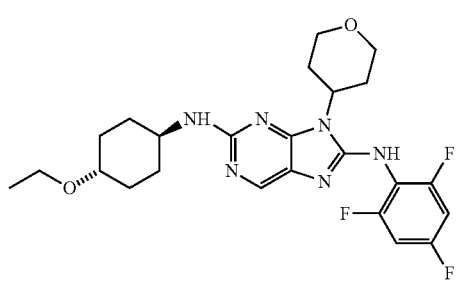 [SMILES: CCO[C@H]1CC[C@H](Nc2ncc3nc(Nc4c(F)cc(F)cc4F)n(C4CCOCC4)c3n2)CC1]
431 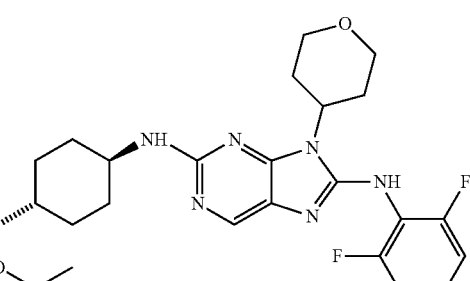
TABLE 1-continued
Compound
432 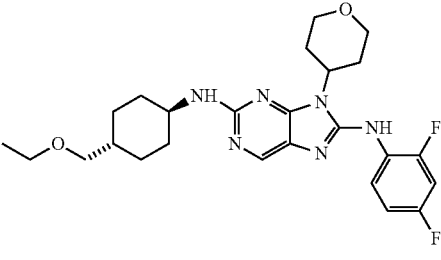 [SMILES: CCOC[C@H]1CC[C@H](Nc2ncc3nc(Nc4ccc(F)cc4F)n(C4CCOCC4)c3n2)CC1]
433 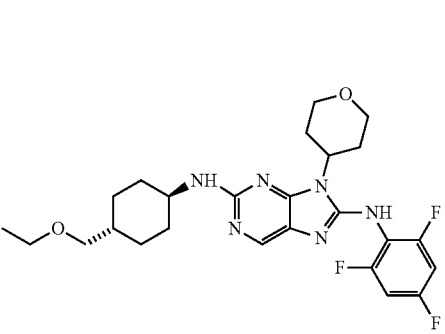 [SMILES: CCOC[C@H]1CC[C@H](Nc2ncc3nc(Nc4c(F)cc(F)cc4F)n(C4CCOCC4)c3n2)CC1]
434 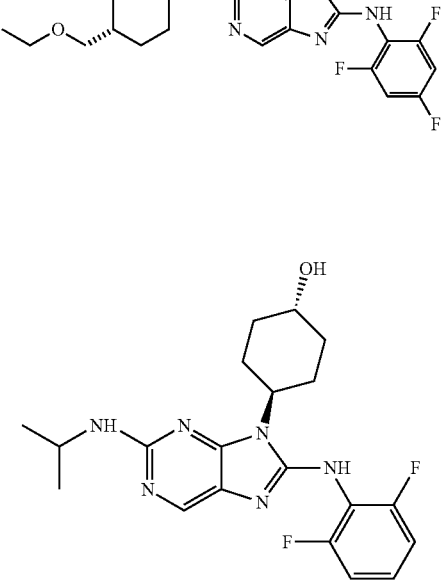
435 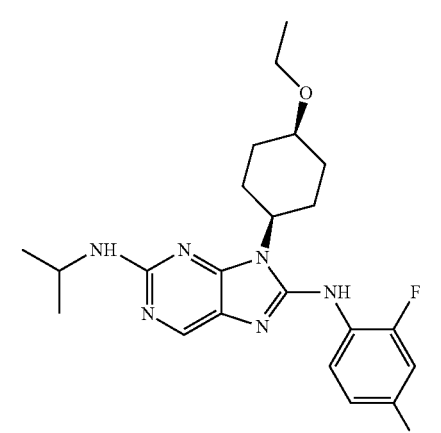

TABLE 1-continued
Compound
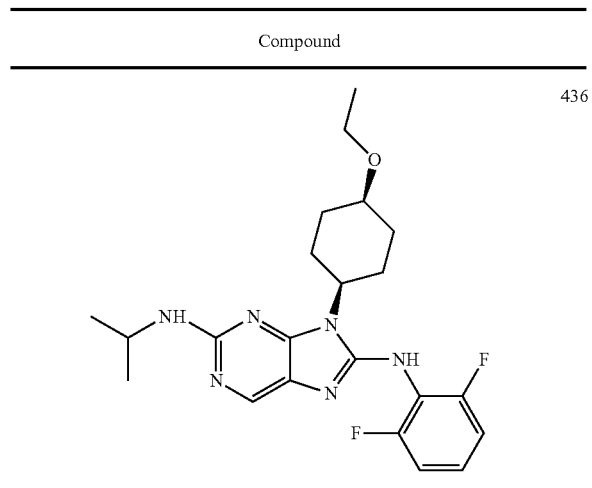 436
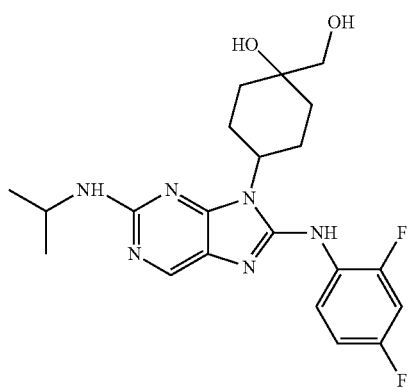 [SMILES: CC(C)Nc1ncc2nc(Nc3ccc(F)cc3F)n(C3CCC(O)(CO)CC3)c2n1] 437
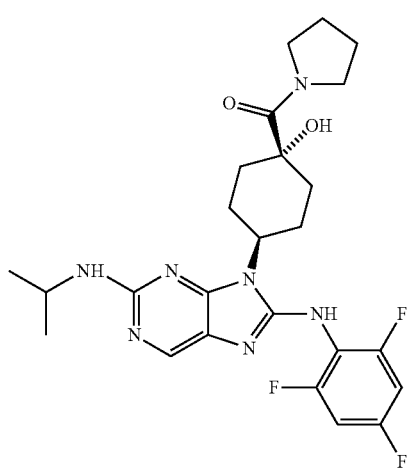 [SMILES: CC(C)Nc1ncc2nc(Nc3c(F)cc(F)cc3F)n([C@H]3CC[C@@](O)(C(=O)N4CCCC4)CC3)c2n1] 438
TABLE 1-continued
Compound
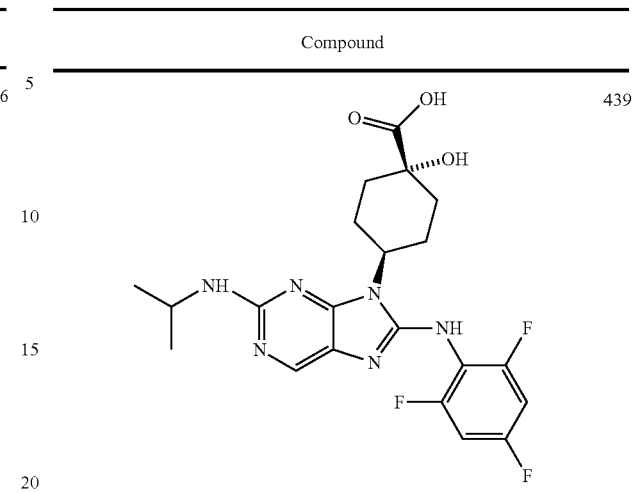 439
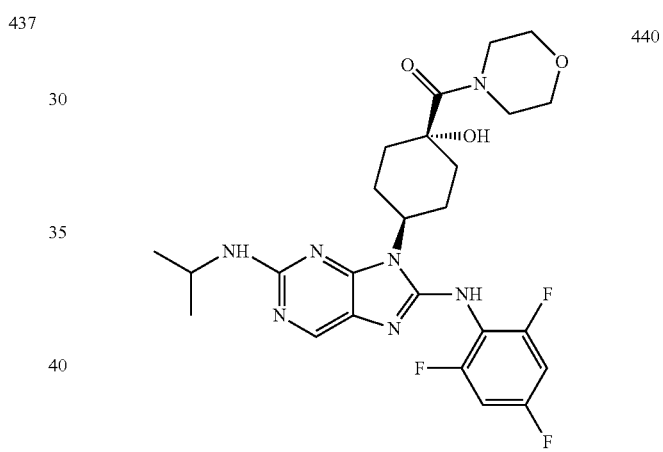 440
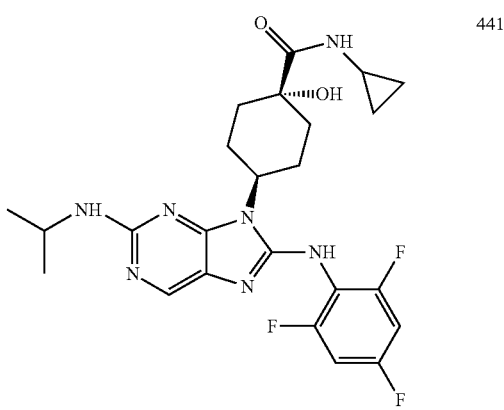 441

TABLE 1-continued
Compound
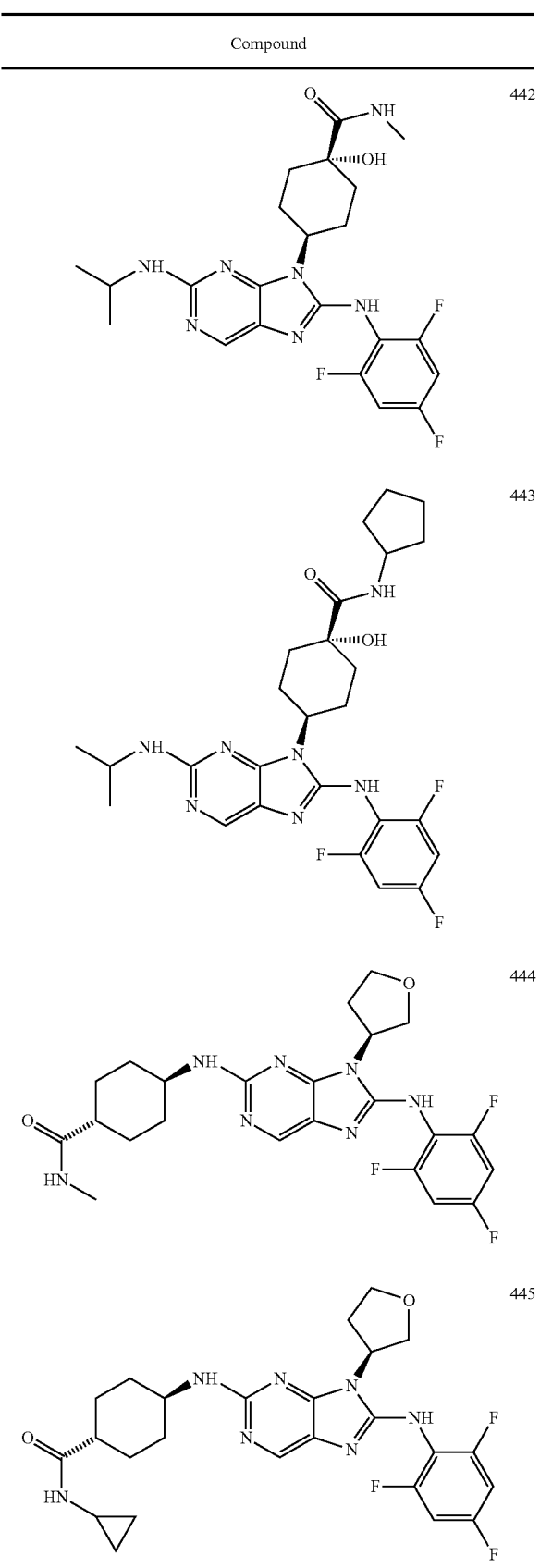
442
443
444
445
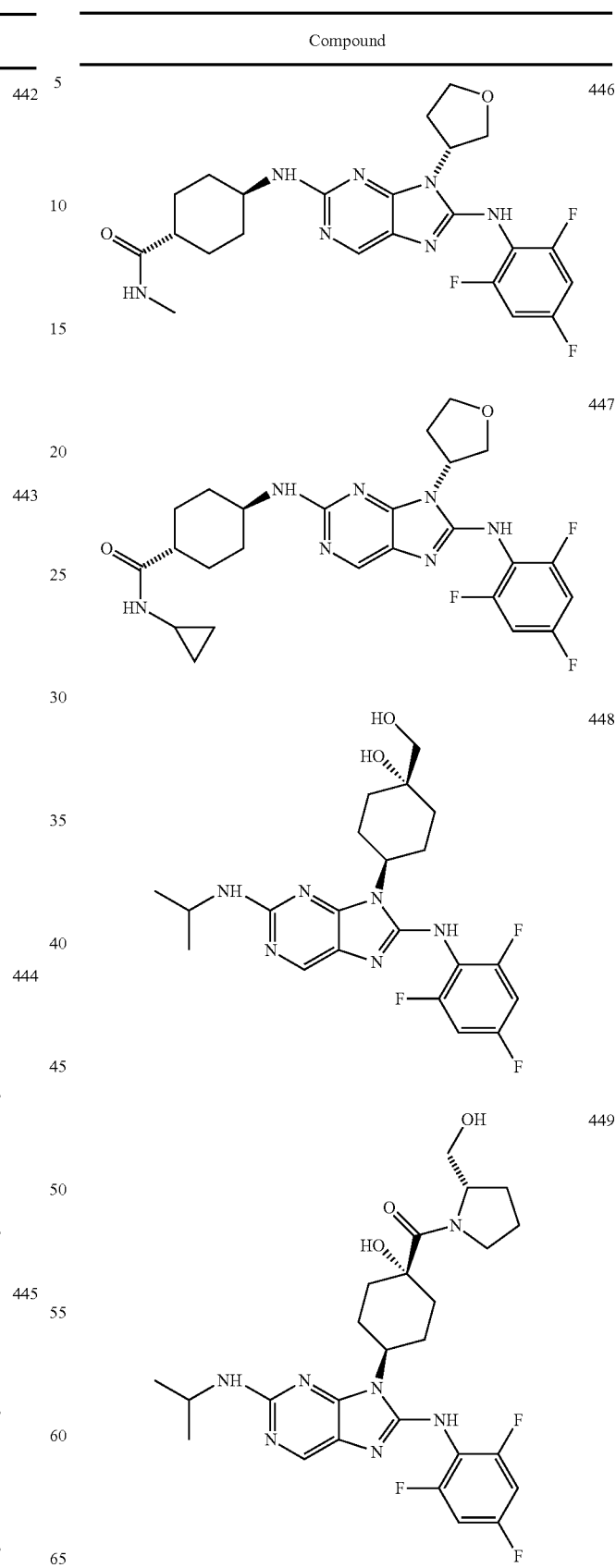
446
447
448
449

TABLE 1-continued
Compound
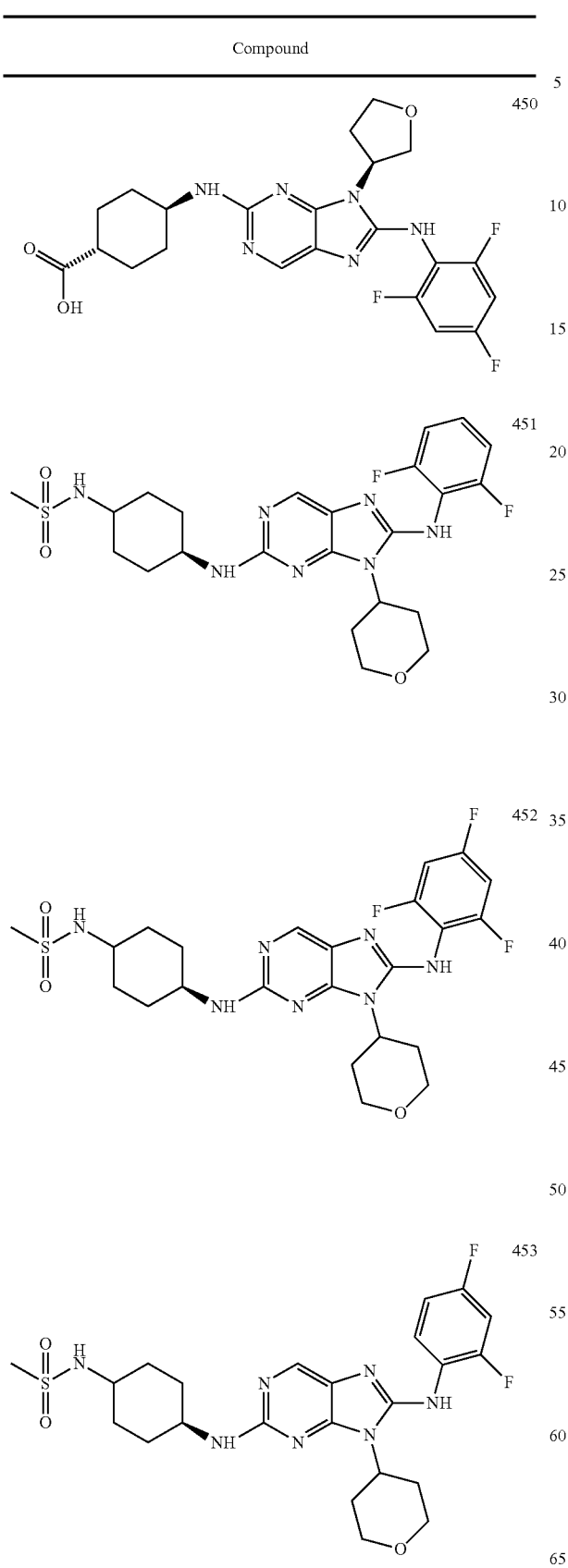
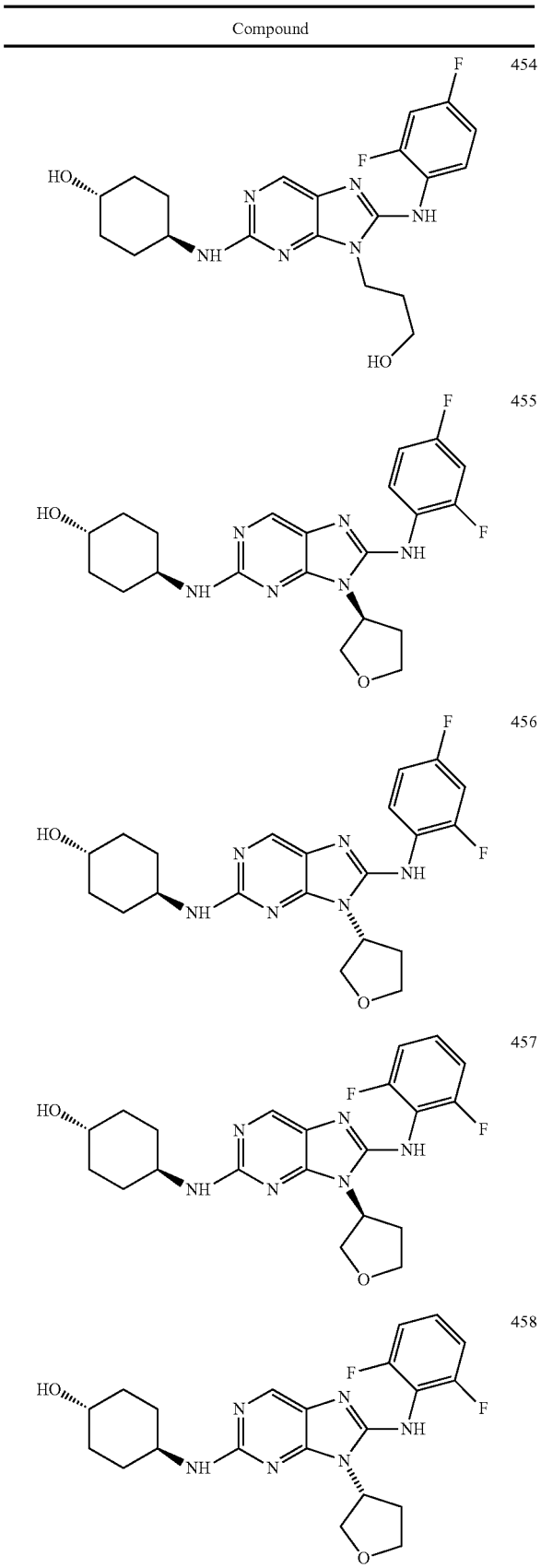

TABLE 1-continued
| Compound | | Compound | |
|---|---|---|---|
| 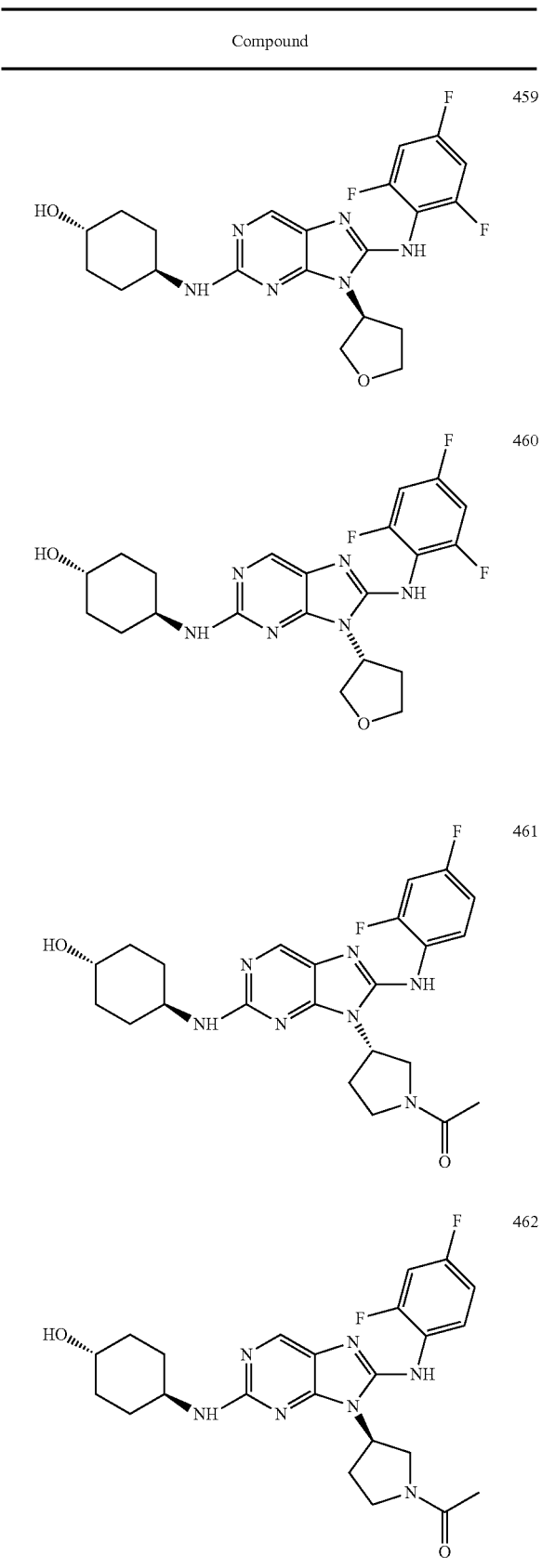 | 459<br><br>460<br><br>461<br><br>462 | 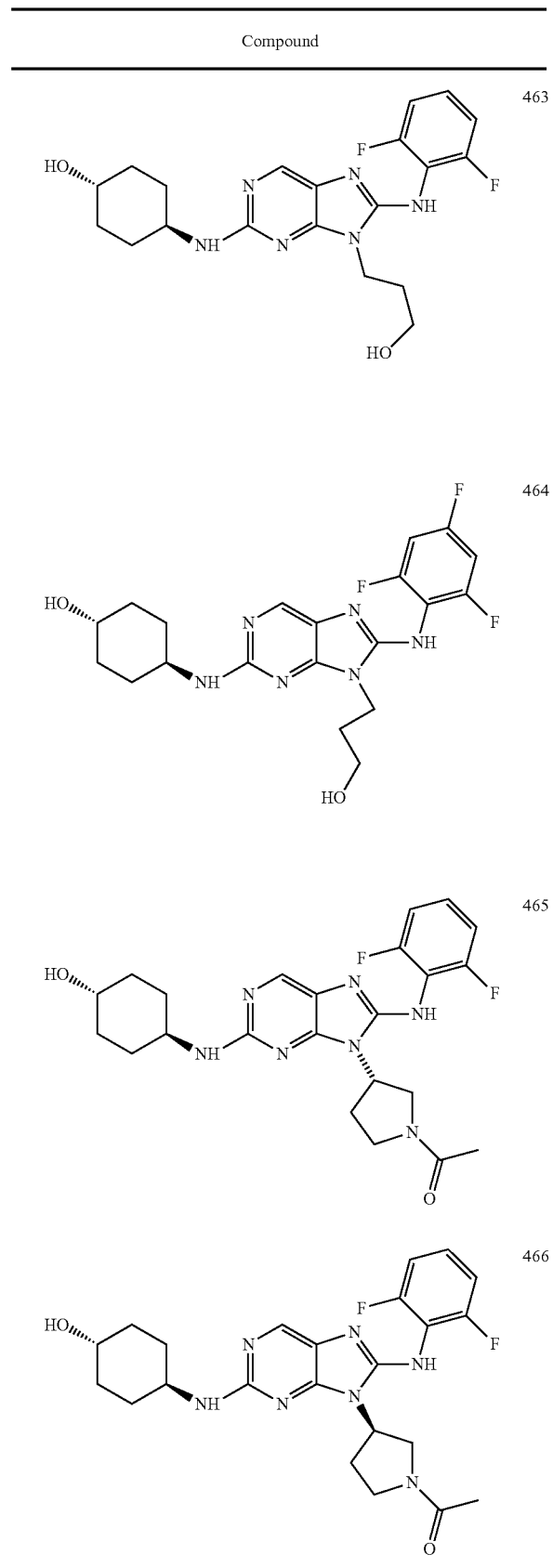 | 463<br><br>464<br><br>465<br><br>466 |

TABLE 1-continued
| Compound | |
|---|---|
| 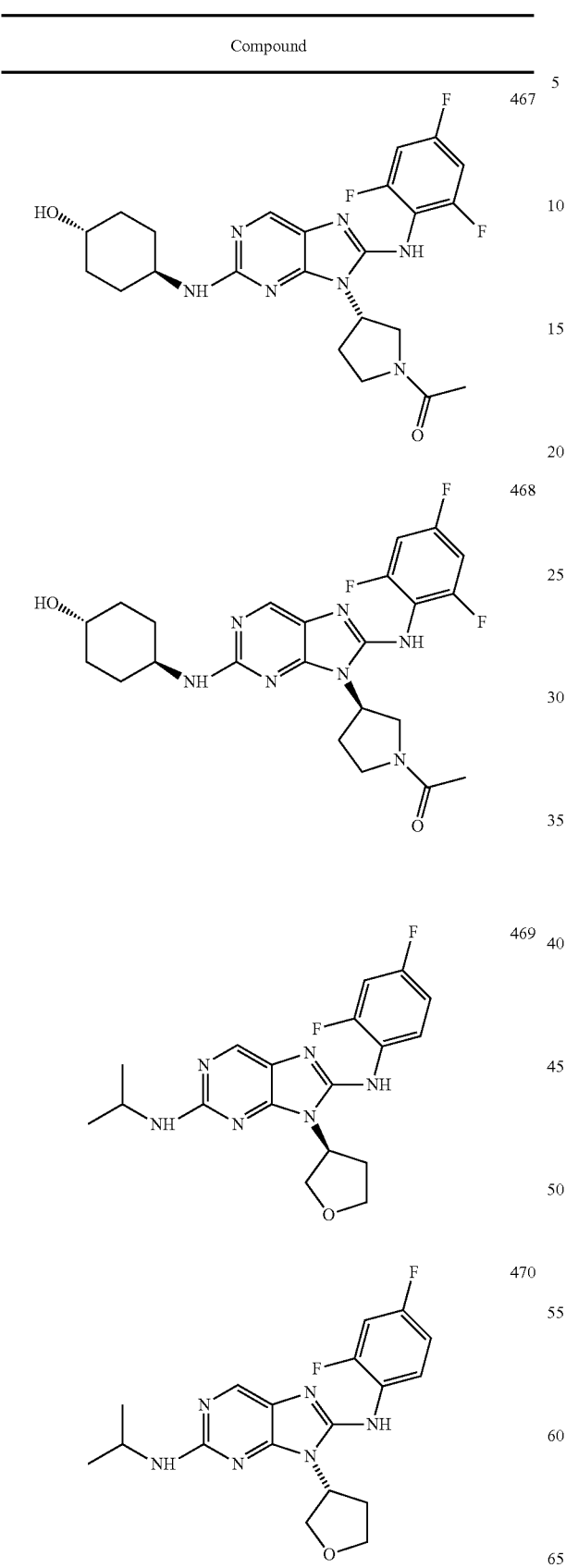 | 467<br><br>468<br><br>469<br><br>470 |
| 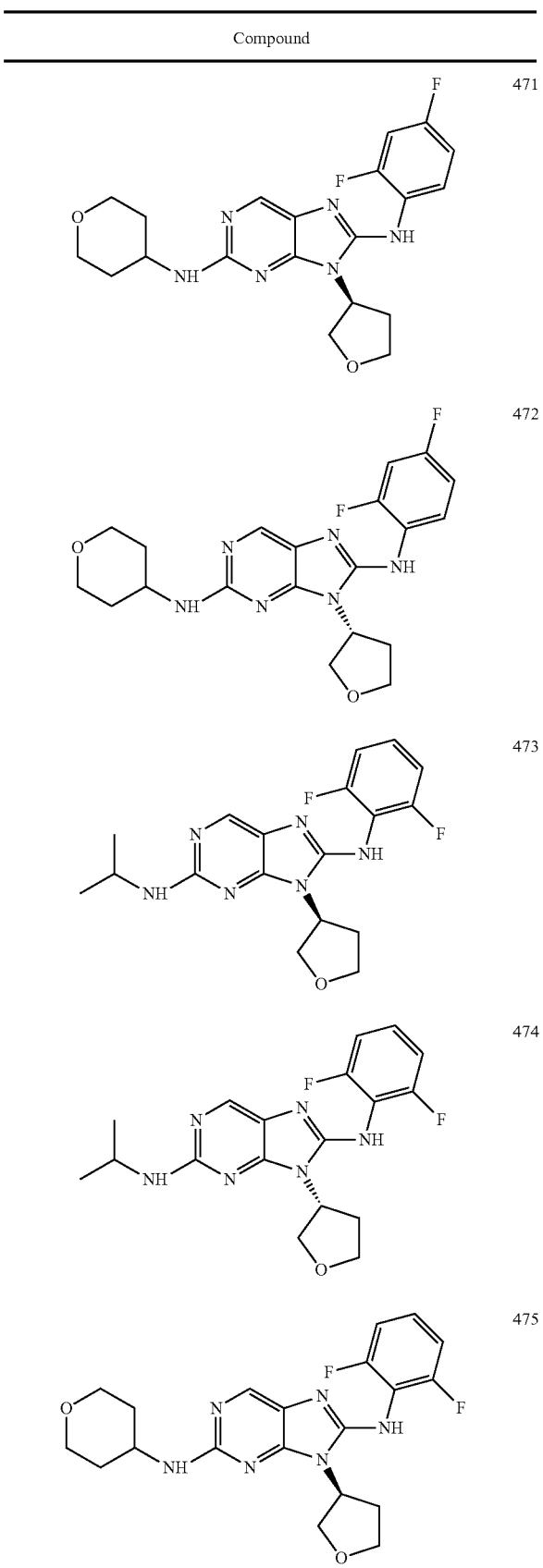 | 471<br><br>472<br><br>473<br><br>474<br><br>475 |

TABLE 1-continued
Compound
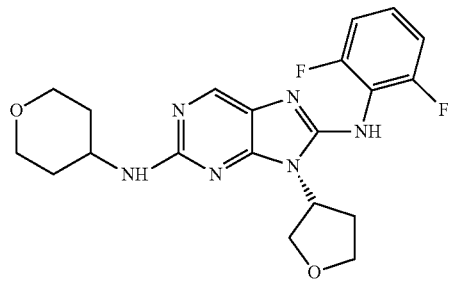
476
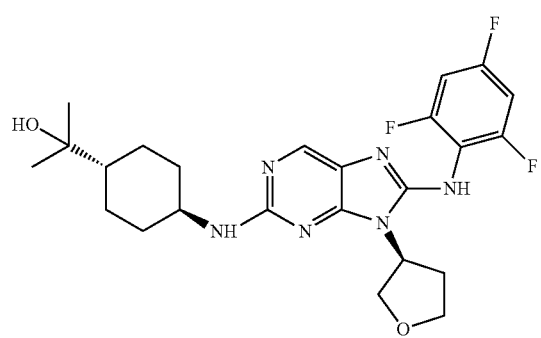 [SMILES: CC(C)(O)[C@H]1CC[C@H](Nc2ncc3nc(Nc4c(F)cc(F)cc4F)n([C@H]4CCOC4)c3n2)CC1]
477
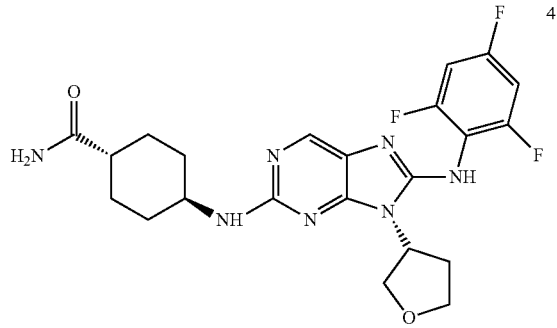
478
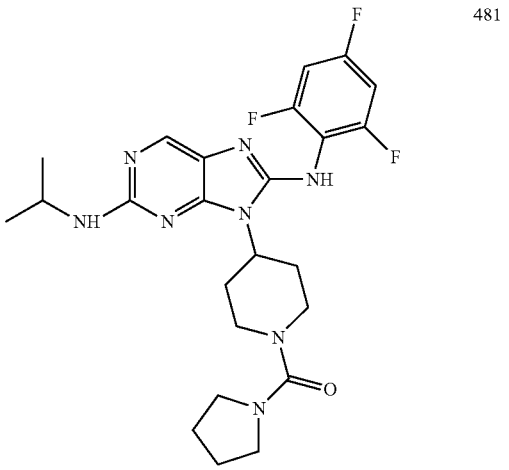
479
TABLE 1-continued
Compound
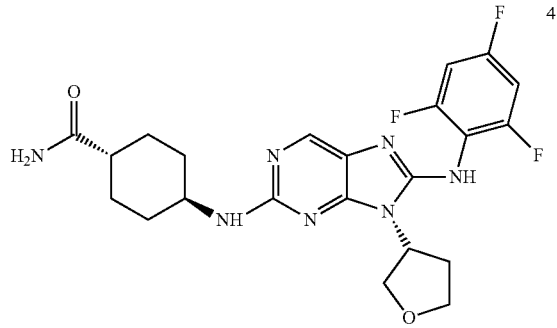
480
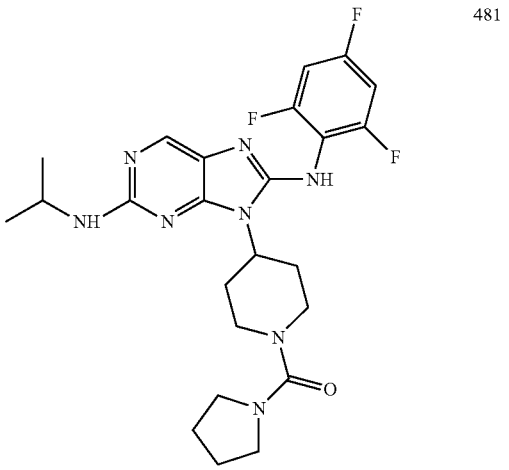
481
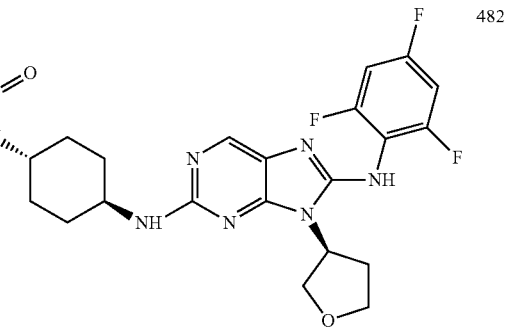
482
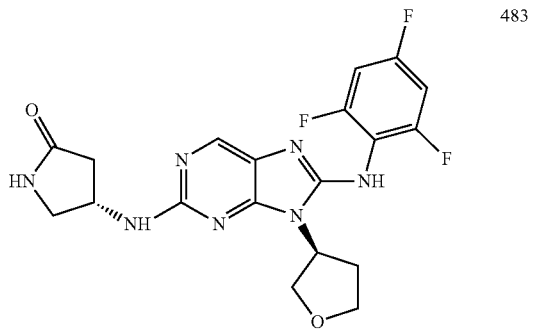
483

TABLE 1-continued
Compound
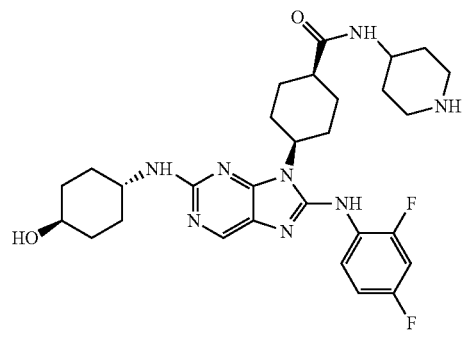 [SMILES: O=C(NC1CCNCC1)[C@H]1CC[C@@H](n2c(Nc3ccc(F)cc3F)nc3cnc(N[C@H]4CC[C@H](O)CC4)nc32)CC1] 484
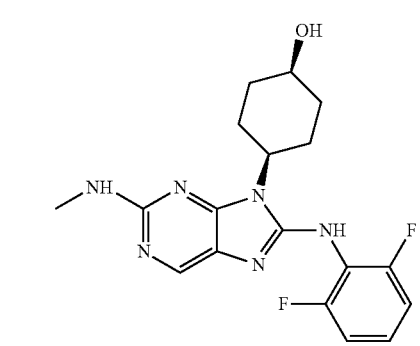 [SMILES: CNc1ncc2nc(Nc3c(F)cccc3F)n([C@H]3CC[C@@H](O)CC3)c2n1] 485
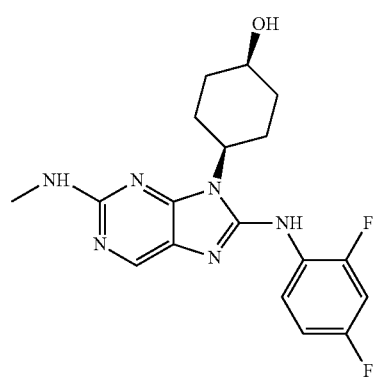 [SMILES: CNc1ncc2nc(Nc3ccc(F)cc3F)n([C@H]3CC[C@@H](O)CC3)c2n1] 486
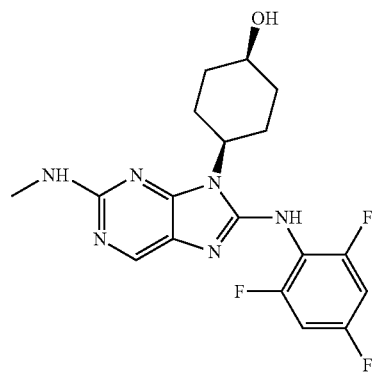 [SMILES: CNc1ncc2nc(Nc3c(F)cc(F)cc3F)n([C@H]3CC[C@@H](O)CC3)c2n1] 487
TABLE 1-continued
Compound
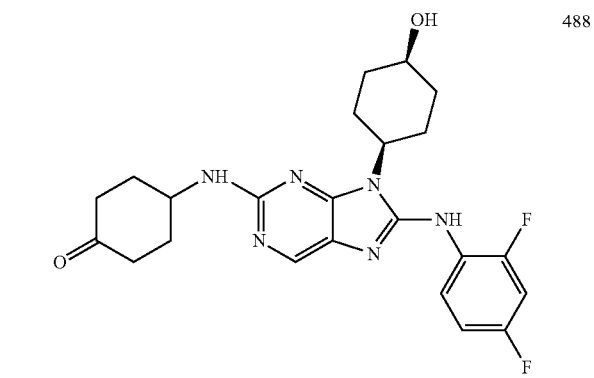 488
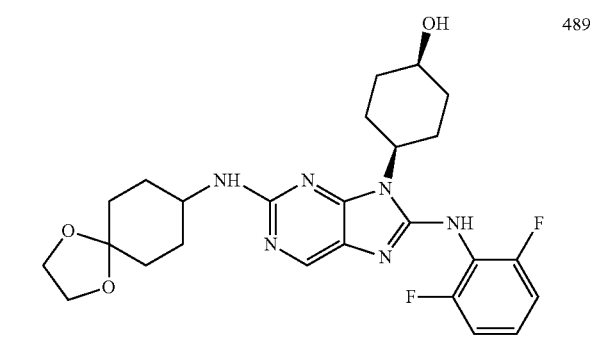 489
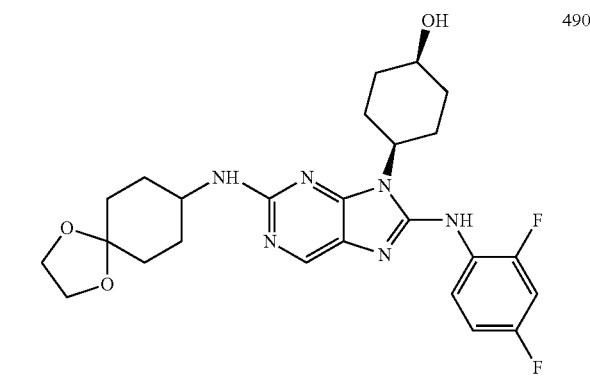 490
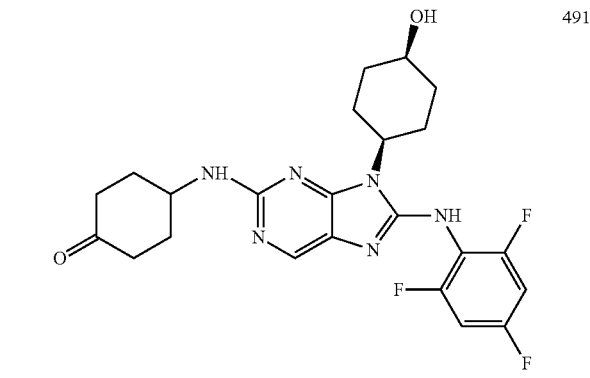 491

TABLE 1-continued
Compound
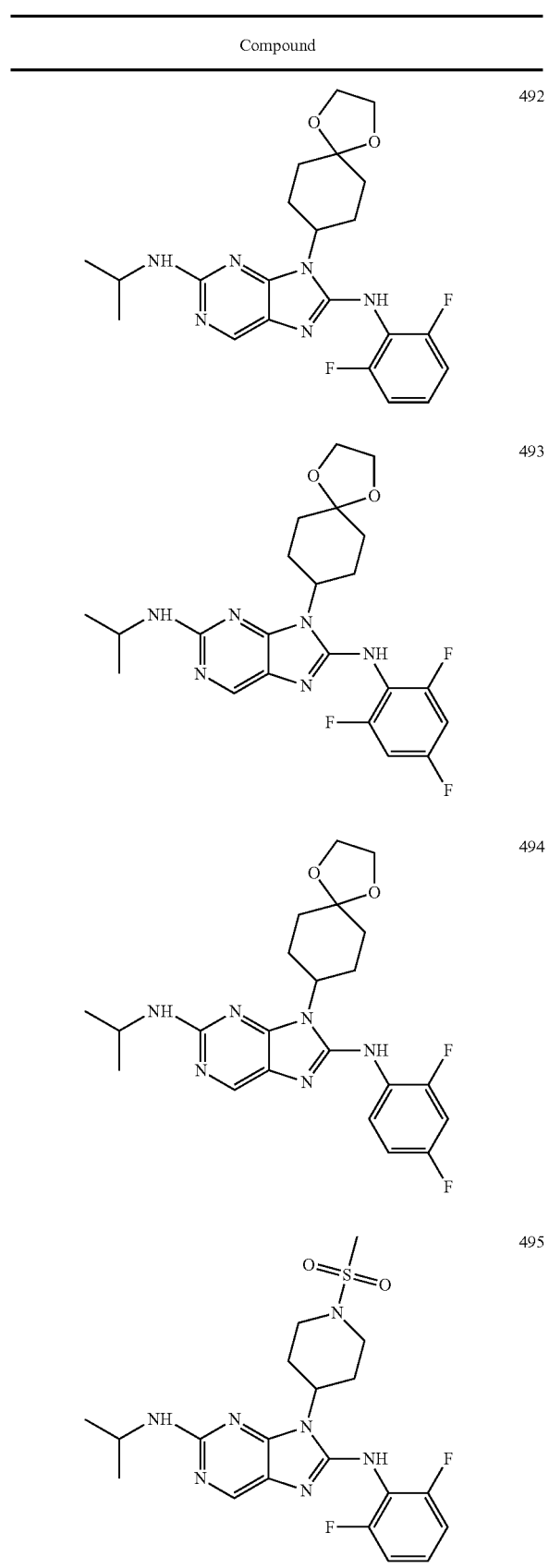
492
493
494
495
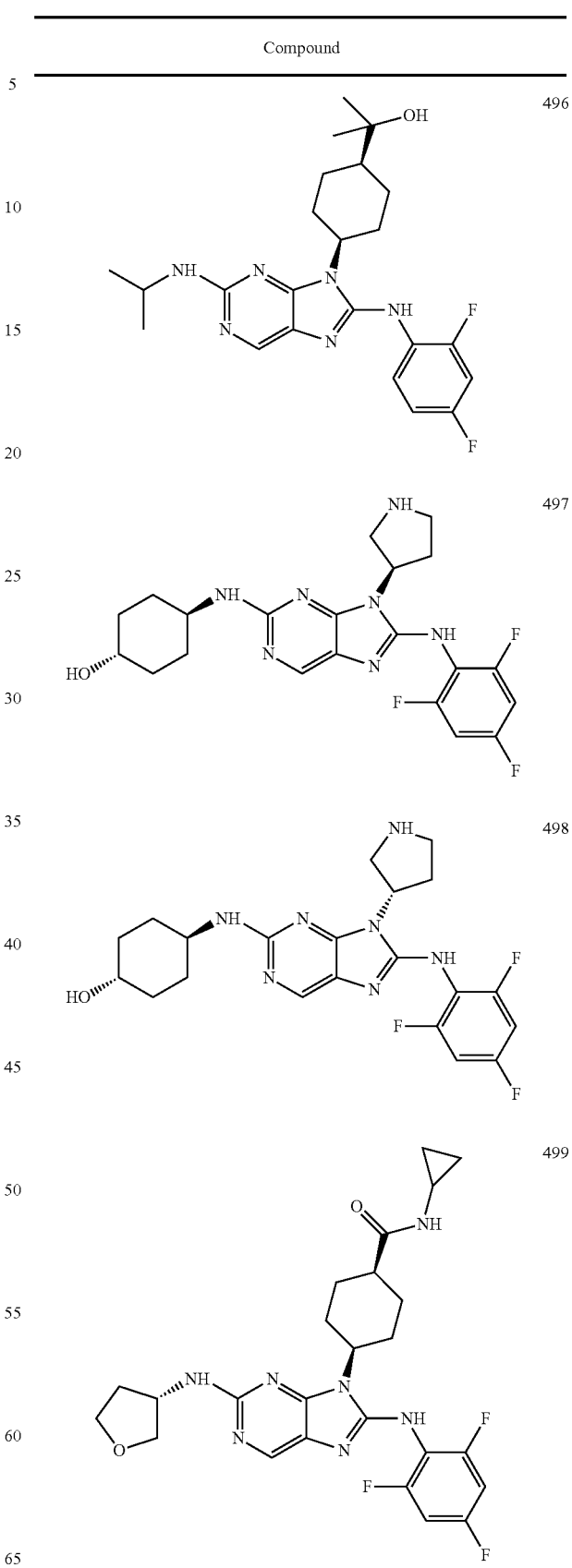
496
497
498
499

TABLE 1-continued

Compound

TABLE 1-continued
Compound
508 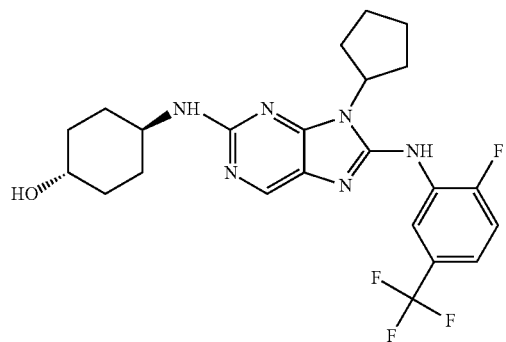 [SMILES: O[C@H]1CC[C@H](Nc2ncc3nc(Nc4cc(C(F)(F)F)ccc4F)n(C4CCCC4)c3n2)CC1]
509 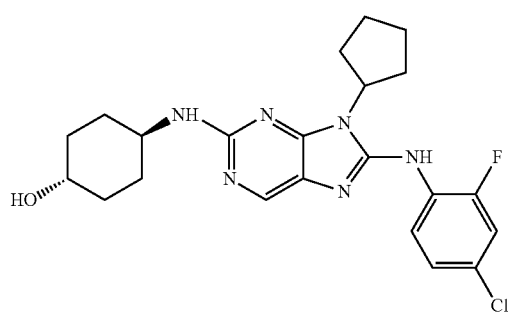 [SMILES: O[C@H]1CC[C@H](Nc2ncc3nc(Nc4ccc(Cl)cc4F)n(C4CCCC4)c3n2)CC1]
510 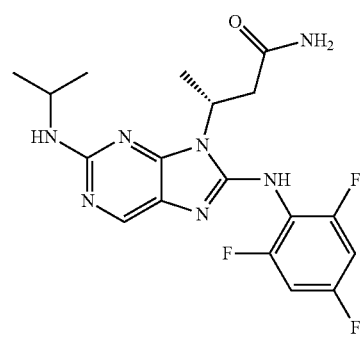 [SMILES: CC(C)Nc1ncc2nc(Nc3c(F)cc(F)cc3F)n([C@H](C)CC(N)=O)c2n1]
511 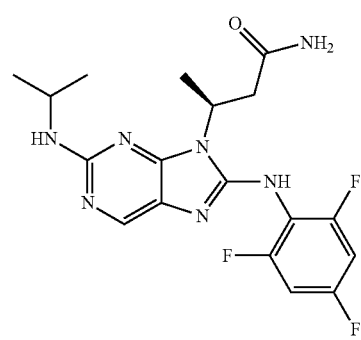 [SMILES: CC(C)Nc1ncc2nc(Nc3c(F)cc(F)cc3F)n([C@@H](C)CC(N)=O)c2n1]
TABLE 1-continued
Compound
512 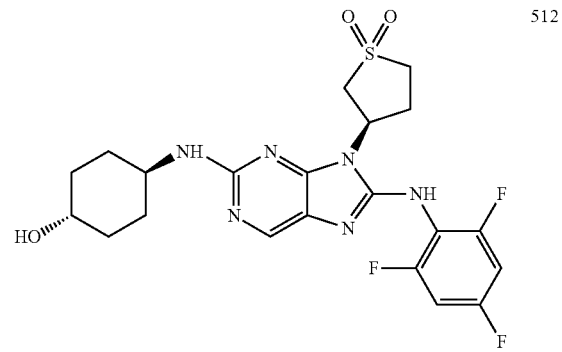
513 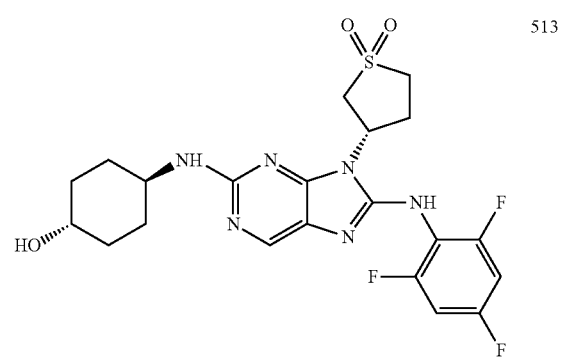
514 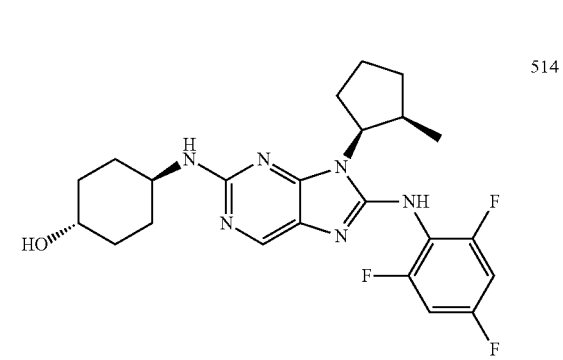
515 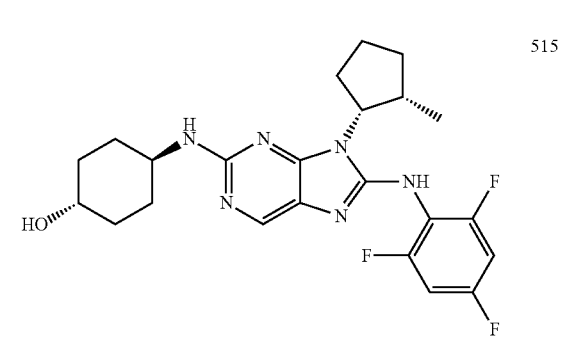

TABLE 1-continued
Compound
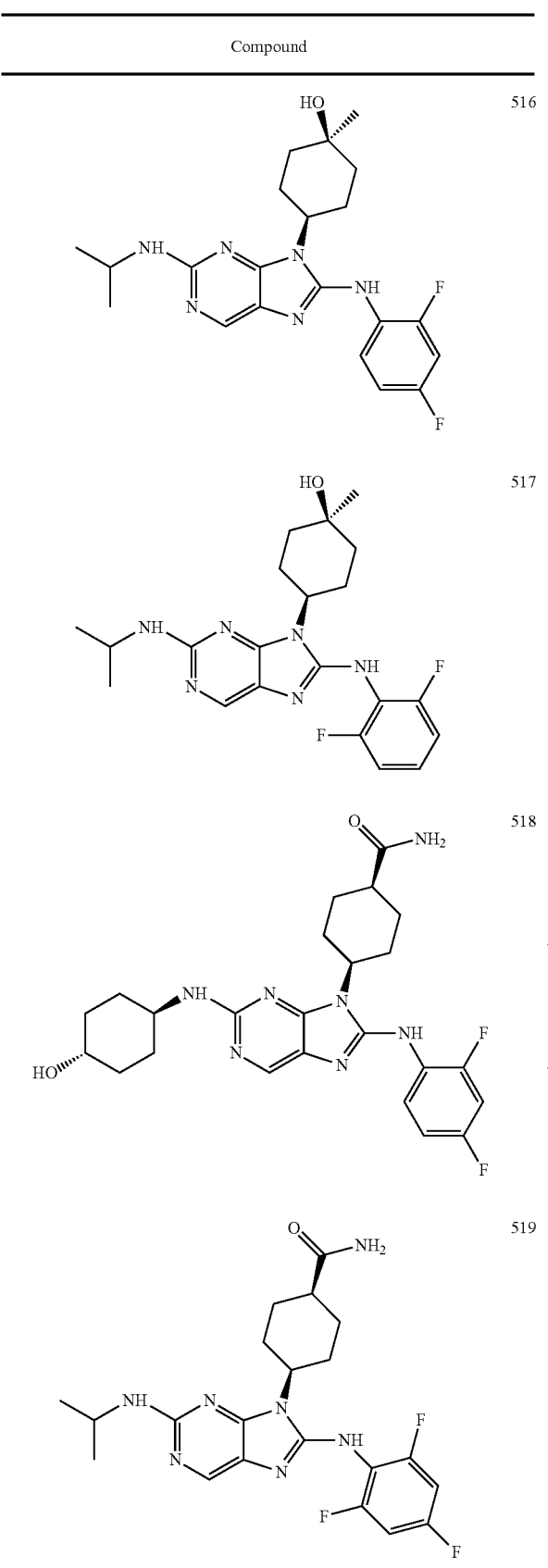
516
517
518
519
TABLE 1-continued
Compound
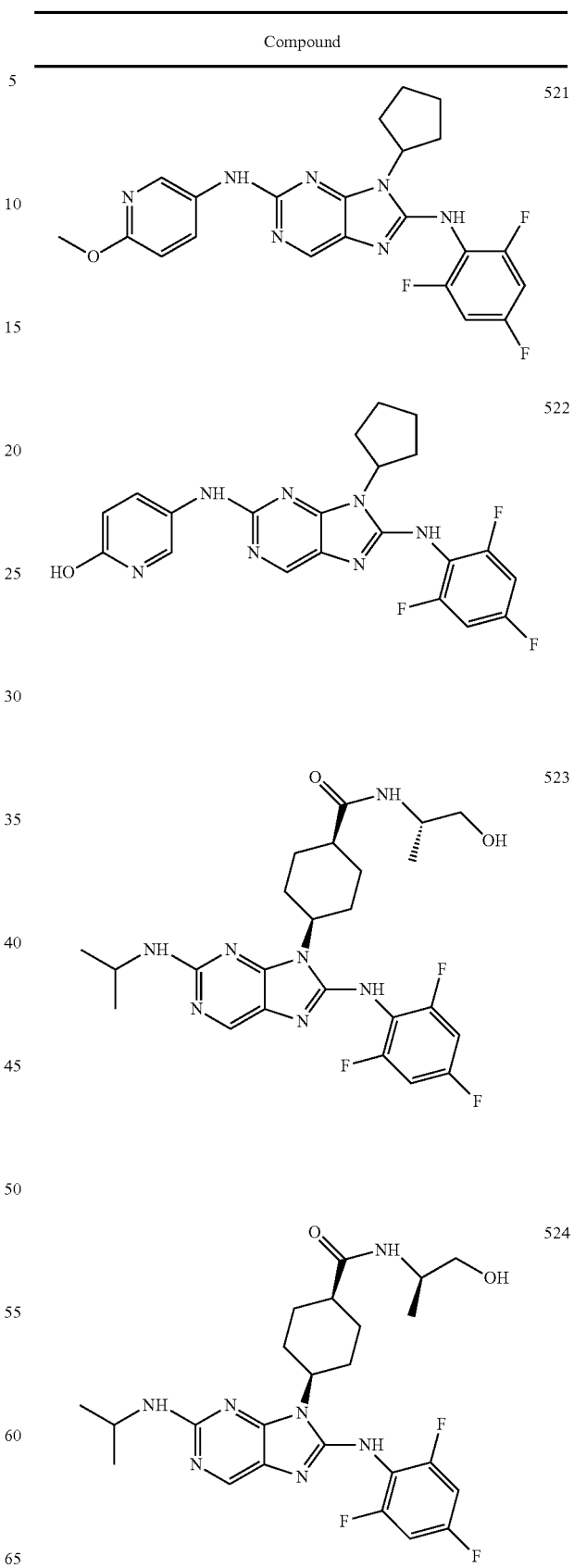
521
522
523
524

TABLE 1-continued

Compound

TABLE 1-continued

Compound

533

534

535

536

Aminopurine Compounds set forth in Table 1 were tested in the JNK inhibitor assays described herein and were found to have activity as JNK inhibitors (see U.S. Pat. Nos. 7,521, 446, 7,723,340 and 7,759,342; and International Pub. Nos. WO 2006/076595 and WO 2007/127382, the disclosure of each of which is incorporated herein by reference in its entirety). In one embodiment, the Aminopurine Compound is compound #425. In one embodiment, the Aminopurine Compound is compound #459, namely, 4-((9-((3S)-tetrahydro-3-furanyl)-8-((2,4,6-trifluorophenyl)amino)-9H-purin-2-yl)amino)-trans-cyclohexanol, having the following structure:

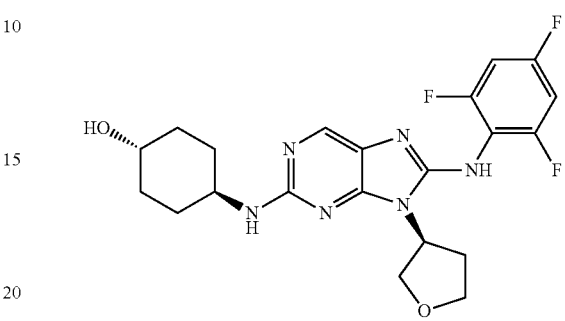

or a pharmaceutically acceptable salt or solvate thereof ("JNKi-1").

In another embodiment, the Aminopurine Compound is the tautomer of 4-((9-((3S)-tetrahydro-3-furanyl)-8-((2,4,6-trifluorophenyl)amino)-9H-purin-2-yl)amino)-trans-cyclohexanol, specifically the compound (S,E)-4-((9-(tetrahydrofuran-3-yl)-8-((2,4,6-trifluorophenyl)imino)-8,9-dihydro-7H-purin-2-yl)amino)cyclohexanol, having the following structure:

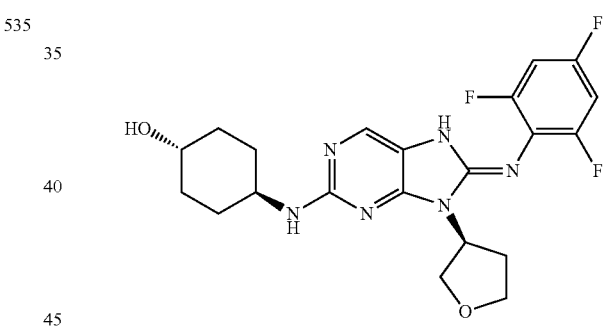

or a pharmaceutically acceptable salt or solvate thereof.

In one embodiment, the Aminopurine Compound is compound #185.

5.4 Methods for Making Aminopurine Compounds

The Aminopurine Compounds can be made using conventional organic syntheses. By way of example and not limitation, Aminopurine Compounds can be prepared according to the methods described in U.S. Pat. Nos. 7,521,446, 7,723,340 and 7,759,342; and International Pub. Nos. WO 2006/076595 and WO 2007/127382, the disclosure of each of which is incorporated herein by reference in its entirety. A hydrate of an Aminopurine Compound in crystalline form can be prepared according to the methods described in U.S. Pat. App. Pub. No. 2009/0048275 (see, e.g., page 4, paragraph (0057) to page 8, paragraph (0098) including the figures referenced therein, and page 5, paragraph (0071) to page 6, paragraph (0077), including the figures referenced therein), the disclosure of which is incorporated herein by reference in its entirety.

In one embodiment, the Aminopurine Compound is a free base. In certain embodiments, the free base is a solid. In certain embodiments, the free base is an amorphous solid. In yet another embodiment, the free base is crystalline. In certain embodiments, the free base is in crystalline Form A. In one embodiment, the crystalline form of the Aminopurine Compound comprises a tautomer of compound (I). In certain embodiments, the free base is in crystalline Form B.

In another embodiment, the Aminopurine Compound is a pharmaceutically acceptable solvate of the free base. In one embodiment, the solvate is a hydrate. In another embodiment, the hydrate is in a crystalline form. In another embodiment, the tautomer of the Aminopurine Compound is in a crystalline form.

5.5 Methods of Use

The Aminopurine Compounds have utility as pharmaceuticals to treat, prevent or improve conditions in animals or humans. Further, the Aminopurine Compounds are active against protein kinases including those involved in scleroderma, keloids, UV injury, sunburn or scar formation. Accordingly, provided herein are many uses of the Aminopurine Compounds, including the treatment, improvement or prevention of those conditions set forth herein. The methods provided herein comprise the administration of an effective amount of an Aminopurine Compound to a patient in need thereof.

Provided herein are methods of treating scleroderma or a symptom thereof, comprising administering an effective amount of an Aminopurine Compound to a patient having scleroderma.

Further provided herein are methods of preventing scleroderma or a symptom thereof, comprising administering an effective amount of an Aminopurine Compound to a patient at risk of having scleroderma.

In certain embodiments, the scleroderma is localized, systemic, limited or diffuse scleroderma.

In certain embodiments, the systemic scleroderma comprises CREST syndrome (Calcinosis, Raynaud's syndrome, esophagaeal dysfunction or dysmotility, sclerodactyl), telangiectasia). Scleroderma is also known as systemic sclerosis or progressive systemic sclerosis. In certain embodiments, provided herein are methods of treating or preventing Raynaud's disease or syndrome. In certain embodiments, systemic sclerosis comprises scleroderma lung disease, scleroderma renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life.

In certain embodiments, limited scleroderma is limited to the hands, the face, neck, or combinations thereof.

In certain embodiments, diffuse scleroderma comprises skin tightening and also occurs above the wrists (or elbows). In certain embodiments, the diffuse systemic sclerosis is sine scleroderma, comprising internal organ fibrosis, but no skin tightening; or familial progressive systemic sclerosis.

In one embodiment, scleroderma is not associated with wasting, such as disease-related wasting.

In one embodiment, provided herein are methods for the reduction, inhibition, or prevention of one or more of the following symptoms of scleroderma: (i) gradual hardening, thickening, and tightening of the skin (e.g., in extremities, such as hands, face, and feet); (ii) skin discoloration; (iii) numbness of extremities; (iv) shiny skin; (v) small white lumps under the surface of the skin that erupt into a chalky white fluid; (vi) Raynaud's esophagaeal dysfunction (pain, numbness, and/or color changes in the hands caused by spasm of the blood vessels upon exposure to cold or emotional stress); (vii) telangiectasia (red spots on, e.g., the hands, palms, forearms, face, and lips); (viii) pain and/or stiffness of the joints; (ix) swelling of the hands and feet; (x) itching of the skin; (xi) stiffening and curling of the fingers; (xii) ulcers (sores) on the outside of certain joints, such as knuckles and elbows; (xiii) digestive problems, such as heartburn, difficulty in swallowing, diarrhea, irritable bowel, and constipation; (xiv) fatigue and weakness; (xv) shortness of breath; (xvi) arthritis; (xvii) hair loss; (xviii) internal organ problems; (xix) digital ulcers; or (xx) digital auto-amputation, comprising administering an effective amount of an Aminopurine Compound to a patient in need thereof.

Further provided herein are methods for treating, preventing or improving keloids (also known as a "keloidal scars") comprising administering an effective amount of an Aminopurine Compound to a patient having or at risk of having keloids. Keloids include raised and ill defined growth of skin in the area of damaged skin.

Further provided herein are methods for treating or preventing UV injury or sunburn comprising administering an effective amount of an Aminopurine Compound to a patient having or at risk of having a UV injury or sunburn. The Aminopurine Compounds are useful for treating or preventing UV injury or sunburn due to exposure of the skin to ultraviolet (UV) radiation (e.g., sunlight), including, but not limited to UVA, UVB, or both UVA and UVB. In one embodiment, the Aminopurine Compounds are useful for preventing UV injury or sunburn due to exposure of the skin to ultraviolet (UV) radiation (e.g., sunlight), including, but not limited to UVA, UVB, or both UVA and UVB.

In one embodiment, provided herein are methods for the reduction, inhibition or prevention of one or more of the following symptoms of UV injury and/or sunburn: (i) apoptotic cell death in the skin; (ii) apoptotic cell death in the epidermis; (iii) skin inflammation, (iv) erythema or tissue damage to skin; (v) immediate pigment darkening reaction; (vi) delayed tanning reaction; (vii) skin redness and irritation; (viii) shock; (ix) skin blistering; (x) chills; (xi) fever; (xii) nausea or vomiting, or both, (xiii) flulike symptoms, such as fever, severe aches and pains in the joints and muscles and around the eyes, and generalized weakness; or (xiii) skin loss, comprising administering an effective amount of an Aminopurine Compound to a patient in need thereof.

Also provided herein are methods for improving or preventing scar formation, comprising administering an effective amount of an Aminopurine Compound to a patient at risk for scar formation (e.g., having a wound or expecting a wound, such as that from a surgical procedure). The Aminopurine Compounds are useful for improving or preventing scar formation. In one embodiment, provided herein are methods for the improvement of prevention of one or more of the following: (i) size reduction of a scar, as measured by the length, width, or thickness of the scar; (ii) reduction in or absence of pain associated with the scar; (iii) reduction in or absence of itching associated with the scar; (iv) reduction in or absence of pigmentation in the scar; (v) increase of pliability in the scar; or (vi) a decrease in vascularity within the scar (evidenced, e.g., by a color change from purple to red to pink to white within the scar) comprising administering an effective amount of an Aminopurine Compound to a patient in need thereof.

Further provided herein are methods of inducing regression of fibrosis comprising administering an effective amount of an Aminopurine Compound to a patient having fibrosis.

Further provided herein are methods of inhibiting or reducing expression or synthesis of extracellular matrix proteins comprising administering an effective amount of an Aminopurine Compound to a patient in need thereof.

Further provided herein are methods for achieving one or more clinical endpoints associated with scleroderma, keloids, UV injury, sunburn or scar formation comprising administering an effective amount of an Aminopurine Compound to a patient or a patient population in need thereof.

Further provided herein are methods for increasing the overall survival, objective response rate, time to progression, progression-free survival and/or time-to-treatment failure of a patient or a patient population having scleroderma comprising administering an effective amount of an Aminopurine Compound to said patient or patient population.

Further provided herein are methods for decreasing mortality, respiratory mortality and/or respiratory hospitalization of a patient or a patient population having scleroderma comprising administering an effective amount of an Aminopurine Compound to said patient or patient population.

Further provided herein are methods for improving the modified Rodnan skin score of a patient or a patient population having scleroderma comprising administering an effective amount of an Aminopurine Compound to said patient or patient population. In one embodiment, the improvement in modified Rodnan skin score is 5, 10, 15 or 20 points or more.

Further provided herein are methods for improving or reducing the skin thickness of a patient or a patient population having scleroderma comprising administering an effective amount of an Aminopurine Compound to said patient or patient population. In one embodiment, the skin thickness is reduced by about 20%, about 25%, about 30%, about 40%, about 50%, about 60%, about 70% about 80%, about 90% or more.

Further provided herein are methods for improving or reducing skin induration of a patient or a patient population having scleroderma comprising administering an effective amount of an Aminopurine Compound to said patient or patient population.

Further provided herein are methods for improving the dermatology quality of life index of a patient or a patient population having scleroderma comprising administering an effective amount of an Aminopurine Compound to said patient or patient population.

Further provided herein are methods for improving the pulmonary function of a patient or a patient population having scleroderma comprising administering an effective amount of an Aminopurine Compound to said patient or patient population.

Further provided herein are methods for improving the carbon monoxide diffusing capacity of a patient or a patient population having scleroderma comprising administering an effective amount of an Aminopurine Compound to said patient or patient population. In one embodiment, the carbon monoxide diffusing capacity of a patient is improved by an improvement in the diffusing capacity of the lung for carbon monoxide ($D_L co$) of about 10%, about 20%, about 25%, about 30%, about 40%, about 50%, about 60%, about 70% about 80%, about 90% or more.

Further provided herein are methods for improving the Mahler Dyspnea index of a patient or a patient population having scleroderma comprising administering an effective amount of an Aminopurine Compound to said patient or patient population. In one embodiment, the improvement in Mahler Dyspnea index is 4, 5, 6, 7, 8, 9 or 10 points or more.

Further provided herein are methods for improving the Saint George's Respiratory Questionnaire score of a patient or a patient population having scleroderma comprising administering an effective amount of an Aminopurine Compound to said patient or patient population. In one embodiment, the improvement in Saint George's Respiratory Questionnaire score is 4, 8, 12, 16, 20, 24, 28, 32, 36, 40, 44, 48, 52 points or more.

Further provided herein are methods for improving the UCLA scleroderma clinical trial consortium gastrointestinal tract score of a patient or a patient population having scleroderma comprising administering an effective amount of an Aminopurine Compound to said patient or patient population.

Further provided herein are methods for treating or preventing digital ulcer of a patient or patient population having scleroderma comprising administering an effective amount of an Aminopurine Compound to said patient or patient population.

Further provided herein are methods improving flow-mediated dilatation of a patient or a patient population having scleroderma comprising administering an effective amount of an Aminopurine Compound to said patient or patient population.

Further provided herein are methods improving or increasing the six minute walk distance of a patient or a patient population having scleroderma comprising administering an effective amount of an Aminopurine Compound to said patient or patient population. In one embodiment, the improvement in the six minute walk distance is about 200 meters, about 250 meters, about 300 meters, about 350 meters, about 400 meters or more.

In certain embodiments, the methods provided herein comprise administering an Aminopurine Compound with one or more second active agents, including a blood pressure medication, an antiinflammatory agent, an immune suppressing agent, a calcium channel blocker, a nitrate, a selective seratonin reuptake inhibitor, a proton pump inhibitor, an antibiotic, an emollient, a calcium antagonist, a blood-thinning agent, an agent useful for treating pulmonary hypertension, relaxin (ConXn™), an endothelin receptor antagonist or a nonsteroidal antiinflammatory (NSAID) agent.

In one embodiment, the blood pressure medication is an angiotensin converting enzyme (ACE) inhibitor, such as captopril.

In one embodiment, the antiinflammatory agent is a corticosteroid. In another embodiment, the antiinflammatory agent is colchicine.

In one embodiment, the immune suppressing agent is azathioprine (Imuran™, Azasan™), methotrexate (Rheumatrex™, Trexall™), penicillamine (Depen™, Cuprimine™), cyclophosphamide (Cytoxan™), mycophenalate (CellCept™, Myfortic™), or prednisone (Deltasone™, Liquid Pred™)

In one embodiment, the calcium channel blocker is nifedipine (Procardia™) or nicardipine.

In one embodiment, the nitrate is nitroglycerin.

In one embodiment, the selective seratonin reuptake inhibitor is fluoxetine (Prozac™).

In one embodiment, the proton pump inhibitor is omeprazole (Prilosec™) esomeprazole (Nexium™) or lansoprazole (Prevacid™).

In one embodiment, the antibiotic is tetracycline or erythromycin.

In one embodiment, the emollient is Lubriderm, Eucerin, a Bag Balm histamine 2 blockers, or trazodone (Desyrel™).

In one embodiment, the blood-thinning agent is heparin.

In one embodiment, the agent useful for treating pulmonary hypertension is prostacyclin (Iloprost™), bosentan (Tracleer™), sildenafil (Viagra™) or tadalafil (Clalis™).

In one embodiment, the endothelin receptor antagonist is sitaxentan, ambrisentan, atrasentan, BQ-123, bosentan, tezosentan or BQ-788.

In one embodiment, the NSAID is naproxen.

5.6 Pharmaceutical Compositions and Routes of Administration

The Aminopurine Compounds can be administered to a patient orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Aminopurine Compounds in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of an Aminopurine Compound to be administered to a patient is rather widely variable and can be subject to the judgment of a health-care practitioner. In general, the Aminopurine Compounds can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of the Aminopurine Compound administered will depend on such factors as the solubility of the active component, the formulation used and the route of administration. In one embodiment, application of a topical concentration provides intracellular exposures or concentrations of about 0.01-10 µM.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of an Aminopurine Compound to a patient in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of an Aminopurine Compound to a patient in need thereof. In a particular embodiment, the methods disclosed herein comprise the administration of 400 mg/day, 600 mg/day or 800 mg/day of an Aminopurine Compound to a patient in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of an Aminopurine Compound. In one embodiment, the unit dosage formulation is about 50 mg or about 100 mg of an Aminopurine compound, for example Jnki-1.

In a particular embodiment, provided herein are unit dosage formulation comprising about 100 mg or 400 mg of an Aminopurine compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of an Aminopurine Compound.

An Aminopurine Compound can be administered once, twice, three, four or more times daily. In a particular embodiment, doses of 600 mg or less are administered as a once daily dose and doses of more than 600 mg are administered twice daily in an amount equal to one half of the total daily dose. In some embodiments, the Aminopurine compound is administered in a dose of 50 mg once daily (i.e. QD), in a dose of 50 mg twice daily (i.e. BID), in a dose of 100 mg daily (i.e. QD), in a dose of 100 mg twice daily (i.e. BID), in a dose of 150 mg daily (i.e. QD), in a dose of 150 mg twice daily (i.e. BID), in a dose of 200 mg daily (i.e. QD), or in a dose of 200 mg twice daily (i.e. BID).

An Aminopurine Compound can be administered orally for reasons of convenience. In one embodiment, when administered orally, an Aminopurine Compound is administered with a meal and water. In another embodiment, the Aminopurine Compound is dispersed in water or juice (e.g., apple juice or orange juice) and administered orally as a suspension.

The Aminopurine Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing an Aminopurine Compound without an additional carrier, excipient or vehicle.

In another embodiment, provided herein are compositions comprising an effective amount of an Aminopurine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing an Aminopurine Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer an Aminopurine Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Aminopurine Compound can be delayed or prolonged by proper formulation. For example, a slowly soluble pellet of the Aminopurine Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Aminopurine Compound in oily or emulsified vehicles that allow it to disperse slowly in the serum.

In certain embodiments, the Aminopurine Compound can be administered in a formulation or dosage for found in U.S. Provisional Pat. App. No. 61/406,292, filed Sep. 25, 2010 or U.S. Provisional Pat. App. No. 61/481,378, filed May 2, 2011, the entire contents of each of which are incorporated by reference herein.

In certain embodiments, the Aminopurine Compound can be cyclically administered to a patient. Cycling therapy involves the administration of the Aminopurine Compound for a period of time, followed by a rest for a period of time and repeating this sequential administration. Cycling therapy can reduce the development of resistance to one or more of the therapies, avoid or reduce the side effects of one of the therapies and/or improves the efficacy of the treatment.

Consequently, in one specific embodiment, an Aminopurine Compound is administered daily in a single or divided doses in a four to six week cycle with a rest period of about a week or two weeks. The methods provided herein further allow the frequency, number and length of dosing cycles to be increased. Thus, in another specific embodiment, the methods provided herein encompasses the administration of an Aminopurine Compound for more cycles than are typical when it is administered alone. In yet another specific embodiment, an Aminopurine Compound is administered for a greater number of cycles than would typically cause dose-limiting toxicity in a patient to whom a second active agent is not also being administered.

In one embodiment, an Aminopurine Compound is administered daily and continuously for three or four weeks at a dose of from about 10 to about 200 mg per day followed by a break of one or two weeks. In another embodiment, an Aminopurine Compound is administered daily and continuously for three or four weeks at a dose of from about 0.1 to 5 mg per day followed by a break of one or two weeks. In a particular embodiment, an Aminopurine Compound is administered in an amount of about 5, 10, 25 or 50 mg/day, preferably in an amount of about 25 mg/day for three to four weeks, followed by one or two weeks of rest in a four or six week cycle.

In another embodiment, an Aminopurine Compound and a second active agent are administered orally, with administration of the Aminopurine Compound occurring 30 to 60 minutes prior to a second active agent, during a cycle of four to six weeks. In another embodiment, the combination of the Aminopurine Compound and a second active agent is administered by intravenous infusion over about 90 minutes every cycle. In a specific embodiment, one cycle comprises the administration of from about 0.1 to about 200 mg/day of an Aminopurine Compound and from about 50 to about 200 mg/m$^2$/day of a second active agent daily for three to four weeks and then one or two weeks of rest. In another specific embodiment, each cycle comprises the administration of from about 1 to about 25 mg/day of an Aminopurine Compound and from about 50 to about 200 mg/m$^2$/day of a second active agent for 3 to 4 weeks followed by one or two weeks of rest. Typically, the number of cycles during which the combinatorial treatment is administered to a patient will be from about one to about 24 cycles, more typically from about two to about 16 cycles and even more typically from about four to about three cycles.

The frequency of administration is in the range of about an hourly dose to a monthly dose. In specific embodiments, administration is from 8 times per day to once every other day or from 1 to 3 times per day. In a specific embodiment, an Aminopurine Compound is administered chronically, e.g., daily.

5.7 Use of Phospho-cJun and cJun as a Biomarker of JNK Activity In Vitro and In Vivo Provided herein are methods for the use of UVB-irradiation of skin and measurement of phospho c-Jun and/or c-Jun using immunohistochemistry as a model to determine the effect of Aminopurine Compounds in human and other patients. The methods can also be used to determine the effect in a patient of selective Aminopurine Compounds alone or in combination with inhibitors of MAP kinase; e.g., whether a compound or combination of compounds inhibits JNK in a patient. The methods herein can accelerate the clinical development of Aminopurine Compounds as the model shows whether the compound at issue hits the JNK target in a patient and also allows the evaluation of dose-response in a patient; which guides the dose selection in clinical development. The methods herein can also be used to identify patient populations who are sensitive to Aminopurine Compounds.

In certain embodiments, provided herein are methods comprising the administration of (an) Aminopurine Compound(s) to a patient and determining the resulting amount of JNK inhibition in said patient using a method provided herein.

Methods provided herein are based, in part, on the discovery that the presence and level of phosphorylated c-Jun or c-Jun in patient skin samples can be utilized as a biomarker to follow the inhibition of JNK. In particular, these biomarkers can be used to predict, assess, and track the effectiveness of Aminopurine Compound therapy in a patient, in particular oral therapy with Aminopurine Compounds, for example, with JNKi-1, or to monitor the patient's compliance to the prescribed regimen of Aminopurine Compound therapy.

The baseline phospho c-Jun immune-reactivity in healthy human skin is low without UVB exposure. UVB-irradiation reliably increases phospho c-Jun immuno-reactivity. The increase starts to plateau at approximately 8 hours post UVB exposure. Oral administration of Aminopurine Compounds, such as those described herein, including but not limited to JNKi-1, at doses of about 75 mg to about 200 mg, partially or completely inhibited the elevation of phospho c-Jun induced by the UVB irradiation, in a majority of patients. The inhibition of JNK is dose-related. UVB-irradiation and phospho c-Jun can be used as a model to evaluate Aminopurine Compounds, including the evaluation of dose-response, and to identify patient populations who are sensitive to Aminopurine Compounds.

Provided herein are methods relating to the use of phospho c-Jun expression induced by UVB-irradiation as a biomarker to evaluate the effectiveness of Aminopurine Compounds. Phospho c-Jun and c-Jun levels can be used to determine whether a treatment is likely to be successful in diseases or conditions associated with JNK.

Without being limited by theory, it is believed that the use of UVB exposure to the skin of a patient and measurement of the amount of phospho c-Jun or c-Jun in said patient's skin prior to and after administration of (an) Aminopurine Compound (s), can be used to evaluate the biological effect of said Aminopurine Compound(s) in said patient. In certain embodiments, the methods provided herein allow for the amount of in vivo inhibition of JNK resulting from administration of (an) Aminopurine Compound(s) to be determined. In certain embodiments, the assays provided herein comprise exposing a first portion of said patient's skin to UVB irradiation, obtaining a sample of said first portion of said patient's skin, measuring the amount of phosphorylated c-Jun or c-Jun in said first portion of said patient's skin immunohistochemically, administering an Aminopurine Compound to said patient, exposing a second portion of said patient's skin to UVB irradiation, obtaining a sample of said second portion of said patient's skin, measuring the amount of phosphorylated c-Jun or c-Jun in said second portion of said patient's skin immunohistochemically, and comparing the levels of phosphorylated c-Jun or c-Jun in said first portion of said patient's skin and said second portion of said patient's skin, wherein a reduction of levels of phosphorylated c-Jun or c-Jun in said second portion of said patient's skin compared to said first portion of said patient's skin indicates inhibition of JNK. In certain embodiments, the assays provided herein comprise using human skin model tissues. In such embodiments, the assays comprise exposing a first sample of said tissue to UVB irradiation, obtaining a sample of said first portion of said tissue, measuring the amount of phosphorylated c-Jun or c-Jun in said first portion of said tissue immunohistochemically, administering an Aminopurine Compound to said tissue, exposing a second portion of said tissue to UVB irradiation, obtaining a sample of said second portion of said tissue, measuring the amount of phosphorylated c-Jun or c-Jun in said second portion of said tissue immunohistochemically, and comparing the levels of phosphorylated c-Jun or c-Jun in said first portion of said tissue and said second portion of said tissue, wherein a reduction of levels of phosphorylated c-Jun or c-Jun in said second portion of said tissue compared to said first portion of said tissue indicates inhibition of JNK.

In such embodiments, human skin model tissues such as EpiDermFT™ may be used. EpiDermFT™ is a reconstituted human skin equivalent, which exhibits morphological and growth characteristics similar to human skin, and has been used widely as a model tissue system in studies relevant to human skin (see, e.g., Zhao J F, Zhang Y J, Kubilus J, Jin X H, Santella R M, Athar M, Wang Z Y, Bickers D R. *Reconstituted 3-Dimensional Human Skin as a Novel in Vitro Model for Studies of Carcinogen*, Biochemical and Biophysical Research Comms. 1999; 254:49-53; Mahns A, Wolber R, Stäb F, Klotz L O, Sies H, *Contribution of UVB and UVA to UV-dependent stimulation of cyclooxygenase-2 expression in artificial epidermis*, Photochem. Photobiol. Sci. 2004; 3:257-62; Sedelnikova O A, Nakamura A, Kovalchuk O, Koturbash I, Mitchell S A, Marino S A, Brenner D J, Bonner W M, *DNA Double-Strand Breaks Form in Bystander Cells after Microbeam Irradiation of Three-dimensional Human Tissue Models*, Cancer Res 2007; 67(9):4295-4302; Hayden P J, Burnham B, Klausner M, Kubilus J, Sheasgreen J E, *Wound Healing Response of the EpiDerm Full Thickness (EpiDermFT) In Vitro Human Skin Equivalent after Solar UV Irradiation*, Presented at the 5th World Congress, Berlin, Germany, August 2005 & The Society of Investigative Dermatology Meeting, Providence, R.I., April-May 2004, TR-328:1-10). EpiDermFT™ samples may be obtained from MatTek Corporation (Ashland, Mass.).

In some embodiments, the immunohistochemistry evaluations of the skin biopsies provided by the methods herein to assess JNK activation comprise a two antibody IHC assay that employs a primary antibody, directed against the target phospho c-Jun or c-Jun, and a secondary antibody conjugated with a chromogenic enzyme. In such embodiments, the secondary antibody-reporter conjugate leaves a differentiating stain when incubated with the substrate reaction mixture, thus marking the location of the primary antibody target complex. This differentiating stain is then recorded with standard bright-field illumination using, e.g., a Nikon microscope. The microscope images are then photographed and electronic images may be scored (blinded) by independent and trained scorers using guidelines as illustrated in the Examples. In certain embodiments, exploratory quantitative IHC analysis may be carried out using a laser scanning cytometer. In such embodiments, the slides are further processed in order to define the nuclear compartment of the epithelial keratinocytes. In such embodiments, the same IHC slides are counterstained with Hematoxylin to tag the nuclear compartment, then scanned using two photodiode channels, 488 nm for the DAB stain (to mark the primary antibody directed against phospho c-Jun or c-Jun) and 633 nm for the Hematoxylin stain, then the nuclei are counted based upon the Hematoxylin signal and the DAB signals are integrated for each nucleus in the epithelium. In some embodiments, the methods provided herein allow for the measurement of phospho c-Jun or c-Jun levels, before and after administration of (an) Aminopurine Compound(s), which can be used as biomarkers for measuring the inhibition of JNK in a patient. In some embodiments of the methods provided herein, a decreased level of phospho c-Jun or c-Jun in said second portion of said patient's skin relative to said first portion of said patient's skin indicates inhibition of JNK. In some embodiments, the methods provided herein allow for the measurement of phospho c-Jun or c-Jun levels before and after administration of (an) Aminopurine Compound(s), which can be used as biomarkers for determining the dose-response relationship for the administration of (an) Aminopurine Compound(s) in a patient. In some embodiments of the methods provided herein, a decreased level of phospho c-Jun or c-Jun in said second portion of said patient's skin relative to said first portion of said patient's skin is proportional to the inhibition of JNK. In some embodiments, the methods provided herein allow for the measurement of phospho c-Jun or c-Jun levels before and after administration of (an) Aminopurine Compound(s), which can be used as biomarkers for determining whether a patient is sensitive to (an) Aminopurine Compound(s). In some embodiments of the methods provided herein, a decreased level of phospho c-Jun or c-Jun in said second portion of said patient's skin relative to said first portion of said patient's skin indicates that said patient is sensitive to said Aminopurine Compound. In some embodiments, the methods provided herein allow for the measurement of phospho c-Jun or c-Jun levels before and after administration of (an) Aminopurine Compound(s), which can be used to determine the effective amount of (an) Aminopurine Compound(s) for the treatment or prevention of a disease or condition associated with JNK in a patient. In some embodiments of the methods provided herein, a decreased level of phospho c-Jun or c-Jun in said second portion of said patient's skin relative to said first portion of said patient's skin may be correlated to indicate the administration of an effective amount of said Aminopurine Compound.

6. EXAMPLES

The following Examples are presented by way of illustration, not limitation.

6.1 Activation of JNK Pathway by Pro-Fibrotic Cytokines and Inhibition of JNK Pathway by Compound JNKi-1

To analyze whether the JNK pathway was activated by TGF-β and PDGF, Western Blot analysis for c-Jun in cultured dermal fibroblasts was performed.

After rinsing twice with PBS, the dermal fibroblasts were trypsinized and lysed with Laemmli Buffer. Five μg of protein from each sample were separated by 10% SDS-PAGE and electrotransferred onto polyvinylidene difluoride (PVDF) membranes according to standard protocols (Distler J H, Jungel A, Kowal-Bielecka O, Michel B A, Gay R E, Sprott H, et al. Expression of interleukin-21 receptor in epidermis from patients with systemic sclerosis. Arthritis Rheum. 2005; 52(3):856-64). Immunoblots were incubated with monoclonal antibodies against c-Jun and phospho-c-Jun (Santa Cruz, Heidelberg, Germany) at a dilution of 1:200 overnight at 4° C. After incubation with horseradish peroxidase-conjugated rabbit anti-mouse antibodies (Dako, Hamburg, Germany) for 1 hour at a dilution of 1:2000, signals were detected with ECL Western Blotting Detection Reagents (Amersham Bioscience, Freiburg, Germany). For confirmation of equal loading of proteins, the amount of β-actin was determined using mouse anti-human β-actin antibodies (Sigma-Aldrich, Munich, Germany; dilution 1:10000).

Stimulation with TGF-β and PDGF potently increased the phosphorylation of c-Jun (FIG. 1). In contrast, pre-incubation with Compound JNKi-1 reduced the stimulatory effects of TGF-β and PDGF on the phosphorylation of c-Jun. In particular, Compound JNKi-1 treatment completely prevented the stimulatory effect of PDGF on c-Jun phosphorylation in fibroblasts (FIG. 1).

6.2 In Vivo Analysis of Antifibrotic Effect of Compound JNKi-1 in Bleomycin-Induced Dermal Fibrosis in the Mouse The selective JNK inhibitor Compound JNKi-1 was tested in a bleomycin-induced dermal fibrosis mouse model, which is considered to represent the early and inflammatory stages of systemic sclerosis (Akhmetshina A, Venalis P, Dees C, Busch N, Zwerina J, Schett G, Distler O, Distler J H, *Treatment with imatinib prevents fibrosis in different preclinical models of systemic sclerosis and induces regression of established fibrosis*, Arthritis Rheum. 2009; 60(1):219-24). Bleomycin is an outmoded anticancer therapeutic that has been demonstrated to cause fibrosis in the lung. In animal models it will similarly induce injury and fibrosis at the site of delivery.

Male and female DBA/2J mice were used. Mice were fed a standard diet with water ad libitum. The room temperature was kept constant at 22° C. with a humidity of 60%.

Compound JNKi-1 was dissolved in 0.5% carboxymethylcellulose (CMC)/0.25% Tween 80 in water. Bleomycin was dissolved in 0.9% sodium chloride (NaCl) at a concentration of 0.5 mg/mL in a total volume of 100 μL. The positive control compound Imatinib mesylate was dissolved in 0.9% NaCl at a concentration of 50 mg/kg/day in a total volume of 100 μL.

Two different dose levels of the JNK-inhibitor Compound JNKi-1 (50 mg/kg and 150 mg/kg, administered twice daily) were used to analyze the anti-fibrotic activity in a mouse model of bleomycin-induced skin fibrosis. For the positive control group, mice were treated intraperitoneally (IP) with imatinib mesylate, which has previously been shown to exert antifibrotic effects. DBA/2J mice (n=5/sex/group) were assigned to one of five treatment groups:

Control group: 0.5% CMC/0.25% Tween 80 in water orally (PO) twice daily (BID) and subcutaneous injections of 100 μL 0.9% NaCl.

Untreated bleomycin group: intradermal injection of bleomycin and 0.5% CMC/0.25% Tween 80 in water orally BID.

50 mg/kg Compound JNKi-1: intradermal injection of bleomycin and Compound JNKi-1 orally BID.

150 mg/kg Compound JNKi-1: intradermal injection of bleomycin and Compound JNKi-1 orally BID.

Positive control group: intradermal injection of bleomycin and imatinib 50 mg/kg/day administered intraperitoneally (IP).

Localized dermal fibrosis was induced by injection of bleomycin every other day for 3 weeks in defined areas of the upper back. Compound JNKi-1 or imatinib was administrated starting from the first dose of bleomycin.

The dermal thickness was determined by staining with hematoxylin and eosin (H & E). The activated fibroblasts (myofibroblasts) at the fibrotic lesions were quantified by immunohistochemistry (IHC) for alpha smooth muscle actin (α-SMA). Collagen concentration in lesional skin was analyzed by hydroxyproline assay. Data are expressed as mean±standard error of the mean (SEM). SPSS17.0 software and the Mann-Whitney-U-test were used for statistical analyses. A p-value of less than 0.05 was considered statistically significant.

In the mouse model of bleomycin-induced fibrosis, dermal thickness decreased dose-dependently by 24%±5% (p=0.012) following treatment with 50 mg/kg Compound JNKi-1 and by 45%±5% (p=0.001) following treatment with 150 mg/kg Compound JNKi-1 (FIG. 2). The number of myofibroblasts was reduced by 80%±10% (p=0.0005) following treatment with 50 mg/kg and by 101%±9% (p=0.001) following treatment with 150 mg/kg of Compound JNKi-1 (FIG. 3). A reduction in dermal thickening by 46%±5% (p=0.002) and decreased myofibroblast count by 51%±10% (p=0.001) were also observed in mice treated with imatinib (FIG. 2 and FIG. 3), a control compound in the study. Furthermore, the collagen content in lesional skin was reduced dose-dependently by 29%±11% (p=0.007) following treatment with 50 mg/kg and by 47%±9% (p=0.001) following treatment with 150 mg/kg of Compound JNKi-1 compared to bleomycin-treated animals (FIG. 4).

Dermal fibrosis with dense accumulation of collagen bundles, inflammatory infiltrates, and replacement of the subcutaneous fat tissue by connective tissue was observed in sham treated bleomycin-challenged mice. In mice treated with Compound JNKi-1, the development of fibrosis by bleomycin was significantly ameliorated (FIG. 5). Treatment with Compound JNKi-1 reduced dermal thickening in a dose-dependent manner by up to 45±2% at doses of 150 mg/kg (p=0.001). This reduction in dermal thickening was comparable to that observed with imatinib at doses of 50 mg/kg (FIG. 5).

The JNK inhibitor Compound JNKi-1 dose-dependently inhibited dermal thickness and accumulation of collagens at the sites of fibrotic lesions in a bleomycin-induced skin fibrosis mouse model. The differentiation of resting fibroblasts into myofibroblasts was completely prevented by Compound JNKi-1 in this mouse model. Compound JNKi-1 has demonstrated in vivo antifibrotic activity.

6.3 Regression of Established Fibrosis by Compound JNKi-1

To evaluate, whether inhibition of JNK might also be effective for the treatment of established fibrosis, a modified model of bleomycin-induced dermal fibrosis was used. Prolonged injections of bleomycin for 6 weeks resulted in progressive fibrosis with increased dermal thickening to 226±6% compared to a dermal thickening of 175±8% after 3 weeks of bleomycin challenge (p=0.021 compared to NaCl injections for 6 weeks). The dermal thickness in mice treated with Compound JNKi-1 for the last 3 weeks was significantly reduced to 127±4% at doses of 150 mg/kg BID (p=0.008 compared to bleomycin for 6 weeks). Thus, Compound JNKi-1 decreased the level of dermal thickness under the pre-treatment level (127±4% vs 175±8% compared to NaCl injections for 6 weeks, p=0.008 and p=0.021) (FIG. 7A). Besides dermal thickness, the number of myofibroblasts was strongly reduced upon treatment with 150 mg/kg Compound JNKi-1 under the pre-treatment level (171±31% vs. 443±15% compared to NaCl injections for 6 weeks, p=0.012 and p=0.014) (FIG. 7C). Additionally, the accumulation of collagen assessed by hydroxyproline assay was significantly reduced in mice treated with 150 mg/kg Compound JNKi-1 for the last 3 weeks of continuous bleomycin challenge for 6 weeks (p=0.025) (FIG. 7B). Thus, inhibition of JNK did not only prevent the development of fibrosis in different models, but also induced regression of pre-existing fibrosis.

6.4 In Vivo Analysis of Antifibrotic Effect of Compound JNKi-1 in Tsk-1 Mice The antifibrotic effects of the JNK inhibitor Compound JNKi-1 were tested in a murine tight skin-1 (Tsk-1) model of systemic sclerosis. In this model, a dominant mutation in the fibrillin 1 gene (Fbn1$^{Tsk}$+/−) leads to a systemic sclerosis-like disease with inflammatory infiltrates and massive fibrosis of the skin (Akhmetshina A, Venalis P, Dees C, Busch N, Zwerina J, Schett G, et al., *Treatment with imatinib prevents fibrosis in different preclinical models of systemic sclerosis and induces regression of established fibrosis*, Arthritis Rheum. 2009; 60(1):219-24).

Male and female TSK-1 mice were used. Mice were fed a standard diet with water ad libitum. The room temperature was kept constant at 22° C. with a humidity of 60%.

Compound JNKi-1 was dissolved in 0.5% carboxymethylcellulose (CMC)/0.25% Tween 80 in water. As vehicle control a solution of 0.5% CMC/0.25% Tween 80 in water was used. Imatinib mesylate was dissolved in 0.9% NaCl at a concentration of 50 mg/kg/day in a total volume of 100 µL.

Groups of Tsk-1 mice (n=4/sex/group) were assigned to one of five treatment groups:

Untreated wildtype (Fbn1$^{Tsk}$−/−) group received 0.5% CMC/0.25% Tween 80 in water orally (PO) twice daily (BID).

Untreated Fbn1Tsk+/− mice received 0.5% CMC/0.25% Tween 80 in water orally BID.

Compound JNKi-1-treated Fbn1$^{Tsk}$+/− received 50 mg/kg orally BID.

Compound JNKi-1-treated Fbn1$^{Tsk}$+/− received 150 mg/kg orally BID.

Imatinib mesylate-treated Fbn1$^{Tsk}$+/− group received 50 mg/kg/day administered intraperitoneally (IP).

Treatments with Compound JNKi-1 and control compound were started at Week 4. After 6 weeks of treatment, mice were sacrificed, and the antifibrotic effects from each treatment were analyzed.

Antifibrotic effects were determined by measuring the dermal thickness and quantifying the numbers of myofibroblasts in the lesional skin. Dermal thickness was determined by measuring the distance from the epidermal/dermal border to the dermal/subdermal border in H & E-stained sections at four different sites. The number of myofibroblasts was quantified by staining for alpha smooth muscle actin (α-SMA) in paraffin-embedded sections. Data are expressed as mean±standard error of the mean (SEM). SPSS17.0 software and the Mann-Whitney-U-test were used for statistical analyses. A p-value of less than 0.05 was considered statistically significant.

Tsk-1 mice showed dramatic hypodermal thickening, which was significantly reduced by 67%±5% (p=0.0005) following treatment with 50 mg/kg of Compound JNKi-1 and by 85%±7% (p=0.0003) following treatment with 150 mg/kg of Compound JNKi-1, compared to untreated mice (FIG. 8). The number of myofibroblasts was decreased by 68%±28% (p=0.008) following treatment with 50 mg/kg of Compound JNKi-1 and by 99%±9% (p=0.004) following treatment with 150 mg/kg of Compound JNKi-1, compared to untreated animals (FIG. 9). Mice treated with imatinib mesylate control compound showed decreased hypodermal thickness by 71%±7% (p=0.003) and decreased number of myofibroblasts by 99%±15% (p=0.004) compared to untreated mice (FIG. 8 and FIG. 9). In addition, the reduction in hypodermal thickening at doses of 150 mg/kg Compound JNKi-1 treatment was more pronounced than with treatment with 50 mg/kg imatinib (FIG. 10).

Compound JNKi-1 was found to dose-dependently reduce hypodermal hypertrophy and myofibroblast counts in the Tsk-1 dermal fibrosis mouse model.

6.5 Effect of Compound JNKi-1 on the Expression of Extracellular Matrix Protein Genes in Dermal Fibroblasts from Human Subjects with Systemic Sclerosis Using fibroblasts isolated from skin biopsies from human systemic sclerosis (SSc) patients, an in vitro study was performed to evaluate whether the selective JNK inhibitor Compound JNKi-1 affects the expression of key extracellular matrix proteins.

Dermal fibroblasts from two SSc patients were treated for 24 hours (hr) with Compound JNKi-1 at concentrations from 0.1 μM to 10 μM (0.5% DMSO/99.5% cell culture media). To study the effect of Compound JNKi-1 on growth factor-induced collagen expression, recombinant transforming growth factor beta (TGF-β) (final concentration of 10 ng/mL) or platelet-derived growth factor-BB (PDGF-BB) (final concentration of 40 ng/mL) were added to cells 2 hr after the addition of JNK-inhibitor Compound JNKi-1 for 24 hr. The expression of collagen proteins was analyzed by SirCol assay. The messenger ribonucleic acid (mRNA) levels of extracellular proteins were measured by real-time polymerase chain reaction (PCR). The β-actin mRNA was used as internal control for the measurement of Collagen 1a1 mRNA using PCR. Fibroblast proliferation assay was performed in the presence or absence of 1 μM Compound JNKi-1 for 24 hr with the (3-(4,5-Dimethylthiazol-2-yl)-2,5-diphenyltetrazolium bromide) (MTT) assay.

The isolation of fibroblasts from human SSc patients and culture conditions used in this study have been previously described (Akhmetshina A, Dees C, Pileckyte M, Maurer B, Axmann R, Jüngel A, et al., *Dual inhibition of c-abl and PDGF receptor signaling by dasatinib and nilotinib for the treatment of dermal fibrosis*, FASEB J. 2008; 22(7):2214-22). Fibroblast cultures were obtained from skin biopsies of SSc patients. All patients fulfilled the criteria for SSc as suggested by LeRoy and colleagues (LeRoy E C, Black C, Fleischmajer R, Jablonska S, Krieg T, Medsger T A Jr, et al., *Scleroderma (systemic sclerosis): classification, subsets and pathogenesis*, J. Rheumatol. 1988; 15(2):202-5). Biopsies from SSc patients were taken from involved skin of the forearm. After enzymatic digestion of the skin biopsies with Dispase II, fibroblasts were cultured in DMEM/F-12 containing 10% heat inactivated fetal calf serum (FCS), 100 U/mL penicillin, 100 μg/mL streptomycin, 2 mM L-glutamine and 2.5 μg/mL amphotericin B (all Invitrogen, Karlsruhe, Germany). Fibroblasts from passages 4-8 were used for the experiments. Data are expressed as mean±standard error of the mean (SEM).

Compound JNKi-1 dose-dependently reduced the expression of extracellular matrix proteins in SSc fibroblasts. Maximal effects were observed at concentrations of 1 μM. At this concentration, Compound JNKi-1 reduced the mRNA levels of col 1a1 and col 1a2 by 71±11% and 61±13%, respectively, and the levels of fibronectin-1 by 55±14% (p<0.02 compared to mock-treated fibroblasts for all) (FIG. 11A). Consistent with the decreased mRNA levels, incubation with 1 μM Compound JNKi-1 also reduced the amount of collagen protein in the supernatant by 21±7% (p=0.001) compared to control (FIG. 11B).

Fibroblasts from SSc patients were used to assess any direct effect of Compound JNKi-1 on cell viability. After a 24-hr incubation, no cytotoxic effect was observed with Compound JNKi-1 in an MTT assay as shown in FIG. 12.

Collagens are major extracellular matrix proteins that are overexpressed in fibrosis. TGF-β and PDGF are the most well-characterized growth factors present in the fibrotic lesion and have been shown to enhance fibrotic pathology in vitro and in vivo. Compound JNKi-1 was tested for its effect on the secretion of total collagens induced by TGF-β or PDGF from fibroblasts from SSc patients. As shown in FIG. 13, Compound JNKi-1 (1 μM) modestly inhibited both TGF-β and PDGF-induced collagen secretion.

6.6 Effect of Compound JNKi-1 on Ultraviolet B-Stimulated Apoptosis in SKH-1 Female Mice' Skin Ultraviolet B (UVB) light is known to induce breaks in DNA (nicks) that can trigger the process of apoptosis, and these nicks can be labeled and visualized with terminal deoxynucleotidyl transferase dUTP nick end labeling (TUNEL). TUNEL technology identifies DNA breaks by labeling free 3'-OH terminals with modified (fluorescing) nucleotides in an enzymatic reaction that makes the damaged apoptotic cells fluoresce. This study was one of a series of pharmacology studies designed to determine the effects of the JNK inhibitor, Compound JNKi-1, on UVB-induced apoptosis in the skin of mice.

Female SKH-1 mice (Charles River, n=17 total) were obtained at a body weight of 15 g to 20 g. Mice were housed in regular shoebox cages and allowed to become acclimated for a minimum of 1 week. Mice were fed Harlan Teklad (No. 7001) 4% mouse/rat diet and water ad libitum and were maintained on a 12-hour light/dark cycle.

Suspensions of Compound JNKi-1 were prepared in aqueous 0.5% CMC and 0.25% Tween-80. The formulations were homogenized using a TEFLON® pestle and mortar (Potter-Elvehjem tissue grinder). Vehicle (aqueous solution of 0.5% CMC and 0.25% Tween-80, stored at 4° C.) and test article compounds were dosed at a volume of 5 mL/kg. Two groups of mice (n=5/group) were dosed with vehicle or Compound JNKi-1 (75 mg/kg) orally (PO) twice daily (BID) for 5 days (9 AM and 12 noon) and exposed to UVB 1 hour (hr) following the final dose.

For determination of compound exposure in plasma and skin, a separate cohort of mice (n=5) was dosed with Compound JNKi-1 (75 mg/kg) for 5 days and samples were collected immediately following UV exposure (within 10 minutes of exposure).

Mice (n=5/group) were anesthetized using ketamine/xylazine (60 mg/kg and 10 mg/mL, respectively) prior to UVB exposure. An all-purpose paper label sticker was placed upon half of the dorsal mouse skin to block UVB stimulation within that area and then mice were subjected to UVB exposure (0.5 J/cm$^2$; Biospectra machine, Vilber Lourmat).

Skin biopsy punches were harvested 24 hr following UVB exposure from both stimulated and nonstimulated skin for TUNEL processing or snap frozen for compound level determination. Blood was drawn via cardiac puncture, spun in plasma separator tubes, and stored at −80° C. until processed for compound level determination. An additional treatment cohort was used to collect skin and blood samples immediately after UV exposure and one hour after drug administration. Skin biopsies processed for TUNEL were placed upon a piece of paper (to prevent curling) and fixed for 2 hr in 10% neutral buffered formalin. Once fixed, samples were placed into 100% ethanol until they could be processed for paraffin embedding. Tissue sections (6 μm thick) were generated and mounted on poly-1-lysine coated slides. Sections were deparaffinized and washed in phosphate buffered saline (PBS). Sections were then incubated in Proteinase K (15 μg/mL) in PBS for 15 minutes and washed in PBS. Sections were then incubated in a TUNEL reaction mixture (Roche 1684795) for 1 hr at 37° C. The sections were washed once more in PBS and cover slipped with Prolong Gold mounting media with antifade.

A Leica microscope with a CoolSNAP digital camera was used to obtain 5 random 20× magnification fluorescent images from five sections of skin epidermis and the number of TUNEL-positive green cells was counted to determine the average number of cells per animal and group (n=5).

Statistical one-way analysis of variance (ANOVA) was performed followed by Bonferroni's multiple comparison test (Graph Pad Prism). The data were expressed as mean±standard error of the mean (SEM).

Twenty-four hours after UVB exposure, a significant induction in TUNEL-positive cells could be measured compared with naive samples (FIG. 14; p<0.001). Chronic pretreatment with Compound JNKi-1 at a dose of 75 mg/kg PO BID for 5 days significantly (p<0.01) decreased the number of TUNEL-positive cells measured 24 hr post UV exposure compared to the vehicle control.

The study results demonstrate that Compound JNKi-1, administered orally prior to UVB exposure, can inhibit apoptotic cell death within the epidermis of SKH-1 mice.

6.7 Effect of Compound JNKi-1 in the Rat Model of Excisional Wound Healing

Wound healing proceeds by a series of highly coordinated events starting with the arrest of hemorrhage, followed by an inflammatory response, scab formation (early granulation tissue), re-epithelialization, collagen remodeling and scab detachment. This sequence of healing is typical of acute injuries and terminates in mature scar formation. Efficient cutaneous wound repair implies carefully orchestrated molecular events allowing fibroblasts to migrate to the wound site, contract the wound, and synthesize extracellular matrix to restore skin integrity. Fibroblasts maintain a limited yet significant pool of phosphorylated c-jun protein that is critical for allowing migration and motility (Javelaud, D., Laboureau, J., Gabison, E., Verrecchia, F., Mauviel, A., *Distruption of basal JNK activity differentially affects key fibroblast functions important for wound healing*, J. Biol. Chem. 2003; 278:24624-24628). Therefore, it is relevant to investigate whether a JNK inhibitor might affect the healing process by impairing fibroblast function.

Male CD-IGS rats (Strain code 001; n=32-52 per experiment) were obtained from Charles River Laboratories at a body weight of 175-195 g. Rats were housed in regular shoe-box cages and allowed to become acclimated for a minimum of 1 week. Rats were fed Harlan Teklad (No. 7001) 4% mouse/rat diet and water ad libitum and were maintained on a 12-hour light/dark cycle.

Suspensions of Compound JNKi-1 were prepared in aqueous 0.5% CMC and 0.25% Tween-80. The formulations were homogenized using a TEFLON® pestle and mortar (Potter-Elvehjem tissue grinder). Vehicle (aqueous solution of 0.5% carboxymethylcellulose, and 0.25% Tween-80) and test article compounds were dosed at a volume of 5 mL/kg. Groups of rats (n=4-8/group) were dosed orally with vehicle, Dexamethasone (0.5 mg/kg) or Compound JNKi-1 (10 mg/kg, 30 mg/kg or 60 mg/kg) daily throughout the study starting 4 days prior to the procedure and continuing for up to 14 days is 10 or 14 days post-wounding post-wounding. Compound JNKi-1 treated groups and the respective vehicle control group were dosed twice daily (bid) with an 8 hr separation between the doses. Dexamethasone treated animals and the respective vehicle control group were dosed once daily (qd) for the duration of the study. The design of the experiments is shown in Table 2.

TABLE 2

| Study | Dose Group (n) | Terminal Time Point |
|---|---|---|
| A | Vehicle bid (n = 8) | Day 10 |
|  | Vehicle qd (n = 8) | Day 10 |
|  | Dexamethasone$^a$ 0.5 mg/kg (n = 8) | Day 10 |
|  | Compound JNKi-1 60 mg/kg (n = 8) | Day 10 |
| B | Vehicle bid (n = 4/timepoint) | Day 1, 5, 10 and 14 |
|  | Dexamethasone$^a$ (n = 4/timepoint) | Day 1, 5 and 10 |
|  | Compound JNKi-1 60 mg/kg (n = 6/timepoint) | Day 1, 5, 10 and 14 |
| C | Vehicle bid (n = 6) | Day 10 |
|  | Dexamethasone$^a$ 0.5 mg/kg (n = 4) | Day 10 |
|  | Compound JNKi-1 10 mg/kg (n = 8) | Day 10 |
|  | Compound JNKi-1 30 mg/kg (n = 8) | Day 10 |
|  | Compound JNKi-1 60 mg/kg (n = 8) | Day 10 |

$^a$Dexamethasone (0.5 mg/kg) is the positive control for the excisional wound healing model (Durmus, M., Karaaslan, E., Ozturk, E., Gulec, M., Iraz, M., Edali, N., Ersoy, M O, *The effects of single-dose dexamethasone on wound healing in rats*, Anesth. Analg. 2003; 97: 1377-80.)

Rats were anesthetized by inhaled isoflurane and the dorsal area was shaved and swabbed with 70% alcohol. Two points were marked 5.5 and 8.5 cm from the base of the skull along the midline. Four further points were marked 1 cm at either side of the midline, two at each of the marked points. These delineated the centers of four excisional wounds. The biopsy punch (6 mm diameter) was aligned vertically over the center of a mark and the epidermis, dermis and panniculus carnosus pierced by applying pressure and twisting at the same time. The skin plug was then removed. This was repeated for the remaining wounds (FIG. 15). The animal was then allowed to recover. All animals were housed singly during the experiment. Rats were monitored twice a day for the first 24 hours following the procedure and then daily until the end of the study. Body weights were recorded two or three times per week. Animals were sacrificed via $CO_2$ asphyxiation at various time-points (day 1, 5, 10 or 14) following wounding.

Each wound size was measured using an electronic digital caliper and the percent of wound remaining open was calculated relative to the initial wound size recorded on day 0 (day of wounding procedure). Four values were averaged for each animal (four wounds on each rat). Measurements were taken at different time-points throughout the study.

Wounds and 2 mm of surrounding tissue were excised using an 8 mm biopsy punch. Wounds were harvested on days 1, 5, 10 and 14 following the procedure. Tissues were fixed in neutral buffered formalin for 3 h then transferred to 100% ethanol. Tissues were paraffin-embedded and four µm cross sections were cut and mounted on poly-lysine slides and stored in slide boxes at room temperature.

One slide for each specimen was stained for H&E to assess granulation-tissue formation and re-epithelialization of the wound gap.

Samples collected on day 10 and 14 were stained with Trichrome Stain (Masson) Kit (Sigma, HT15) to evaluate collagen deposition and remodeling.

Tissue sections were deparaffinized and hydrated to deionized (DI) water. Sections were incubated in preheated Bouin' Solution (Sigma, HT10-132) at 56° C. overnight and then thoroughly rinsed in tap water. Sections were stained in Weigert's Iron Hematoxylin solution (Sigma, HT10-79) for 15 min, washed, and counterstained with Biebrich Scarlet Acid Fuchsin solution. After washing, sections were incubated with Phosphotungstic-Phosphomolybdic acid solution for 15 min and then stained with Aniline Blue solution. Sections were dehydrated and cleared in xylene.

Wound healing was evaluated on day 10 and day 14 after the procedure. H&E sections were scored for re-epithelialization using the following criteria:

Score 0 Absence of new epidermis on one or both wound edges

Score 1 Incomplete re-epithelialization

Score 2 Complete re-epithelialization of the wound gap

Masson's Trichrome sections were scored for collagen deposition and remodeling using the following criteria:

Score 0 Absence of collagen deposition and reorganization

Score 1 Partial collagen remodeling

Score 2 Complete collagen remodeling (non-reticular appearance)

H&E and Masson's Trichrome scores were combined to calculate the overall healing score. Wounds that completely healed had a score=4.

The expression of alpha-smooth muscle actin (α-SMA) was evaluated by IHC on tissue samples harvested on day 5 after the procedure to investigate the migration of myofibroblasts into the wound site. Tissue sections were deparaffinized and hydrated to deionized (DI) water. Sections were incubated in 0.6% $H_2O_2$ for 15 min to quench endogenous peroxidase, washed and blocked in 5% goat serum for 10 min. Primary Ab (Sigma, A2547) was added for 60 min and biotinylated secondary Ab (Sigma, B9904) for 20 min at room temperature. Sections were then incubated with ExtrAvidin-Peroxidase (Sigma, E2886) for an additional 20 min. AEC (Sigma, AEC101) was used as chromogen to localize peroxidase in tissue. A qualitative assessment of α-SMA positive staining was made.

The levels of myeloperoxidase (MPO) were evaluated by IHC on tissue samples harvested on day 1 after the procedure to investigate the neutrophil influx into the wound site. Staining was performed according to manufacture instruction. Briefly, deparafinized tissues were boiled for 10 minutes in 10 mM citrate buffer (Lab Vision, AP-9003) for antigen retrieval. Primary Ab (Thermo Scientific Lab Vision, RB-373-A) was diluted 1:100 in blocking buffer and added for 60 min and the secondary Ab for 30 min at room temperature. Secondary Ab and ABC reagent were from Vectastain Elite ABC Kit (Vector Lab, Rabbit IgG, PK-6101). DAB was used as chromogen to localize peroxidase in tissue. A qualitative assessment of myeloperoxidase positive staining was made.

Body weight, wound size and healing score are expressed as the mean+/−SEM. Statistical analysis was performed using one way ANOVA followed by Dunnet's comparison to Vehicle control animals. *$P<0.05$, $P<0.01$ and *$P<0.001$ denotes statistical significance. The PK data are presented as the mean ($\mu M$)+/−SD.

Results. Body weight gain was comparable between vehicle and Compound JNKi-1 dosed groups. Dexamethasone treated rats lost about 10% of the initial body weight mass (FIG. 16, result is representative of three experiments).

Vehicle dosed groups completely healed by day 10 post-wounding. All animals in the positive control group that received Dexamethasone at 0.5 mg/kg showed a significant ($p<0.0001$) delay in the healing process and approximately 70% of the wound gap remained open at day 10 post wounding. A less dramatic (only 27%, n=3 studies), but still significant ($p<0.05$-$p<0.01$) delay in wound healing was observed in rats dosed with Compound JNKi-1 at 60 mg/kg b.i.d (FIG. 17). However, no difference was observed in rats dosed with Compound JNKi-1 at 30 or 10 mg/kg (FIG. 17, panel C). Complete skin repair was achieved by day 14 post wounding in all Compound JNKi-1 treated groups (FIG. 17, panel B). No difference was observed in the once daily (q.d.) or twice daily (b.i.d.) dosed vehicle groups (FIG. 17, panel A).

Healing score was evaluated based on re-epithelialization and collagen deposition/remodeling as described in the Experimental Procedures sections. On day 10 after wounding almost all vehicle dosed rats (6 out of 8) had completed new epidermis and collagen fibers remodeled in a non-reticular pattern. As expected, none of the animals that received Dexamethasone showed complete re-epithelialization and collagen remodeling. In the Compound JNKi-1 treated group, only 5 out of 14 rats had completely healed by day 10: two rats showed incomplete new epidermis, 4 rats had only partial collagen remodeling and 3 rats displayed both incomplete re-epithelialization and collagen remodeling. By day 14 all animals receiving Compound JNKi-1 had fully healed (FIG. 18, panel A). In the dose-response study (Study C) both 60 and 30 mg/kg doses showed a significant delay in healing compare to vehicle control group. None of the rats treated at 60 mg/kg had completely healed by day 10 and 5 out of 8 rats treated at 30 mg/kg displayed both incomplete re-epithelialization and collagen remodeling. No significant effect was observed in the group that received Compound JNKi-1 at 10 mg/kg (FIG. 18, panel B).

Myofibroblast Migration into the Wound Gap:

Early during healing of an open wound, resident dermal fibroblasts proliferate from the wound margin and migrate into the provisional matrix composed of a fibrin clot. About 1 week after wounding, the provisional matrix is replaced by neo-formed connective tissue, known as granulation tissue, essentially composed of small vessels, extracellular matrix, and fibroblastic cells that become activated myofibroblasts (Kwon, A H., Qiu, Z., and Hirao, Y., *Topical application of plasma fibronectin in full-thickness skin wound healing in rats*, Exp. Biol. Med. 2007; 232:935-941). The main marker of myofibroblasts is the neo-expression of α-smooth muscle actin (α-SMA), the actin isoform typical of vascular smooth muscle cells (Skalli, O., Ropraz, P., Trzeciak, A., Benzonana, G., Gillessen, D., and Gabbiani, G A, *Monoclonal antibody against alpha-smooth muscle actin: a new probe for smooth muscle differentiation*, J. Cell Biol. 1986; 103:2787-2796).

During model validation we demonstrated that myofibroblast migration into the wound gap peaks on day 5 after wounding. Therefore, we choose this time point to monitor α-SMA expression by immunohistochemistry on tissue sections. All vehicle dosed rats showed intense myofibroblast infiltration at the wound site (FIG. 19, panel A). In contrast, animals from the 60 mg/kg Compound JNKi-1 treated group displayed an earlier stage of the healing process with few myofibroblasts migrating at the wound edges and highly perfuse granulation tissue throughout the entire wound gap (FIG. 19, panel B). This suggests that JNK inhibitor Compound JNKi-1 might affect the healing process by reducing and/or delaying myofibroblast migration into the wound site.

Neutrophil Migration into the Wound Gap:

Neutrophil influx is an early inflammatory response that is essential for the clearance of bacteria and cellular debris during cutaneous wounding (Kim, M H., Liu, Wei., Borjesson, D L., Curry, F R E., Miller, L S., Cheung, A L., Liu, F T., Isseroff, R., Simon, S I., *Dynamics of neutrophil infiltration during cutaneous wound healing and infection using fluorescence imaging*, J. Invest. Dermatol. 2008; 128:1812-20). We have previously evaluated neutrophil infiltration in the excisional wound model and determined that their numbers peak on day 1 after wounding. Neutrophil migration was monitored using an anti-myeloperoxidase (MPO) antibody on skin sections. The number of neutrophils recruited into the wounds was comparable between controls and Compound JNKi-1 dosed rats (FIG. 20). This result suggests that inflammatory cell infiltration during the response to tissue damage is not affected by Compound JNKi-1 treatment at 60 mg/kg.

The study results demonstrate that by inhibiting JNK activity with Compound JNKi-1, the inflammatory response to tissue damage is not affected and complete skin repair can be achieved. However, the delay in the healing process observed with Compound JNKi-1 treatment suggests that basal JNK activity is critical for fibroblast migration and/or motility into the wound site.

6.8 Effect of Compound JNKi-1 on Ultraviolet B-Stimulated Human Skin

Study Design.

The inhibitory effect of JNKi-1 on JNK was evaluated by assessing the status of the downstream substrate c-Jun ("cJun") and phospho-c-Jun (or "p-cJun") following UV irradiation of human skin.

The study was designed as randomized, double blind, placebo controlled, multiple dose, 3-way crossover study. Fifteen subjects were randomized to one of 3 sequences (5 subjects per sequence) as outlined below (see Table 3). There was a 7-day to 10 day washout period (no more than 14 days) from the last dose of the previous period to the first dose of the next period.

TABLE 3

|  | Period 1 | Period 2 | Period 3 |
| --- | --- | --- | --- |
| Sequence I | A | B | C |
| Sequence II | B | C | A |
| Sequence III | C | A | B |

Treatment A = 75 mg JNKi-1, QD x 6 days
Treatment B = 200 mg JNKi-1, QD x 6 days
Treatment C = Placebo to JNKi-1, QD x 6 days The eligibility of the subjects was assessed during an approximately 28 day screening period. The minimal erythema dose (MED) was determined during screening and within 7 days of enrollment of Period 1 (i.e. Day-7 to Day-1).

To determine the MED, each subject received UC-irradiation to 6 areas on their buttock. The UV dose on each area was increased incrementally for the previous dose. The spectrum of UV-irradiation was UV light B spectrum (UVB). MED determination was done approximately 22 to 24 hours post UVB exposure.

Fifteen patients enrolled, 14 completed the study and were included in the PD and PK analyses; all were healthy Caucasian male volunteers with Fitzpatrick skin type 2. The mean age was 31 years old (20-49 years) and weight was 81 kg (64-96 kg). On the evening of Day-1, patients started fasting (at least an 8-hour fast prior to dosing on Day 1). Subjects received treatment A, B or C in Periods 1 to 3 under fasting conditions in an order based on the randomization scheme. Subjects went through the same procedures (except for the change in treatment) for all 3 periods, with the required washout in between periods. No strenuous activities were permitted during confinement. All efforts were made to keep activities, environment, food, procedures, and schedule between treatment periods identical.

On Day 6, subjects received a 2×MED UV dose to two sites on the buttock. One punch biopsy (approximately 3 mm in diameter by 0.8 mm in depth) was taken from one of the two UV irradiated sites. The punch biopsies were taken at 8 (±5 minutes) hours post UV exposure on Day 6.

Assessment of erythema was performed at 24 hours post-UV irradiation on the lower UV irradiated site. Three assessments of erythema were performed throughout the study with one assessment per period.

Skin specimens from the biopsies was analyzed for phospho c-Jun and total c-Jun using IHC assay. Phospho c-Jun was quantified using a 0-4 subjective grading scales and/or objective scoring using an automated system, i.e. a laser scanning cytometer (LSC), evaluating the integrated intensity of staining measured optically.

Plasma samples were collected on Day 6 from 0 to 24 hours postdose in each period to determine the concentrations and PK of JNKi-1.

Methods.

UV Exposure Equipment: The DermaPal UV unit (manufactured by Daavlin) uses a FS Fluorescent Sunlamp and exposure is regulated by a built-in digital timer. The DermaPal was adapted to position a 12 oz styrofoam coffee cup over the bulbs, which thus became a device establishing all exposure distances and preventing unwanted exposure. A separate device consisting of six graded neutral density filters was supplied to provide a graded series of UV doses to establish each patient's MED.

IHC Subjective Scoring Parameters:

Biopsies were analyzed following the procedures described below to evaluate phospho c-Jun and c-Jun expression using IHC assay. The method employed to assess JNK activation was a two antibody IHC assay that employed a primary antibody, directed against the target, and a secondary antibody conjugated with a chromogenic enzyme. Thus, the method was a two-step immunohistochemical assay designed to interrogate the target, c-Jun and phospho c-Jun. Any changes in JNK activity were measurable in the amounts of these target molecules, c-Jun and phospho c-Jun. The secondary antibody-reporter conjugate deposited a red color when incubated with the substrate reaction mix, thus marking the location of the primary antibody target complex. The red color was then recorded with standard bright-field illumination using a Nikon microscope. The microscope images were then photographed and electronic images were scored (blinded) by three independent and trained scorers using the following guidelines. A score of 0 indicated staining of 0-19% of the epithelial keratinocyte nuclei; a score of 1 indicated staining of 20-39% of the epithelial keratinocyte nuclei; a score of 2 indicated staining of 40-59% of the epithelial keratinocyte nuclei; a score of 3 indicated staining of 60-79% of the epithelial keratinocyte nuclei; and a score of 4 indicated staining of 80-100% of the epithelial keratinocyte nuclei. FIG. 21 depicts representative immunostaining for the respective scores.

Laser Scanning Cytometry Analysis:

For each tissue, a count of nuclei in the epithelial layer was obtained. All phospho c-Jun or c-Jun positive nuclei were counted as well as their integral (intensity). A score was calculated for each: score=(p-cJun or cJun positive nuclei× average Intensity)/Total nuclei.

Results.

JNKi-1 is a competitive, reversible JNK inhibitor. It was observed that 2×MED UVB elevated phospho c-Jun and c-Jun expression and that 2×MED UVB and biopsy protocols described herein are well-tolerated by patients.

The results determined that 200 mg of JNKi-1 inhibited phospho c-Jun in 11/14 (78%) patients; 75 mg of JNKi-1 reduced phospho c-Jun in 8/14 (57%) patients, based on subjective scoring (see FIG. 22).

Phospho c-Jun immunostaining of skin biopsy results for Patient 15 shows that the percentage of epithelial c-Jun positive nuclei is significantly decreased in the presence of JNK inhibitor over placebo (see FIG. 23).

JNKi-1 decreased the median subjective score of phospho c-Jun, in a manner that appears dose-related: placebo score 4, 75 mg score 3, 200 mg score 1 (See FIG. 24).

Table 4 shows the data for phospho c-Jun scores (see above) and inter-evaluator variability for the patients treated with JNKi-1.

TABLE 4

| Patient # | 200 mg | | | 75 mg | | | Placebo | | |
|---|---|---|---|---|---|---|---|---|---|
| | Scorer 1 | Scorer 2 | Scorer 3 | Scorer 1 | Scorer 2 | Scorer 3 | Scorer 1 | Scorer 2 | Scorer 3 |
| 1 | 1 | 2 | 1 | 2 | 1 | 2 | 4 | 4 | 4 |
| 2 | 1 | 2 | 1 | 4 | 4 | 4 | 3 | 3 | 3 |
| 3 | 1 | 2 | 1 | 0 | 0 | 0 | 4 | 4 | 4 |
| 4 | 2 | 2 | 2 | 3 | 3 | 3 | 4 | 4 | 3 |
| 5 | 4 | 4 | 3 | 2 | 2 | 2 | 4 | 4 | 4 |
| 6 | 1 | 2 | 1 | 4 | 4 | 4 | 3 | 3 | 3 |
| 7 | 4 | 3 | 3 | 3 | 3 | 3 | 4 | 4 | 4 |
| 9 | 1 | 2 | 1 | 4 | 4 | 4 | 4 | 4 | 4 |
| 10 | 0 | 0 | 0 | 3 | 3 | 4 | 4 | 4 | 4 |
| 11 | 3 | 3 | 3 | 3 | 2 | 3 | 3 | 3 | 3 |
| 12 | 2 | 3 | 2 | 1 | 1 | 1 | 4 | 4 | 4 |
| 13 | 4 | 4 | 4 | 1 | 1 | 0 | 0 | 0 | 0 |
| 14 | 0 | 0 | 0 | 3 | 3 | 3 | 3 | 4 | 3 |
| 15 | 0 | 0 | 0 | 2 | 2 | 2 | 4 | 4 | 4 |

Decrease in phospho c-Jun was confirmed using objective LSC analysis (see FIG. 25).

The data are statistically significant: following treatment with JNKi-1, fewer patients had high scores for phospho c-Jun (see FIG. 26). Logistic regression analysis on scores 0, 1, 2 vs. scores 3, 4 determined that for 75 mg vs. placebo, the odds ratio was 10.96, P-value 0.0164; and for 200 mg vs. placebo, the odds ratio was 41.89, P-value 0.0045.

Figure 28:
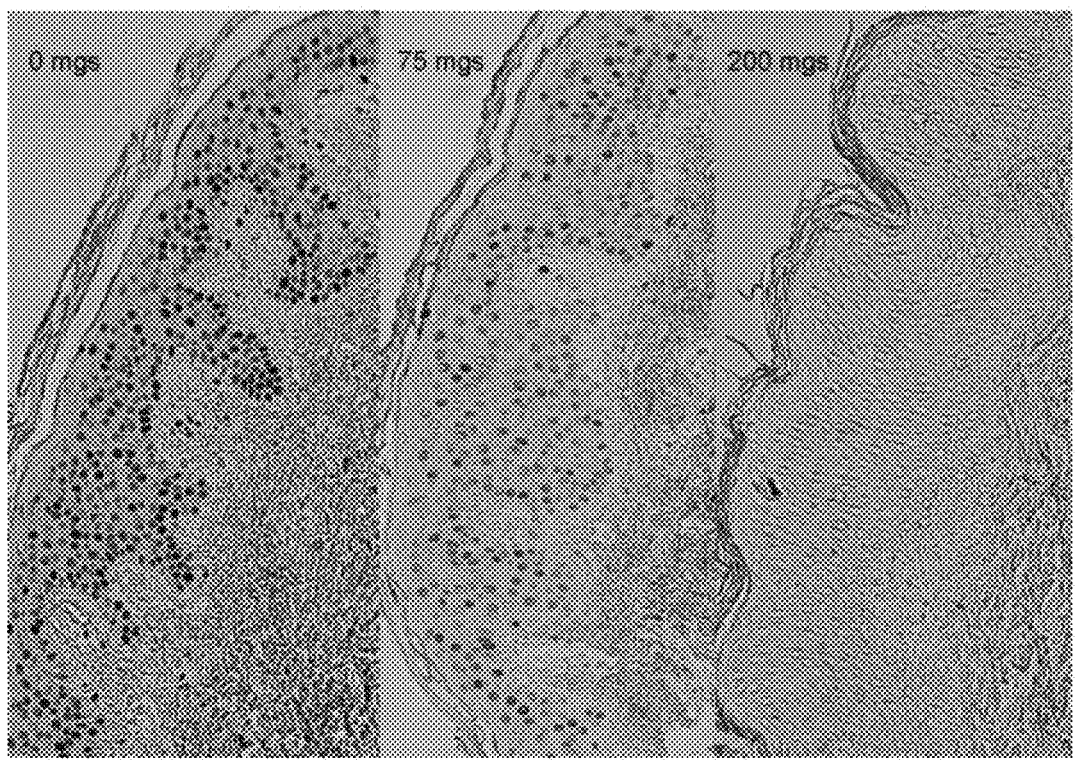

The data show a similar pattern of c-Jun inhibition by JNKi-1, but to a lesser extent: 200 mg of JNKi-1 inhibited c-Jun in 8/14 (57%) patients; 75 mg of JNKi-1 reduced c-Jun in 5/14 (36%) patients, based on subjective scoring (see FIG. 27).

c-Jun immunostaining of skin biopsy results for Patient 15 shows that the percentage of epithelial c-Jun positive nuclei is significantly decreased in the presence of JNK inhibitor over placebo (See FIG. 28).

JNKi-1 also decreased the median subjective score of c-Jun, in a manner that appears dose-related: placebo score 3, 75 mg score 3, 200 mg score 2 (See FIG. 29).

The c-Jun data are also statistically significant: following treatment with 200 mg of JNKi-1, fewer patients had high scores for c-Jun (See FIG. 30). Logistic regression analysis on scores 0, 1, 2 vs. scores 3, 4 determined that for 75 mg vs. placebo, the odds ratio was 3.69, P-value 0.1809; and for 200 mg vs. placebo, the odds ratio was 9.30, P-value 0.0427. Thus, JNKi-1 inhibits JNK activation in human patients.

6.9 Effect of JNK Inhibitors on Ultraviolet B-Stimulated JNK Activation in Model Systems Two in vitro systems, nHEK and the EpiDermFT™ skin model, were used in this study. The nHEK cells and EpiDermFT™ samples were pretreated with JNKi-1 at concentrations of 0.1, 3, and 10 µM prior to 60 mJ/cm$^2$ and 135 mJ/cm$^2$ UVB irradiation, respectively. After UV stimulation, the activities of JNK were measured as levels of phospho-c-Jun via immunoblotting of cell lysates using an anti-phospho-c-Jun S63 antibody. Phospho-Stat3 was also evaluated as a marker of JNK activation.

Methods.

nHEK Model system. Normal human epithelial keratinocytes (nHEK) cells were grown after three passages. Cells were plated at 2×10$^6$/plate in 100 mm plates. Plates were incubated at 37° C., 5% $CO_2$ for 5 days until ~80% confluent. Each plate was washed with warm phosphate buffered saline (PBS) and replenished with 10 mL of media containing either 0, 0.1, 3, or 10 µM of JNKi-1 and incubated for 1 hour (hr) at 37° C. Eight mL of media were removed and set aside. Plates were irradiated with 60 mJ/cm$^2$ of UVB in a UV cross-linker machine and control plates were sham irradiated. The 8 mL of media set aside were returned to each plate and stored at 37° C. Cells were harvested at 30 minutes and 4 hr post UV treatment and lysed in ice cold cell extraction buffer. Lysates were stored at −80° C.

EpiDermFT™ Model System.

Samples were cultured in 2 mL of serum-free maintenance media (EFT-200-MM) for 72 hr. After 72 hr, the media was replaced with 2 mL of fresh media containing 0, 0.1, 3, and 10 µM of JNKi-1, respectively). Samples were allowed to soak at 37° C., 5% $CO_2$ for 6 hr, then removed from the media and placed into 2 mL of PBS and irradiated with 135 mJ/cm$^2$ of UVB. Controls were sham irradiated. Samples were placed back into 2 mL of media containing JNKi-1. Samples were harvested at 30 minutes and 3 hr post UV treatment. Each sample was cut in half; one half was snap frozen in liquid nitrogen, homogenized in lysis buffer, and lysates stored at −80° C. The other half was placed in 10% neutral buffer formalin for 3 hr and transferred to 100% ethanol for processing Study Design. In the nHEK Model, cells were pre-incubated with either dimethyl sulfoxide (DMSO) (FIG. 31, lanes 1, 2, and 12 to 15) or JNKi-1 at the indicated concentration (lanes 3 to 11) for 1 hr and then irradiated without (Control, lanes 1 and 2) or with UVB at 60 mJ/cm$^2$ (lanes 3 to 15). Cells were lysed 30 minutes after UV irradiation and cell lysates were subjected to sodium dodecyl sulfate polyacrylamide gel electrophoresis (SDS-PAGE) before Western blotting with anti-phospho-c-Jun antibody. The lysates were also blotted for β-actin as loading control In the EpiDermFT™ model, cells were pre-incubated with either DMSO (FIG. 32, lanes 1 to 3) or JNKi-1 at an indicated concentration (lanes 4 to 12) for 2 hr and then irradiated without (Control, lanes 1 and 2) or with UVB at 135 mJ/cm$^2$ (lanes 4 to 12). Cells were lysed 30 minutes after UV irradiation and cell lysates were subjected to SDS-PAGE before Western blotting with anti-phospho-c-Jun antibody. The lysates were also blotted for β-actin as loading control Western analysis: For Western blot analysis, 20 to 25 μg of total protein were applied to SDS-PAGE gels followed by electrophoresis and blotting. Immunodetection was performed with anti-phospho-cJun (S63), anti-phospho-JNK (T183/Y185), and anti-phospho-Stat3 (S727) antibodies. Western blot imaging was performed on an Odyssey® Infrared Imaging System (LI-COR Biosciences, Lincoln, Nebr.). The intensity of each band was quantified by the Odyssey 2.1 software and exported into Excel for further analysis. The raw intensities p-JNK, pc-Jun, and p-Stat3 were normalized against the loading control, β-actin.

Results.

Stimulation with UVB caused strong elevation of phospho-c-Jun at 30 minutes (FIG. 31, lanes 12 to 15; FIG. 32, lanes 2 and 3) and the levels of phospho-c-Jun were sustained for 3 hours (data not shown). Pretreatment of cells with JNKi-1 significantly blocked the activation of JNK in a dose-dependent manner in both systems as shown by decreased levels of phospho-c-Jun (FIG. 31, lanes 3 to 11; FIG. 32, lanes 4 to 12). UV stimulation produced a slight increase in phospho-Stat3 levels at 30 minutes, however, inhibition by JNKi-1 was minimal (data not shown). The effect of JNKi-1 on c-Jun phosphorylation in nHEKs is shown by Western blot analysis (A). Quantitation of Western blot is shown in panel B.

As shown in the Figures, pretreatment with JNKi-1 significantly blocks UVB-induced JNK activation in nHEK and EpiDermFT™ skin models in a dose-dependent manner. The $IC_{50}$ for p-cJun in both systems is between 0.1 μM and 3 μM.

A number of references have been cited, the disclosures of which are incorporated herein by reference in their entirety.

What is claimed is:

1. A method for treating scleroderma, comprising administering to a patient having scleroderma an effective amount of a compound having the formula (I):

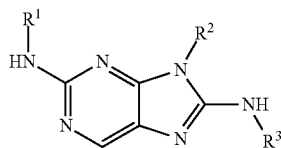

(I)

or a pharmaceutically acceptable salt, solid form, solvate, hydrate or tautomer thereof, wherein:

$R^1$ is substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl;

$R^2$ is H, substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl; and $R^3$ is aryl substituted with one or more halogens or $C_{3-10}$heteroaryl substituted with one or more halogens, wherein the aryl or $C_{3-10}$heteroaryl group is optionally further substituted with one or more $C_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

2. The method of claim 1, wherein $R^1$ is $C_{3-10}$cycloalkyl substituted with one or more $C_{1-6}$alkyl, hydroxy, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

3. The method of claim 1, wherein $R^2$ is substituted or unsubstituted 3-oxetanyl, 3-tetrahydrofuranyl, 4-tetrahydropyranyl, 4-piperidinyl, 4-(1-acyl)-piperidinyl, 4-(1-alkanesulfonyl)piperidinyl, 3-pyrrolidinyl, 3-(1-acyl)pyrrolidinyl, and 3-(1-alkanesulfonyl)pyrrolidinyl.

4. The method of claim 1, wherein $R^3$ is fluoro substituted phenyl.

5. The method of claim 1, wherein the compound is a compound from Table 1, or a pharmaceutically acceptable salt, solid form, solvate, hydrate or tautomer thereof.

6. A method for improving the modified Rodnan skin score, reducing or improving the skin thickness, reducing or improving skin induration, improving the pulmonary function, improving the dermatology quality of life index, improving the carbon monoxide diffusing capacity, improving the Mahler Dyspnea index, improving the Saint George's Respiratory Questionnaire score, improving the UCLA scleroderma clinical trial consortium gastrointestinal tract score, improving flow-mediated dilatation or improving or increasing the six minute walk distance of a patient having scleroderma, comprising administering to said patient an effective amount of a compound having the formula (I):

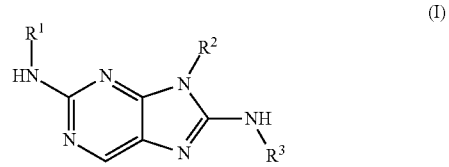

(I)

or a pharmaceutically acceptable salt, solid form, solvate, hydrate or tautomer thereof, wherein:

$R^1$ is substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl;

$R^2$ is H, substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl; and $R^3$ is aryl substituted with one or more halogens or $C_{3-10}$heteroaryl substituted with one or more halogens, wherein the aryl or $C_{3-10}$heteroaryl group is optionally further substituted with one or more $C_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

7. The method of claim 6, wherein $R^1$ is $C_{3-10}$cycloalkyl substituted with one or more $C_{1-6}$alkyl, hydroxy, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

8. The method of claim 6, wherein $R^2$ is substituted or unsubstituted 3-oxetanyl, 3-tetrahydrofuranyl, 4-tetrahydropyranyl, 4-piperidinyl, 4-(1-acyl)-piperidinyl, 4-(1-alkanesulfonyl)piperidinyl, 3-pyrrolidinyl, 3-(1-acyl)pyrrolidinyl, and 3-(1-alkanesulfonyl)pyrrolidinyl.

9. The method of claim 6, wherein $R^3$ is fluoro substituted phenyl.

10. The method of claim 6, wherein the compound is a compound from Table 1, or a pharmaceutically acceptable salt, solid form, solvate, hydrate or tautomer thereof.

11. A method for reducing or inhibiting a symptom of scleroderma selected from the group consisting of (i) gradual hardening, thickening, and tightening of the skin; (ii) skin discoloration; (iii) numbness of extremities; (iv) shiny skin; (v) small white lumps under the surface of the skin that erupt into a chalky white fluid; (vi) Raynaud's esophagaeal dysfunction; (vii) telangiectasia; (viii) pain and/or stiffness of the joints; (ix) swelling of the hands and feet; (x) itching of the skin; (xi) stiffening and curling of the fingers; (xii) ulcers (sores) on the outside of certain joints; (xiii) digestive problems; (xiv) fatigue and weakness; (xv) shortness of breath; (xvi) arthritis; (xvii) hair loss; (xviii) internal organ problems; (xix) digital ulcers; and (xx) digital auto-amputation, comprising administering to a patient having scleroderma an effective amount of a compound having the formula (I):

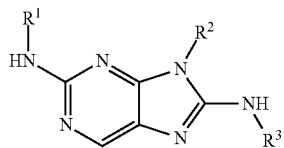

(I)

or a pharmaceutically acceptable salt, solid form, solvate, hydrate or tautomer thereof, wherein:

$R^1$ is substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl;

$R^2$ is H, substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl; and $R^3$ is aryl substituted with one or more halogens or $C_{3-10}$heteroaryl substituted with one or more halogens, wherein the aryl or $C_{3-10}$heteroaryl group is optionally further substituted with one or more $C_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

12. The method of claim 11, wherein $R^1$ is $C_{3-10}$cycloalkyl substituted with one or more $C_{1-6}$alkyl, hydroxy, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

13. The method of claim 11, wherein $R^2$ is substituted or unsubstituted 3-oxetanyl, 3-tetrahydrofuranyl, 4-tetrahydropyranyl, 4-piperidinyl, 4-(1-acyl)-piperidinyl, 4-(1-alkanesulfonyl)piperidinyl, 3-pyrrolidinyl, 3-(1-acyl)pyrrolidinyl, and 3-(1-alkanesulfonyl)pyrrolidinyl.

14. The method of claim 11, wherein $R^3$ is fluoro substituted phenyl.

15. The method of claim 11, wherein the compound is a compound from Table 1, or a pharmaceutically acceptable salt, solid form, solvate, hydrate or tautomer thereof.

16. The method of claim 11, wherein the symptom of scleroderma is gradual hardening, thickening, and tightening of skin of the hands, face or feet.

17. The method of claim 11, wherein the symptom of scleroderma is an ulcer on the outside of a knuckle or elbow.

18. The method of claim 11, wherein the symptom of scleroderma is heartburn, difficulty in swallowing, diarrhea, irritable bowel or constipation.

* * * * *